United States Patent
Myers et al.

(10) Patent No.: US 9,775,915 B2
(45) Date of Patent: Oct. 3, 2017

(54) TRIOXACARCINS, TRIOXACARCIN-ANTIBODY CONJUGATES, AND USES THEREOF

(71) Applicant: President and Fellows of Harvard College, Cambridge, MA (US)

(72) Inventors: Andrew G. Myers, Boston, MA (US); Daniel J. Smaltz, Cambridge, MA (US); Andreas Schumacher, Bottmingen (CH)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/647,198

(22) PCT Filed: Nov. 26, 2013

(86) PCT No.: PCT/US2013/071924
§ 371 (c)(1),
(2) Date: May 26, 2015

(87) PCT Pub. No.: WO2014/082065
PCT Pub. Date: May 30, 2014

(65) Prior Publication Data
US 2015/0297747 A1    Oct. 22, 2015

Related U.S. Application Data

(60) Provisional application No. 61/729,826, filed on Nov. 26, 2012.

(51) Int. Cl.
*A61K 39/00* (2006.01)
*C07K 16/00* (2006.01)
(Continued)

(52) U.S. Cl.
CPC ...... *A61K 47/48569* (2013.01); *A61K 47/484* (2013.01); *A61K 47/48484* (2013.01); *C07K 16/18* (2013.01)

(58) Field of Classification Search
CPC ............ A61K 47/48484; A61K 47/484; A61K 47/48569; A61K 39/00; C07K 16/18; C07K 16/00
(Continued)

(56) References Cited

U.S. PATENT DOCUMENTS

| 4,270,537 A | 6/1981 | Romaine |
| 4,355,023 A | 10/1982 | Ehrlich et al. |

(Continued)

FOREIGN PATENT DOCUMENTS

| JP | 58-065293 A | 4/1983 |
| JP | 63-135389 A | 6/1988 |

(Continued)

OTHER PUBLICATIONS

International Search Report and Written Opinion for PCT/US2011/029343, mailed Jul. 22, 2011.
(Continued)

*Primary Examiner* — T. Victor Oh
(74) *Attorney, Agent, or Firm* — Wolf, Greenfield & Sacks, P.C.

(57) ABSTRACT

Provided herein are trioxacarcin-antibody drug conjugates of Formula (A): and pharmaceutically acceptable salts thereof, comprising at least one instance of the group $-L^1-(A-L^2)a-B$ attached thereto, wherein a is an integer between 1 and 10, inclusive, $L^1$ is absent or is a linking group, A is a moiety formed from the reaction of two complimentary groups (X and Y), $L^2$ is absent or is another linking group, and B is an antibody or antibody fragment.

(Continued)

Also provided are methods of preparing these antibody-drug conjugates, pharmaceutically acceptable compositions thereof, and methods of their use and treatment. Further provided are precursors to the trioxacarcin-antibody drug conjugates, novel trioxacarcins without an antibody conjugated thereto, pharmaceutical compositions thereof, and methods of their use and treatment.

(A)

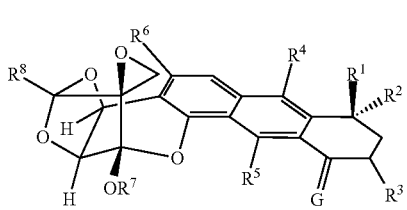

24 Claims, 31 Drawing Sheets

(51) Int. Cl.
*A61K 47/48* (2006.01)
*C07K 16/18* (2006.01)
(58) Field of Classification Search
USPC .................................. 424/181.1; 530/391.9
See application file for complete search history.

(56) References Cited

U.S. PATENT DOCUMENTS

| | | | |
|---|---|---|---|
| 4,459,291 A | 7/1984 | Shirahata et al. |
| 4,470,925 A | 9/1984 | Auditore-Hargreaves |
| 4,511,560 A | 4/1985 | Tomita et al. |
| 4,596,556 A | 6/1986 | Morrow et al. |
| 4,626,503 A | 12/1986 | Lee et al. |
| 4,790,824 A | 12/1988 | Morrow et al. |
| 4,816,567 A | 3/1989 | Cabilly et al. |
| 4,886,499 A | 12/1989 | Cirelli et al. |
| 4,940,460 A | 7/1990 | Casey, I. et al. |
| 4,941,880 A | 7/1990 | Burns |
| 4,946,778 A | 8/1990 | Ladner et al. |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,202,238 A | 4/1993 | Fell et al. |
| 5,204,244 A | 4/1993 | Fell et al. |
| 5,312,335 A | 5/1994 | McKinnon et al. |
| 5,328,483 A | 7/1994 | Jacoby |
| 5,334,144 A | 8/1994 | Alchas et al. |
| 5,383,851 A | 1/1995 | McKinnon, Jr. et al. |
| 5,399,163 A | 3/1995 | Peterson et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,565,354 A | 10/1996 | Ostberg |
| 5,567,610 A | 10/1996 | Borrebaeck et al. |
| 5,569,189 A | 10/1996 | Parsons |
| 5,569,825 A | 10/1996 | Lonberg et al. |
| 5,599,302 A | 2/1997 | Lilley et al. |
| 5,649,912 A | 7/1997 | Peterson |
| 5,704,911 A | 1/1998 | Parsons |
| 5,893,397 A | 4/1999 | Peterson et al. |
| 5,993,412 A | 11/1999 | Deily et al. |
| 7,846,915 B2 | 12/2010 | Wong et al. |
| 9,102,697 B2 | 8/2015 | Myers et al. |
| 2011/0165155 A1 | 7/2011 | Agresta et al. |
| 2013/0150314 A1 | 6/2013 | Myers et al. |

FOREIGN PATENT DOCUMENTS

| | | |
|---|---|---|
| JP | 63-135390 A | 6/1988 |
| JP | 63-135391 A | 6/1988 |
| WO | WO 97/13537 A1 | 4/1997 |
| WO | WO 97/37705 A1 | 10/1997 |
| WO | WO 99/34850 A1 | 7/1999 |
| WO | WO 2005/080549 A2 | 9/2005 |
| WO | WO 2011/119549 A1 | 9/2011 |

OTHER PUBLICATIONS

International Preliminary Report on Patentability for PCT/US2011/029343, mailed Oct. 4, 2012.
International Search Report and Written Opinion for PCT/US2013/071924, mailed Feb. 6, 2014.
International Preliminary Report on Patentability for PCT/US2013/071924, mailed Jun. 4, 2015.
Anelli et al., Fast and selective oxidation of primary alcohols to aldehydes or to carboxylic acids and of secondary alcohols to ketones mediated by oxoammonium salts under two-phase conditions. J Org Chem. 1987;52(12):2559-2562.
Boeckman et al., Catechol Boron Halides: Mild and Selective Reagents for Cleavage of Common Protecting Groups. Tetrahedron Lett. 1985;26:1411-14.
Bondar et al., Pectenotoxin-2 synthetic studies. 2. Construction and conjoining of ABC and DE Eastern hemisphere subtargets. Org Lett. Apr. 28, 2005;7(9):1813-6.
Brubaker et al., A practical, enantioselective synthetic route to a key precursor to the tetracycline antibiotics. Org Lett. Aug. 30, 2007;9(18):3523-5. Epub Aug. 11, 2007.
Brzezinski et al., The Asymmetric Baylis-Hillman Reaction. J Am Chem Soc. 1997;119(18):4317-4318.
Cassidy et al., Phase I clinical study of LL-D49194 alpha 1 with retrospective pharmacokinetic investigations in mice and humans. The EORTC ECTG. Cancer Chemother Pharmacol. 1993;31(5):395-400.
Collum et al., Synthesis of the polyether antibiotic monensin. 2. Preparation of intermediates. J Am Chem Soc. 1980;102(6):2118-2120.
Dimond, Antibody-Drug Conjugates Stage a Comeback. GEN Genetic Engineering & Biotechnology News. Mar. 10, 2010. 3 pages. Accessed at http://www.genengnews.com/insight-and-intelligenceand153/antibody-drug-conjugates-stage-a-comeback/77899350.
Drewes et al., Facile Diastereoselective Synthesis of 2,6-Dialkyl-5-methylene-1,3-dioxan-4-ones via α-Activated Vinyl Esters. Chem Ber. 1990;123:1447-48.
Ducry et al., Antibody-drug conjugates: linking cytotoxic payloads to monoclonal antibodies. Bioconjug Chem. Jan. 2010;21(1):5-13. doi: 10.1021/bc9002019.
Fitzner et al., Formation of gutingimycin: analytical investigation of trioxacarcin A-mediated alkylation of dsDNA. Anal Bioanal Chem. Feb. 2008;390(4):1139-47. Epub Jan. 22, 2008.
Fujimoto et al., Antitumor activity of trioxacarcin C. J Antibiot (Tokyo). Sep. 1983;36(9):1216-21.
Garegg et al., Synthesis of Methyl 2,6-Dideoxy-3-C-methyl-α-L-xylo-hexopyranoside ("Methyl-α-Axenoside"). Acta Chemica Scandinavica B. 1975;29:507-12.
Hill et al., Anhydrous tert-butyl hydroperoxide in toluene: the preferred reagent for applications requiring dry TBHP. J Org Chem. 1983;48(20):3607-3608.
Kato et al., Fluorescence study on the nyctinasty of *Phyllanthus urinaria* L. using novel-fluorescence-labeled probe compounds. Tetrahedron. 2006;62:7307-18.
Kovtun et al., Antibody-drug conjugates designed to eradicate tumors with homogeneous and heterogeneous expression of the target antigen. Cancer Res. Mar. 15, 2006;66(6):3214-21.

(56) References Cited

OTHER PUBLICATIONS

Kovtun et al., Cell killing by antibody-drug conjugates. Cancer Lett. Oct. 8, 2007;255(2):232-40. Epub Jun. 5, 2007.

Kraus et al., An Annelation Route to Quinones. Tetrahedron Lett. 1978;19(26):2263-66.

Le Pecq et al., A new fluorometric method for RNA and DNA determination. Anal Biochem. Oct. 1966;17(1):100-7.

Lim et al., A method for the preparation of differentiated trans-1,2-diol derivatives with enantio- and diastereocontrol. J Am Chem Soc. Apr. 29, 2009;131(16):5763-5.

Magauer et al., Component-based syntheses of trioxacarcin A, DC-45-A1 and structural analogues. Nat Chem. Oct. 2013;5(10):886-93. doi: 10.1038/nchem.1746. Epub Sep. 8, 2013.

Maiese et al., LL-D49194 antibiotics, a novel family of antitumor agents: taxonomy, fermentation and biological properties. J Antibiot (Tokyo). Mar. 1990;43(3):253-8.

Marshall et al., Synthesis of Protected Carbohydrate Derivatives Through Homologation of Threose and Erythrose Derivatives with Chiral .gamma.-Alkoxy Allylic Stannanes. J Org Chem. 1994;59(12):3413-3420.

Maskey et al., Anti-cancer and antibacterial trioxacarcins with high anti-malaria activity from a marine Streptomycete and their absolute stereochemistry. J Antibiot (Tokyo). Dec. 2004;57(12):771-9.

Maskey et al.. Gutingimycin: a highly complex metabolite from a marine streptomycete. Angew Chem Int Ed Engl. Feb. 27, 2004;43(10):1281-3.

Mattes et al., Mechanism of DNA strand breakage by piperidine at sites of N7-alkylguanines. Biochim Biophys Acta. Oct. 16, 1986;868(1):71-6.

Oppolzer et al., Enantioselective Addition of (Z)- and (E)-Alkenylzinc Bromides to Aldehydes: Asymmetric Synthesis of Sec-Allylalcohols. Tetrahedron Lett. 1991;32:5777-80.

Pangborn et al., Safe and Convenient Procedure for Solvent Purification. Organometallics. 1996;15(5):1518-1520.

Pfoh et al., Crystal structure of trioxacarcin A covalently bound to DNA. Nucleic Acids Res. Jun. 2008;36(10):3508-14. Epub May 3, 2008.

Pröpper et al., Crystalline guanine adducts of natural and synthetic trioxacarcins suggest a common biological mechanism and reveal a basis for the instability of trioxacarcin A. Bioorg Med Chem Lett. Sep. 15, 2014;24(18):4410-3. doi: 10.1016/j.bmcl.2014.08.016.

Schinzer et al., Syntheses of (−)-Epothilone B. J Chem-Euro J. 1999;5:2492-500.

Sharpless et al., Metal-Catalyzed, Highly Selective Oxygenations of Olefins and Acetylenes with tert-Butyl Hydroperoxide. Practical Considerations and Mechanisms. Aldrichimica Acta. 1979;12:63-74.

Smaltz et al., Diastereoselective additions of allylmetal reagents to free and protected syn-α,β-dihydroxyketones enable efficient synthetic routes to methyl trioxacarcinoside A. Org Lett. Apr. 6, 2012;14(7):1812-5. Epub Mar. 9, 2012.

Still et al., Rapid chromatographic technique for preparative separations with moderate resolution. J Org Chem. 1978;43(14):2923-2925.

Suami et al., Synthesis of Methyl α-Trioxacarcinoside B. Chem Lett. 1982:1245-48.

Suami et al., Synthetic Studies on Methyl α-Trioxacarcinoside B. Bull Chem Soc Jpn. 1983;56:1431-34.

Švenda et al., A multiply convergent platform for the synthesis of trioxacarcins. Proc Natl Acad Sci U S A. Apr. 26, 2011;108(17):6709-14. Epub Jan. 18, 2011.

Svenda et al., Anti-selective epoxidation of methyl alpha-methylene-beta-tert-butyldimethylsilyloxycarboxylate esters. Evidence for stereospecific oxygen atom transfer in a nucleophilic epoxidation process. Org Lett. Jun. 4, 2009;11(11):2437-40.

Tamaoki et al., Trioxacarcins, novel antitumor antibiotics. II. Isolation, physico-chemical properties and mode of action. J Antibiot (Tokyo). Dec. 1981;34(12):1525-30.

Teicher et al., Antibody conjugate therapeutics: challenges and potential. Clin Cancer Res. Oct. 15, 2011;17(20):6389-97. doi: 10.1158/1078-0432.CCR-11-1417.

Tomita et al., Trioxacarcins, Novel Antitumor Antibiotics. I. Producing Organism, Fermentation and Biological Activities. J Antibiotics. 1981;34(12):1519-24.

Wahl et al., Improved radioimaging and tumor localization with monoclonal F(ab')2. J Nucl Med. Apr. 1983;24(4):316-25.

Williams et al., A New General Method of Preparation of N-Methoxy-N-Methylamides. Applications in Direct Conversion of an Ester to a Ketone. Tetrahedron. 1995;36:5461-64.

Yu et al., Improved procedure for the oxidative cleavage of olefins by OsO4—NaIO4. Org Lett. Sep. 16, 2004;6(19):3217-9.

Nicolaou et al., Total Synthesis of Trioxacarcins DC-45-A1, A, D, C, and C7"-epi-C and Full Structural Assignment of Trioxacarcin C. J Am Chem Soc. Mar. 9, 2016;138(9):3118-24. doi: 10.1021/jacs.5b12687. Epub Feb. 24, 2016.

Nicolaou et al., Total Synthesis of Trioxacarcin DC-45-A2. Angew Chem. 2015;127:3117-3121.

| Compound | GI₅₀ (nM) | | | | | | | | % Prolif (100 nM) |
|---|---|---|---|---|---|---|---|---|---|
| | H460 | T-47D | HEKα93 | M87 | MDA-MB-468/072 | HT 29 | HL-60 | HEL 92.1.7 (MDR+) | |
|  | 0.85 | 3.5 | 0.85 | | | | | | |
|  | 57 | 47 | 27 | 10.3 | 41.0 | 56.1 | 13.7 | 80.6 | 37 |

| Compound | GI50 (nM) | | | | | | | | % Prolif (100 nM) |
|---|---|---|---|---|---|---|---|---|---|
| | H460 | T-47D | HEK293 | N87 | MDA MB 468PTX2 | MT 29 | HL 64 | TB1 92.1.7 (MDR+) | |
| 3 | 19 | 28 | 5.1 | 5.7 | 27.4 | 12.6 | 6.0 | 0.3 | 5 |
| 4 | 44 | 36 | 16 | 11.7 | 93.0 | 52.3 | 11.6 | 0.7 | 49 |
| 5 | 38 | | | 8.4 | 78.4 | 31.8 | 22.9 | 2.7 | 38 |

| Compound | IC50 (nM) | | | | | | | | % Prolif (100 nM) |
|---|---|---|---|---|---|---|---|---|---|
| | H460 | T-47D | HEK293 | N87 | MDA-MB-468/TT2 | HT-29 | HT-60 | HEL 92.1.7 (MDM2-+) | |
| 9 | >5000 | | | | | | | | 99 |
| 10 | >5000 | | | | | | | | 98 |
| 11 | 331 | | | | | | | | 83 |

| Compound | HMEC | T-47D | HEK293 | N87 | GI$_{50}$ (nM) MDA 468 2400 YFX | HT 29 | HL 60 | HBL 92.1.7 (MDR+) | % Prolif (100 nM) |
|---|---|---|---|---|---|---|---|---|---|
| 18 (structure) | 397 | | | | | | | | 88 |
| 19 (structure) | 10 | | | 9.9 | 28.2 | 11.3 | 2.3 | 0.2 | 7 |
| 20 (structure) | 10 | | | 13.1 | 48.4 | 39.1 | 14.7 | 1.0 | 36 |

Figure 10 (continued)

| Compound | CI₅₀ (nM) | | | | | | | | % Prolif (100 nM) |
|---|---|---|---|---|---|---|---|---|---|
| | H460 | T-47D | HEK293 | A87 | MDA-MB-231/ATCC | HT-29 | HL-60 | MES SA/DX (MDR+) | |
| 31 | 4.5 | | | 4.2 | 33.8 | 12.0 | 2.2 | 0.3 | 20 |
| 32 | 59 | | | | | | | | 65 |

Figure 10 (continued)

| Compound | GI₅₀ (nM) | | | | | | | | % Prolif (100 nM) |
|---|---|---|---|---|---|---|---|---|---|
| | H460 | T-47D | HEK293 | N87 | MCF7 xen (A549YT) | HT 29 | HL 60 | HH1 92.1.7 (MDR+) | |
| 23 | >2500 | | | | | | | | |
| 24 | <0.042 | | | 5.9 | 57.8 | 13.5 | 2.0 | 0.4 | 21 |
| 25 | <1.1 | | | 2.4 | 43.1 | 9.4 | 1.8 | 0.3 | 16 |

Figure 10 (continued)

| Compound | GI₅₀ (nM) | | | | | | | | % Prolif (100 nM) |
|---|---|---|---|---|---|---|---|---|---|
| | H460 | T47D | HEK293 | X87 | MDA MB 361/DYT2 | HT 29 | HL 60 | HBL 92.1.7 (MJW+) | |
| 26  | 2.5 | | | 4.4 | 24.7 | 8.2 | 2.1 | 0.3 | 6 |
| 27  | 2.6 | | | 7.4 | 58.8 | 22.7 | 2.1 | 0.2 | 25 |
| 28  | 3.8 | | | 9.3 | 62.2 | 24.6 | 10.6 | 0.5 | 28 |

| Compound | IC₅₀ (nM) | | | | | | | | % Prolif (100 nM) |
|---|---|---|---|---|---|---|---|---|---|
| | H460 | T-47D | HEK293 | K87 | MDA MB-468 | | HT 29 | 10T 1/2 | BJ-1 92-117 (MDR+) | |
| 29 | 4.4 | | | | | | | | | |
| 30 | 46 | | | | | | | | | 76 |
| 32 | 62 | | | | | | | | | 77 |

Figure 10 (continued)

| Compound | GI₅₀ (nM) | | | | | | | % Prolif (100 nM) |
|---|---|---|---|---|---|---|---|---|
| | H460 | T47D | HEK293 | N87 | MDA MB 468/ATCC | HT 29 | HL 60 | HEL 92.1.7 (MDR+) |
| 33 | 2303 | | | | | | | 92 |
| 34 | 313 | | | | | | | 89 |
| 35 | 374 | | | | | | | 96 |
| 36 | 7.8 | | | | | | | 67 |

Figure 10 (continued)

| Compound | H460 | P-470 | HEK293 | 1887 | MDA MB 435MDR2 | HT-29 | HL-60 | HL3 9-212 (MDR+) | % Prolif <100 nM |
|---|---|---|---|---|---|---|---|---|---|
| 37 | 17 | | | 13.2 | 111.4 | 57.9 | 20.3 | 0.9 | 54 |
| 38 | 17 | | | 17.7 | 42.8 | 31.9 | 15.6 | 1.6 | 33 |
| 39 | 6480 | | | | | | | | |

Figure 10 (continued)

| Compound | GI₅₀ (nM) | | | | | | | | % Prolif (100 nM) |
|---|---|---|---|---|---|---|---|---|---|
| | H460 | T-47D | HEK293 | N87 | MDA/MB/MDCT2 | HT | HL-60 | HH1 92.1.7 (MDK-) | |
| 40  | 670 | | | | | | | | 92 |
| 41  | > 2500 | | | | | | | | |
| 44  | 83 | | | | | | | | 81 |

| compound | CI₅₀ (nM) | | | | | | | % Prolif (100 nM) |
|---|---|---|---|---|---|---|---|---|
| | H460 | T-47D | HEK293 | N87 | MDA MB 435/LCC6 | HT 29 | HL 60 | MB 231 92.17 (MDR+) |
| 49 | | | | | | | | |
| 50 | | | | | | | | |
| 51 | | | | | | | | |

Figure 10 (continued)

| Compound | IC₅₀ (nM) | | | | | | | % Prolif (100 nM) |
|---|---|---|---|---|---|---|---|---|
| | H460 | T-47D | HEK293 | NK7 | MDA-MB-231/ATCC | HT-29 | HT-60 | MCF-7/ADR (MDR+) | |
| 52 (structure) | | | | | | | | | 67 |
| 53 (structure) | | | | | | | | | |
| 54 (structure) | | | | | | | | | 96 |

Figure 10 (continued)

| Compound | IC₅₀ (nM) | | | | | | | | % Prolif. <100 nM |
|---|---|---|---|---|---|---|---|---|---|
| | HeLa | T-47D | HEK293 | H69 | MDA-MB-468/12 | KB-3 | KB-V1/VLB | HL-60 | HL-60/MDR-1 | |
| 55 | | | | | | | | | | |
| 56 | | | | | | | | | | |
| 57 | | | | | 3.8 | 37.6 | 12% | 2.0 | 0.8 | 23 |

Figure 10 (continued)

TRIOXACARCINS, TRIOXACARCIN-ANTIBODY CONJUGATES, AND USES THEREOF

RELATED APPLICATIONS

The present application is a national stage filing under 35 U.S.C. §371 of international PCT application, PCT/US2013/071924, filed Nov. 26, 2013, which claims priority under 35 U.S.C. §119(e) to U.S. provisional patent application, U.S.S.N. 61/729,826, filed Nov. 26, 2012, each of which is incorporated herein by reference.

BACKGROUND OF THE INVENTION

Antibody-drug conjugates (ADCs) are a new type of targeted therapy consisting of three components: a target-specific antibody (e.g., a monoclonal antibody, mAb) or antibody fragment (e.g., a single-chain variable fragment (scFv)); a payload, often a cytotoxic drug; and a linker connecting the drug to the antibody. Upon administration, the antibody binds to a target cell and the drug exerts its therapeutic effect, for example, by optional cleavage from the ADC and/or by internalization in the cell or proximity to the outside of the cell. See, e.g., Ducry et al., *Bioconjugate Chemistry* (2010) 21: 5-13; Kovtun et al., *Cancer Research* (2006) 66: 3214-21; and Kovtun et al., *Cancer Letters* (2007) 255 (2): 232-40. Targeted therapies are envisioned to provide many advantages including, but not limited to, decreased side effects and a wider therapeutic window as compared to untargeted therapies.

The type of linker used is an important consideration in the design of the ADC. For example, ADCs with cleavable linkers are thought to have a less favorable therapeutic window, and are best designed for targets, such as tumor cell surface antigens that are internalized efficiently. Hydrophilic linkers, such as linkers which contain multiple polyethyleneglycol (PEG) units, are known to help prevent the drug being pumped out of resistant cancer cells through MDR (multiple drug resistance) transporters. See, e.g., P. Diamond, *Genetic Engingeering & Biotechnology News*, "Antibody-Drug Conjugates Stage a Comeback" (Mar. 9, 2010). The linker should also be designed in a manner that ensures stability during circulation in blood but allows for the rapid release of the drug, preferably inside the target cell. Several types of enzymatically degradable and non-degradable linkers for ADCs have also been explored, such as cleavable acid- and peptidase-labile linkers and non-cleavable linkers such as thioethers. See, e.g., Ducry et al., *Bioconjugate Chemistry* (2010) 21: 5-13.

SUMMARY OF THE INVENTION

Natural products that bind and often covalently modify duplex DNA figure prominently in chemotherapy for human cancers. The trioxacarcins are a new class of DNA-modifying natural products with antiproliferative effects. The trioxacarcins were first described in 1981 by Tomita and coworkers. See, e.g., Tomita et al., *J. Antibiotics*, 34(12): 1520-1524, 1981; Tamaoki et al., *J. Antibiotics* 34(12):1525-1530, 1981; Fujimoto et al., *J. Antibiotics* 36(9):1216-1221, 1983. Trioxacarcin A, B, and C were isolated by Tomita and coworkers from the culture broth of *Streptomyces bottropensis* DO-45 and shown to possess anti-tumor activity in murine models as well as gram-positive antibiotic activity. Subsequent work led to the discovery of other members of this family. Trioxacarcin A is a powerful anticancer agent with subnanmolar $IC_{70}$ values against lung (LXFL 529L, H-460), mammary (MCF-7), and CNS (SF-268) cancer cell lines. The trioxacarcins have also been shown to have antimicrobial activity, e.g., anti-bacterial and anti-malarial activity. See, e.g., Maskey et al., *J. Antibiotics* (2004) 57:771-779. An X-ray crystal structure of trioxacarcin A bound to N-7 of a guanidylate residue in a duplex DNA oligonucleotide substrate has provided compelling evidence for a proposed pathyway of DNA modification that proceeds by duplex intercalation and alkylation. See, e.g., Pfoh et al., *Nucleic Acids Research* (2008) 36:3508-3514. All trioxacarcins appear to be derivatives of the aglycone, which is itself a bacterial isolate referred to in the patent literature as DC-45-$A_2$. U.S. Pat. No. 4,459,291, issued Jul. 10, 1984, describes the preparation of DC-45-$A_2$ by fermentation. DC-45-$A_2$ is the algycone of trioxacarcins A, B, and C and is prepared by the acid hydrolysis of the fermentation products trioxacarcins A and C or the direct isolation from the fermentation broth of *Streptomyces bottropensis*.

Prior to this work, the inventors developed a fully synthetic method to access known trioxacarcins and new and novel trioxacarcin analogs. See, e.g., PCT Application Publication No. WO 2011/119549, incorporated herein by reference. See also FIG. 1. A wide variety of fully synthetic natural and nonnatural trioxacarcin compounds have been prepared by a process that is amenable to scaling. The synthetic route produces a key diversifiable precursor 2 through the union of three building blocks of similar complexity: a diazodiketone, cyanophthalide compound, and an enone compound. The process developed is a robust and scalable chemistry that allows for the preparation of each of these building blocks in multigram amounts. Notably, only six chemical steps are required to transform these building blocks into precursor 2, which contains all of the key structural features of the trioxacarcins. The differentially-protected precursor may then be transformed into two potent members of the trioxacarcin family, trioxacarcin A and DC-45-A1, through stereoselective glycosylation reactions. Structure-activity relationship studies have been performed on the trioxacarcins using the several non-natural as well as natural trioxacarcins prepared following this synthetic method. See, e.g., FIGS. 2A-2D.

The inventors now build from this synthetic method access to trioxacarcins covalently bonded ("conjugated") through a linking group to an antibody. Preliminary studies suggest that the trioxacarcins are highly toxic to a variety of cell types. The inventors envision linking a trioxacarcin to an antibody would preserve the trioxacarcin's potency against the cell type while increasing specificity to the target cell, and optionally increasing endocytosis of the trioxacarcin. These effects would enable lowering the overall amount of trioxacarcin to be delivered, thereby reducing the associated toxicity. Exploration of various linking groups conjugating the trioxacarcin to the antibody, the chemistry used in such conjugation, and the site of conjugation is described herein.

In one aspect, provided is a trioxacarcin antibody-drug conjugate of Formula (A):

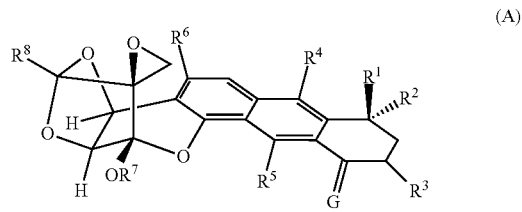

or a pharmaceutically acceptable salt thereof, wherein G is O or N—R$^G$, comprising at least one instance of the group -L$^1$-(A-L$^2$)$_a$-B attached thereto, wherein a is an integer between 1 and 10, inclusive, L$^1$ is absent or a linking group, A is a moiety formed from the reaction of two complimentary groups (X and Y), L$^2$ is absent or is another linking group, and B is an antibody or antibody fragment.

In certain embodiments, the trioxacarcin antibody-drug conjugate of Formula (A) is of Formula (I):

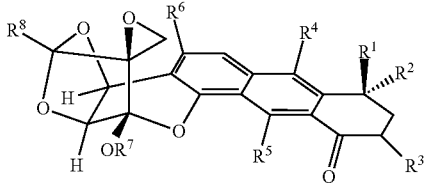

(I)

or a pharmaceutically acceptable salt thereof.

In certain embodiments, the trioxacarcin antibody-drug conjugate of Formula (A) is of Formula (II):

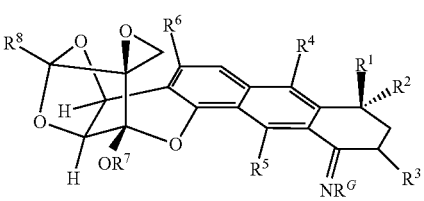

(II)

or a pharmaceutically acceptable salt thereof.

Further provided are precursor compounds to Formula (A), referred to herein as compounds of Formula (P-A):

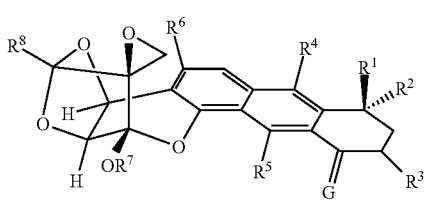

(P-A)

or pharmaceutically acceptable salts thereof; comprising at least one instance of the group -L$^1$-X attached thereto, wherein L$^1$ is absent or a linking group and X is a reactive moiety.

In certain embodiments, the precursor compounds of Formula (P-A) are compounds of Formula (P-I):

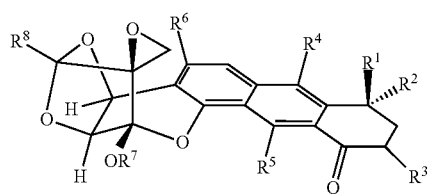

(P-I)

or pharmaceutically acceptable salts thereof.

In certain embodiments, the precursor compounds of Formula (P-A) are compounds of Formula (P-II):

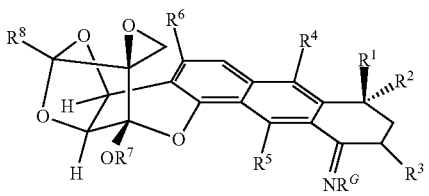

(P-II)

or pharmaceutically acceptable salts thereof.

Compounds of Formula (A), (I), and (II) are prepared by coupling a compound of Formula (P-A), (P-I), or (P-II), comprising at least one -L$^1$-X group attached thereto, with a compound of formula Y-L$^2$-B, or iteratively coupling with one or more independent instances of a compound of formula Y-L$_2$-X before coupling (capping) with a compound of formula Y-L$^2$-B, wherein X and Y react together to form a group A.

Also provided are methods of preparing these antibody-drug conjugates, pharmaceutically acceptable compositions thereof, and methods of their use in treating disease, e.g., such as cancer.

Further provided are precursors to the antibody-drug conjugates (which do not comprise an antibody conjugated thereto), pharmaceutical compositions thereof, and methods of their use and treatment.

Further provided are novel trioxacarins which do not comprise an antibody conjugated thereto, pharmaceutical compositions thereof, and methods of their use and treatment.

Further provided are products of nucleophilic addition, e.g., by water or hydroxide addition or by addition of guanine via DNA alkylation, of the trioxacarcins as described herein, contemplated useful, for example, as control compounds for assay and compound development.

The details of one or more embodiments of the invention are set forth in the accompanying Figures and the Detailed Description below. Other features, objects, and advantages of the invention will be apparent from the Examples and the Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein may comprise one or more asymmetric centers, and thus may exist as stereoisomers, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). Compounds may exist as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "heteroalkyl" refers to an alkyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl").

In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-4}$ cycloalkyl"). In some embodiments, a cycloalkyl group has 5 to 6 ring carbon atoms ("$C_{5-10}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-4}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as described herein, substituted by an aryl group, as described herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as described herein, substituted by a heteroaryl group, as described herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as described herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —CN, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C($OR^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)N($R^{bb}$)$_2$, —OC(=$NR^{bb}$)N($R^{bb}$)$_2$, —$NR^{bb}$C(=$NR^{bb}$)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$—C(=S)N($R^{bb}$)$_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)$_2R^{aa}$, —OP(=O)$_2R^{aa}$, —P(=O)($R^{aa}$)$_2$, —OP(=O)($R^{aa}$)$_2$, —OP(=O)($OR^{cc}$)$_2$, —P(=O)$_2N(R^{bb})_2$, —OP(=O)$_2N(R^{bb})_2$, —P(=O)(N$R^{bb}$)$_2$, —OP(=O)(N$R^{bb}$)$_2$, —$NR^{bb}$P(=O)($OR^{cc}$)$_2$, —$NR^{bb}$P(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B($OR^{cc}$)$_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, $C_{3-14}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =$NNR^{bb}$C(=O)$R^{aa}$, =$NNR^{bb}$C(=O)$OR^{aa}$, =$NNR^{bb}$S(=O)$_2R^{aa}$, =$NR^{bb}$, or =$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —ON($R^{ff}$)$_2$, —N($R^{ff}$)$_2$, —N($R^{ff}$)$_3^+X^-$, —N($OR^{ee}$)$R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)N($R^{ff}$)$_2$, —OC(=O)N($R^{ff}$)$_2$, —$NR^{ff}$C(=O)$R^{ee}$, —$NR^{ff}CO_2R^{ee}$, —$NR^{ff}$C(=O)N($R^{ff}$)$_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)N($R^{ff}$)$_2$, —OC(=$NR^{ff}$)N($R^{ff}$)$_2$, —$NR^{ff}$C(=$NR^{ff}$)N($R^{ff}$)$_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —Si($R^{ee}$)$_3$, —OSi($R^{ee}$)$_3$, —C(=S)N($R^{ff}$)$_2$, —C(=O)$SR^{ee}$, —C(=S)$SR^{ee}$, —SC(=S)$SR^{ee}$, —P(=O)$_2R^{ee}$, —P(=O)($R^{ee}$)$_2$, —OP(=O)($R^{ee}$)$_2$, —OP(=O)($OR^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH (OH), —SH, —S$C_{1-6}$ alkyl, —SS($C_{1-6}$ alkyl), —C(=O) ($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N ($C_{1-6}$ alkyl)$_2$, —OC(=O)NH($C_{1-6}$ alkyl), —NHC(=O) ($C_{1-6}$ alkyl), —N($C_{1-6}$ alkyl)C(=O)($C_{1-6}$ alkyl), —NHCO$_2$ ($C_{1-6}$ alkyl), —NHC(=O)N($C_{1-6}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH) NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-4}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C (=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S) S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, "acyl" refers to a group of the formula —C(=O)$R^{aa}$, wherein $R^{aa}$ is as described herein.

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

A "leaving group" is an art-understood term referring to a molecular fragment that departs with a pair of electrons in heterolytic bond cleavage, wherein the molecular fragment is an anion or neutral molecule. See, for example, Smith, *March's Advanced Organic Chemistry* 6th ed. (501-502). Exemplary leaving groups include, but are not limited to, halo (e.g., chloro, bromo, iodo) and activated substituted hydroxyl groups (e.g., —OC(=O)S$R^{aa}$, —OC(=O)$R^{aa}$, —OCO$_2$$R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O) $R^{aa}$, —OSO$_2$$R^{aa}$, —OP($R^{cc}$)$_2$, —OP($R^{cc}$)$_3$, —OP(=O)$_2$ $R^{aa}$, —OP(=O)($R^{aa}$)$_2$, —OP(=O)(O$R^{cc}$)$_2$, —OP(=O)$_2$N ($R^{bb}$)$_2$, and —OP(=O)(N$R^{bb}$)$_2$ wherein $R^{aa}$, $R^{bb}$ and $R^{cc}$ are as described herein).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON ($R^{bb}$)$_2$, —OC(=O)S$R^{aa}$, —OC(=O)$R^{aa}$, —OCO$_2$$R^{aa}$, —OC(=O)N($R^{bb}$)$_2$, —OC(=N$R^{bb}$)$R^{aa}$, —OC(=N$R^{bb}$) O$R^{aa}$, —OC(=N$R^{bb}$)N($R^{bb}$)$_2$, —OS(=O)$R^{aa}$, —OSO$_2$$R^{aa}$, —OSi($R^{aa}$)$_3$, —OP($R^{cc}$)$_2$, —OP($R^{cc}$)$_3$, —OP (=O)$_2$$R^{aa}$, —OP(=O)($R^{aa}$)$_2$, —OP(=O)(O$R^{cc}$)$_2$, —OP (=O)$_2$N($R^{bb}$)$_2$, and —OP(=O)(N$R^{bb}$)$_2$, wherein $R^{aa}$, $R^{bb}$, and $R^{cc}$ are as described herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —S$R^{aa}$, —S=S$R^{cc}$, —SC(=S)S$R^{aa}$, —SC (=O)S$R^{aa}$, —SC(=O)O$R^{aa}$, and —SC(=O)$R^{aa}$, wherein $R^{aa}$ and $R^{cc}$ are as described herein.

As used herein, the term, "amino" refers to the group —NH$_2$. The term "substituted amino," by extension, refers to a monosubstituted amino, a disubstituted amino, or a trisubstituted amino, as described herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2$$R^{aa}$, —NHC(=O)N($R^{bb}$)$_2$, —NHC(=N$R^{bb}$)N ($R^{bb}$)$_2$, —NHSO$_2$$R^{aa}$, —NHP(=O)(O$R^{cc}$)$_2$, and —NHP (=O)(N$R^{bb}$)$_2$, wherein $R^{aa}$, $R^{bb}$ and $R^{cc}$ are as described herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2$$R^{aa}$, —N$R^{bb}$C (=O)N($R^{bb}$)$_2$, —N$R^{bb}$C(=N$R^{bb}$)N($R^{bb}$)$_2$, —N$R^{bb}$SO$_2$$R^{aa}$, —N$R^{bb}$P(=)(O$R^{cc}$)$_2$, and —N$R^{bb}$P(=O)(N$R^{bb}$)$_2$, wherein $R^{aa}$, $R^{bb}$, and $R^{cc}$ are as described herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb}$)$_3$ and —N($R^{bb}$)$_3$$^+$ X$^-$, wherein $R^{bb}$ and X$^-$ are as described herein.

As used herein, the term "oxo" refers to the group =O, and the term "thiooxo" refers to the group =S.

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —O$R^{aa}$, —N($R^{cc}$)$_2$, —CN, —C(=O)$R^{aa}$, —C(=O) N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O) ($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, hetero $C_{1-10}$alkyl, hetero$C_{2-10}$alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as described herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —$C(=O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —$S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)($OR^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as described herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)($OR^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as described herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

The term "salt" and "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "peptidyl group" refers to a divalent amino acid moiety. A "dipeptidyl" group refers to a divalent moiety comprising two amino acid residues linked together by peptide bonds, i.e., —C(=O)—N— (amide) bonds. A "polypeptidyl" group refers to a divalent moiety comprising three or more consecutively linked amino acid residues (e.g., 3, 4, 5, 6, 7, 8, 9, 10, 11, 12, 13, 14, 15, 16, 17, 18 19, 20, or more linked amino acid residues).

Peptidyl, dipeptidyl, and polypeptidyl moieties may contain only natural amino acids, although non-natural amino acids (i.e., compounds that do not occur in nature but that can be incorporated into a polypeptide chain) and/or amino acid analogs as are known in the art may alternatively be employed. Furthermore, one or more of the amino acids in a peptidyl, dipeptidyl, or polypeptidyl moiety may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification. For example, a cysteine (—CH$_2$SH) side chain may be modified to a formyl (—CHO) side chain.

Exemplary amino acids contemplated useful in providing the peptidyl, dipeptidyl, and polypeptidyl moieties of interest include, without limitation, natural alpha-amino acids such as D- and L-isomers of the 20 common naturally occurring alpha-amino acids found in peptides (e.g., A, R, N, C, D, Q, E, G, H, I, L, K, M, F, P, S, T, W, Y, V), natural beta-amino acids (e.g., beta-alanine), and unnatural amino acids. There are many known unnatural amino acids any of which may be included in the peptides of the present invention. See for example, S. Hunt, *The Non-Protein Amino Acids: In Chemistry and Biochemistry of the Amino Acids*, edited by G. C. Barrett, Chapman and Hall, 1985. Additional examples of amino acids contemplated useful in providing the peptidyl, dipeptidyl, and polypeptidyl moieties of interest include without limitation, ornithine, citrulline (Cit), α-methyl-Alanine (Aib), 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-aminocyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo; —NO$_2$; CH$_3$), and statine.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as rodents (e.g., mice, rats), guinea pigs, cattle, pigs, horses, sheep, goats, cats, and/or dogs. The non-human animal may be male or female and at any stage of development. A non-human animal may be a transgenic animal.

"Disease," "disorder," and "condition" are used interchangeably herein.

As used herein, and unless otherwise specified, the terms "treat," "treating" and "treatment" contemplate an action that occurs while a subject is suffering from the specified disease, disorder, or condition, which reduces the severity of the disease, disorder, or condition, or retards or slows the progression of the disease, disorder, or condition ("therapeutic treatment" or "therapeutically treating"), and also contemplates an action that occurs before a subject begins to suffer from the specified disease, disorder, or condition, and which inhibits or reduces the severity of the disease, disorder, or condition ("prophylactic treatment" or "prophylactically treating").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. For example, the effective amount of a compound with anti-proliferative activity is the amount that results in a sufficient concentration to inhibit the proliferation of cells. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder, or condition, or to delay or minimize one or more symptoms associated with the disease, disorder, or condition. A therapeutically effective amount of a compound means an amount of therapeutic agent, alone or in combination with other therapies, which provides a therapeutic benefit in the treatment of the disease, disorder, or condition. The term "therapeutically effective amount" can encompass an amount that improves overall therapy, reduces or avoids symptoms or causes of the disease, disorder, or condition, or enhances the therapeutic efficacy of another therapeutic agent.

As used herein, and unless otherwise specified, a "prophylactically effective amount" of a compound is an amount sufficient to prevent a disease, disorder, or condition, or one or more symptoms associated with the disease, disorder, or condition, or prevent its recurrence. A prophylactically effective amount of a compound means an amount of a therapeutic agent, alone or in combination with other agents, which provides a prophylactic benefit in the prevention of the disease, disorder, or condition. The term "prophylactically effective amount" can encompass an amount that improves overall prophylaxis or enhances the prophylactic efficacy of another prophylactic agent.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

DETAILED DESCRIPTION OF CERTAIN EMBODIMENTS OF THE INVENTION

Figure 1:
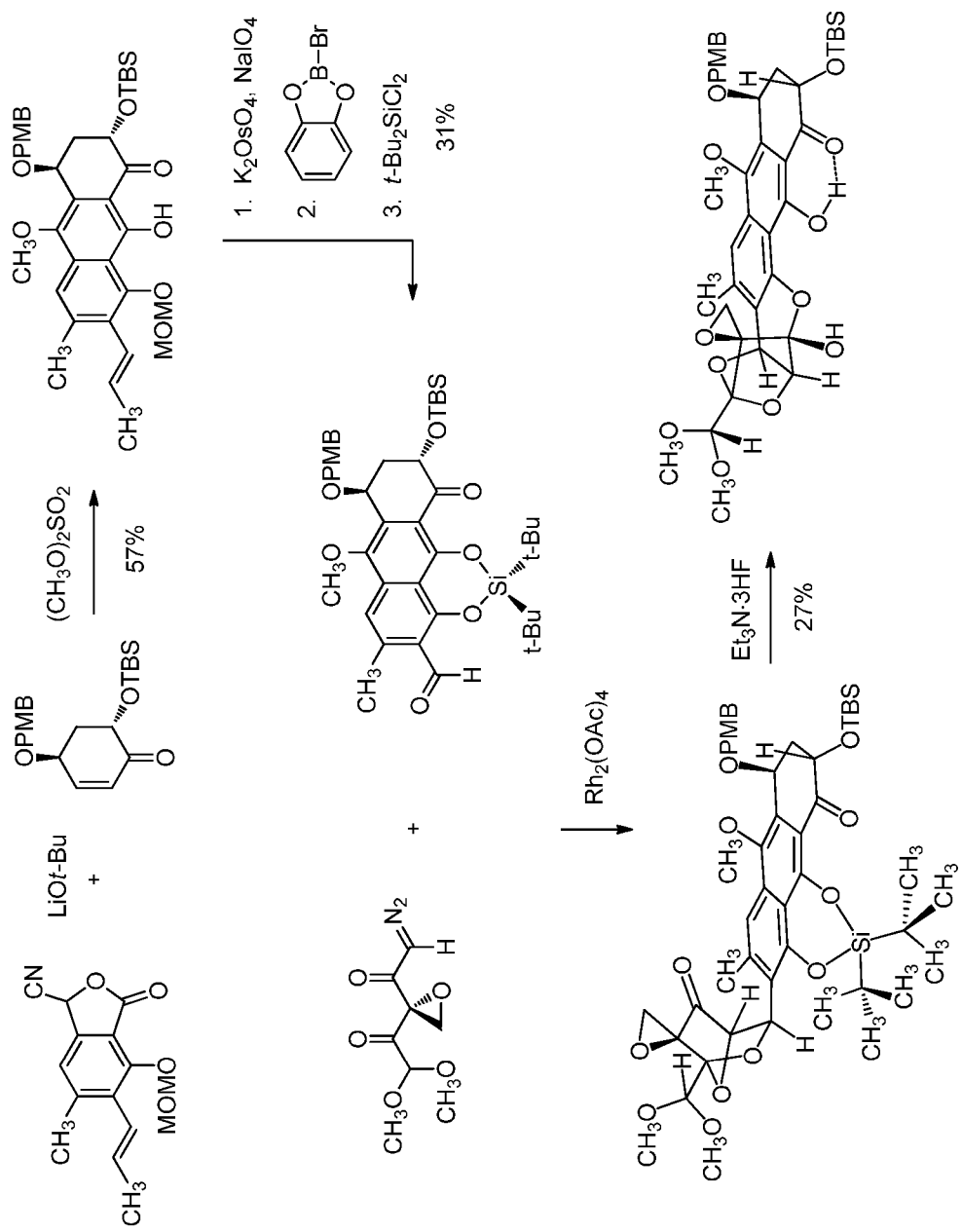
FIG. 1 depicts the convergent synthesis of scaffold (2), a differentially-protected precursor to the trioxacarcins useful in the synthesis of trioxacarcins.
Figure 2A:
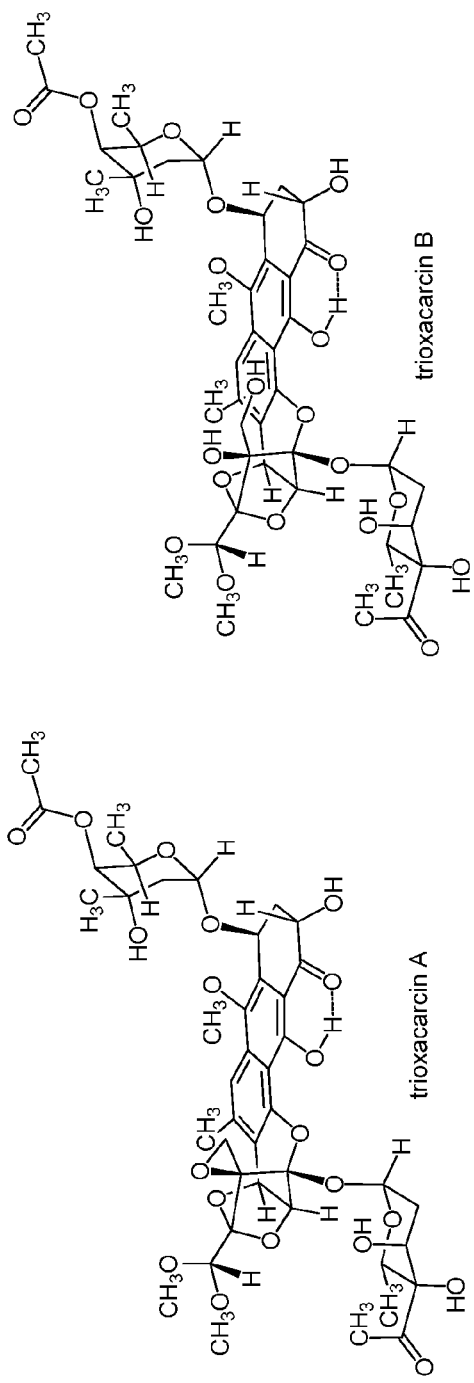
FIGS. 2A-2D depict natural and unnatural trioxacarcins of interest.
Figure 2A:
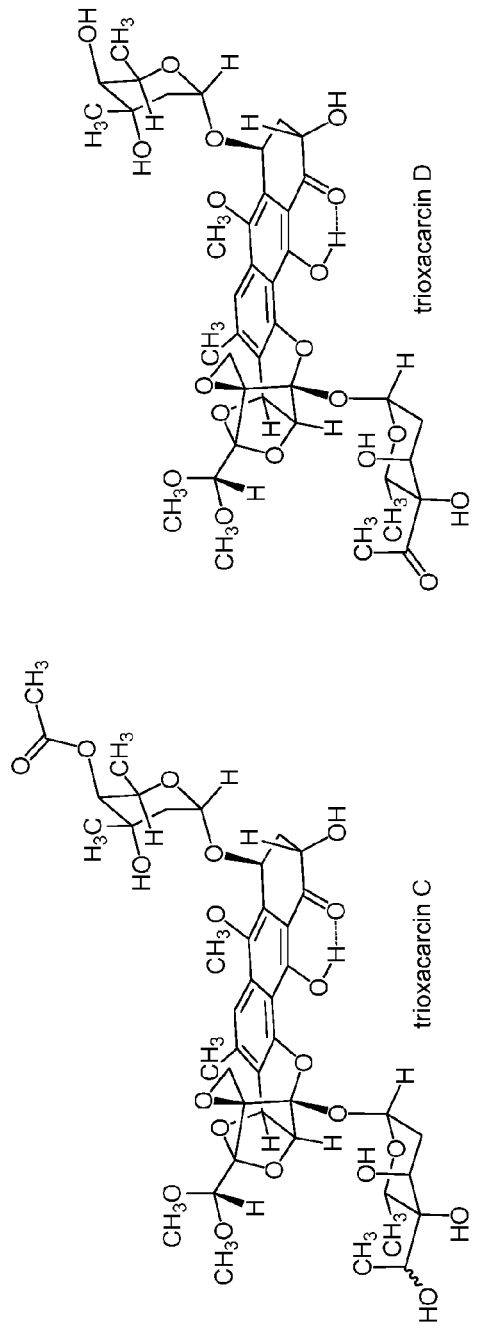
Figure 2B:
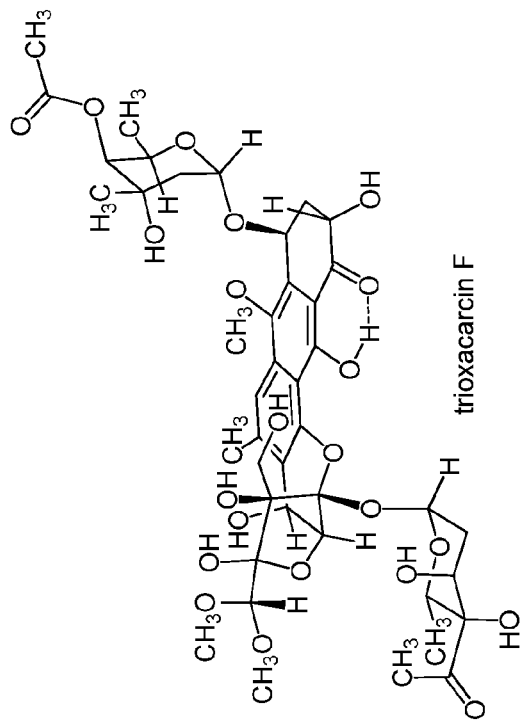
Figure 2B:
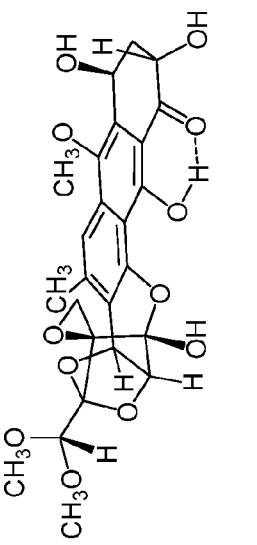
Figure 2B:
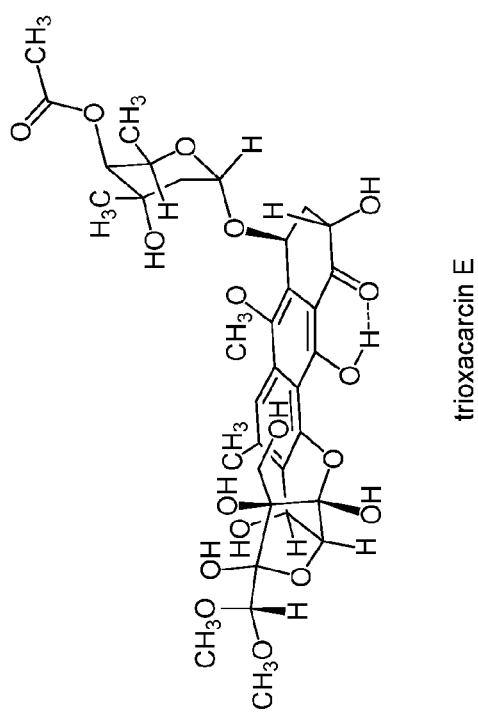
Figure 2B:
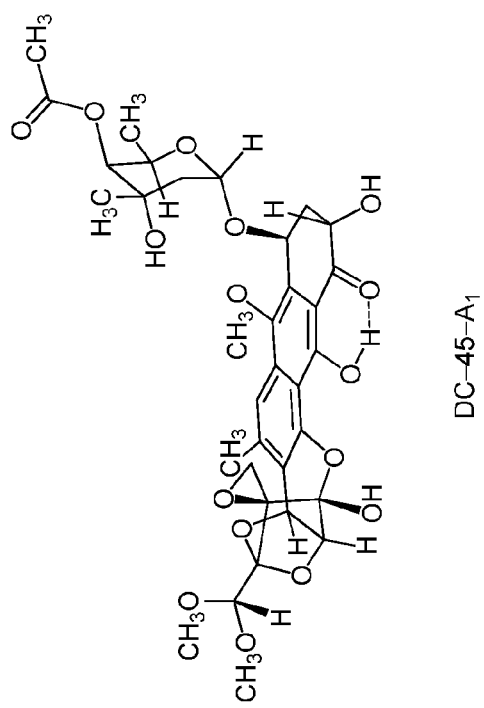
Figure 2C:
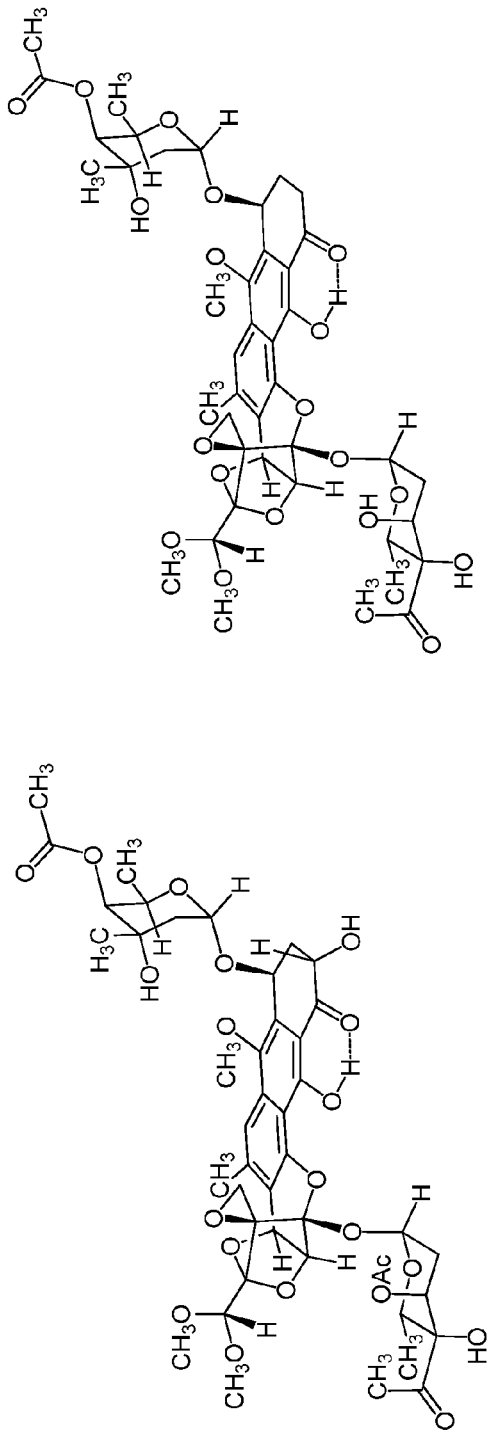
Figure 2C:
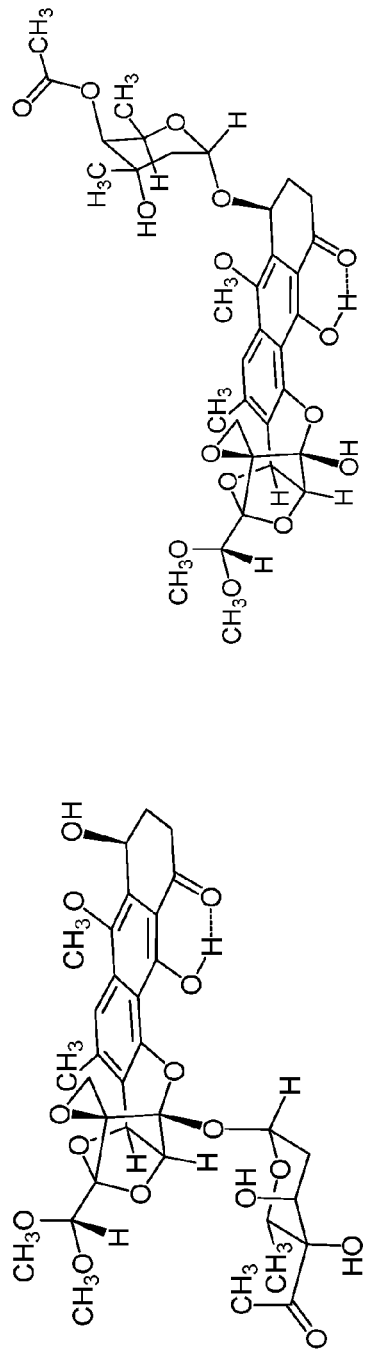
Figure 2D:
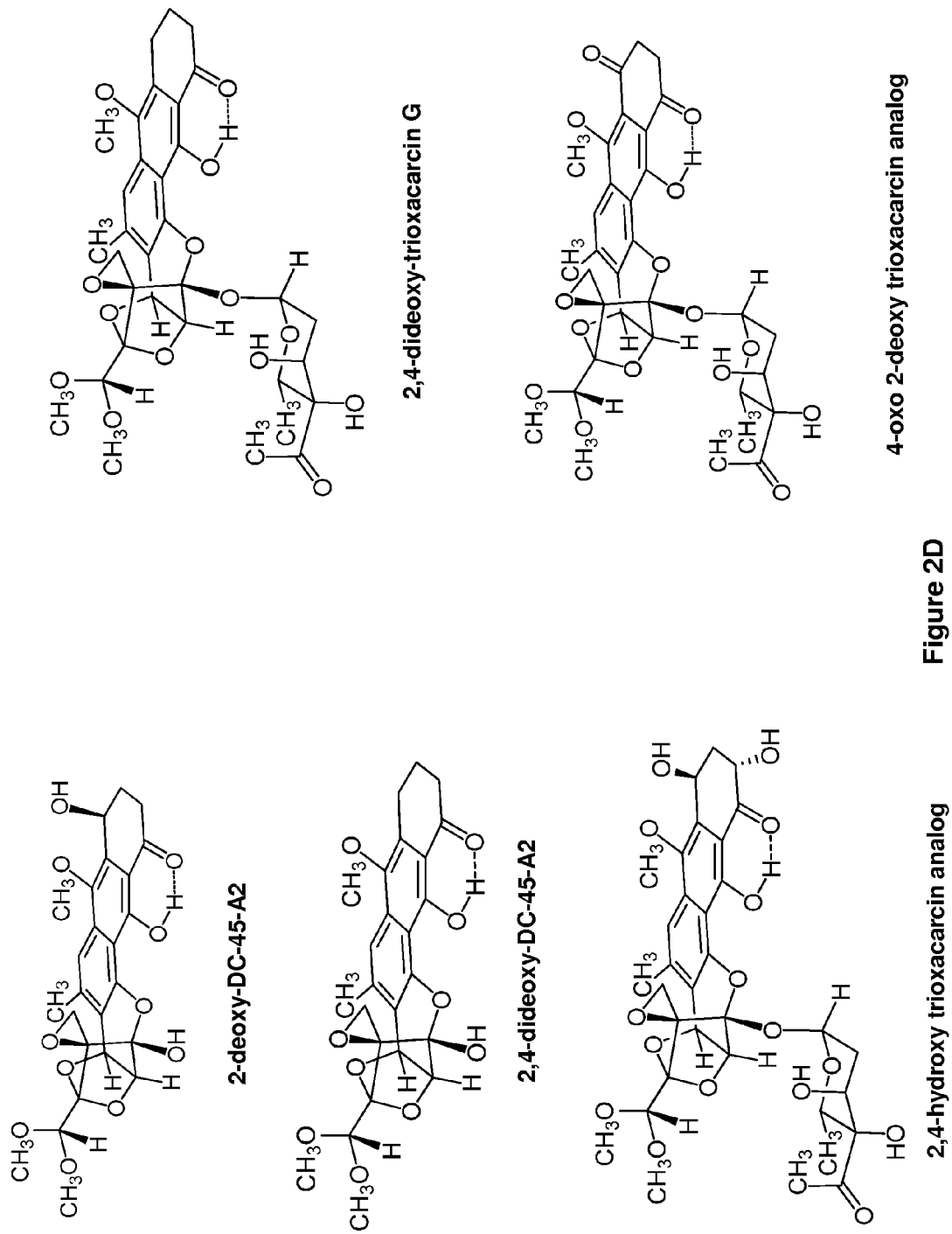

As described herein, prior to this work, the inventors developed a fully synthetic method to access known trioxacarcins and new and novel trioxacarcin analogs. See, e.g., PCT Application Publication No. WO 2011/119549, incorporated herein by reference. See also FIG. 1. A wide variety of fully synthetic natural and nonnatural trioxacarcin compounds have been prepared by a process that is amenable to scaling. Structure-activity relationship studies have been performed on the trioxacarcins using the several non-natural as well as natural trioxacarcins prepared following this synthetic method. See, e.g., FIGS. 2A-2D.

The inventors now build from this synthetic method access to trioxacarcins covalently bonded ("conjugated") through a linking group to an antibody. Preliminary studies suggest that the trioxacarcins are highly toxic to a variety of cell types. The inventors envision linking a trioxacarcin to an antibody would preserve the trioxacarcin's potency against the cell type while increasing specificity to the target cell, and optionally increasing endocytosis of the trioxacarcin. These effects would enable lowering the overall amount of trioxacarcin to be delivered, thereby reducing the associated toxicity. Exploration of various linking groups conjugating the trioxacarcin to the antibody, the chemistry used in such conjugation, and the site of conjugation is contemplated herein.

In one aspect, provided is a trioxacarcin antibody-drug conjugate of Formula (A):

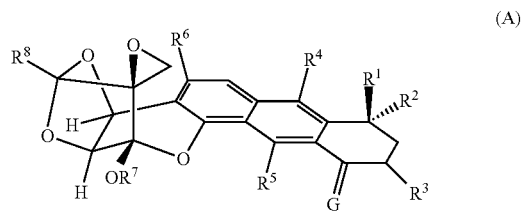

(A)

or a pharmaceutically acceptable salt thereof; comprising at least one instance of the group $-L^1-(A-L^2)_a-B$ attached thereto;

wherein:

G is O or N—$R^G$, wherein $R^G$ is hydrogen or —$OR^{G1}$, and wherein $R^{G1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a group $-L^1-(A-L^2)_a-B$;

a is an integer between 1 and 10, inclusive;

$L^1$ is absent or is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; peptidyl groups; dipeptidyl groups; and polypeptidyl groups; and combinations thereof;

$L^2$ is absent or is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; peptidyl groups; dipeptidyl groups; and polypeptidyl groups; and combinations thereof;

A is a group of the formula —NH—, —NH—NH—, —NH—O—, —O—NH—, —S—, —O—,

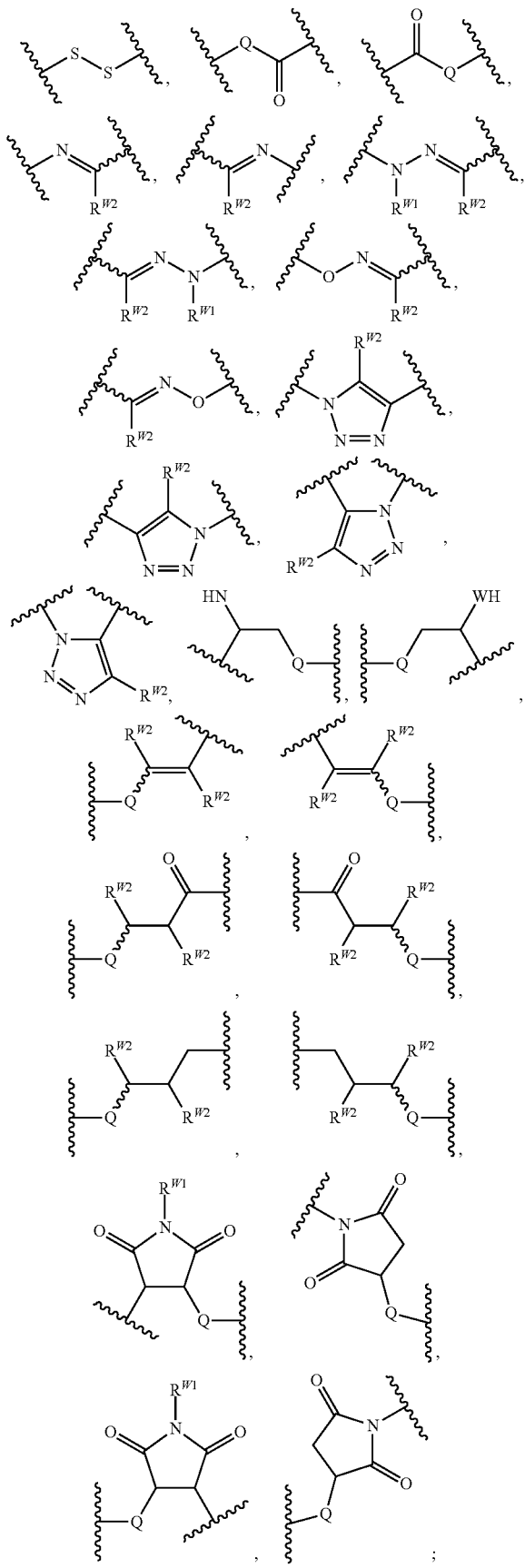

Q is —NH—, —NH—NH—, —O—NH—, —NH—O—, —S—, or —O—;

W is —O—, —S—, or —NR$^{W1}$—, wherein R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

R$^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl, or two R$^{W2}$ groups are joined to form a 5-6 membered ring;

B is an antibody or antibody fragment;

R$^1$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{A1}$; —C(=O)R$^{A2}$; —CO$_2$R$^{A2}$; —CN; —SCN; —SR$^{A1}$; —SOR$^{A1}$; —SO$_2$R$^{A2}$; —NO$_2$; —N$_3$; —N(R$^{A2}$)$_2$; —NR$^{A2}$C(=O)R$^{A2}$; —NR$^{A2}$C(=O)N(R$^{A2}$)$_2$; —OC(=O)OR$^{A1}$; —OC(=O)R$^{A2}$; —OC(=O)N(R$^{A2}$)$_2$; —NR$^{A2}$C(=O)OR$^{A1}$; —C(R$^{A2}$)$_3$; or a group -L$^1$-(A-L$^2$)$_a$-B; and R$^2$ is hydrogen; or R$^1$ and R$^2$ are joined to form =O; =N(R$^{A2}$); or =S;

each occurrence of R$^{A1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; or a group -L$^1$-(A-L$^2$)$_a$-B;

each occurrence of R$^{A2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; or substituted amino; or a group -L$^1$-(A-L$^2$)$_a$-B; or two R$^{A2}$ groups are optionally joined to form a heterocyclyl or heteroaryl ring;

or R$^{A1}$ or R$^{A2}$ represent a group of Formula (i):

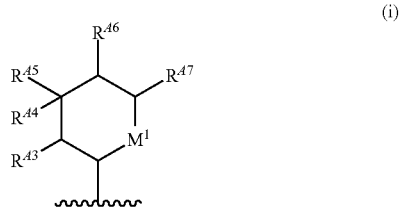

(i)

each occurrence of R$^{A3}$, R$^{A4}$, R$^{A5}$, R$^{A6}$, and R$^{A7}$ is independently hydrogen, substituted or unsubstituted alkyl; —OR$^{A9}$; —OC(=O)R$^{A9}$; —N(R$^{A9}$)$_2$; —NHC(=O)R$^{A9}$; or a group -L$^1$-(A-L$^2$)$_a$-B; wherein each occurrence of R$^{A9}$ is independently hydrogen; substituted or unsubstituted alkyl; an oxygen protecting group when attached to an oxygen atom; a nitrogen protecting group when attached to a nitrogen atom; or a group -L$^1$-(A-L$^2$)$_a$-B; or two R$^{A9}$ groups are joined to form a substituted or unsubstituted heterocyclic or substituted or unsubstituted heteroaryl ring;

$M^1$ is —O—, —NR$^{A8}$—, or —CHR$^{A8}$—, wherein R$^{A8}$ is hydrogen; substituted or unsubstituted alkyl; a nitrogen protecting group if attached to nitrogen; —OR$^{A9}$; or a group -L$^1$-(A-L$^2$)$_a$-B; wherein R$^{A9}$ is independently hydrogen; substituted or unsubstituted alkyl; acyl; an oxygen protecting group; or a group -L$^1$-(A-L$^2$)$_a$-B;

R$^3$ is hydrogen or —OR$^{C1}$, wherein R$^{C1}$ is hydrogen; an oxygen protecting group; substituted or unsubstituted alkyl; substituted or unsubstituted alkenyl; substituted or unsubstituted carbocyclyl; substituted or unsubstituted heterocyclyl; substituted or unsubstituted aryl; substituted or unsubstituted heteroaryl; acyl; or a group -L$^1$-(A-L$^2$)$_a$-B;

R$^4$ is hydrogen or —OR$^{D1}$, wherein R$^{D1}$ is hydrogen; an oxygen protecting group; substituted or unsubstituted alkyl; substituted or unsubstituted alkenyl; substituted or unsubstituted carbocyclyl; substituted or unsubstituted heterocyclyl; substituted or unsubstituted aryl; substituted or unsubstituted heteroaryl; acyl; or a group -L$^1$-(A-L$^2$)$_a$-B;

R$^5$ is hydrogen or —OR$^{E1}$, wherein R$^{E1}$ is hydrogen; an oxygen protecting group; substituted or unsubstituted alkyl; substituted or unsubstituted alkenyl; substituted or unsubstituted carbocyclyl; substituted or unsubstituted heterocyclyl; substituted or unsubstituted aryl; substituted or unsubstituted heteroaryl; acyl; or a group -L$^1$-(A-L$^2$)$_a$-B;

R$^6$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{F1}$; —C(=O)R$^{F2}$; —CO$_2$R$^{F1}$; —CN; —SCN; —SR$^{F1}$; —SOR$^{F1}$; —SO$_2$R$^{F2}$; —NO$_2$; —N$_3$; —N(R$^{F2}$)$_2$; —NR$^{F2}$C(=O)R$^{F2}$; —NR$^{F2}$C(=O)N(R$^{F2}$)$_2$; —OC(=O)OR$^{F1}$; —OC(=O)R$^{F2}$; —OC(=O)N(R$^{F2}$)$_2$; —NR$^{F2}$C(=O)OR$^{F1}$; —C(R$^{F2}$)$_3$, or a group -L$^1$-(A-L$^2$)$_a$-B;

each occurrence of R$^{F1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; or a group -L$^1$-(A-L$^2$)$_a$-B;

each occurrence of R$^{F2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; substituted amino, or a group -L$^1$-(A-L$^2$)$_a$-B; or two R$^{F2}$ groups are optionally joined to form a heterocyclyl or heteroaryl ring;

R$^7$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —C(=O)R$^{H1}$; a group -L$^1$-(A-L$^2$)$_a$-B; or a group of Formula (ii):

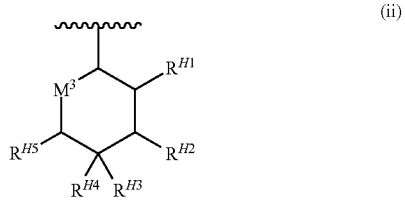

wherein:

each occurrence of R$^{H1}$, R$^{H3}$, and R$^{H5}$ is independently hydrogen, substituted or unsubstituted alkyl; —OR$^{H9}$; —OC(=O)R$^{H9}$; —N(R$^{H9}$)$_2$; —NHC(=O)R$^{H9}$; a group -L$^1$-A-L$^2$-B; wherein each occurrence of R$^{H9}$ is independently hydrogen; substituted or unsubstituted alkyl; an oxygen protecting group when attached to an oxygen atom; a nitrogen protecting group when attached to a nitrogen atom; or a group -L$^1$-(A-L$^2$)$_a$-B; or two R$^{H9}$ groups are joined to form a substituted or unsubstituted heterocyclic or substituted or unsubstituted heteroaryl ring;

each instance of R$^{H2}$ and R$^{H4}$ is independently, hydrogen; —OR$^{H7}$; —N(R$^{H7}$)$_2$; —OC(=O)R$^{H7}$; —NHC(=O)R$^{H8}$; —C(=O)R$^{H7}$; —C(=NR$^{H7}$)R$^{H8}$; —C(=N—OR$^{H7}$)R$^{H8}$; —C(=N—NHR$^{H7}$)R$^{H8}$; —C(R$^{H8}$)$_2$NHR$^{H7}$; —C(R$^{H8}$)$_2$OR$^{H7}$; or a group -L$^1$-(A-L$^2$)$_a$-B; wherein R$^{H7}$ is independently hydrogen; substituted or unsubstituted alkyl; an oxygen protecting group if attached to an oxygen atom; a nitrogen protecting group if attached to a nitrogen atom; a group -L$^1$-(A-L$^2$)$_a$-B; and R$^{H8}$ is hydrogen or substituted or unsubstituted alkyl; or R$^{H7}$ and R$^{H8}$ or two R$^{H7}$ groups are joined to form a substituted or unsubstituted heterocyclic or substituted or unsubstituted heteroaryl ring;

$M^3$ is —O—, —NR$^{H6}$—, or —CHR$^{H6}$—, wherein R$^{H6}$ is hydrogen; substituted or unsubstituted alkyl; a nitrogen protecting group if attached to nitrogen; —OR$^{H9}$; or a group -L$^1$-(A-L$^2$)$_a$-B; wherein each occurrence of R$^{H9}$ is independently hydrogen; an oxygen protecting group; substituted or unsubstituted alkyl; acyl; or a group -L$^1$-(A-L$^2$)$_a$-B;

R$^8$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{I1}$; —C(=O)R$^{I2}$; —CO$_2$R$^{I1}$; —CN; —SCN; —SR$^{I1}$; —SOR$^{I1}$; —SO$_2$R$^{I2}$; —NO$_2$; —N$_3$; —N(R$^{I2}$)$_2$; —NR$^{I2}$C(=O)R$^{I2}$; —NR$^{I2}$C(=O)N(R$^{I2}$)$_2$; —OC(=O)OR$^{I1}$; —OC(=O)R$^{I2}$; —OC(=O)N(R$^{I2}$)$_2$; —NR$^{I2}$C(=O)OR$^{I1}$; —CH$_2$(OR$^{I1}$), —CH(OR$^{I1}$)$_2$, —CH$_2$OC(=O)R$^{I2}$, or a group -L$^1$-(A-L$^2$)$_a$-B;

each occurrence of R$^{I1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; a group of Formula (iii) or (iv), or a group -L$^1$-(A-L$^2$)$_a$-B; and each occurrence of R$^{I2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; substituted amino, a group of Formula (iii) or (iv); or a group -L¹-(A-L²)ₐ-B; or two R^{J2} groups are optionally joined to form a heterocyclyl or heteroaryl ring;

wherein Formula (iii) and (iv) is:

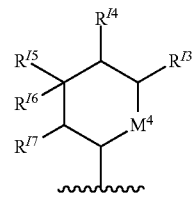
(iii)

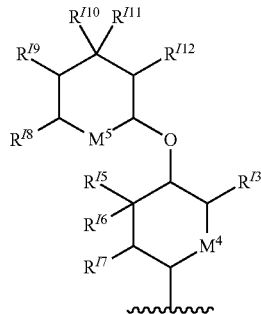
(iv)

wherein:

each occurrence of $R^{J3}$, $R^{J5}$, $R^{J6}$, $R^{J7}$, $R^{J8}$, $R^{J10}$, $R^{J11}$, and $R^{J12}$, is independently hydrogen, substituted or unsubstituted alkyl; —$OR^{J13}$; —OC(=O)$R^{J13}$; —N($R^{J13}$)₂; —NHC(=O)$R^{J13}$; a group -L¹-(A-L²)ₐ-B; wherein each occurrence of $R^{J13}$ is independently hydrogen; substituted or unsubstituted alkyl; an oxygen protecting group when attached to an oxygen atom; a nitrogen protecting group when attached to a nitrogen atom; or a group -L¹ (A-L²)ₐ-B; or two $R^{J13}$ groups are joined to form a substituted or unsubstituted heterocyclic or substituted or unsubstituted heteroaryl ring;

each occurrence of $R^{J4}$ and $R^{J9}$ is independently, hydrogen; substituted or unsubstituted alkyl; —$OR^{J14}$; —N($R^{J14}$)₂; —OC(=O)$R^{J14}$; —NHC(=O)$R^{J15}$; —OC(=O)$R^{J14}$; —C(=O)$R^{J14}$; —C(=N$R^{J14}$)$R^{J15}$; —C(=N—$OR^{J14}$)$R^{J15}$; —C(=N—NH$R^{J14}$)$R^{J15}$; —C($R^{J15}$)₂NH$R^{J14}$; —C($R^{J15}$)₂$OR^{J14}$; or a group -L¹-(A-L²)ₐ-B; wherein $R^{J14}$ is independently hydrogen; substituted or unsubstituted alkyl; an oxygen protecting group if attached to an oxygen atom; a nitrogen protecting group if attached to a nitrogen atom; a group -L¹-(A-L²)ₐ-B; and $R^{J15}$ is hydrogen, or substituted or unsubstituted alkyl; and each occurrence of $M^4$ and $M^5$ is independently —O—, —$NR^{J16}$—, or —$CHR^{J16}$—, wherein $R^{J16}$ is hydrogen; substituted or unsubstituted alkyl; a nitrogen protecting group if attached to nitrogen; —$OR^{J13}$; a group -L¹-(A-L²)ₐ-B; wherein each occurrence of $R^{J13}$ is independently hydrogen; an oxygen protecting group; substituted or unsubstituted alkyl; acyl; or a group -L¹-(A-L²)ₐ-B.

In certain embodiments, the trioxacarcin antibody-drug conjugate of Formula (A) is of Formula (I):

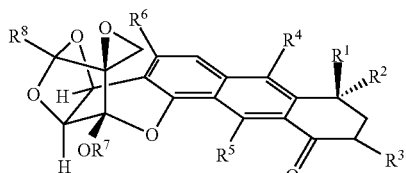
(I)

or a pharmaceutically acceptable salt thereof.

In certain embodiments, the trioxacarcin antibody-drug conjugate of Formula (A) is of Formula (II):

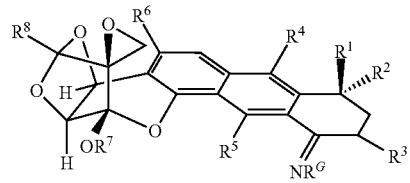
(II)

or a pharmaceutically acceptable salt thereof.

In certain embodiments, the compound of Formula (A), (I), and (II) comprises only one instance of a group -L¹-(A-L²)ₐ-B attached thereto. In certain embodiments, the compound of Formula (A), (I), and (II) comprises two independent instances of a group -L¹-(A-L²)ₐ-B attached thereto. In certain embodiments, the compound of Formula (A), (I), and (II) comprises three independent instances of a group -L¹-(A-L²)ₐ-B attached thereto.

The antibody or antibody fragment B is a large molecule with many sites of attachment, and thus may have many instances of a [compound of Formula (A), (I), and (II)-L¹-(A-L²)ₐ-] attached thereto. In certain embodiments, the antibody or antibody fragment comprises 1 to 200 independent instances of a [compound of Formula (I)-L¹-(A-L²)ₐ-] attached thereto, inclusive, e.g., 1 to 150, 1 to 100, 1 to 75, 1 to 50, 1 to 25, 1 to 15, 1 to 10, inclusive, e.g., 1, 2, 3, 4, 5, 6, 7, 8, 9, or 10 independent instances.

Further provided are precursor compounds to Formula (A), referred to herein as compounds of Formula (P-A):

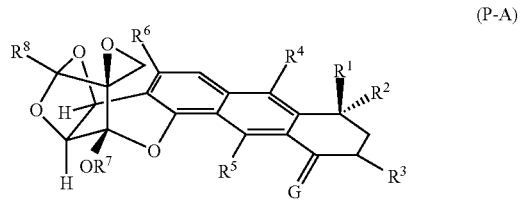
(P-A)

or pharmaceutically acceptable salts thereof; comprising at least one instance of the group -L¹-X attached thereto, wherein:

G is O or N—$R^G$, wherein $R^G$ is hydrogen or —$OR^{G1}$, and wherein $R^{G1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a group -L¹-X;

L¹ is absent or is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; peptidyl groups; dipeptidyl groups; and polypeptidyl groups; and combinations thereof;

X is selected from the group consisting of —SH, —OH, —NH$_2$, —NH—NH$_2$, —N$_3$, —O—NH$_2$, halogen (or other leaving group), —C(=O)R$^{X1}$,

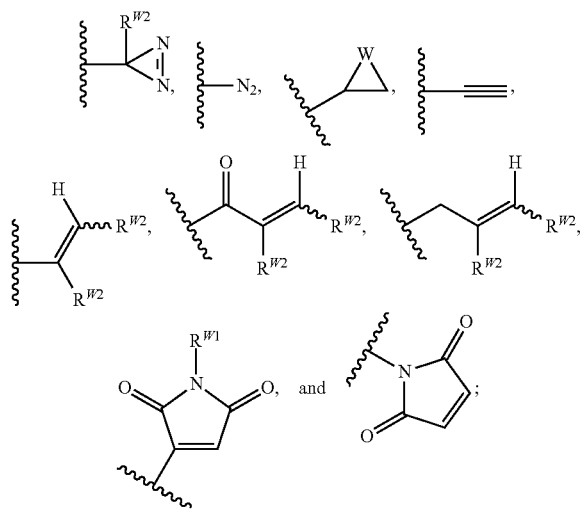

wherein:

R$^{X1}$ is hydrogen, halogen, or —OR$^{X2}$, wherein R$^{X2}$ is hydrogen, substituted or unsubstituted alkyl, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; an oxygen protecting group;

W is —O—, —S—, or —NR$^{W1}$—;

R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group; and R$^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl, or two R$^{W2}$ groups are joined to form a 5-6 membered ring;

R$^1$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{A1}$; —C(=O)R$^{A2}$; —CO$_2$R$^{A2}$; —CN; —SCN; —SR$^{A1}$; —SOR$^{A1}$; —SO$_2$R$^{A2}$; —NO$_2$; —N$_3$; —N(R$^{A2}$)$_2$; —NR$^{A2}$C(=O)R$^{A2}$; —NR$^{A2}$C(=O)N(R$^{A2}$)$_2$; —OC(=O)OR$^{A1}$; —OC(=O)R$^{A2}$; —OC(=O)N(R$^{A2}$)$_2$; —NR$^{A2}$C(=O)OR$^{A1}$; —C(R$^{A2}$)$_3$; or a group -L$^1$-X; and R$^2$ is hydrogen; or R$^1$ and R$^2$ are joined to form =O; =N(R$^{A2}$); or =S;

each occurrence of R$^{A1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; or a group -L$^1$-X;

each occurrence of R$^{A2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; or substituted amino; or a group -L$^1$-X; or two R$^{A2}$ groups are optionally joined to form a heterocyclyl or heteroaryl ring;

or R$^{A1}$ or R$^{A2}$ represent a group of Formula (i):

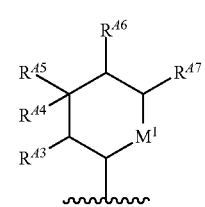

(i)

each occurrence of R$^{A3}$, R$^{A4}$, R$^{A5}$, R$^{A6}$, and R$^{A7}$ is independently hydrogen, substituted or unsubstituted alkyl; —OR$^{A9}$; —OC(=O)R$^{A9}$; —N(R$^{A9}$)$_2$; —NHC(=O)R$^{A9}$; or a group -L$^1$-X; wherein each occurrence of R$^{A9}$ is independently hydrogen; substituted or unsubstituted alkyl; an oxygen protecting group when attached to an oxygen atom; a nitrogen protecting group when attached to a nitrogen atom; or a group -L$^1$-X; or two R$^{A9}$ groups are joined to form a substituted or unsubstituted heterocyclic or substituted or unsubstituted heteroaryl ring;

M is —O—, —NR$^{A8}$, or —CHR$^{A8}$—, wherein R$^{A8}$ is hydrogen; substituted or unsubstituted alkyl; a nitrogen protecting group if attached to nitrogen; —OR$^{A9}$; or a group -L$^1$-X; wherein R$^{A9}$ is independently hydrogen; substituted or unsubstituted alkyl; acyl; an oxygen protecting group; or a group -L$^1$-X;

R$^3$ is hydrogen or —OR$^{C1}$, wherein R$^{C1}$ is hydrogen; an oxygen protecting group; substituted or unsubstituted alkyl; substituted or unsubstituted alkenyl; substituted or unsubstituted carbocyclyl; substituted or unsubstituted heterocyclyl; substituted or unsubstituted aryl; substituted or unsubstituted heteroaryl; acyl; or a group -L$^1$-X;

R$^4$ is hydrogen or —OR$^{D1}$, wherein R$^{D1}$ is hydrogen; an oxygen protecting group; substituted or unsubstituted alkyl; substituted or unsubstituted alkenyl; substituted or unsubstituted carbocyclyl; substituted or unsubstituted heterocyclyl; substituted or unsubstituted aryl; substituted or unsubstituted heteroaryl; acyl; or a group -L$^1$-X;

R$^5$ is hydrogen or —OR$^{E1}$, wherein R$^{E1}$ is hydrogen; an oxygen protecting group; substituted or unsubstituted alkyl; substituted or unsubstituted alkenyl; substituted or unsubstituted carbocyclyl; substituted or unsubstituted heterocyclyl; substituted or unsubstituted aryl; substituted or unsubstituted heteroaryl; acyl; or a group -L$^1$-X;

R$^6$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{F1}$; —C(=O)R$^{F2}$; —CO$_2$R$^{F1}$; —CN; —SCN; —SR$^{F1}$; —SOR$^{F1}$; —SO$_2$R$^{F2}$; —NO$_2$; —N$_3$; —N(R$^{F2}$)$_2$; —NR$^{F2}$C(=O)R$^{F2}$; —NR$^{F2}$C(=O)N(R$^{F2}$)$_2$; —OC(=O)OR$^{F1}$; —OC(=O)R$^{F2}$; —OC(=O)N(R$^{F2}$)$_2$; —NR$^{F2}$C(=O)OR$^{F1}$; —C(R$^{F2}$)$_3$, or a group -L$^1$-X;

each occurrence of R$^{F1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; or a group -L$^1$-X;

each occurrence of R$^{F2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; substituted amino, or a group -L$^1$-X; or two R$^{F2}$ groups are optionally joined to form a heterocyclyl or heteroaryl ring;

R$^7$ is hydrogen, an oxygen protecting group, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —C(=O)R$^{H1}$; a group -L$^1$-X; or a group of Formula (ii):

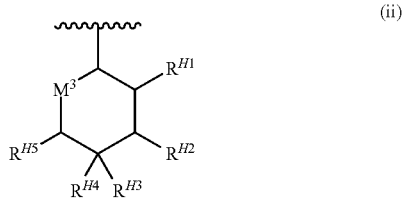

(ii)

wherein:

each occurrence of R$^{H1}$, R$^{H3}$, and R$^{H5}$ is independently hydrogen, substituted or unsubstituted alkyl; —OR$^{H9}$; —OC(=O)R$^{H9}$; —N(R$^{H9}$)$_2$; —NHC(=O)R$^{H9}$; a group -L$^1$-X; wherein each occurrence of R$^{H9}$ is independently hydrogen; substituted or unsubstituted alkyl; an oxygen protecting group when attached to an oxygen atom; a nitrogen protecting group when attached to a nitrogen atom; or a group -L$^1$-X; or two R$^{H9}$ groups are joined to form a substituted or unsubstituted heterocyclic or substituted or unsubstituted heteroaryl ring;

each instance of R$^{H2}$ and R$^{H4}$ is independently, hydrogen; —OR$^{H7}$; —N(R$^{H7}$)$_2$; —OC(=O)R$^{H7}$; —NHC(=O)R$^{H8}$; —C(=O)R$^{H7}$; —C(=NR$^{H7}$)R$^{H8}$; —C(=N—OR$^{H7}$)R$^{H8}$; —C(=N—NHR$^{H7}$)R$^{H8}$; —C(R$^{H8}$)$_2$NHR$^{H7}$; —C(R$^{H8}$)$_2$OR$^{H7}$; -L$^1$-X; wherein R$^{H7}$ is independently hydrogen; substituted or unsubstituted alkyl; an oxygen protecting group if attached to an oxygen atom; a nitrogen protecting group if attached to a nitrogen atom; a group -L$^1$-X; and R$^{H8}$ is hydrogen or substituted or unsubstituted alkyl; or R$^{H7}$ and R$^{H8}$ or two R$^{H7}$ groups are joined to form a substituted or unsubstituted heterocyclic or substituted or unsubstituted heteroaryl ring;

M$^3$ is O, NR$^{H6}$, or CHR$^{H6}$, wherein R$^{H6}$ is hydrogen; substituted or unsubstituted alkyl; a nitrogen protecting group if attached to nitrogen; —OR$^{H9}$; or a group -L$^1$-X; wherein each occurrence of R$^{H9}$ is independently hydrogen; an oxygen protecting group; substituted or unsubstituted alkyl; acyl; or a group -L$^1$-X;

R$^8$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{I1}$; —C(=O)R$^{I2}$; —CO$_2$R$^{I1}$; —CN; —SCN; —SR$^{I1}$; —SOR$^{I1}$; —SO$_2$R$^{I2}$; —NO$_2$; —N$_3$; —N(R$^{I2}$)$_2$; —NR$^{I2}$C(=O)R$^{I2}$; —NR$^{I2}$C(=O)N(R$^{I2}$)$_2$; —OC(=O)OR$^{I1}$; —OC(=O)R$^{I2}$; —OC(=O)N(R$^{I2}$)$_2$; —NR$^{I2}$C(=O)OR$^{I1}$; —CH$_2$(OR$^{I1}$), —CH(OR$^{I1}$)$_2$, —C(R$^{I2}$)$_3$, —CH$_2$OC(=O)R$^{I2}$, or a group -L$^1$-X;

each occurrence of R$^{I1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; a group of Formula (iii) or (iv); or a group -L$^1$-X; and each occurrence of R$^{I2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; substituted amino; a group of Formula (iii) or (iv); or a group -L$^1$-X; or two R$^{I2}$ groups are optionally joined to form a heterocyclyl or heteroaryl ring;

wherein Formula (iii) and (iv) is:

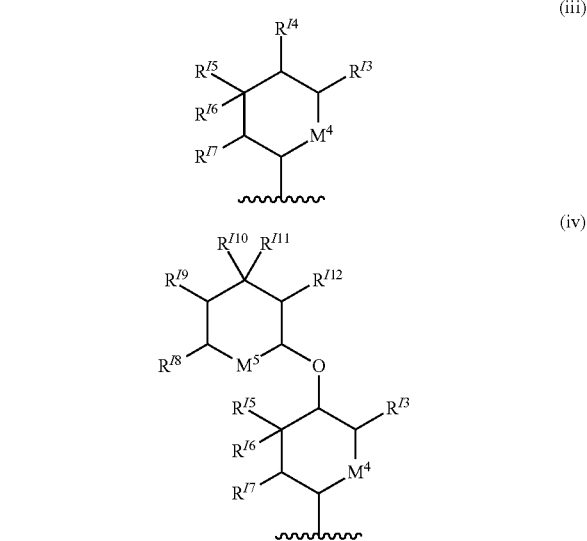

wherein:

each occurrence of R$^{I3}$, R$^{I5}$, R$^{I6}$, R$^{I7}$, R$^{I8}$, R$^{I10}$, R$^{I11}$, and R$^{I12}$, is independently hydrogen, substituted or unsubstituted alkyl; —OR$^{I13}$; —OC(=O)R$^{I13}$; —N(R$^{I13}$)$_2$; —NHC(=O)R$^{I13}$; a group -L$^1$-X; wherein each occurrence of R$^{I13}$ is independently hydrogen; substituted or unsubstituted alkyl; an oxygen protecting group when attached to an oxygen atom; a nitrogen protecting group when attached to a nitrogen atom; or a group -$L^1$-X; or two $R^{J13}$ groups are joined to form a substituted or unsubstituted heterocyclic or substituted or unsubstituted heteroaryl ring;

each occurrence of $R^{J4}$ and $R^{J9}$ is independently, hydrogen; substituted or unsubstituted alkyl; —$OR^{J14}$; —$N(R^{J14})_2$; —$OC(=O)R^{J14}$; —$NHC(=O)R^{J15}$; —$OC(=O)R^{J14}$; —$C(=O)R^{J14}$; —$C(=NR^{J14})R^{J15}$; —$C(=N-OR^{J14})R^{J15}$; —$C(=N-NHR^{J14})R^{J15}$; —$C(R^{J15})_2NHR^{J14}$; —$C(R^{J15})_2OR^{J14}$; or a group -$L^1$-A-$L^2$-B; wherein $R^{J14}$ is independently hydrogen; substituted or unsubstituted alkyl; an oxygen protecting group if attached to an oxygen atom; a nitrogen protecting group if attached to a nitrogen atom; a group -$L^1$-X; and $R^{J15}$ is hydrogen, or substituted or unsubstituted alkyl; and each occurrence of $M^4$ and $M^5$ is independently —O—, —$NR^{J16}$, or —$CHR^{J16}$—, wherein $R^{J16}$ is hydrogen; substituted or unsubstituted alkyl; a nitrogen protecting group if attached to nitrogen; —$OR^{J13}$; a group -$L^1$-X; wherein each occurrence of $R^{J13}$ is independently hydrogen; an oxygen protecting group; substituted or unsubstituted alkyl; acyl; or a group -$L^1$-X.

In certain embodiments, the precursor compounds of Formula (P-A) are compounds of Formula (P-I):

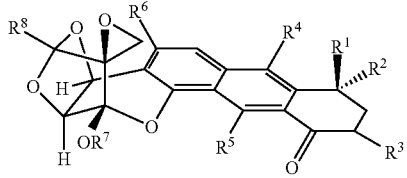

(P-I)

or pharmaceutically acceptable salts thereof.

In certain embodiments, the precursor compounds of Formula (P-A) are compounds of Formula (P-II):

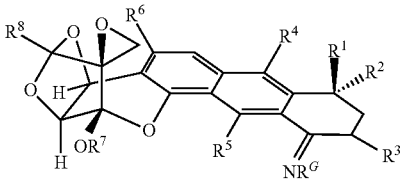

(P-II)

or pharmaceutically acceptable salts thereof.

Compounds of Formula (A), (I), and (II) are prepared by coupling a compound of Formula (P-A), (P-I), or (P-II), comprising at least one -$L^1$-X group attached thereto, with a compound of formula Y-$L^2$-B, or iteratively coupling with one or more independent instances of a compound of formula Y-$L_2$-X before coupling (capping) with a compound of formula Y-$L^2$-B, wherein X and Y react together to form a group A.

In certain embodiments, the compound of Formula (P-A), (P-I), or (P-II) comprises only one instance of a group -$L^1$-X attached thereto. In certain embodiments, the compound of Formula (P-A), (P-I), or (P-II) comprises two independent instances of a group -$L^1$-X attached thereto. In certain embodiments, the compound of Formula (P-A), (P-I), or (P-II) comprises three independent instances of a group -$L^1$-X attached thereto.

Also provided are pharmaceutically acceptable compositions of Formula (A), (I), and (II), methods of use and treatment, and methods of preparation.

Groups $R^1$ and $R^2$

As generally defined above, $R^1$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —$OR^{41}$; —$C(=O)R^{42}$; —$CO_2R^{42}$; —CN; —SCN; —$SR^{41}$; —$SOR^{41}$; —$SO_2R^{42}$; —$NO_2$; —$N_3$; —$N(R^{42})_2$; —$NR^{42}C(=O)R^{42}$; —$NR^{42}C(=O)N(R^{42})_2$; —$OC(=O)OR^{41}$; —$OC(=O)R^{42}$; —$OC(=O)N(R^{42})_2$; —$NR^{42}C(=O)OR^{41}$; —$C(R^{42})_3$; a group -$L^1$-(A-$L^2$)$_a$-B for Formula (A), (I), and (II), or a group -$L^1$-X for Formula (P-A), (P-I), and (P-II); and $R^2$ is hydrogen; or $R^1$ and $R^2$ are joined to form =O; =$N(R^{42})$; or =S.

In certain embodiments, $R^1$ is hydrogen; and $R^2$ is hydrogen.

In certain embodiments, $R^1$ is halogen (e.g., —F, —Cl, Br, or —I); and $R^2$ is hydrogen.

In certain embodiments, $R^1$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, and $R^2$ is hydrogen. Exemplary $R^1C_{1-6}$ alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$).

In certain embodiments, $R^1$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl, and $R^2$ is hydrogen.

In certain embodiments, $R^1$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl, and $R^2$ is hydrogen.

In certain embodiments, $R^1$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl, and $R^2$ is hydrogen.

In certain embodiments, $R^1$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl, and $R^2$ is hydrogen.

In certain embodiments, $R^1$ is substituted or unsubstituted aryl, e.g., substituted or unsubstituted phenyl, and $R^2$ is hydrogen.

In certain embodiments, $R^1$ is substituted or unsubstituted heteroaryl, e.g., substituted or unsubstituted 5-6 membered heteroaryl, and $R^2$ is hydrogen.

In certain embodiments, $R^1$ is —$OR^{41}$, and $R^2$ is hydrogen. In certain embodiments, $R^1$ is —C(=O)$R^{42}$ and $R^2$ is hydrogen. In certain embodiments, $R^1$ is —$CO_2R^{42}$ and $R^2$ is hydrogen. In certain embodiments, $R^1$ is —CN and $R^2$ is hydrogen. In certain embodiments, $R^1$ is —SCN and $R^2$ is hydrogen. In certain embodiments, $R^1$ is —$SR^{41}$ and $R^2$ is hydrogen. In certain embodiments, $R^1$ is —$SOR^{41}$ and $R^2$ is hydrogen. In certain embodiments, $R^1$ is —$SO_2R^{42}$ and $R^2$ is hydrogen. In certain embodiments, $R^1$ is —$NO_2$ and $R^2$ is hydrogen. In certain embodiments, $R^1$ is —$N_3$ and $R^2$ is hydrogen. In certain embodiments, $R^1$ is —$N(R^{42})_2$ and $R^2$ is hydrogen. In certain embodiments, $R^1$ is —$NR^{42}C(=O)R^{42}$ and $R^2$ is hydrogen. In certain embodiments, $R^1$ is —$NR^{42}C(=O)N(R^{42})_2$ and $R^2$ is hydrogen. In certain embodiments, $R^1$ is —OC(=O)$OR^{41}$ and $R^2$ is hydrogen. In certain embodiments, $R^1$ is —OC(=O)$R^{42}$ and $R^2$ is hydrogen. In certain embodiments, $R^1$ is —OC(=O)$N(R^{42})_2$ and $R^2$ is hydrogen. In certain embodiments, $R^1$ is —$NR^{42}C(=O)OR^{41}$ and $R^2$ is hydrogen. In certain embodiments, $R^1$ is —$C(R^{42})_3$ and $R^2$ is hydrogen.

In certain embodiments, $R^1$ is a group -$L^1$-(A-$L^2$)$_a$-B for Formula (I), or a group -$L^1$-X for Formula (P-A), (P-I), and (P-II) and $R^2$ is hydrogen.

In certain embodiments, $R^1$ and $R^2$ are joined to form =O. In certain embodiments, $R^1$ and $R^2$ are joined to form =$N(R^{42})$. In certain embodiments, $R^1$ and $R^2$ are joined to form =S.

As generally defined above, each occurrence of $R^{41}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; a group -$L^1$-(A-$L^2$)$_a$-B for Formula (A), (I), and (II), or a group -$L^1$-X for Formula (P-A), (P-I), and (P-II); each occurrence of $R^{42}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; or substituted amino; a group -$L^1$-(A-$L^2$)$_a$-B for Formula (A), (I), and (II), or a group -$L^1$-X for Formula (P-A), (P-I), and (P-II); or two $R^{42}$ groups are optionally joined to form a heterocyclyl or heteroaryl ring;

or $R^{41}$ or $R^{42}$ represent a group of Formula (i):

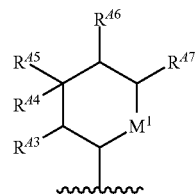

(i)

each occurrence of $R^{43}$, $R^{44}$, $R^{45}$, $R^{46}$, and $R^{47}$ is independently hydrogen, substituted or unsubstituted alkyl; —$OR^{49}$; —OC(=O)$R^{49}$; —$N(R^{49})_2$; —NHC(=O)$R^{49}$; a group -$L^1$-(A-$L^2$)$_a$-B for Formula (A), (I), and (II), or a group -$L^1$-X for Formula (P-A), (P-I), and (P-II); wherein each occurrence of $R^{49}$ is independently hydrogen; substituted or unsubstituted alkyl; an oxygen protecting group when attached to an oxygen atom; a nitrogen protecting group when attached to a nitrogen atom; or a group -$L^1$-(A-$L^2$)$_a$-B for Formula (A), (I), and (II), or a group -$L^1$-X for Formula (P-A), (P-I), and (P-II); or two $R^{49}$ groups are joined to form a substituted or unsubstituted heterocyclic or substituted or unsubstituted heteroaryl ring; and $M^1$ is —O—, —$NR^{48}$—, or —$CHR^{48}$— wherein $R^{48}$ is hydrogen; substituted or unsubstituted alkyl; a nitrogen protecting group if attached to nitrogen; —$OR^{49}$; a group -$L^1$-(A-$L^2$)$_a$-B for Formula (A), (I), and (II), or a group -$L^1$-X for Formula (P-A), (P-I), and (P-II); wherein $R^{49}$ is independently hydrogen; substituted or unsubstituted alkyl; acyl; an oxygen protecting group; a group -$L^1$-(A-$L^2$)$_a$-B for Formula (A), (I), and (II), or a group -$L^1$-X for Formula (P-A), (P-I), and (P-II).

In certain embodiments, $R^{41}$ or $R^{42}$ is hydrogen. In certain embodiments, $R^{41}$ or $R^{42}$ is a group -$L^1$-(A-$L^2$)$_a$-B for Formula (A), (I), and (II), or a group -$L^1$-X for Formula (P-A), (P-I), and (P-II). In certain embodiments, $R^{41}$ or $R^{42}$ is represents a group of Formula (i).

In certain embodiments, $R^{43}$ is hydrogen, substituted or unsubstituted alkyl; —$OR^{49}$; —OC(=O)$R^{49}$; —NHC(=O)$R^{49}$; or a group -$L^1$-(A-$L^2$)$_a$-B for Formula (A), (I), and (II), or a group -$L^1$-X for Formula (P-A), (P-I), and (P-II); wherein each occurrence of $R^{49}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{43}$ is hydrogen. In certain embodiments, $R^{43}$ is substituted or unsubstituted alkyl, e.g., methyl. In certain embodiments, $R^{43}$ is —$OR^{49}$, e.g., —OH or —O-alkyl. In certain embodiments, $R^{43}$ is —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{43}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{44}$ is hydrogen, substituted or unsubstituted alkyl; —$OR^{49}$; —OC(=O)$R^{49}$; —NHC(=O)$R^{49}$; or a group -$L^1$-(A-$L^2$)$_a$-B for Formula (A), (I), and (II), or a group -$L^1$-X for Formula (P-A), (P-I), and (P-II); wherein each occurrence of $R^{49}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{44}$ is hydrogen. In certain embodiments, $R^{44}$ is substituted or unsubstituted alkyl, e.g., methyl. In certain embodiments, $R^{44}$ is —$OR^{49}$, e.g., —OH or —O-alkyl. In certain embodiments, $R^{44}$ is —OC(=O-$L^1$-(A-$L^2$)$_a$-B for Formula (A), (I), and (II), or a group —OC(=O)-$L^1$-X for Formula (P-A), (P-I), and (P-II). In certain embodiments, $R^{44}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{45}$ is hydrogen, substituted or unsubstituted alkyl; —$OR^{49}$; —OC(=O)$R^{49}$; —NHC(=O)$R^{49}$; or a group -$L^1$-(A-$L^2$)$_a$-B for Formula (A), (I), and (II), or a group -$L^1$-X for Formula (P-A), (P-I), and (P-II); wherein each occurrence of $R^{49}$ is independently hydrogen; substituted or unsubstituted alkyl; an oxygen protecting group; a group -L¹-(A-L²)ₐ-B for Formula (A), (I), and (II), or a group -L¹-X for Formula (P-A), (P-I), and (P-II), e.g., -L¹-N₃. In certain embodiments, R$^{45}$ is hydrogen. In certain embodiments, R$^{45}$ is substituted or unsubstituted alkyl, e.g., methyl. In certain embodiments, R$^{45}$ is —OR$^{49}$, e.g., —OH or —O-alkyl. In certain embodiments, R$^{45}$ is —OC(=O)-L¹-(A-L²)ₐ-B for Formula (A), (I), and (II), or a group —OC(=O)-L¹-X for Formula (P-A), (P-I), and (P-II). In certain embodiments, R$^{45}$ is —NHC(=O-L¹-(A-L²)ₐ-B for Formula (A), (I), and (II), or a group —NHC(=O)-L¹-X for Formula (P-A), (P-I), and (P-II).

In certain embodiments, R$^{46}$ is hydrogen, substituted or unsubstituted alkyl; —OR$^{49}$; —OC(=O)R$^{49}$; —NHC(=O)R$^{49}$; or a group -L¹-(A-L²)ₐ-B for Formula (A), (I), and (II), or a group -L¹-X for Formula (P-A), (P-I), and (P-II); wherein each occurrence of R$^{49}$ is independently hydrogen; substituted or unsubstituted alkyl; an oxygen protecting group; a group -L¹-(A-L²)ₐ-B for Formula (A), (I), and (II), or a group -L¹-X for Formula (P-A), (P-I), and (P-II). In certain embodiments, R$^{46}$ is hydrogen. In certain embodiments, R$^{46}$ is substituted or unsubstituted alkyl, e.g., methyl. In certain embodiments, R$^{46}$ is —OR$^{49}$, e.g., —OH or —O-alkyl. In certain embodiments, R$^{46}$ is —OC(=O-L¹-(A-L²)ₐ-B for Formula (A), (I), and (II), or a group —OC(=O)-L¹-X for Formula (P-A), (P-I), and (P-II). In certain embodiments, R$^{46}$ is —NHC(=O-L¹-(A-L²)ₐ-B for Formula (A), (I), and (II), or a group —NHC(=O)-L¹-X for Formula (P-A), (P-I), and (P-II).

In certain embodiments, R$^{47}$ is hydrogen, substituted or unsubstituted alkyl; —OR$^{49}$; —OC(=O)R$^{49}$; —NHC(=O)R$^{49}$; or a group -L¹-(A-L²)ₐ-B for Formula (A), (I), and (II), or a group -L¹-X for Formula (P-A), (P-I), and (P-II); wherein each occurrence of R$^{49}$ is independently hydrogen; substituted or unsubstituted alkyl; an oxygen protecting group; a group -L¹-(A-L²)ₐ-B for Formula (A), (I), and (II), or a group -L¹-X for Formula (P-A), (P-I), and (P-II). In certain embodiments, R$^{47}$ is hydrogen. In certain embodiments, R$^{47}$ is substituted or unsubstituted alkyl, e.g., methyl. In certain embodiments, R$^{46}$ is —OR$^{49}$, e.g., —OH or —O-alkyl. In certain embodiments, R$^{47}$ is —OC(=O)-L¹-(A-L²)ₐ-B for Formula (A), (I), and (II), or a group —OC(=O)-L¹-X for Formula (P-A), (P-I), and (P-II). In certain embodiments, R$^{47}$ is —NHC(=O)-L¹-(A-L²)ₐ-B for Formula (A), (I), and (II), or a group —NHC(=O)-L¹-X for Formula (P-A), (P-I), and (P-II).

In certain embodiments, M¹ is —O—, —NR$^{48}$—, or —CHR$^{48}$—, wherein R$^{48}$ is hydrogen; substituted or unsubstituted alkyl; a nitrogen protecting group if attached to nitrogen; —OR$^{49}$; or a group -L¹-(A-L²)ₐ-B for Formula (A), (I), and (II), or a group -L¹-X for Formula (P-A), (P-I), and (P-II); wherein R$^{49}$ is independently hydrogen; substituted or unsubstituted alkyl; acyl; an oxygen protecting group; or a group -L¹-(A-L²)ₐ-B for Formula (A), (I), and (II), or a group -L¹-X for Formula (P-A), (P-I), and (P-II).

In certain embodiments, M¹ is —O—. In certain embodiments, M¹ is —NR$^{48}$—, e.g., —NH—. In certain embodiments, M¹ is —CHR$^{48}$—, e.g., —CH₂—.

In certain embodiments, R$^{43}$ is hydrogen; R$^{44}$ is hydrogen or —OR$^{49}$; R$^{45}$ is methyl, —NHC(=O)R$^{49}$, a group -L¹-(A-L²)ₐ-B for Formula (A), (I), and (II), or a group -L¹-X for Formula (P-A), (P-I), and (P-II); R$^{46}$ is hydrogen; —OR$^{49}$; —OC(=O)R$^{49}$; or —NHC(=O)R$^{49}$; R$^{47}$ is methyl; and M¹ is —O—.

In certain embodiments, the group of Formula (i) is of Formula (i-a):

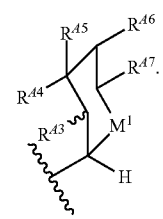

In certain embodiments, M¹ is —O—. In certain embodiments, M¹ is —NH—. In certain embodiments, M¹ is —CH₂—. In certain embodiments, R$^{43}$ is hydrogen; R$^{44}$ is hydrogen or —OR$^{49}$; R$^{45}$ is methyl, —NHC(=O)R$^{49}$, a group -L¹-(A-L²)ₐ-B for Formula (A), (I), and (II), or a group -L¹-X for Formula (P-A), (P-I), and (P-II), e.g., -L¹-N₃.; R$^{46}$ is hydrogen; —OR$^{49}$; —OC(=O)R$^{49}$; or —NHC(=O)R$^{49}$; and R$^{47}$ is methyl. In certain embodiments, R$^{46}$ is a group —OC(=O)-L¹-(A-L²)ₐ-B for Formula (A), (I), and (II), or a group —OC(=O)-L¹-X for Formula (P-A), (P-I), and (P-II). In certain embodiments, R$^{43}$ is a non-hydrogen equatorial group.

In certain embodiments, the group of Formula (i-a) is of Formula (i-b1), (i-b2), (i-b3), or (i-b4):

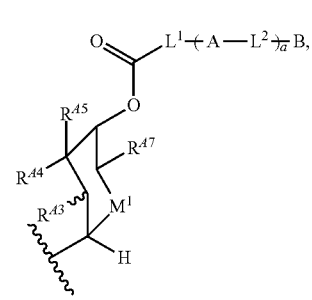

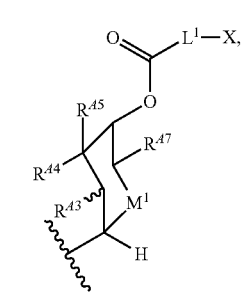

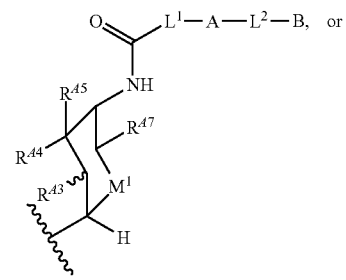

(i-b4)

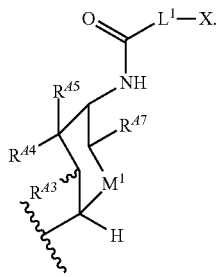

In certain embodiments, $M^1$ is —O—. In certain embodiments, $M^1$ is —NH—. In certain embodiments, M is —CH$_2$—. In certain embodiments, $R^{43}$ is hydrogen; $R^{44}$ is hydrogen or —OR$^{49}$; $R^{45}$ is methyl; and $R^{47}$ is methyl. In certain embodiments, $R^{43}$ Is a non-hydrogen equatorial group.

In certain embodiments, the group of Formula (i-b) is of Formula (i-c1), (i-c2), (i-c3), or (i-c4):

(i-c1)

[structure]

(i-c2)

[structure]

(i-c1)

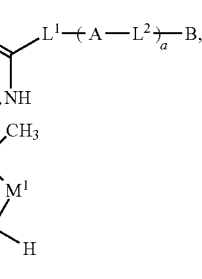

(i-c2)

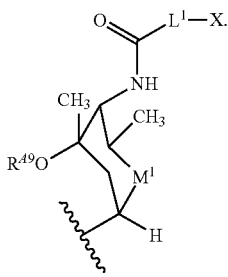

In certain embodiments, the group of Formula (i) is of Formula (i-d):

(i-d)

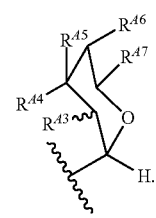

In certain embodiments, $R^{43}$ is hydrogen; $R^{44}$ is hydrogen or —OR$^{49}$; $R^{45}$ is methyl, —NHC(=O)R$^{49}$, a group -L$^1$-(A-L$^2$)$_a$-B for Formula (A), (I), and (II), or a group -L$^1$-X for Formula (P-A), (P-I), and (P-II), e.g., -L$^1$-N$_3$; $R^{46}$ is hydrogen; —OR$^{49}$; —OC(=O)R$^{49}$; or —NHC(=O)R$^{49}$; and $R^{47}$ is methyl. In certain embodiments, $R^{46}$ is a group —OC(=O)-L$^1$-(A-L$^2$)$_a$-B for Formula (A), (I), and (II), or a group —OC(=O)-L$^1$-X for Formula (P-A), (P-I), and (P-II). In certain embodiments, $R^{43}$ is a non-hydrogen equatorial group.

In certain embodiments, the group of Formula (i) is of Formula (i-e1) or (i-e2):

(i-e1)

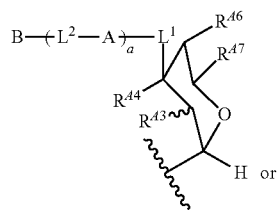 or (i-e2)

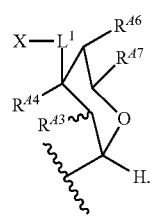

In certain embodiments, $R^{43}$ is hydrogen; $R^{44}$ is hydrogen or —OR$^{49}$; $R^{46}$ is hydrogen; —OR$^{49}$; —OC(=O)R$^{49}$; or —NHC(=O)R$^{49}$; and $R^{47}$ is methyl. In certain embodiments, $R^{43}$ is a non-hydrogen equatorial group.

In certain embodiments, the group of Formula (i) is of Formula (i-f):

(i-f)

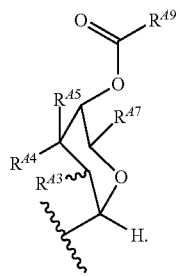

In certain embodiments, $R^{A3}$ is hydrogen; $R^{A4}$ is hydrogen or —$OR^{A9}$; $R^{A5}$ is methyl, —NHC(=O)$R^{A9}$, a group -$L^1$-(A-$L^2$)$_a$-B for Formula (A), (I), and (II), or a group -$L^1$-X for Formula (P-A), (P-I), and (P-II), e.g., -$L^1$-$N_3$; and $R^{A7}$ is methyl. In certain embodiments, $R^{A3}$ is a non-hydrogen equatorial group.

In certain embodiments, the group of Formula (i) is of Formula (i-g):

(i-g)

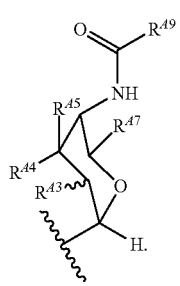

In certain embodiments, $R^{A3}$ is hydrogen; $R^{A4}$ is hydrogen or —$OR^{A9}$; $R^{A5}$ is methyl, —NHC(=O)$R^{A9}$, a group -$L^1$-(A-$L^2$)$_a$-B for Formula (A), (I), and (II), or a group -$L^1$-X for Formula (P-A), (P-I), and (P-II), e.g., -$L^1$-$N_3$; and $R^{A7}$ is methyl. In certain embodiments, $R^{A3}$ is a non-hydrogen equatorial group.

In certain embodiments, the group of Formula (i) is of Formula (i-h):

(i-h)

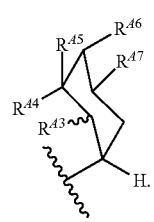

In certain embodiments, $R^{A3}$ is hydrogen; $R^{A4}$ is hydrogen or —$OR^{A9}$; $R^{A5}$ is methyl, —NHC(=O)$R^{A9}$, a group -$L^1$-(A-$L^2$)$_a$-B for Formula (A), (I), and (II), or a group -$L^1$-X for Formula (P-A), (P-I), and (P-II), e.g., -$L^1$-$N_3$; $R^{A6}$ is hydrogen; —$OR^{A9}$; —OC(=O)$R^{A9}$; or —NHC(=O)$R^{A9}$; and $R^{A7}$ is methyl. In certain embodiments, $R^{A6}$ is a group —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{A3}$ is a non-hydrogen equatorial group.

In certain embodiments, the group of Formula (i) is of Formula (i-i1) or (i-i2):

(i-i1)

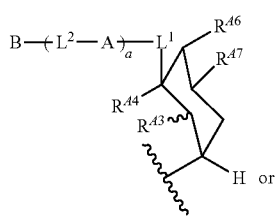

or (i-i2)

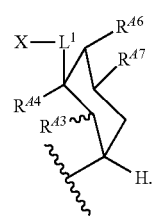

In certain embodiments, $R^{A3}$ is hydrogen; $R^{A4}$ is hydrogen or —$OR^{A9}$; $R^{A6}$ is hydrogen; —$OR^{A9}$; —OC(=O)$R^{A9}$; or —NHC(=O)$R^{A9}$; and $R^{A7}$ is methyl. In certain embodiments, $R^{A3}$ is a non-hydrogen equatorial group.

In certain embodiments, the group of Formula (i) is of Formula (i-j):

(i-j)

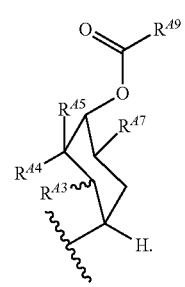

In certain embodiments, $R^{A3}$ is hydrogen; $R^{A4}$ is hydrogen or —$OR^{A9}$; $R^{A5}$ is methyl, —NHC(=O)$R^{A9}$, a group -$L^1$-(A-$L^2$)$_a$-B for Formula (A), (I), and (II), or a group -$L^1$-X for Formula (P-A), (P-I), and (P-II), e.g., -$L^1$-$N_3$; and $R^{A7}$ is methyl. In certain embodiments, $R^{A3}$ is a non-hydrogen equatorial group.

In certain embodiments, the group of Formula (i) is of Formula (i-k):

(i-k)

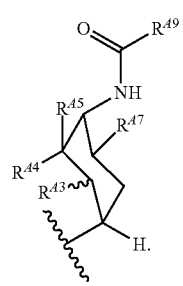

In certain embodiments, $R^{A3}$ is hydrogen; $R^{A4}$ is hydrogen or —$OR^{A9}$; $R^{A5}$ is methyl, —NHC(=O)$R^{A9}$, a group -$L^1$-

(A-L$^2$)$_a$-B for Formula (A), (I), and (II), or a group -L$^1$-X for Formula (P-A), (P-I), and (P-II), e.g., -L$^1$-N$_3$; and R$^{A7}$ is methyl. In certain embodiments, R$^{A3}$ is a non-hydrogen equatorial group.

Groups R$^3$, R$^4$, R$^5$, and R$^6$

As generally defined above, R$^3$ is hydrogen or —OR$^{C1}$, wherein R$^{C1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; a group -L$^1$-(A-L$^2$)$_a$-B for Formula (A), (I), and (II), or a group -L$^1$-X for Formula (P-A), (P-I), and (P-II). In certain embodiments, R$^3$ is hydrogen.

In certain embodiments, R$^3$ is —OR$^{C1}$, e.g., —OH or —OCH$_3$.

As generally defined above, R$^4$ is hydrogen or —OR$^{D1}$, wherein R$^{D1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; a group -L$^1$-(A-L$^2$)$_a$-B for Formula (A), (I), and (II), or a group -L$^1$-X for Formula (P-A), (P-I), and (P-II). In certain embodiments, R$^4$ is hydrogen.

In certain embodiments, R$^4$ is —OR$^{D1}$, e.g., —OH or —OCH$_3$.

As generally defined above, R$^5$ is hydrogen or —OR$^{E1}$, wherein R$^{E1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; a group -L$^1$-(A-L$^2$)$_a$-B for Formula (A), (I), and (II), or a group -L$^1$-X for Formula (P-A), (P-I), and (P-II). In certain embodiments, R$^5$ is hydrogen. In certain embodiments, R$^5$ is —OR$^{E1}$, e.g., —OH or —OCH$_3$.

As generally defined above, R$^6$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{F1}$; —C(=O)R$^{F2}$; —CO$_2$R$^{F1}$; —CN; —SCN; —SR$^{F1}$; —SOR$^{F1}$; —SO$_2$R$^{F2}$; —NO$_2$; —N$_3$; —N(R$^{F2}$)$_2$; —NR$^{F2}$C(=O)R$^{F2}$; —NR$^{F2}$C(=O)N(R$^{F2}$)$_2$; —OC(=O)OR$^{F1}$; —OC(=O)R$^{F2}$; —OC(=O)N(R$^{F2}$)$_2$; —NR$^{F2}$C(=O)OR$^{F1}$; —C(R$^{F2}$)$_3$; a group -L$^1$-(A-L$^2$)$_a$-B for Formula (A), (I), and (II), or a group -L$^1$-X for Formula (P-A), (P-I), and (P-II).

In certain embodiments, R$^6$ is hydrogen.

In certain embodiments, R$^6$ is halogen; e.g., —F, —Cl, Br, or —I.

In certain embodiments, R$^6$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^6$C$_{1-6}$ alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), n-hexyl (C$_6$).

In certain embodiments, R$^6$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In certain embodiments, R$^6$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl.

In certain embodiments, R$^6$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl. In certain embodiments, R$^6$ is substituted or unsubstituted cyclopropyl.

In certain embodiments, R$^6$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, R$^6$ is substituted or unsubstituted aryl, e.g., substituted or unsubstituted phenyl.

In certain embodiments, R$^6$ is substituted or unsubstituted heteroaryl, e.g., substituted or unsubstituted 5-6 membered heteroaryl.

In certain embodiments, R$^6$ is —OR$^{F1}$. In certain embodiments, R$^6$ is —C(=O)R$^{F2}$. In certain embodiments, R$^6$ is —CO$_2$R$^{F1}$. In certain embodiments, R$^6$ is —CN. In certain embodiments, R$^6$ is —SCN. In certain embodiments, R$^6$ is —SR$^{F1}$. In certain embodiments, R$^6$ is —SOR$^{F1}$. In certain embodiments, R$^6$ is —SO$_2$R$^{F2}$. In certain embodiments, R$^6$ is —NO$_2$. In certain embodiments, R$^6$ is —N$_3$. In certain embodiments, R$^6$ is —N(R$^{F2}$)$_2$. In certain embodiments, R$^6$ is —NR$^{F2}$C(=O)R$^{F2}$. In certain embodiments, R$^6$ is —NR$^{F2}$C(=O)N(R$^{F2}$)$_2$. In certain embodiments, R$^6$ is —OC(=O)OR$^{F1}$. In certain embodiments, R$^6$ is —OC(=O)R$^{F2}$. In certain embodiments, R$^6$ is —OC(=O)N(R$^{F2}$)$_2$. In certain embodiments, R$^6$ is —NR$^{F2}$C(=O)OR$^{F1}$. In certain embodiments, R$^6$ is —C(R$^{F2}$)$_3$.

In certain embodiments, R$^6$ is a group -L$^1$-(A-L$^2$)$_a$-B for Formula (A), (I), and (II), or a group -L$^1$-X for Formula (P-A), (P-I), and (P-II).

As generally defined above, each occurrence of R$^{F1}$ is independently hydrogen; an oxygen protecting group if attached to oxygen; a sulfur protecting group if attached to sulfur; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; a group -L$^1$-(A-L$^2$)$_a$-B for Formula (A), (I), and (II), or a group -L$^1$-X for Formula (P-A), (P-I), and (P-II); and each occurrence of R$^{F2}$ is independently hydrogen; a nitrogen protecting group if attached to nitrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; acyl; hydroxyl; substituted hydroxyl; thiol; substituted thiol; amino; substituted amino, a group -L$^1$-(A-L$^2$)$_a$-B for Formula (A), (I), and (II), or a group -L$^1$-X for Formula (P-A), (P-I), and (P-II); or two R$^{F2}$ groups are optionally joined to form a heterocyclyl or heteroaryl ring.

In certain embodiments, $R^{F1}$ or $R^{F2}$ is hydrogen or a group -$L^1$-(A-$L^2$)$_a$-B for Formula (A), (I), and (II), or a group -$L^1$-X for Formula (P-A), (P-I), and (P-II).

In certain embodiments, $R^3$ is hydrogen or —OH, $R^4$ is —OCH$_3$, and $R^5$ is —OH.

In certain embodiments, $R^3$ is hydrogen or —OH, $R^4$ is —OCH$_3$, $R^5$ is —OH, and $R^6$ substituted or unsubstituted alkyl or —O$R^{F1}$.

Group $R^7$

As generally defined above, $R^7$ is hydrogen, an oxygen protecting group, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —C(=O)$R^{H1}$; a group -$L^1$-(A-$L^2$)$_a$-B for Formula (A), (I), and (II), or a group -$L^1$-X for Formula (P-A), (P-I), and (P-II); or a group of Formula (ii):

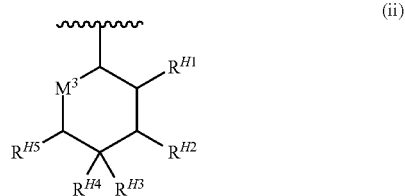

(ii)

wherein:

each occurrence of $R^{H1}$, $R^{H3}$, and $R^{H5}$ is independently hydrogen, substituted or unsubstituted alkyl; —O$R^{H9}$; —OC(=O)$R^{H9}$; —N($R^{H9}$)$_2$; —NHC(=O)$R^{H9}$; a group -$L^1$-(A-$L^2$)$_a$-B for Formula (A), (I), and (II), or a group -$L^1$-X for Formula (P-A), (P-I), and (P-II); wherein each occurrence of $R^{H9}$ is independently hydrogen; substituted or unsubstituted alkyl; an oxygen protecting group when attached to an oxygen atom; a nitrogen protecting group when attached to a nitrogen atom; or a group -$L^1$-(A-$L^2$)$_a$-B for Formula (A), (I), and (II), or a group -$L^1$-X for Formula (P-A), (P-I), and (P-II); or two $R^{H9}$ groups are joined to form a substituted or unsubstituted heterocyclic or substituted or unsubstituted heteroaryl ring;

each instance of $R^{H2}$ and $R^{H4}$ is independently, hydrogen; —O$R^{H7}$; —N($R^{H7}$)$_2$; —OC(=O)$R^{H7}$; —NHC(=O)$R^{H8}$; —C(=O)$R^{H7}$; —C(=N$R^{H7}$)$R^{H8}$; —C(=N—O$R^{H7}$)$R^{H8}$; —C(=N—NH$R^{H7}$)$R^{H8}$; —C($R^{H8}$)$_2$NH$R^{H7}$; —C($R^{H8}$)$_2$O$R^{H7}$; a group -$L^1$-(A-$L^2$)$_a$-B for Formula (A), (I), and (II), or a group -$L^1$-X for Formula (P-A), (P-I), and (P-II); wherein $R^{H7}$ is independently hydrogen; substituted or unsubstituted alkyl; an oxygen protecting group if attached to an oxygen atom; a nitrogen protecting group if attached to a nitrogen atom; a group -$L^1$-(A-$L^2$)$_a$-B for Formula (A), (I), and (II), or a group -$L^1$-X for Formula (P-A), (P-I), and (P-II); and $R^{H8}$ is hydrogen or substituted or unsubstituted alkyl; or $R^{H7}$ and $R^{H8}$ or two $R^{H7}$ groups are joined to form a substituted or unsubstituted heterocyclic or substituted or unsubstituted heteroaryl ring;

$M^3$ is O, NR$^{H6}$, or CHR$^{H6}$, wherein $R^{H6}$ is hydrogen; substituted or unsubstituted alkyl; a nitrogen protecting group if attached to nitrogen; —O$R^{H9}$; a group -$L^1$-(A-$L^2$)$_a$-B for Formula (A), (I), and (II), or a group -$L^1$-X for Formula (P-A), (P-I), and (P-II); wherein each occurrence of $R^{H9}$ is independently hydrogen; an oxygen protecting group; substituted or unsubstituted alkyl; acyl; a group -$L^1$-(A-$L^2$)$_a$-B for Formula (A), (I), and (II), or a group -$L^1$-X for Formula (P-A), (P-I), and (P-II).

In certain embodiments, $R^7$ is hydrogen.

In certain embodiments, $R^7$ is an oxygen protecting group.

In certain embodiments, $R^7$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl.

In certain embodiments, $R^7$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In certain embodiments, $R^7$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl.

In certain embodiments, $R^7$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, $R^7$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, $R^7$ is substituted or unsubstituted aryl, e.g., substituted or unsubstituted phenyl.

In certain embodiments, $R^7$ is substituted or unsubstituted heteroaryl, e.g., substituted or unsubstituted 5-6 membered heteroaryl.

In certain embodiments, $R^7$ is —C(=O)$R^{H1}$, e.g., —C(=O)CH$_3$.

In certain embodiments, $R^7$ is a group -$L^1$-(A-$L^2$)$_a$-B for Formula (A), (I), and (II), or a group -$L^1$-X for Formula (P-A), (P-I), and (P-II).

In certain embodiments, $R^7$ is a group of Formula (ii).

In certain embodiments, $R^{H1}$ is hydrogen, substituted or unsubstituted alkyl; —O$R^{H9}$; —OC(=O)$R^{H9}$; —NHC(=O)$R^{H9}$; or a group -$L^1$-(A-$L^2$)$_a$-B for Formula (A), (I), and (II), or a group -$L^1$-X for Formula (P-A), (P-I), and (P-II); wherein each occurrence of $R^{H9}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{H1}$ is hydrogen. In certain embodiments, $R^{H1}$ is substituted or unsubstituted alkyl, e.g., methyl. In certain embodiments, $R^{H1}$ is —O$R^{A9}$, e.g., —OH or —O-alkyl. In certain embodiments, $R^{H1}$ is —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{H1}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{H3}$ is hydrogen, substituted or unsubstituted alkyl; —O$R^{H9}$; —OC(=O)$R^{H9}$; —NHC(=O)$R^{H9}$; or a group -$L^1$-(A-$L^2$)$_a$-B for Formula (A), (I), and (II), or a group -$L^1$-X for Formula (P-A), (P-I), and (P-II); wherein each occurrence of $R^{H9}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{H3}$ is hydrogen. In certain embodiments, $R^{H3}$ is substituted or unsubstituted alkyl, e.g., methyl. In certain embodiments, $R^{H3}$ is —$OR^{A9}$, e.g., —OH or —O-alkyl. In certain embodiments, $R^{H3}$ is —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{H3}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{H5}$ is hydrogen, substituted or unsubstituted alkyl; —$OR^{H9}$; —OC(=O)$R^{H9}$; —NHC(=O)$R^{H9}$; or a group -$L^1$-(A-$L^2$)$_a$-B for Formula (A), (I), and (II), or a group -$L^1$-X for Formula (P-A), (P-I), and (P-II); wherein each occurrence of $R^{H9}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{H5}$ is hydrogen. In certain embodiments, $R^{H5}$ is substituted or unsubstituted alkyl, e.g., methyl. In certain embodiments, $R^{H5}$ is —$OR^{A9}$, e.g., —OH or —O-alkyl. In certain embodiments, $R^{H5}$ is —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{H5}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{H1}$ is hydrogen, $R^{H3}$ is —$OR^{H9}$ or —OC(=O)$R^{H9}$, and $R^{H5}$ is methyl.

In certain embodiments, $R^{H2}$ is hydrogen.

In certain embodiments, $R^{H2}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl.

In certain embodiments, $R^{H2}$ is -$L^1$-(A-$L^2$)$_a$-B for Formula (A), (I), and (II), or a group -$L^1$-X for Formula (P-A), (P-I), and (P-II), e.g., -$L^1$-$N_3$.

In certain embodiments, $R^{H2}$ is —$OR^{H7}$. In certain embodiments, $R^{H2}$ is —N($R^{H7}$)$_2$. In certain embodiments, $R^{H2}$ is —OC(=O)$R^{H7}$. In certain embodiments, $R^{H2}$ is —NHC(=O)$R^{H9}$ In certain embodiments, $R^{H2}$ is —C(=O)$R^{H7}$. In certain embodiments, $R^{H2}$ is —C(=N$R^{H7}$)$R^{H8}$ In certain embodiments, $R^{H2}$ is —C(=N—O$R^{H7}$)$R^{H8}$. In certain embodiments, $R^{H2}$ is —C(=N—NH$R^{H7}$)$R^{H8}$. In certain embodiments, $R^{H2}$ is —C($R^{H8}$)$_2$NH$R^{H7}$. In certain embodiments, $R^{H2}$ is —C($R^{H8}$)$_2$O$R^{H7}$. In certain embodiments of $R^{H2}$, $R^{H7}$ is hydrogen. In certain embodiments of $R^{H2}$, $R^{H7}$ is substituted or unsubstituted alkyl, e.g., methyl. In certain embodiments of $R^{H2}$, $R^{H7}$ is an oxygen protecting group if attached to an oxygen atom or a nitrogen protecting group if attached to a nitrogen atom. In certain embodiments of $R^{H2}$, $R^{H7}$ is a group -$L^1$-(A-$L^2$)$_a$-B for Formula (A), (I), and (II), or a group -$L^1$-X for Formula (P-A), (P-I), and (P-II). In certain embodiments of $R^{H2}$, $R^{H8}$ is hydrogen. In certain embodiments of $R^{H2}$, $R^{H8}$ is substituted or unsubstituted alkyl, e.g., methyl.

However, in certain embodiments of $R^{H2}$, X is not —$N_3$. In certain embodiments of $R^{H2}$, $L^1$ is not —CH$_2$CH$_2$—. In certain embodiments of $R^{H2}$, the group -$L^1$-X is not —CH$_2$CH$_2$N$_3$, e.g., when attached to a group —C(=O)—. In certain embodiments of $R^{H2}$, $R^{H7}$ is not —CH$_2$CH$_2$N$_3$. In certain embodiments of $R^{H2}$, $R^{H8}$ is not —CH$_2$CH$_2$N$_3$.

In certain embodiments, $R^{H4}$ is hydrogen.

In certain embodiments, $R^{H4}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl.

In certain embodiments, $R^{H4}$ is -$L^1$-(A-$L^2$)$_a$-B for Formula (A), (I), and (II), or a group -$L^1$-X for Formula (P-A), (P-I), and (P-II).

In certain embodiments, $R^{H4}$ is —$OR^{H7}$. In certain embodiments, $R^{H4}$ is —OC(=O)$R^{H7}$. In certain embodiments, $R^{H4}$ is —C(=O)$R^{H7}$. In certain embodiments, $R^{H4}$ is —C(=N$R^{H7}$)$R^{H8}$. In certain embodiments, $R^{H4}$ is —C(=N—O$R^{H7}$)$R^{H8}$. In certain embodiments, $R^{H4}$ is —C(=N—NH$R^{H7}$)$R^{H8}$. In certain embodiments, $R^{H4}$ is —C($R^{H8}$)$_2$NH$R^{H7}$. In certain embodiments, $R^{H4}$ is —C($R^{H8}$)$_2$O$R^{H7}$. In certain embodiments of $R^{H4}$, $R^{H7}$ is hydrogen. In certain embodiments of $R^{H4}$, $R^{H7}$ is substituted or unsubstituted alkyl, e.g., methyl. In certain embodiments of $R^{H4}$, $R^{H7}$ is an oxygen protecting group if attached to an oxygen atom or a nitrogen protecting group if attached to a nitrogen atom. In certain embodiments of $R^{H4}$, $R^{H7}$ is a group -$L^1$-(A-$L^2$)$_a$-B for Formula (A), (I), and (II), or a group -$L^1$-X for Formula (P-A), (P-I), and (P-II). In certain embodiments of $R^{H4}$, $R^{H8}$ is hydrogen. In certain embodiments of $R^{H4}$, $R^{H8}$ is substituted or unsubstituted alkyl, e.g., methyl.

In certain embodiments, $R^{H2}$ is —$OR^{H7}$ (e.g., OH) or —N($R^{H7}$)$_2$, and $R^{H4}$ is —C(=N—O$R^{H7}$)$R^{H8}$ wherein $R^{H7}$ of $R^{H4}$ is a group -$L^1$-(A-$L^2$)$_a$-B for Formula (A), (I), and (II), or a group -$L^1$-X for Formula (P-A), (P-I), and (P-II). In this instance, in certain embodiments, $R^{H1}$ is hydrogen, $R^{H3}$ is —$OR^{H9}$ or —OC(=O)$R^{H9}$, and $R^{H5}$ is methyl.

In certain embodiments, $R^{H2}$ is —OC(=O)$R^{H7}$ (e.g., —OAc) or —NHC(=O)$R^{H7}$, and $R^{H4}$ is —C(=N—O$R^{H7}$)$R^{H8}$ wherein $R^{H7}$ of $R^{H4}$ is a group -$L^1$-(A-$L^2$)$_a$-B for Formula (A), (I), and (II), or a group -$L^1$-X for Formula (P-A), (P-I), and (P-II). In this instance, in certain embodiments, $R^{H1}$ is hydrogen, $R^{H3}$ is —$OR^{H9}$ or —OC(=O)$R^{H9}$, and $R^{H5}$ is methyl.

In certain embodiments, $R^{H4}$ is —C(=O)$R^{H7}$ (e.g., —C=OCH$_3$), and $R^{H2}$ is —OC(=O)$R^{H7}$ or —NHC(=O)$R^{H7}$ wherein $R^{H7}$ of $R^{H2}$ is a group -$L^1$-(A-$L^2$)$_a$-B for Formula (A), (I), and (II), or a group -$L^1$-X for Formula (P-A), (P-I), and (P-II). In this instance, in certain embodiments, $R^{H1}$ is hydrogen, $R^{H3}$ is —$OR^{H9}$ or —OC(=O)$R^{H9}$, and $R^{H5}$ is methyl.

In certain embodiments, $R^{H4}$ is hydrogen and $R^{H2}$ is —NHC(=O)$R^{H7}$, a group -$L^1$-(A-$L^2$)$_a$-B for Formula (A), (I), and (II), or a group -$L^1$-X for Formula (P-A), (P-I), and (P-II), e.g., -$L^1$-$N_3$. In this instance, in certain embodiments, $R^{H1}$ is hydrogen, $R^{H3}$ is —$OR^{H9}$ or —OC(=O)$R^{H9}$, and $R^{H5}$ is methyl.

In certain embodiments, $M^3$ is —O—. In certain embodiments, $M^3$ is —N$R^{H6}$—, e.g., NH. In certain embodiments, $M^3$ is —CH$R^{H6}$, e.g., —CH$_2$—.

In certain embodiments, the group of Formula (ii) is of Formula (ii-a):

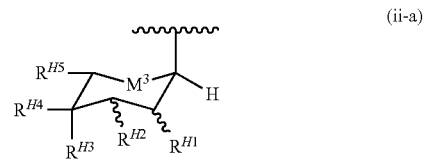

(ii-a)

In certain embodiments, $M^3$ is —O—. In certain embodiments, $M^3$ is —NH—. In certain embodiments, $M^3$ is —CH$_2$—. In certain embodiments, R$^{H1}$ is hydrogen, R$^{H3}$ is —OR$^{H9}$ or —OC(=O)R$^{H9}$, and R$^{H5}$ is methyl. In certain embodiments, R$^{H1}$ is a non-hydrogen equatorial group. In certain embodiments, R$^{H2}$ is a non-hydrogen equatorial group. In certain embodiments, R$^{H2}$ is a non-hydrogen axial group. In certain embodiments, R$^{H2}$ is —OR$^{H7}$ (e.g., OH) or —OC(=O)R$^{H7}$ (e.g., —OAc), and R$^{H4}$ is —C(=N—OR$^{H7}$)R$^{H8}$ wherein R$^{H7}$ of R$^{H4}$ is a group -L$^1$-(A-L$^2$)$_a$-B for Formula (A), (I), and (II), or a group -L$^1$-X for Formula (P-A), (P-I), and (P-II). In certain embodiments, R$^{H4}$ is —C(=O)R$^{H7}$ (e.g., —C=OCH$_3$), and R$^{H2}$ is —OC(=O)R$^{H7}$ wherein R$^{H7}$ of R$^{H2}$ is a group -L$^1$-(A-L$^2$)$_a$-B for Formula (A), (I), and (II), or a group -L$^1$-X for Formula (P-A), (P-I), and (P-II). In certain embodiments, R$^{H4}$ is hydrogen and R$^{H2}$ is —NHC(=O)R$^{H7}$, a group -L$^1$-(A-L$^2$)$_a$-B for Formula (A), (I), and (II), or a group -L$^1$-X for Formula (P-A), (P-I), and (P-II), e.g., -L$^1$-N$_3$.

In certain embodiments, the group of Formula (ii) is of Formula (ii-b1) or (ii-b2):

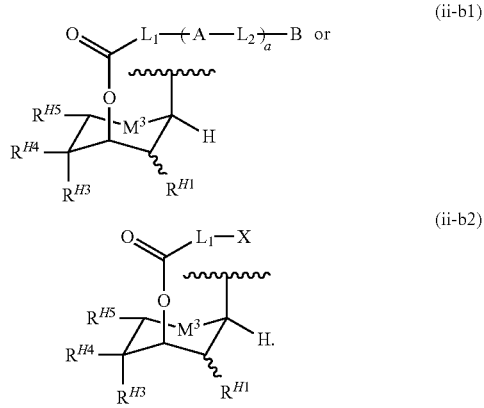

In certain embodiments, M$^3$ is —O—. In certain embodiments, M$^3$ is —NH—. In certain embodiments, M$^3$ is —CH$_2$—. In certain embodiments, R$^{H1}$ is hydrogen, R$^{H3}$ is —OR$^{H9}$ or —OC(=O)R$^{H9}$, and R$^{H5}$ is methyl. In certain embodiments, R$^{H1}$ is a non-hydrogen equatorial group.

In certain embodiments, the group of Formula (ii) is of Formula (ii-c1) or (ii-c2):

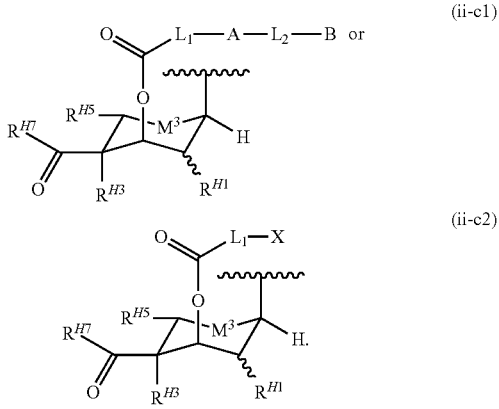

In certain embodiments, M$^3$ is —O—. In certain embodiments, M$^3$ is —NH—. In certain embodiments, M$^3$ is —CH$_2$—. In certain embodiments, R$^{H1}$ is hydrogen, R$^{H3}$ is —OR$^{H9}$ or —OC(=O)R$^{H9}$, and R$^{H5}$ is methyl. In certain embodiments, R$^{H1}$ is a non-hydrogen equatorial group.

In certain embodiments, the group of Formula (ii) is of Formula (ii-d1) or (ii-d2):

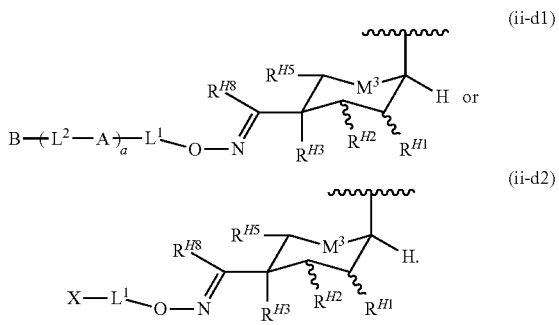

In certain embodiments, M$^3$ is —O—. In certain embodiments, M$^3$ is —NH—. In certain embodiments, M$^3$ is —CH$_2$—. In certain embodiments, R$^{H1}$ is hydrogen, R$^{H3}$ is —OR$^{H9}$ or —OC(=O)R$^{H9}$, and R$^{H5}$ is methyl. In certain embodiments, R$^{H2}$ is —OR$^{H7}$ (e.g., OH) or —OC(=O)R$^{H7}$ (e.g., —OAc). In certain embodiments, R$^{H1}$ is a non-hydrogen equatorial group. In certain embodiments, R$^{H2}$ is a non-hydrogen equatorial group. In certain embodiments, R$^{H2}$ is a non-hydrogen axial group.

In certain embodiments, the group of Formula (ii) is of Formula (ii-e):

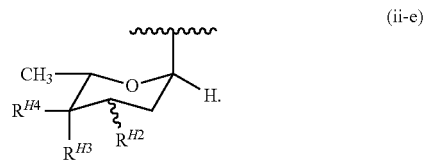

In certain embodiments, R$^{H3}$ is —OR$^{H9}$ or —OC(=O)R$^{H9}$. In certain embodiments, R$^{H2}$ is —OR$^{H7}$ (e.g., OH) or —OC(=O)R$^{H7}$ (e.g., —OAc), and R$^{H4}$ is —C(=N—OR$^{H7}$)R$^{H8}$, wherein R$^{H7}$ of R$^{H4}$ is a group -L$^1$-(A-L$^2$)$_a$-B for Formula (A), (I), and (II), or a group -L$^1$-X for Formula (P-A), (P-I), and (P-II). In certain embodiments, R$^{H4}$ is —C(=O)R$^{H7}$ (e.g., —C=OCH$_3$), and R$^{H2}$ is —OC(=O)R$^{H7}$, wherein R$^{H7}$ of R$^{H2}$ is a group -L$^1$-(A-L$^2$)$_a$-B for Formula (A), (I), and (II), or a group -L$^1$-X for Formula (P-A), (P-I), and (P-II). In certain embodiments, R$^{H4}$ is hydrogen and R$^{H2}$ is —NHC(=O)R$^{H7}$, a group -L$^1$-(A-L$^2$)$_a$-B for Formula (A), (I), and (II), or a group -L$^1$-X for Formula (P-A), (P-I), and (P-II), e.g., -L$^1$-N$_3$. In certain embodiments, R$^{H2}$ is a non-hydrogen equatorial group. In certain embodiments, R$^{H2}$ is a non-hydrogen axial group.

Group R$^8$

As generally defined above, R$^8$ is hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; —OR$^{I1}$; —C(=O)R$^{I2}$; —CO$_2$R$^{I1}$; —CN; —SCN; —SR$^{I1}$; —SOR$^{I1}$; —SO$_2$R$^{I2}$; —NO$_2$; —N$_3$; —N(R$^{I2}$)$_2$; —NR$^{I2}$C(=O)R$^{I2}$; —NR$^{I2}$C(=O)N(R$^{I2}$)$_2$; —OC(=O)OR$^{I1}$; —OC(=O)R$^{I2}$; —OC(=O)N(R$^{I2}$)$_2$; —NR$^{I2}$C(=O)OR$^{I1}$; —CH$_2$(OR$^{I1}$), —CH(OR$^{I1}$)$_2$, —CH$_2$OC(=O)R$^{I2}$, —C(R$^{I2}$)$_3$, a group -L$^1$-

(A-L$^2$)$_a$-B for Formula (A), (I), and (II), or a group -L$^1$-X for Formula (P-A), (P-I), and (P-II).

In certain embodiments, R$^8$ is hydrogen.

In certain embodiments, R$^8$ is halogen, e.g., —F, —Cl, —Br, or —I.

In certain embodiments, R$^8$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl.

In certain embodiments, R$^8$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In certain embodiments, R$^8$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl.

In certain embodiments, R$^8$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, R$^8$ is substituted or unsubstituted heterocyclyl, e.g., substituted or unsubstituted 3-6 membered heterocyclyl, substituted or unsubstituted 3-4 membered heterocyclyl, or substituted or unsubstituted 4-5 membered heterocyclyl.

In certain embodiments, R$^8$ is substituted or unsubstituted aryl, e.g., substituted or unsubstituted phenyl.

In certain embodiments, R$^8$ is substituted or unsubstituted heteroaryl, e.g., substituted or unsubstituted 5-6 membered heteroaryl.

In certain embodiments, R$^8$ is —OR$^{J1}$. In certain embodiments, R$^8$ is —C(=O)R$^{J2}$. In certain embodiments, R$^8$ is —CO$_2$R$^{J1}$. In certain embodiments, R$^8$ is —CN. In certain embodiments, R$^8$ is —SCN. In certain embodiments, R$^8$ is —SR$^{J1}$. In certain embodiments, R$^8$ is —SOR$^{J1}$. In certain embodiments, R$^8$ is —SO$_2$R$^{J2}$. In certain embodiments, R$^8$ is —NO$_2$. In certain embodiments, R$^8$ is —N$_3$. In certain embodiments, R$^8$ is —N(R$^{J2}$)$_2$. In certain embodiments, R$^8$ is —NR$^{J2}$C(=O)R$^{J2}$. In certain embodiments, R$^8$ is —NR$^{J2}$C(=O)N(R$^{J2}$)$_2$. In certain embodiments, R$^8$ is —OC(=O)OR$^{J1}$. In certain embodiments, R$^8$ is —OC(=O)R$^{J2}$. In certain embodiments, R$^8$ is —OC(=O)N(R$^{J2}$)$_2$. In certain embodiments, R$^8$ is —NR$^{J2}$C(=O)OR$^{J1}$. In certain embodiments, R$^8$ is —CH$_2$(OR$^{J1}$). In certain embodiments, R$^8$ is —CH(OR$^{J1}$)$_2$. In certain embodiments, R$^8$ is —CH$_2$OC(=O)R$^{J2}$. In certain embodiments, R$^8$ is —C(R$^{J2}$)$_3$.

In certain embodiments, R$^8$ is a group -L$^1$-(A-L$^2$)$_a$-B for Formula (A), (I), and (II), or a group -L$^1$-X for Formula (P-A), (P-I), and (P-II).

In certain embodiments, at least one instance of R$^{J1}$ is independently hydrogen.

In certain embodiments, at least one instance of R$^{J1}$ is an oxygen protecting group if attached to oxygen or a sulfur protecting group if attached to sulfur.

In certain embodiments, at least one instance of R$^{J1}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl.

In certain embodiments, at least one instance of R$^{J1}$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In certain embodiments, at least one instance of R$^{J1}$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl.

In certain embodiments, at least one instance of R$^{J1}$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, at least one instance of R$^{J1}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, at least one instance of R$^{J1}$ is substituted or unsubstituted aryl, e.g., substituted or unsubstituted phenyl.

In certain embodiments, at least one instance of R$^{J1}$ is substituted or unsubstituted heteroaryl, e.g., substituted or unsubstituted 5-6 membered heteroaryl.

In certain embodiments, at least one instance of R$^{J1}$ is acyl.

In certain embodiments, at least one instance of R$^{J1}$ is a group -L$^1$-(A-L$^2$)$_a$-B for Formula (A), (I), and (II), or a group -L$^1$-X for Formula (P-A), (P-I), and (P-II).

In certain embodiments, at least one instance of R$^{J2}$ is independently hydrogen.

In certain embodiments, at least one instance of R$^{J2}$ is a nitrogen protecting group if attached to nitrogen.

In certain embodiments, at least one instance of R$^{J2}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl.

In certain embodiments, at least one instance of R$^{J2}$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In certain embodiments, at least one instance of R$^{J2}$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl.

In certain embodiments, at least one instance of R$^{J2}$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, at least one instance of R$^{J2}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, at least one instance of $R^{J2}$ is substituted or unsubstituted aryl, e.g., substituted or unsubstituted phenyl.

In certain embodiments, at least one instance of $R^{J2}$ is substituted or unsubstituted heteroaryl, e.g., substituted or unsubstituted 5-6 membered heteroaryl.

In certain embodiments, at least one instance of $R^{J2}$ is acyl.

In certain embodiments, at least one instance of $R^{J2}$ is hydroxyl; substituted hydroxyl; thiol; substituted thiol; amino; or substituted amino.

In certain embodiments, at least one instance of $R^{J2}$ is a group -$L^1$-(A-$L^2$)$_a$-B for Formula (A), (I), and (II), or a group -$L^1$-X for Formula (P-A), (P-I), and (P-II).

In certain embodiments, two $R^{J2}$ groups are optionally joined to form a heterocyclyl or heteroaryl ring In certain embodiments, $R^{J1}$ or $R^{J2}$ is a group of Formula (iii) or (iv):

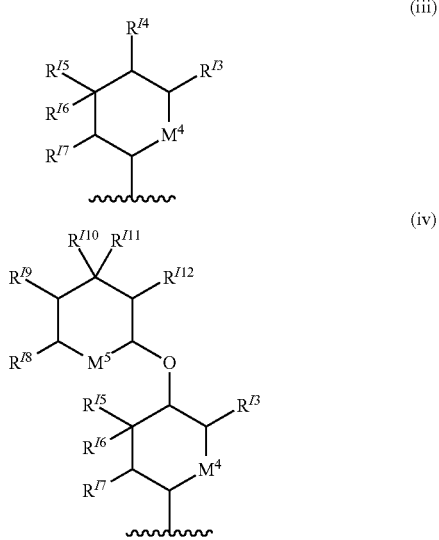

wherein:

each occurrence of $R^{J3}$, $R^{J5}$, $R^{J6}$, $R^{J7}$, $R^{J8}$, $R^{J10}$, $R^{J11}$, and $R^{J12}$, is independently hydrogen, substituted or unsubstituted alkyl; —$OR^{J13}$; —OC(=O)$R^{J13}$; —N($R^{J13}$)$_2$; —NHC(=O)$R^{J13}$; a group -$L^1$-(A-$L^2$)$_a$-B for Formula (A), (I), and (II), or a group -$L^1$-X for Formula (P-A), (P-I), and (P-II); wherein each occurrence of $R^{J13}$ is independently hydrogen; substituted or unsubstituted alkyl; an oxygen protecting group when attached to an oxygen atom; a nitrogen protecting group when attached to a nitrogen atom; or a group -$L^1$-(A-$L^2$)$_a$-B for Formula (A), (I), and (II), or a group -$L^1$-X for Formula (P-A), (P-I), and (P-II); or two $R^{J13}$ groups are joined to form a substituted or unsubstituted heterocyclic or substituted or unsubstituted heteroaryl ring;

each occurrence of $R^{J4}$ and $R^{J9}$ is independently, hydrogen; substituted or unsubstituted alkyl; —$OR^{J14}$; —N($R^{J14}$)$_2$; —OC(=O)$R^{J14}$; —NHC(=O)$R^{J15}$; —OC(=O)$R^{J14}$; —C(=O)$R^{J14}$; —C(=N$R^{J14}$)$R^{J15}$; —C(=N—$OR^{J14}$)$R^{J15}$; —C(=N—NH$R^{J14}$)$R^{J15}$; —C($R^{J15}$)$_2$NH$R^{J14}$; —C($R^{J15}$)$_2$$OR^{J14}$; a group -$L^1$-(A-$L^2$)$_a$-B for Formula (A), (I), and (II), or a group -$L^1$-X for Formula (P-A), (P-I), and (P-II); wherein $R^{J14}$ is independently hydrogen; substituted or unsubstituted alkyl; an oxygen protecting group if attached to an oxygen atom; a nitrogen protecting group if attached to a nitrogen atom; a group -$L^1$-(A-$L^2$)$_a$-B for Formula (A), (I), and (II), or a group -$L^1$-X for Formula (P-A), (P-I), and (P-II); and $R^{J15}$ is hydrogen, or substituted or unsubstituted alkyl; and each occurrence of $M^4$ and $M^5$ is independently —O—, —$NR^{J16}$—, or —CH$R^{J16}$—, wherein $R^{J16}$ is hydrogen; substituted or unsubstituted alkyl; a nitrogen protecting group if attached to nitrogen; —$OR^{J13}$; a group -$L^1$-(A-$L^2$)$_a$-B for Formula (A), (I), and (II), or a group -$L^1$-X for Formula (P-A), (P-I), and (P-II); wherein each occurrence of $R^{J13}$ is independently hydrogen; an oxygen protecting group; substituted or unsubstituted alkyl; acyl; or a group -$L^1$-(A-$L^2$)$_a$-B for Formula (A), (I), and (II), or a group -$L^1$-X for Formula (P-A), (P-I), and (P-II).

In certain embodiments, $R^{J3}$ is hydrogen, substituted or unsubstituted alkyl; —$OR^{J13}$; —OC(=O)$R^{J13}$; —NHC(=O)$R^{J13}$; or a group -$L^1$-(A-$L^2$)$_a$-B for Formula (A), (I), and (II), or a group -$L^1$-X for Formula (P-A), (P-I), and (P-II); wherein each occurrence of $R^{J13}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{J3}$ is hydrogen. In certain embodiments, $R^{J3}$ is substituted or unsubstituted alkyl, e.g., methyl. In certain embodiments, $R^{J3}$ is —$OR^{J13}$, e.g., —OH or —O-alkyl. In certain embodiments, $R^{J3}$ is —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{J3}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{J5}$ is hydrogen, substituted or unsubstituted alkyl; —$OR^{J13}$; —OC(=O)$R^{J13}$; —NHC(=O)$R^{J13}$; or a group -$L^1$-(A-$L^2$)$_a$-B for Formula (A), (I), and (II), or a group -$L^1$-X for Formula (P-A), (P-I), and (P-II); wherein each occurrence of $R^{J13}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{J5}$ is hydrogen. In certain embodiments, $R^{J5}$ is substituted or unsubstituted alkyl, e.g., methyl. In certain embodiments, $R^{J5}$ is —$OR^{J13}$, e.g., —OH or —O-alkyl. In certain embodiments, $R^{J5}$ is —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{J5}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{J6}$ is hydrogen, substituted or unsubstituted alkyl; —$OR^{J13}$; —OC(=O)$R^{J13}$; —NHC(=O)$R^{J13}$; or a group -$L^1$-(A-$L^2$)$_a$-B for Formula (A), (I), and (II), or a group -$L^1$-X for Formula (P-A), (P-I), and (P-II); wherein each occurrence of $R^{J13}$ is independently hydrogen; substituted or unsubstituted alkyl; an oxygen protecting group; a group -$L^1$-(A-$L^2$)$_a$-B for Formula (A), (I), and (II), or a group -$L^1$-X for Formula (P-A), (P-I), and (P-II). In certain embodiments, $R^{J6}$ is hydrogen. In certain embodiments, $R^{J6}$ is substituted or unsubstituted alkyl, e.g., methyl. In certain embodiments, $R^{J6}$ is —$OR^{J13}$, e.g., —OH or —O-alkyl. In certain embodiments, $R^{J6}$ is —OC(=O)-$L^1$-(A-$L^2$)$_a$-B for Formula (A), (I), and (II), or a group —OC(=O)-$L^1$-X for Formula (P-A), (P-I), and (P-II). In certain embodiments, $R^{J6}$ is —NHC(=O)-$L^1$-(A-$L^2$)$_a$-B for Formula (A), (I), and (II), or a group —NHC(=O)-$L^1$-X for Formula (P-A), (P-I), and (P-II).

In certain embodiments, $R^{J7}$ is hydrogen, substituted or unsubstituted alkyl; —$OR^{J13}$; —OC(=O)$R^{J13}$; —NHC(=O)$R^{J13}$; or a group -$L^1$-(A-$L^2$)$_a$-B for Formula (A), (I), and (II), or a group -L$^1$-X for Formula (P-A), (P-I), and (P-II); wherein each occurrence of R$^{J13}$ is independently hydrogen; substituted or unsubstituted alkyl; an oxygen protecting group; a group -L$^1$-(A-L$^2$)$_a$-B for Formula (A), (I), and (II), or a group -L$^1$-X for Formula (P-A), (P-I), and (P-II). In certain embodiments, R$^{J7}$ is hydrogen. In certain embodiments, R$^{J7}$ is substituted or unsubstituted alkyl, e.g., methyl. In certain embodiments, R$^{J7}$ is —OR$^{J13}$, e.g., —OH or —O-alkyl. In certain embodiments, R$^{J7}$ is —OC(=O)-L$^1$-(A-L$^2$)$_a$-B for Formula (A), (I), and (II), or a group —OC(=O)-L$^1$-X for Formula (P-A), (P-I), and (P-II). In certain embodiments, R$^{J7}$ is —NHC(=O)-L$^1$-(A-L$^2$)$_a$-B for Formula (A), (I), and (II), or a group —NHC(=O)-L$^1$-X for Formula (P-A), (P-I), and (P-II).

In certain embodiments, R$^{J8}$ is hydrogen, substituted or unsubstituted alkyl; —OR$^{J13}$; —OC(=O)R$^{J13}$; —NHC(=O)R$^{J13}$; or a group -L$^1$-(A-L$^2$)$_a$-B for Formula (A), (I), and (II), or a group -L$^1$-X for Formula (P-A), (P-I), and (P-II); wherein each occurrence of R$^{J13}$ is independently hydrogen; substituted or unsubstituted alkyl; an oxygen protecting group; a group -L$^1$-(A-L$^2$)$_a$-B for Formula (A), (I), and (II), or a group -L$^1$-X for Formula (P-A), (P-I), and (P-II). In certain embodiments, R$^{J8}$ is hydrogen. In certain embodiments, R$^{J8}$ is substituted or unsubstituted alkyl, e.g., methyl. In certain embodiments, R$^{J8}$ is —OR$^{J13}$, e.g., —OH or —O-alkyl. In certain embodiments, R$^{J8}$ is —OC(=O)-L$^1$-(A-L$^2$)$_a$-B for Formula (A), (I), and (II), or a group —OC(=O)-L$^1$-X for Formula (P-A), (P-I), and (P-II). In certain embodiments, R$^{J8}$ is —NHC(=O)-L$^1$-(A-L$^2$)$_a$-B for Formula (A), (I), and (II), or a group —NHC(=O)-L$^1$-X for Formula (P-A), (P-I), and (P-II).

In certain embodiments, R$^{J10}$ is hydrogen, substituted or unsubstituted alkyl; —OR$^{J13}$; —OC(=O)R$^{J13}$; —NHC(=O)R$^{J13}$; or a group -L$^1$-(A-L$^2$)$_a$-B for Formula (A), (I), and (II), or a group -L$^1$-X for Formula (P-A), (P-I), and (P-II); wherein each occurrence of R$^{J13}$ is independently hydrogen; substituted or unsubstituted alkyl; an oxygen protecting group; a group -L$^1$-(A-L$^2$)$_a$-B for Formula (A), (I), and (II), or a group -L$^1$-X for Formula (P-A), (P-I), and (P-II). In certain embodiments, R$^{J10}$ is hydrogen. In certain embodiments, R$^{J8}$ is substituted or unsubstituted alkyl, e.g., methyl. In certain embodiments, R$^{J10}$ is —OR$^{J13}$, e.g., —OH or —O-alkyl. In certain embodiments, R$^{J10}$ is —OC(=O)-L$^1$-(A-L$^2$)$_a$-B for Formula (A), (I), and (II), or a group —OC(=O)-L$^1$-X for Formula (P-A), (P-I), and (P-II). In certain embodiments, R$^{J10}$ is —NHC(=O)-L$^1$-(A-L$^2$)$_a$-B for Formula (A), (I), and (II), or a group —NHC(=O)-L$^1$-X for Formula (P-A), (P-I), and (P-II).

In certain embodiments, R$^{J11}$ is hydrogen, substituted or unsubstituted alkyl; —OR$^{J13}$; —OC(=O)R$^{J13}$; —NHC(=O)R$^{J13}$; or a group -L$^1$-(A-L$^2$)$_a$-B for Formula (A), (I), and (II), or a group -L$^1$-X for Formula (P-A), (P-I), and (P-II); wherein each occurrence of R$^{J13}$ is independently hydrogen; substituted or unsubstituted alkyl; an oxygen protecting group; a group -L$^1$-(A-L$^2$)$_a$-B for Formula (A), (I), and (II), or a group -L$^1$-X for Formula (P-A), (P-I), and (P-II). In certain embodiments, R$^{J11}$ is hydrogen. In certain embodiments, R$^{J11}$ is substituted or unsubstituted alkyl, e.g., methyl. In certain embodiments, R$^{J11}$ is —OR$^{J13}$, e.g., —OH or —O-alkyl. In certain embodiments, R$^{J11}$ is —OC(=O)-L$^1$-(A-L$^2$)$_a$-B for Formula (A), (I), and (II), or a group —OC(=O)-L$^1$-X for Formula (P-A), (P-I), and (P-II). In certain embodiments, R$^{J11}$ is —NHC(=O)-L$^1$-(A-L$^2$)$_a$-B for Formula (A), (I), and (II), or a group —NHC(=O)-L$^1$-X for Formula (P-A), (P-I), and (P-II).

In certain embodiments, R$^{J12}$ is hydrogen, substituted or unsubstituted alkyl; —OR$^{J13}$; —OC(=O)R$^{J13}$; —NHC(=O)R$^{J13}$; or a group -L$^1$-(A-L$^2$)$_a$-B for Formula (A), (I), and (II), or a group -L$^1$-X for Formula (P-A), (P-I), and (P-II); wherein each occurrence of R$^{J13}$ is independently hydrogen; substituted or unsubstituted alkyl; an oxygen protecting group; a group -L$^1$-(A-L$^2$)$_a$-B for Formula (A), (I), and (II), or a group -L$^1$-X for Formula (P-A), (P-I), and (P-II). In certain embodiments, R$^{J12}$ is hydrogen. In certain embodiments, R$^{J12}$ is substituted or unsubstituted alkyl, e.g., methyl. In certain embodiments, R$^{J11}$ is —OR$^{J13}$, e.g., —OH or —O-alkyl. In certain embodiments, R$^{J12}$ is —OC(=O)-L$^1$-(A-L$^2$)$_a$-B for Formula (A), (I), and (II), or a group —OC(=O)-L$^1$-X for Formula (P-A), (P-I), and (P-II). In certain embodiments, R$^{J12}$ is —NHC(=O)-L$^1$-(A-L$^2$)$_a$-B for Formula (A), (I), and (II), or a group —NHC(=O)-L$^1$-X for Formula (P-A), (P-I), and (P-II).

In certain embodiments, R$^{J4}$ is hydrogen.

In certain embodiments, R$^{J4}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl.

In certain embodiments, R$^{J4}$ is -L$^1$-(A-L$^2$)$_a$-B for Formula (A), (I), and (II), or a group -L$^1$-X for Formula (P-A), (P-I), and (P-II).

In certain embodiments, R$^{J4}$ is —OR$^{J14}$. In certain embodiments, R$^{J4}$ is —N(R$^{J14}$)$_2$. In certain embodiments, R$^{J4}$ is —OC(=O)R$^{J14}$. In certain embodiments, R$^{J4}$ is —NHC(=O)R$^{J15}$. In certain embodiments, R$^{J4}$ is —C(=O)R$^{J14}$. In certain embodiments, R$^{J4}$ is —C(=NR$^{J14}$)R$^{J15}$. In certain embodiments, R$^{J4}$ is —C(=N—OR$^{J14}$)R$^{J15}$. In certain embodiments, R$^{J4}$ is —C(=N—NHR$^{J14}$)R$^{J15}$. In certain embodiments, R$^{J4}$ is —C(R$^{J15}$)$_2$NHR$^{J14}$. In certain embodiments, R$^{J4}$ is —C(R$^{J15}$)$_2$OR$^{J14}$. In certain embodiments of R$^{J4}$, R$^{J14}$ is hydrogen. In certain embodiments of R$^{J4}$, R$^{J14}$ is substituted or unsubstituted alkyl, e.g., methyl. In certain embodiments of R$^{J4}$, R$^{J14}$ is an oxygen protecting group if attached to an oxygen atom or a nitrogen protecting group if attached to a nitrogen atom. In certain embodiments of R$^{J4}$, R$^{J14}$ is a group -L$^1$-(A-L$^2$)$_a$-B for Formula (A), (I), and (II), or a group -L$^1$-X for Formula (P-A), (P-I), and (P-II). In certain embodiments of R$^{J4}$, R$^{J15}$ is hydrogen. In certain embodiments of R$^{J4}$, R$^{J15}$ is substituted or unsubstituted alkyl, e.g., methyl.

In certain embodiments, R$^{J9}$ is hydrogen.

In certain embodiments, R$^{J9}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl.

In certain embodiments, R$^{J9}$ is -L$^1$-(A-L$^2$)$_a$-B for Formula (A), (I), and (II), or a group -L$^1$-X for Formula (P-A), (P-I), and (P-II).

In certain embodiments, R$^{J9}$ is —OR$^{J4}$. In certain embodiments, R$^{J9}$ is —N(R$^{J14}$)$_2$. In certain embodiments, R$^{J9}$ is —OC(=O)R$^{J14}$. In certain embodiments, R$^{J9}$ is —NHC(=O)R$^{J15}$. In certain embodiments, R$^{J9}$ is —C(=NR$^{J14}$)R$^{J15}$. In certain embodiments, R$^{J9}$ is —C(=N—OR$^{J14}$)R$^{J15}$. In certain embodiments, R$^{J9}$ is —C(=N—NHR$^{J14}$)R$^{J15}$. In certain embodiments, R$^{J9}$ is —C(R$^{J15}$)$_2$NHR$^{J14}$. In certain embodiments, R$^{J9}$ is —C(R$^{J15}$)$_2$OR$^{J14}$. In certain embodiments of R$^{J9}$, R$^{J14}$ is hydrogen. In certain embodiments of R$^{J9}$, R$^{J14}$ is substituted or unsubstituted alkyl, e.g., methyl. In certain embodiments of R$^{J9}$, R$^{J14}$ is an oxygen protecting group if attached to an oxygen atom or a nitrogen protecting group if attached to a nitrogen atom. In certain embodiments of $R^{J9}$, $R^{J14}$ is a group -L$^1$-(A-L$^2$)$_a$-B for Formula (A), (I), and (II), or a group -L$^1$-X for Formula (P-A), (P-I), and (P-II). In certain embodiments of $R^{J9}$, $R^{J15}$ is hydrogen. In certain embodiments of $R^{J9}$, $R^{J15}$ is substituted or unsubstituted alkyl, e.g., methyl.

In certain embodiments, M$^4$ is —O—. In certain embodiments, M$^4$ is —NR$^{J16}$—, e.g., NH. In certain embodiments, M$^4$ is —CHR$^{J16}$, e.g., —CH$_2$—.

In certain embodiments, M$^5$ is —O—. In certain embodiments, M$^5$ is —NR$^{J16}$—, e.g., NH. In certain embodiments, M$^5$ is —CHR$^{J16}$, e.g., —CH$_2$—.

In certain embodiments, both M$^4$ and M$^5$ are —O—.

In certain embodiments, the group of Formula (iii) is of Formula (iii-a):

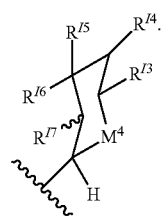

(iii-a)

In certain embodiments, $R^{J3}$ is substituted or unsubstituted alkyl, e.g., methyl. In certain embodiments, $R^{J5}$ is substituted or unsubstituted alkyl, e.g., methyl. In certain embodiments, $R^{J6}$ is —OR$^{J13}$, e.g., —OH. In certain embodiments, $R^{J7}$ is hydrogen. In certain embodiments, $R^{J4}$ is —OR$^{J14}$. In certain embodiments, $R^{J4}$ is —OC(=O)R$^{J14}$. In certain embodiments $R^{J14}$ is substituted or unsubstituted alkyl, e.g., methyl. In certain embodiments $R^{J14}$ is an oxygen protecting group. In certain embodiments $R^{J14}$ is a group -L$^1$-(A-L$^2$)$_a$-B for Formula (A), (I), and (II), or a group -L$^1$-X for Formula (P-A), (P-I), and (P-II). In certain embodiments, M$^4$ is —O—.

In certain embodiments, the group of Formula (iv) is of Formula (iv-a):

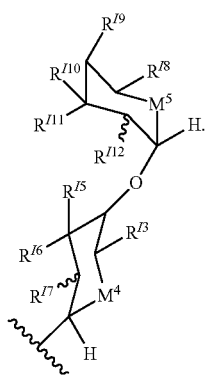

(iv-a)

In certain embodiments, $R^{J3}$ is substituted or unsubstituted alkyl, e.g., methyl. In certain embodiments, $R^{J5}$ is substituted or unsubstituted alkyl, e.g., methyl. In certain embodiments, $R^{J6}$ is —OR$^{J13}$, e.g., —OH. In certain embodiments, $R^{J7}$ is hydrogen. In certain embodiments, $R^{J8}$ is substituted or unsubstituted alkyl, e.g., methyl. In certain embodiments, $R^{J10}$ is substituted or unsubstituted alkyl, e.g., methyl. In certain embodiments, $R^{J11}$ is —OR$^{J13}$, e.g., —OH. In certain embodiments, $R^{J12}$ is hydrogen. In certain embodiments, $R^{J9}$ is —OR$^{J14}$. In certain embodiments, $R^{J9}$ is —OC(=O)R$^{J14}$. In certain embodiments $R^{J14}$ is substituted or unsubstituted alkyl, e.g., methyl. In certain embodiments $R^{J14}$ is an oxygen protecting group. In certain embodiments $R^{J14}$ is a group -L$^1$-(A-L$^2$)$_a$-B for Formula (A), (I), and (II), or a group -L$^1$-X for Formula (P-A), (P-I), and (P-II). In certain embodiments, M$^4$ is —O—. In certain embodiments, M$^5$ is —O—.

In certain embodiments, the group of Formula (iv) is of Formula (iv-b1) or (iv-b2):

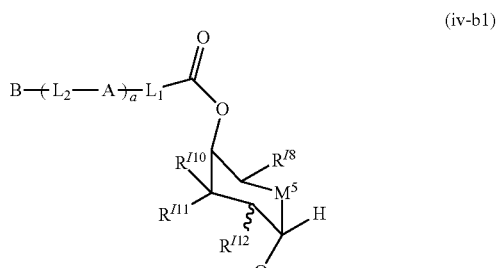

(iv-b1)

or

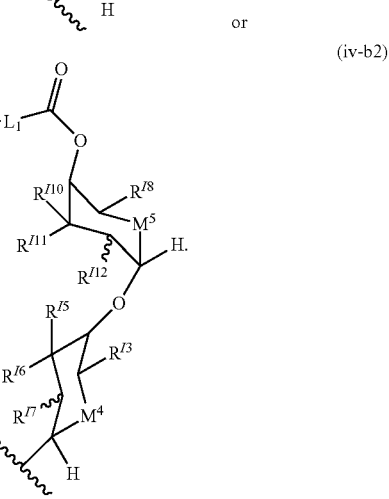

(iv-b2)

In certain embodiments, $R^{J3}$ is substituted or unsubstituted alkyl, e.g., methyl. In certain embodiments, $R^{J5}$ is substituted or unsubstituted alkyl, e.g., methyl. In certain embodiments, $R^{J6}$ is —OR$^{J13}$, e.g., —OH. In certain embodiments, $R^{J7}$ is hydrogen. In certain embodiments, $R^{J8}$ is substituted or unsubstituted alkyl, e.g., methyl. In certain embodiments, $R^{J10}$ is substituted or unsubstituted alkyl, e.g., methyl. In certain embodiments, $R^{J11}$ is —OR$^{J13}$, e.g., —OH. In certain embodiments, $R^{J12}$ is hydrogen. In certain embodiments, M$^4$ is —O—. In certain embodiments, M$^5$ is —O—.

In certain embodiments, R$^8$ is —CH$_2$(OR$^{J1}$), —CH(OR$^{J1}$)$_2$, or —CH$_2$OC(=O)R$^{J2}$ and at least one instance of R$^{J1}$ or R$^{J2}$ is hydrogen. In certain embodiments, R$^8$ is —CH$_2$(OR$^{J1}$), —CH(OR$^{J1}$)$_2$, or —CH$_2$OC(=O)R$^{J2}$ and at least one instance of R$^{J1}$ or R$^{J2}$ is substituted or unsubstituted alkyl, e.g., methyl. In certain embodiments, R$^8$ is —CH$_2$ (OR$^{J1}$), —CH(OR$^{J1}$)$_2$, or —CH$_2$OC(=O)R$^{J2}$, and at least one instance of R$^{J1}$ or R$^{J2}$ is substituted or unsubstituted alkenyl. In certain embodiments, R$^8$ is —CH$_2$(OR$^{J1}$), —CH (OR$^{J1}$)$_2$, or —CH$_2$OC(=O)R$^{J2}$, and at least one instance of R$^{J1}$ or R$^{J2}$ is substituted or unsubstituted alkynyl. In certain embodiments, R$^8$ is —CH$_2$(OR$^{J1}$), —CH(OR$^{J1}$)$_2$, or —CH$_2$OC(=O)R$^{J2}$ and at least one instance of R$^{J1}$ or R$^{J2}$ is substituted or unsubstituted carbocyclyl. In certain embodiments, R$^8$ is —CH$_2$(OR$^{J1}$), —CH(OR$^{J1}$)$_2$, or —CH$_2$OC(=O)R$^{J2}$ and at least one instance of R$^{J1}$ or R$^{J2}$ is substituted or unsubstituted heterocyclyl. In certain embodiments, R$^8$ is —CH$_2$(OR$^{J1}$) or —CH(OR$^{J1}$)$_2$, and at least one instance of R$^{J1}$ or R$^{J2}$ is substituted or unsubstituted aryl. In certain embodiments, R$^8$ is —CH$_2$(OR$^{J1}$), —CH(OR$^{J1}$)$_2$, or —CH$_2$OC(=O)R$^{J2}$, and at least one instance of R$^{J1}$ or R$^{J2}$ is substituted or unsubstituted heteroaryl. In certain embodiments, R$^8$ is —CH$_2$(OR$^{J1}$), —CH(OR$^{J1}$)$_2$, or —CH$_2$OC (=O)R$^{J2}$, and one instance of R$^{J1}$ or R$^{J2}$ is acyl. In certain embodiments, R$^8$ is —CH$_2$(OR$^{J1}$), —CH(OR$^{J1}$)$_2$, or —CH$_2$OC(=O)R$^{J2}$, and at least one instance of R$^{J1}$ or R$^{J2}$ is a group -L$^1$-(A-L$^2$)$_a$-B for Formula (A), (I), and (II), or a group -L$^1$-X for Formula (P-A), (P-I), and (P-II). In certain embodiments, R$^8$ is —CH$_2$(OR$^{J1}$), —CH(OR$^{J1}$)$_2$, or —CH$_2$OC(=O)R$^{J2}$, and at least one instance of R$^{J1}$ or R$^{J2}$ is a group of Formula (iii). In certain embodiments, R$^8$ is —CH$_2$(OR$^{J1}$), —CH(OR$^{J1}$)$_2$, or —CH$_2$OC(=O)R$^{J2}$, and at least one instance of R$^{J1}$ or R$^{J2}$ is a group of Formula (iv).

Group G

As generally defined herein, G is O or N—R$^G$, wherein R$^G$ is hydrogen or —OR$^{G1}$ and wherein R$^{G1}$ is hydrogen; an oxygen protecting group; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a group -L$^1$-(A-L$^2$)$_a$-B for Formula (A) or (II), or a group -L$^1$-X for Formula (P-A) or (P-II).

In certain embodiments, G is O.

In certain embodiments, G is N—R$^G$. In certain embodiments, R$^G$ is —OR$^{G1}$. In certain embodiments, R$^{G1}$ is a group -L$^1$-(A-L$^2$)$_a$-B for Formula (A) or (II), or a group -L$^1$-X for Formula (P-A) or (P-II), as defined herein.

Additional Embodiments of Formula (I), (P-I), (II) and (P-II)

Various combinations of the above embodiments are further contemplated herein.

One of skill in the art would appreciate that the various embodiments described herein may be combined in various ways and are contemplated by the inventors.

For example, in certain embodiments, the compound of Formula (I) or (P-I) is, respectively, a compound of Formula (I-a), comprising at least one group of formula -L$^1$-(A-L$^2$)$_a$-B attached thereto, or a compound of Formula (P-I-a), comprising at least one group of formula -L$^1$-X attached thereto:

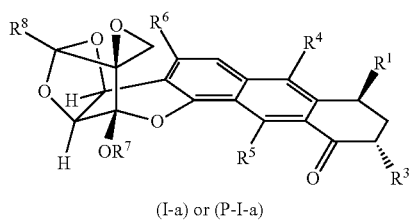

(I-a) or (P-I-a)

or a pharmaceutically acceptable salt thereof. In certain embodiments, R$^1$ is —OH or —OR$^{A1}$ In certain embodiments, R$^{A1}$ is a group of Formula (i). In certain embodiments of Formula (i), R$^{A6}$ is hydrogen; —OR$^{A9}$; —OC(=O)R$^{A9}$; or —NHC(=O)R$^{A9}$. In certain embodiments, R$^{A6}$ is a group —OC(=O)-L$^1$-(A-L$^2$)$_a$-B for Formula (I), or a group —OC (=O)-L$^1$-X for Formula (P-I). In certain embodiments, R$^1$ is hydrogen. In certain embodiments, R$^3$ is hydrogen. In certain embodiments, R$^3$ is —OR$^{C1}$, e.g., —OH. In certain embodiments, R$^1$ and R$^3$ are both hydrogen. In certain embodiments, R$^4$ is —OR$^{D1}$, e.g., —OCH$_3$. In certain embodiments, R$^5$ is —OR$^{E1}$, e.g., —OH. In certain embodiments, R$^6$ is substituted or unsubstituted alkyl or —OR$^{F1}$ In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$.

In certain embodiments, the compound of Formula (I) or (P-I) is, respectively, a compound of Formula (I-b), comprising at least one group of formula -L$^1$-(A-L$^2$)$_a$-B attached thereto, or a compound of Formula (P-I-b), comprising at least one group of formula -L$^1$-X attached thereto:

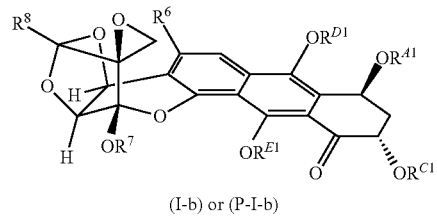

(I-b) or (P-I-b)

or a pharmaceutically acceptable salt thereof. In certain embodiments, R$^{A1}$ is a group of Formula (i). In certain embodiments of Formula (i), R$^{A6}$ is hydrogen; —OR$^{A9}$; —OC(=O)R$^{A9}$; or —NHC(=O)R$^{A9}$. In certain embodiments, R$^{A6}$ is a group —OC(=O)-L$^1$-(A-L$^2$)$_a$-B for Formula (I), or a group —OC(=O)-L$^1$-X for Formula (P-I). In certain embodiments, R$^6$ is substituted or unsubstituted alkyl or —OR$^{F1}$. In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$.

In certain embodiments, the compound of Formula (I) or (P-I) is, respectively, a compound of Formula (I-c), comprising at least one group of formula -L$^1$-(A-L$^2$)$_a$-B attached thereto, or a compound of Formula (P-I-c), comprising at least one group of formula -L$^1$-X attached thereto:

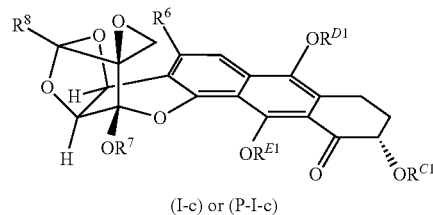

(I-c) or (P-I-c)

or a pharmaceutically acceptable salt thereof. In certain embodiments, R$^6$ is substituted or unsubstituted alkyl or —OR$^{F1}$. In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$.

In certain embodiments, the compound of Formula (I) or (P-I) is, respectively, a compound of Formula (I-d), comprising at least one group of formula -L$^1$-(A-L$^2$)$_a$-B attached thereto, or a compound of Formula (P-I-d), comprising at least one group of formula -L$^1$-X attached thereto:

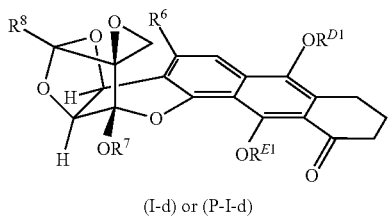

(I-d) or (P-I-d)

or a pharmaceutically acceptable salt thereof. In certain embodiments, R$^6$ is substituted or unsubstituted alkyl or —OR$^{F1}$. In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$.

In certain embodiments, the compound of Formula (I) or (P-I) is, respectively, a compound of Formula (I-e), comprising at least one group of formula -L$^1$-(A-L$^2$)$_a$-B attached thereto, or a compound of Formula (P-I-e), comprising at least one group of formula -L$^1$-X attached thereto:

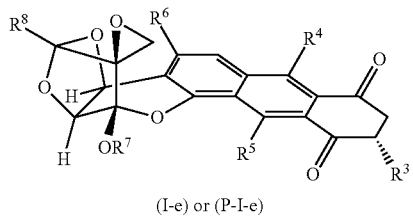

(I-e) or (P-I-e)

or a pharmaceutically acceptable salt thereof. In certain embodiments, R$^3$ is hydrogen. In certain embodiments, R$^3$ is —OR, e.g., —OH. In certain embodiments, R$^6$ is substituted or unsubstituted alkyl or —OR$^{F1}$. In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$.

In certain embodiments, the compound of Formula (I) or (P-I) is, respectively, a compound of Formula (I-f), comprising at least one group of formula -L$^1$-(A-L$^2$)$_a$-B attached thereto, or a compound of Formula (P-I-f), comprising at least one group of formula -L$^1$-X attached thereto:

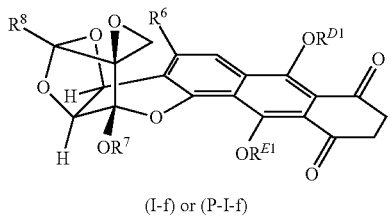

(I-f) or (P-I-f)

or a pharmaceutically acceptable salt thereof. In certain embodiments, R$^6$ is substituted or unsubstituted alkyl or —OR$^{F1}$. In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$.

In certain embodiments, the compound of Formula (I) or (P-I) is, respectively, a compound of Formula (I-x), comprising at least one group of formula -L$^1$-(A-L$^2$)$_a$-B attached thereto, or a compound of Formula (P-I-x), comprising at least one group of formula -L$^1$-X attached thereto:

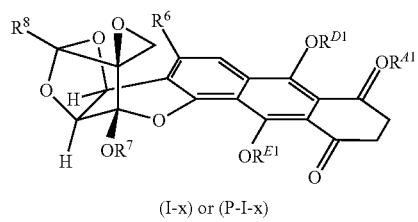

(I-x) or (P-I-x)

or a pharmaceutically acceptable salt thereof. In certain embodiments, R$^{A1}$ is a group of Formula (i). In certain embodiments of Formula (i), R$^{A6}$ is hydrogen; —OR$^{A9}$; —OC(=O)R$^{A9}$; or —NHC(=O)R$^{A9}$. In certain embodiments, R$^{A6}$ is a group —OC(=O)-L$^1$-(A-L$^2$)$_a$-B for Formula (I), or a group —OC(=O)-L$^1$-X for Formula (P-I). In certain embodiments, R$^6$ is substituted or unsubstituted alkyl or —OR$^{F1}$. In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$.

In certain embodiments, the compound of Formula (II) or (P-II) is, respectively, a compound of Formula (II-a), comprising at least one group of formula -L$^1$-(A-L$^2$)$_a$-B attached thereto, or a compound of Formula (P-II-a), comprising at least one group of formula -L$^1$-X attached thereto:

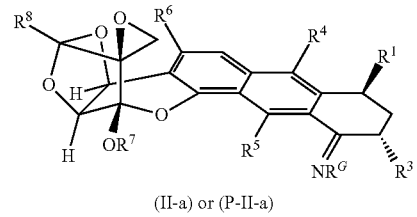

(II-a) or (P-II-a)

or a pharmaceutically acceptable salt thereof. In certain embodiments, R$^1$ is —OH or —OR$^{A1}$. In certain embodiments, R$^{A1}$ is a group of Formula (i). In certain embodiments of Formula (i), R$^{A6}$ is hydrogen; —OR$^{A9}$; —OC(=O)R$^{A9}$; or —NHC(=O)R$^{A9}$. In certain embodiments, R$^{A6}$ is a group —OC(=O)-L$^1$-(A-L$^2$)$_a$-B for Formula (II), or a group —OC(=O)-L$^1$-X for Formula (P-II). In certain embodiments, R$^1$ is hydrogen. In certain embodiments, R$^3$ is hydrogen. In certain embodiments, R$^3$ is —OR$^{C1}$, e.g., —OH. In certain embodiments, R$^1$ and R$^3$ are both hydrogen. In certain embodiments, R$^4$ is —OR$^{D1}$, e.g., —OCH$_3$. In certain embodiments, R$^5$ is —OR$^{E1}$, e.g., —OH. In certain embodiments, R$^6$ is substituted or unsubstituted alkyl or —OR$^{F1}$. In certain embodiments, R$^7$ is hydrogen. In certain embodiments, R$^7$ is a group of Formula (ii). In certain embodiments, R$^8$ is hydrogen, —CH$_2$(OR$^{J1}$), or —CH(OR$^{J1}$)$_2$. In certain embodiments, R$^G$ is —OR$^{G1}$. In certain embodiments, R$^{G1}$ is a group -L$^1$-(A-L$^2$)$_a$-B for Formula (II), or a group -L$^1$-X for Formula (P-II).

In certain embodiments, the compound of Formula (II) or (P-II) is, respectively, a compound of Formula (II-b), comprising at least one group of formula -$L^1$-(A-$L^2$)$_a$-B attached thereto, or a compound of Formula (P-II-b), comprising at least one group of formula -$L^1$-X attached thereto:

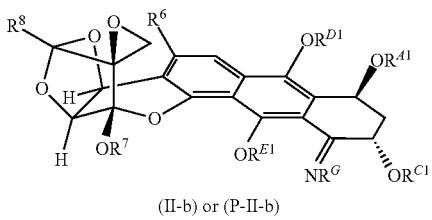

(II-b) or (P-II-b)

or a pharmaceutically acceptable salt thereof. In certain embodiments, $R^{A1}$ is a group of Formula (i). In certain embodiments of Formula (i), $R^{A6}$ is hydrogen; —$OR^{A9}$; —OC(=O)$R^{A9}$; or —NHC(=O)$R^{A9}$. In certain embodiments, $R^{A6}$ is a group —OC(=O)-$L^1$-(A-$L^2$)$_a$-B for Formula (II), or a group —OC(=O)-$L^1$-X for Formula (P-II). In certain embodiments, $R^6$ is substituted or unsubstituted alkyl or —$OR^{F1}$. In certain embodiments, $R^7$ is hydrogen. In certain embodiments, $R^7$ is a group of Formula (ii). In certain embodiments, $R^8$ is hydrogen, —CH$_2$(OR$^{J1}$), or —CH(OR$^{J1}$)$_2$. In certain embodiments, $R^G$ is —$OR^{G1}$. In certain embodiments, $R^{G1}$ is a group -$L^1$-(A-$L^2$)$_a$-B for Formula (II), or a group -$L^1$-X for Formula (P-II).

In certain embodiments, the compound of Formula (II) or (P-II) is, respectively, a compound of Formula (II-c), comprising at least one group of formula -$L^1$-(A-$L^2$)$_a$-B attached thereto, or a compound of Formula (P-II-c), comprising at least one group of formula -$L^1$-X attached thereto:

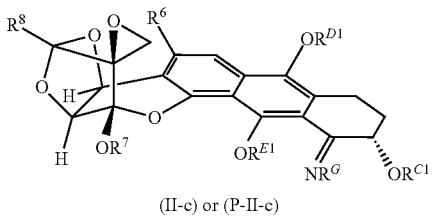

(II-c) or (P-II-c)

or a pharmaceutically acceptable salt thereof. In certain embodiments, $R^6$ is substituted or unsubstituted alkyl or —$OR^{F1}$. In certain embodiments, $R^7$ is hydrogen. In certain embodiments, $R^7$ is a group of Formula (ii). In certain embodiments, $R^8$ is hydrogen, —CH$_2$(OR$^{J1}$), or —CH(OR$^{J1}$)$_2$. In certain embodiments, $R^G$ is —$OR^{G1}$. In certain embodiments, $R^{G1}$ is a group -$L^1$-(A-$L^2$)$_a$-B for Formula (II), or a group -$L^1$-X for Formula (P-II).

In certain embodiments, the compound of Formula (II) or (P-II) is, respectively, a compound of Formula (II-d), comprising at least one group of formula -$L^1$-(A-$L^2$)$_a$-B attached thereto, or a compound of Formula (P-II-d), comprising at least one group of formula -$L^1$-X attached thereto:

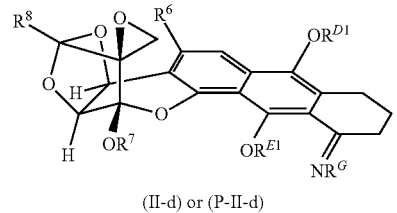

(II-d) or (P-II-d)

or a pharmaceutically acceptable salt thereof. In certain embodiments, $R^6$ is substituted or unsubstituted alkyl or —$OR^{F1}$. In certain embodiments, $R^7$ is hydrogen. In certain embodiments, $R^7$ is a group of Formula (ii). In certain embodiments, $R^8$ is hydrogen, —CH$_2$(OR$^{J1}$), or —CH(OR$^{J1}$)$_2$. In certain embodiments, $R^G$ is —$OR^{G1}$. In certain embodiments, $R^{G1}$ is a group -$L^1$-(A-$L^2$)$_a$-B for Formula (II), or a group -$L^1$-X for Formula (P-II).

In certain embodiments, the compound of Formula (II) or (P-II) is, respectively, a compound of Formula (II-e), comprising at least one group of formula -$L^1$-(A-$L^2$)$_a$-B attached thereto, or a compound of Formula (P-II-e), comprising at least one group of formula -$L^1$-X attached thereto:

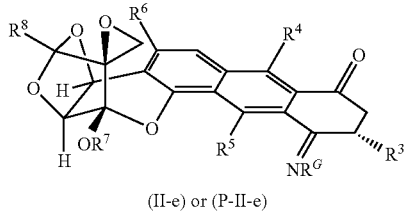

(II-e) or (P-II-e)

or a pharmaceutically acceptable salt thereof. In certain embodiments, $R^3$ is hydrogen. In certain embodiments, $R^3$ is —$OR^{C1}$, e.g., —OH. In certain embodiments, $R^6$ is substituted or unsubstituted alkyl or —$OR^{F1}$. In certain embodiments, $R^7$ is hydrogen. In certain embodiments, $R^7$ is a group of Formula (ii). In certain embodiments, $R^8$ is hydrogen, —CH$_2$(OR$^{J1}$), or —CH(OR$^{J1}$)$_2$. In certain embodiments, $R^G$ is —$OR^{G1}$. In certain embodiments, $R^{G1}$ is a group -$L^1$-(A-$L^2$)$_a$-B for Formula (II), or a group -$L^1$-X for Formula (P-II).

In certain embodiments, the compound of Formula (II) or (P-II) is, respectively, a compound of Formula (II-f), comprising at least one group of formula -$L^1$-(A-$L^2$)$_a$-B attached thereto, or a compound of Formula (P-II-f), comprising at least one group of formula -$L^1$-X attached thereto:

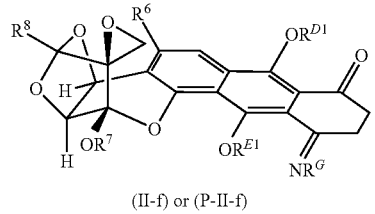

(II-f) or (P-II-f)

or a pharmaceutically acceptable salt thereof. In certain embodiments, $R^6$ is substituted or unsubstituted alkyl or —$OR^{F1}$. In certain embodiments, $R^7$ is hydrogen. In certain embodiments, $R^7$ is a group of Formula (ii). In certain embodiments, $R^8$ is hydrogen, —CH$_2$(OR$^{J1}$), or —CH(OR$^{J1}$)$_2$. In certain embodiments, $R^G$ is —$OR^{G1}$. In certain embodiments, $R^{G1}$ is a group $-L^1-(A-L^2)_a-B$ for Formula (II), or a group $-L^1-X$ for Formula (P-II).

In certain embodiments, the compound of Formula (II) or (P-II) is, respectively, a compound of Formula (II-x), comprising at least one group of formula $-L^1-(A-L^2)_a-B$ attached thereto, or a compound of Formula (P-II-x), comprising at least one group of formula $-L^1-X$ attached thereto:

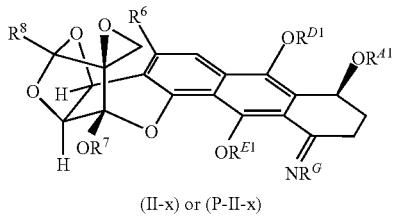

(II-x) or (P-II-x)

or a pharmaceutically acceptable salt thereof. In certain embodiments, $R^{41}$ is a group of Formula (i). In certain embodiments of Formula (i), $R^{46}$ is hydrogen; $-OR^{49}$; $-OC(=O)R^{49}$; or $-NHC(=O)R^{49}$. In certain embodiments, $R^{46}$ is a group $-OC(=O)-L^1-(A-L^2)_a-B$ for Formula (I), or a group $-OC(=O)-L^1-X$ for Formula (P-II). In certain embodiments, $R^6$ is substituted or unsubstituted alkyl or $-OR^{F1}$. In certain embodiments, $R^7$ is hydrogen. In certain embodiments, $R^7$ is a group of Formula (ii). In certain embodiments, $R^8$ is hydrogen, $-CH_2(OR^{J1})$, or $-CH(OR^{J1})_2$. In certain embodiments, $R^G$ is $-OR^{G1}$. In certain embodiments, $R^{G1}$ is a group $-L^1-(A-L^2)_a-B$ for Formula (II), or a group $-L^1-X$ for Formula (P-II).

Linker Group $L^1$

As generally defined herein, $L^1$ is absent or is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; peptidyl groups; dipeptidyl groups; polypeptidyl groups; and combinations thereof.

In certain embodiments, $L^1$ is absent. It is generally understood that if $L^1$ is absent, the group A is directly attached to the compound of Formula (A), (I), and (II) and the group X is directly attached to the compound of Formula (P-I).

In certain embodiments, $L^1$ is a linking group comprising at least one instance of substituted or unsubstituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^1$ is a substituted or unsubstituted alkylene as described herein.

In certain embodiments, $L^1$ is a linking group comprising at least one instance of substituted or unsubstituted alkenylene, e.g., substituted or unsubstituted $C_{2-6}$ alkenylene, substituted or unsubstituted $C_{3-4}$alkenylene, substituted or unsubstituted $C_{4-6}$alkenylene, substituted or unsubstituted $C_{5-6}$alkenylene, substituted or unsubstituted $C_{2-5}$alkenylene, substituted or unsubstituted $C_{2-4}$alkenylene, substituted or unsubstituted $C_{2-3}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene. In certain embodiments, $L^1$ is a substituted or unsubstituted alkenylene as described herein.

In certain embodiments, $L^1$ is a linking group comprising at least one instance of substituted or unsubstituted alkynylene, e.g., substituted or unsubstituted $C_{2-6}$alkynylene, substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene. In certain embodiments, $L^1$ is a substituted or unsubstituted alkynylene as described herein.

In certain embodiments, $L^1$ is a linking group comprising at least one instance of substituted or unsubstituted heteroalkylene, e.g., substituted or unsubstituted heteroC$_{1-6}$alkylene, substituted or unsubstituted heteroC$_{2-6}$alkylene, substituted or unsubstituted heteroC$_{3-6}$alkylene, substituted or unsubstituted heteroC$_{4-6}$alkylene, substituted or unsubstituted heteroC$_{5-6}$alkylene, substituted or unsubstituted heteroC$_{2-5}$alkylene, substituted or unsubstituted heteroC$_{2-4}$alkylene, substituted or unsubstituted heteroC$_{2-3}$alkylene, substituted or unsubstituted heteroC$_1$alkylene, substituted or unsubstituted heteroC$_2$alkylene, substituted or unsubstituted heteroC$_3$alkylene, substituted or unsubstituted heteroC$_4$alkylene, substituted or unsubstituted heteroC$_5$alkylene, or substituted or unsubstituted heteroC$_6$alkylene. In certain embodiments, $L^1$ is a substituted or unsubstituted heteroalkylene as described herein.

In certain embodiments, $L^1$ is a linking group comprising at least one instance of substituted or unsubstituted heteroalkenylene, e.g., substituted or unsubstituted heteroC$_{2-6}$alkenylene, substituted or unsubstituted heteroC$_{3-6}$alkenylene, substituted or unsubstituted heteroC$_{4-6}$alkenylene, substituted or unsubstituted heteroC$_{5-6}$alkenylene, substituted or unsubstituted heteroC$_{2-5}$alkenylene, substituted or unsubstituted heteroC$_{2-4}$alkenylene, substituted or unsubstituted heteroC$_{2-3}$alkenylene, substituted or unsubstituted heteroC$_2$alkenylene, substituted or unsubstituted heteroC$_3$alkenylene, substituted or unsubstituted heteroC$_4$alkenylene, substituted or unsubstituted heteroC$_5$alkenylene, or substituted or unsubstituted heteroC$_6$alkenylene. In certain embodiments, $L^1$ is a substituted or unsubstituted heteroalkenylene as described herein.

In certain embodiments, $L^1$ is a linking group comprising at least one instance of substituted or unsubstituted heteroalkynylene, e.g., substituted or unsubstituted heteroC$_{2-6}$alkynylene, substituted or unsubstituted heteroC$_{3-6}$alkynylene, substituted or unsubstituted heteroC$_{4-6}$alkynylene, substituted or unsubstituted heteroC$_{5-6}$alkynylene, substituted or unsubstituted heteroC$_{2-5}$alkynylene, substituted or unsubstituted heteroC$_{2-4}$alkynylene, substituted or unsubstituted heteroC$_{2-3}$alkynylene, substituted or unsubstituted heteroC$_2$alkynylene, substituted or unsubstituted heteroC$_3$alkynylene, substituted or unsubstituted heteroC$_4$alkynylene, substituted or unsubstituted heteroC$_5$alkynylene, or substituted or unsubstituted heteroC$_6$alkynylene. In certain embodiments, L$^1$ is a substituted or unsubstituted heteroalkynylene as described herein.

In certain embodiments, L$^1$ is a linking group comprising at least one instance of substituted or unsubstituted heterocyclylene, e.g., substituted or unsubstituted 5- to 8-membered heterocyclylene, substituted or unsubstituted 5- to 7-membered heterocyclylene, substituted or unsubstituted 5- to 6-membered heterocyclylene, substituted or unsubstituted 5-membered heterocyclylene, substituted or unsubstituted 6-membered heterocyclylene, substituted or unsubstituted 7-membered heterocyclylene, or substituted or unsubstituted 8-membered heterocyclylene. In certain embodiments, L$^1$ is a substituted or unsubstituted heterocyclylene as described herein.

In certain embodiments, L$^1$ is a linking group comprising at least one instance of substituted or unsubstituted carbocyclylene, e.g., substituted or unsubstituted C$_{3-6}$ carbocyclylene, substituted or unsubstituted C$_{3-5}$ carbocyclylene, substituted or unsubstituted C$_{3-4}$ carbocyclylene, substituted or unsubstituted C$_3$ carbocyclylene, substituted or unsubstituted C$_4$ carbocyclylene, substituted or unsubstituted C$_5$ carbocyclylene, or substituted or unsubstituted C$_6$ carbocyclylene. In certain embodiments, L$^1$ is a substituted or unsubstituted carbocyclylene as described herein.

In certain embodiments, L$^1$ is a linking group comprising at least one instance of substituted or unsubstituted arylene, e.g., substituted or unsubstituted C$_6$ arylene (phenylene) or substituted or unsubstituted C$_{10}$ arylene (naphthylene). In certain embodiments, L$^1$ is a substituted or unsubstituted arylene as described herein.

In certain embodiments, L$^1$ is a linking group comprising at least one instance of substituted or unsubstituted heteroarylene, e.g., substituted or unsubstituted 5-membered heteroarylene or substituted or unsubstituted 6-membered heteroarylene. In certain embodiments, L$^1$ is a substituted or unsubstituted heteroarylene as described herein.

In certain embodiments, L$^1$ is a linking group comprising at least one instance of a peptidyl group as described herein. In certain embodiments, L$^1$ is a linking group comprising at least one instance of a dipeptidyl group as described herein. In certain embodiments, L$^1$ is a linking group comprising at least one instance of a polypeptidyl group as described herein.

In certain embodiments, L$^1$ represents a linking group comprising a combination of one or more groups (e.g., 1, 2, 3, 4, 5, 6, 7, 8, 9, or 10 groups) of the formula:

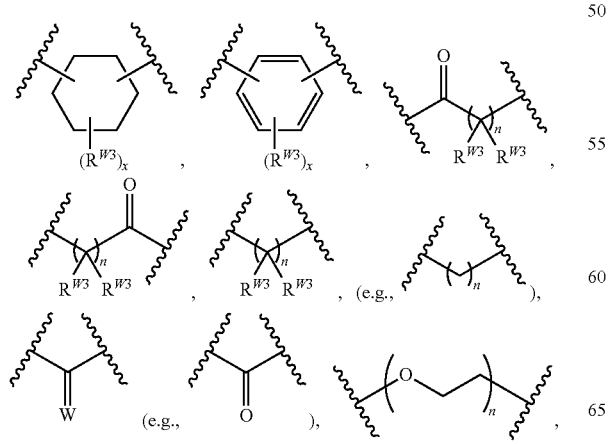

-continued

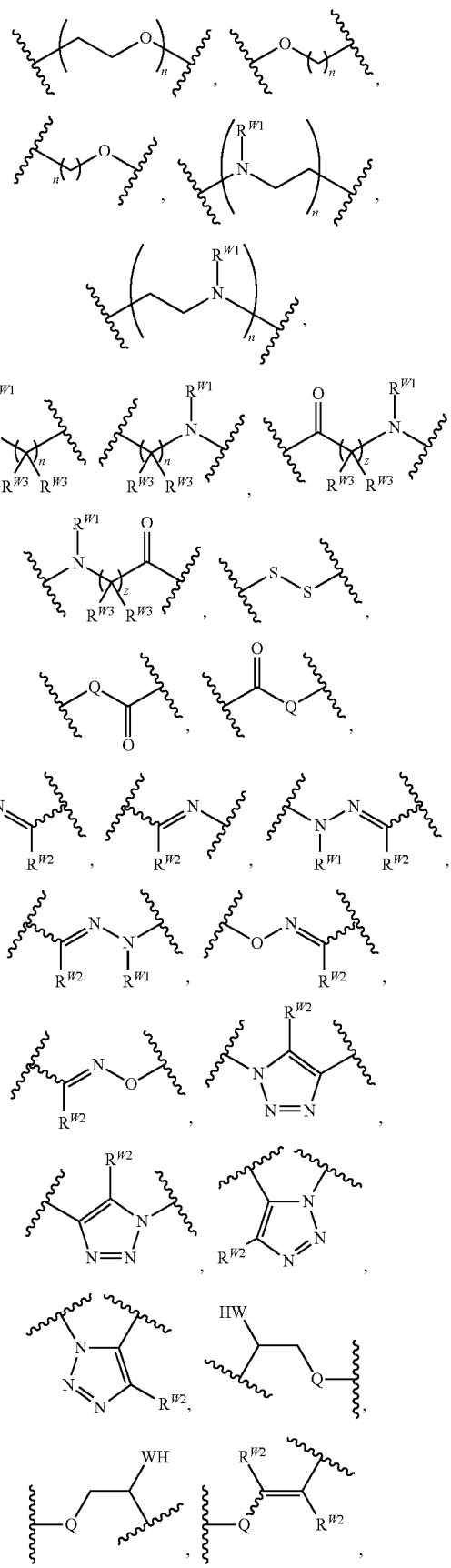

-continued

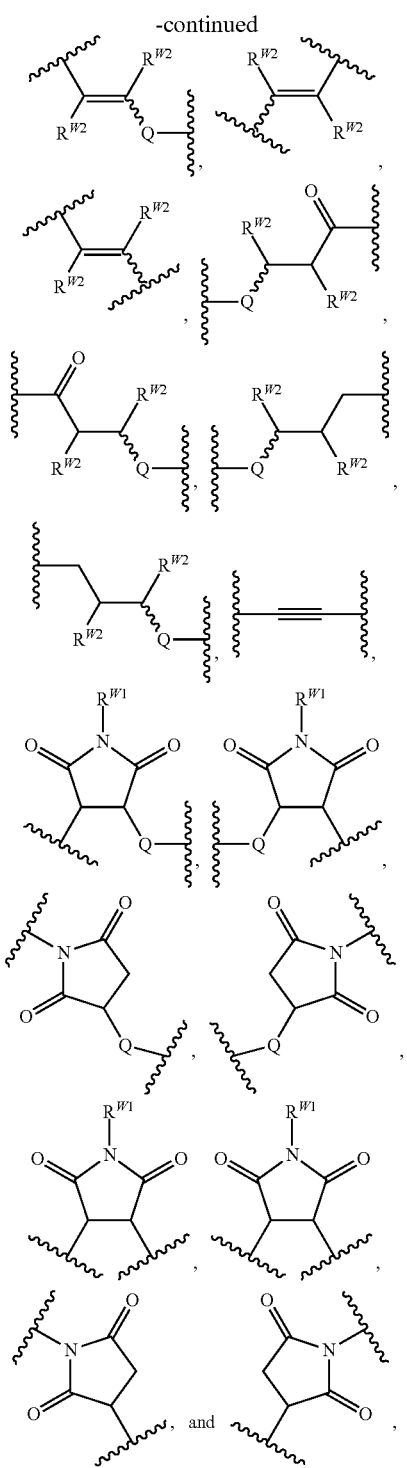

wherein:
n is an integer between 1 to 10, inclusive;
x is 0, 1, or 2;
z is 1 or 2;
Q is —NH—, —NH—NH—, —O—NH—, —NH—O—, —S—, —O—;
W is O, S, or $NR^{W1}$;
$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

$R^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or two $R^{W2}$ groups are joined to form a 5-6 membered ring; and each instance of $R^{W3}$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; substituted or unsubstituted hydroxyl; substituted or unsubstituted thiol; substituted or unsubstituted amino; or two $R^{W3}$ groups are joined to form a 3-6 membered ring;

or $R^{W1}$ and $R^{W3}$ are joined to form a 5-6 membered heterocyclic ring.

In certain embodiments, n is 1, 2, 3, 4, 5, 6, 7, 8, 9, or 10.
In certain embodiments, x is 0. In certain embodiments, x is 1. In certain embodiments, x is 2.
In certain embodiments, z is 1. In certain embodiments, z is 2.
In certain embodiments, Q is —NH—. In certain embodiments, Q is —NH—NH—. In certain embodiments, Q is —S—. In certain embodiments, Q is —O—.
In certain embodiments, W is O. In certain embodiments, W is S. In certain embodiments, W is $NR^{W1}$. In certain embodiments, $R^{W1}$ is hydrogen. In certain embodiments, $R^{W1}$ is substituted or unsubstituted alkyl, e.g., methyl.
In certain embodiments, $R^{W2}$ is hydrogen. In certain embodiments, $R^{W2}$ is substituted or unsubstituted alkyl, e.g., methyl.
In certain embodiments, each instance of $R^{W3}$ is independently hydrogen; substituted or unsubstituted alkyl; substituted or unsubstituted aryl; or substituted or unsubstituted heteroaryl, or two $R^{W3}$ groups are joined to form a 3-6 membered ring; or $R^{W1}$ and $R^{W3}$ are joined to form a 5-6 membered heterocyclic ring.
In certain embodiments, $L^1$ represents a linking group comprising a combination of one or more groups (e.g., 1, 2, 3, 4, 5, 6, 7, 8, 9, or 10 groups) of the formula:

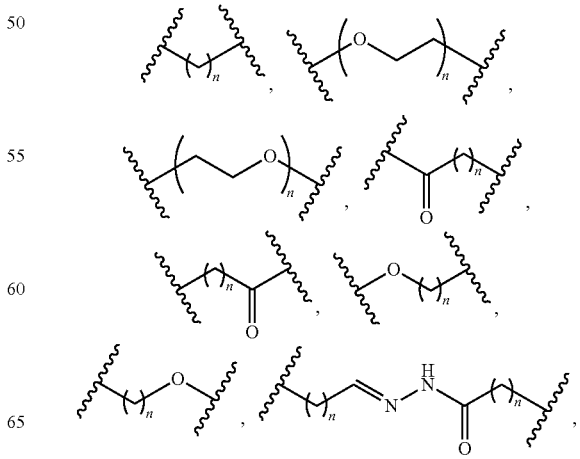

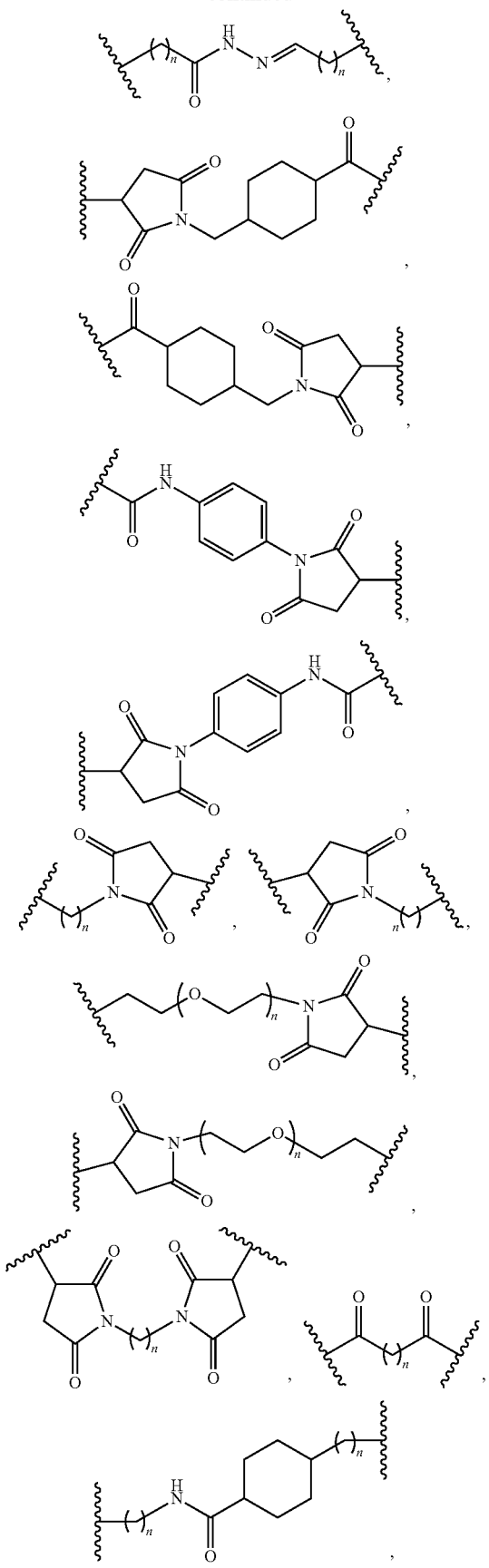

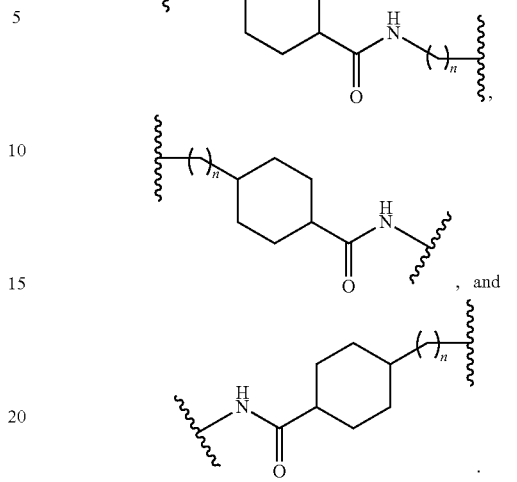

Alternatively, in certain embodiments, $L^1$ is a dendrimeric linking group comprising multiple and independent trioxacarcin compounds attached thereto. A dendrimeric linking group, as used herein, is a repetitively branched linking groups selected from the group consisting of repetitively branched substituted or unsubstituted alkylene; repetitively branched substituted or unsubstituted alkenylene; repetitively branched substituted or unsubstituted alkynylene; repetitively branched substituted or unsubstituted heteroalkylene; repetitively branched substituted or unsubstituted heteroalkenylene; repetitively branched substituted or unsubstituted heteroalkynylene; repetitively branched substituted or unsubstituted heterocyclylene; repetitively branched substituted or unsubstituted carbocyclylene; repetitively branched substituted or unsubstituted arylene; repetitively branched substituted or unsubstituted heteroarylene; repetitively branched peptidyl groups; repetitively branched dipeptidyl groups; repetitively branched polypeptidyl groups; and combinations thereof. In certain embodiments, the dendrimeric linking group comprises 1 to 200 independent instances of a trioxacarcin compound attached thereto, inclusive, e.g., 1 to 150, 1 to 100, 1 to 75, 1 to 50, 1 to 25, 1 to 15, 1 to 10, inclusive, e.g., 1, 2, 3, 4, 5, 6, 7, 8, 9, or 10 independent instances.

In one non-limiting embodiment, $L^1$ is attached to a compound of Formula (A), (I), and (II) or (P-I) via an oxime moiety of the compound of Formula (A), (I), and (II) or (P-I). For example, in certain embodiments, $L^1$ is attached via the oxime moiety —C(=N—OR$^{H7}$)R$^{H8}$ as defined for R$^{H2}$ or R$^{H4}$.

Linker Group $L^2$

As generally defined herein, $L^2$ is absent or is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; peptidyl groups; dipeptidyl groups; polypeptidyl groups; and combinations thereof.

In certain embodiments, $L^2$ is absent. It is generally understood for a compound of Formula (A), (I), and (II) that if $L^2$ is absent, B is directly attached to group A. It is also generally understood that for a compound of Formula Y-$L^2$-B that if $L^2$ is absent, then Y is a functional group directly attached to the antibody or antibody fragment B.

Figure 5:
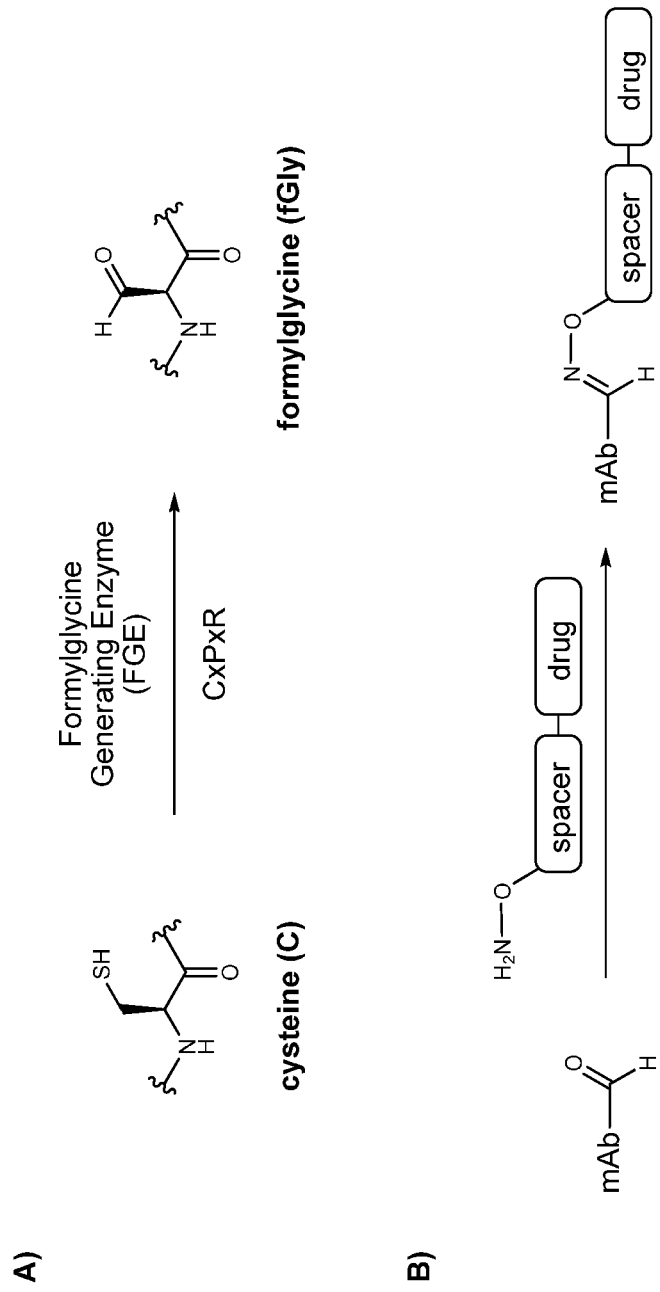
FIG. 5 depicts site specific chemical modification of monoclonoal antibodies.

In certain embodiments, Y is a functional group of the antibody or antibody fragment, e.g., a functional group attached to the side chain of an amino acid moiety of the antibody or antibody fragment. For example, in certain embodiments, when $L^2$ is absent, Y is an —SH group of a cysteine moiety of the antibody or antibody fragment. In certain embodiments, when $L^2$ is absent, Y is an —NH$_2$ group from a lysine, arginine, asparagine, or glutamine moiety or the N-terminus of the antibody or antibody fragment. In certain embodiments, when $L^2$ is absent, Y is an —CO$_2$H group from an aspartic acid or glutamic acid moiety of the antibody or antibody fragment. In certain embodiments, when $L^2$ is absent, Y is an —OH group from a serine or threonine moiety of the antibody or antibody fragment. Cysteine side chains (—CH$_2$SH) may be chemically or enzymatically modified, for example, by conversion to formyl (—CHO) groups. See, e.g., FIG. 5. In such an instance, the $L^2$ group is also understood to be absent since Y is a —CHO functional group directly attached to the side chain of an amino acid moiety of the antibody or antibody fragment.

In certain embodiments, $L^2$ is a linking group comprising at least one instance of substituted or unsubstituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^2$ is a substituted or unsubstituted alkylene as described herein.

In certain embodiments, $L^2$ is a linking group comprising at least one instance of substituted or unsubstituted alkenylene, e.g., substituted or unsubstituted $C_{2-6}$alkenylene, substituted or unsubstituted $C_{3-6}$alkenylene, substituted or unsubstituted $C_{4-6}$alkenylene, substituted or unsubstituted $C_{5-6}$alkenylene, substituted or unsubstituted $C_{2-5}$alkenylene, substituted or unsubstituted $C_{2-4}$alkenylene, substituted or unsubstituted $C_{2-3}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene. In certain embodiments, $L^2$ is a substituted or unsubstituted alkenylene as described herein.

In certain embodiments, $L^2$ is a linking group comprising at least one instance of substituted or unsubstituted alkynylene, e.g., substituted or unsubstituted $C_{2-6}$alkynylene, substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene. In certain embodiments, $L^2$ is a substituted or unsubstituted alkynylene as described herein.

In certain embodiments, $L^2$ is a linking group comprising at least one instance of substituted or unsubstituted heteroalkylene, e.g., substituted or unsubstituted heteroC$_{1-6}$alkylene, substituted or unsubstituted heteroC$_{2-6}$alkylene, substituted or unsubstituted heteroC$_{3-6}$alkylene, substituted or unsubstituted heteroC$_{4-6}$alkylene, substituted or unsubstituted heteroC$_{5-6}$alkylene, substituted or unsubstituted heteroC$_{2-5}$alkylene, substituted or unsubstituted heteroC$_{2-4}$alkylene, substituted or unsubstituted heteroC$_{2-3}$alkylene, substituted or unsubstituted heteroC$_1$alkylene, substituted or unsubstituted heteroC$_2$alkylene, substituted or unsubstituted heteroC$_3$alkylene, substituted or unsubstituted heteroC$_4$alkylene, substituted or unsubstituted heteroC$_5$alkylene, or substituted or unsubstituted heteroC$_6$alkylene. In certain embodiments, $L^2$ is a substituted or unsubstituted heteroalkylene as described herein.

In certain embodiments, $L^2$ is a linking group comprising at least one instance of substituted or unsubstituted heteroalkenylene, e.g., substituted or unsubstituted heteroC$_{2-6}$alkenylene, substituted or unsubstituted heteroC$_{3-6}$alkenylene, substituted or unsubstituted heteroC$_{4-6}$alkenylene, substituted or unsubstituted heteroC$_{5-6}$alkenylene, substituted or unsubstituted heteroC$_{2-5}$alkenylene, substituted or unsubstituted heteroC$_{2-4}$alkenylene, substituted or unsubstituted heteroC$_{2-3}$alkenylene, substituted or unsubstituted heteroC$_2$alkenylene, substituted or unsubstituted heteroC$_3$alkenylene, substituted or unsubstituted heteroC$_4$alkenylene, substituted or unsubstituted heteroC$_5$alkenylene, or substituted or unsubstituted heteroC$_6$alkenylene. In certain embodiments, $L^2$ is a substituted or unsubstituted heteroalkenylene as described herein.

In certain embodiments, $L^2$ is a linking group comprising at least one instance of substituted or unsubstituted heteroalkynylene, e.g., substituted or unsubstituted heteroC$_{2-6}$alkynylene, substituted or unsubstituted heteroC$_{3-6}$alkynylene, substituted or unsubstituted heteroC$_{4-6}$alkynylene, substituted or unsubstituted heteroC$_{5-6}$alkynylene, substituted or unsubstituted heteroC$_{2-5}$alkynylene, substituted or unsubstituted heteroC$_{2-4}$alkynylene, substituted or unsubstituted heteroC$_{2-3}$alkynylene, substituted or unsubstituted heteroC$_2$alkynylene, substituted or unsubstituted heteroC$_3$alkynylene, substituted or unsubstituted heteroC$_4$alkynylene, substituted or unsubstituted heteroC$_5$alkynylene, or substituted or unsubstituted heteroC$_6$alkynylene. In certain embodiments, $L^2$ is a substituted or unsubstituted heteroalkynylene as described herein.

In certain embodiments, $L^2$ is a linking group comprising at least one instance of substituted or unsubstituted heterocyclylene, e.g., substituted or unsubstituted 5- to 8-membered heterocyclylene, substituted or unsubstituted 5- to 7-membered heterocyclylene, substituted or unsubstituted 5- to 6-membered heterocyclylene, substituted or unsubstituted 5-membered heterocyclylene, substituted or unsubstituted 6-membered heterocyclylene, substituted or unsubstituted 7-membered heterocyclylene, or substituted or unsubstituted 8-membered heterocyclylene. In certain embodiments, $L^2$ is a substituted or unsubstituted heterocyclylene as described herein.

In certain embodiments, $L^2$ is a linking group comprising at least one instance of substituted or unsubstituted carbocyclylene, e.g., substituted or unsubstituted $C_{3-6}$ carbocyclylene, substituted or unsubstituted $C_{3-5}$ carbocyclylene, substituted or unsubstituted $C_{3-4}$ carbocyclylene, substituted or unsubstituted $C_3$ carbocyclylene, substituted or unsubstituted $C_4$ carbocyclylene, substituted or unsubstituted $C_5$ carbocyclylene, or substituted or unsubstituted $C_6$ carbocyclylene. In certain embodiments, L² is a substituted or unsubstituted carbocyclylene as described herein.

In certain embodiments, L² is a linking group comprising at least one instance of substituted or unsubstituted arylene, e.g., substituted or unsubstituted C₆ arylene (phenylene) or substituted or unsubstituted C₁₀ arylene (naphthylene). In certain embodiments, L² is a substituted or unsubstituted arylene as described herein.

In certain embodiments, L² is a linking group comprising at least one instance of substituted or unsubstituted heteroarylene, e.g., substituted or unsubstituted 5-membered heteroarylene or substituted or unsubstituted 6-membered heteroarylene. In certain embodiments, L² is a substituted or unsubstituted heteroarylene as described herein.

In certain embodiments, L² is a linking group comprising at least one instance of a peptidyl group as described herein. In certain embodiments, L² is a linking group comprising at least one instance of a dipeptidyl group as described herein. In certain embodiments, L² is a linking group comprising at least one instance of a polypeptidyl group as described herein.

In certain embodiments, L² represents a linking group comprising a combination of one or more groups (e.g., 1, 2, 3, 4, 5, 6, 7, 8, 9, or 10 groups) of the formula:

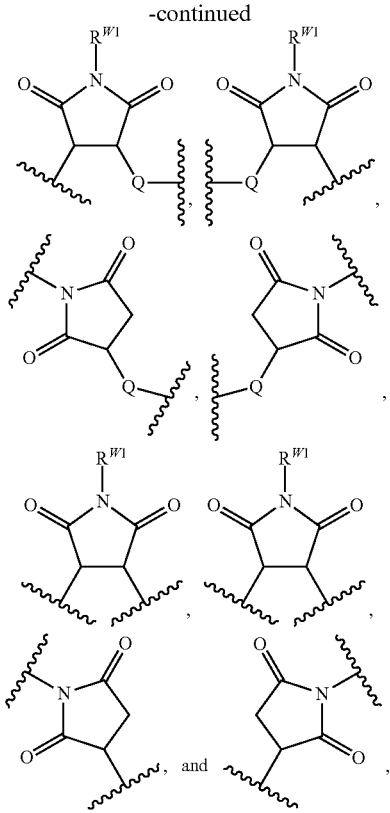

wherein:
n is an integer between 1 to 10, inclusive;
x is 0, 1 or 2;
z is 1 or 2;
Q is —NH—, —NH—NH—, —O—NH—, —NH—O—, —S—, —O—;
W is O, S, or NR$^{W1}$;
R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;
R$^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or two R$^{W2}$ groups are joined to form a 5-6 membered ring; and each instance of R$^{W3}$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; substituted or unsubstituted hydroxyl; substituted or unsubstituted thiol; substituted or unsubstituted amino; or two R$^{W3}$ groups are joined to form a 3-6 membered ring;
or R$^{W1}$ and R$^{W3}$ are joined to form a 5-6 membered heterocyclic ring.

In certain embodiments, n is 1, 2, 3, 4, 5, 6, 7, 8, 9, or 10.
In certain embodiments, x is 0. In certain embodiments, x is 1. In certain embodiments, x is 2.
In certain embodiments, z is 1. In certain embodiments, z is 2.

In certain embodiments, Q is —NH—. In certain embodiments, Q is —NH—NH—. In certain embodiments, Q is —S—. In certain embodiments, Q is —O—.

In certain embodiments, W is O. In certain embodiments, W is S. In certain embodiments, W is NR$^{W1}$. In certain embodiments, R$^{W1}$ is hydrogen. In certain embodiments, R$^{W1}$ is substituted or unsubstituted alkyl, e.g., methyl.

In certain embodiments, R$^{W2}$ is hydrogen. In certain embodiments, R$^{W2}$ is substituted or unsubstituted alkyl, e.g., methyl.

In certain embodiments, each instance of R$^{W3}$ is independently hydrogen; substituted or unsubstituted alkyl; substituted or unsubstituted aryl; or substituted or unsubstituted heteroaryl; or two R$^{W3}$ groups are joined to form a 3-6 membered ring; or R$^{W1}$ and R$^{W3}$ are joined to form a 5-6 membered heterocyclic ring.

In certain embodiments, L$^2$ represents a linking group comprising a combination of one or more groups (e.g., 1, 2, 3, 4, 5, 6, 7, 8, 9, or 10 groups) of the formula:

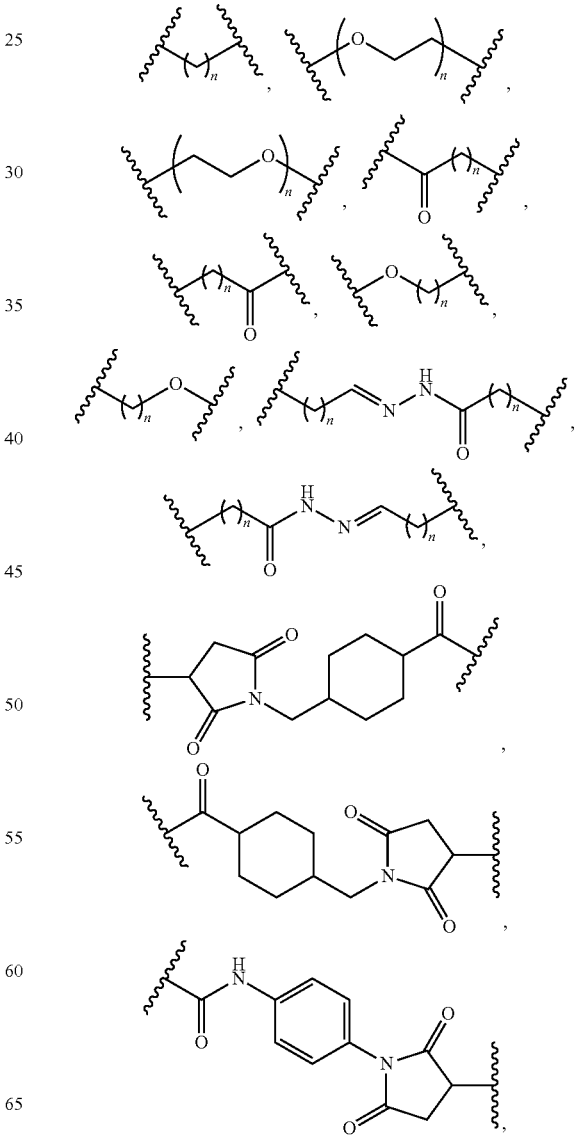

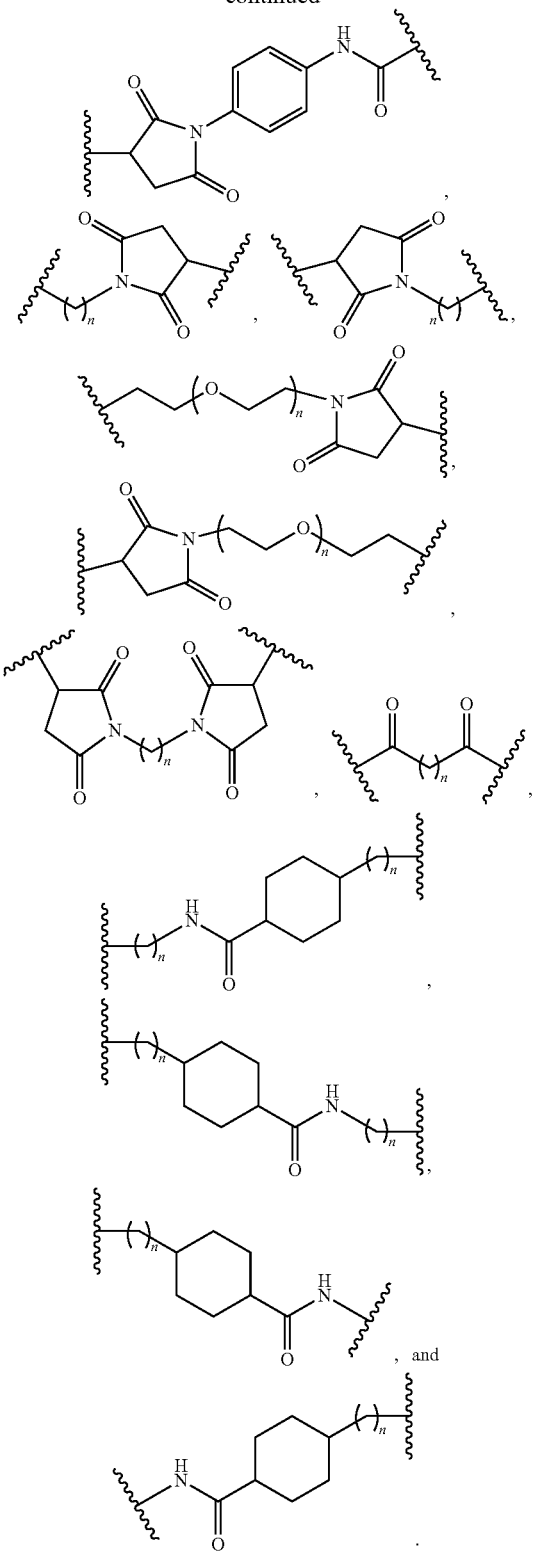

Group B

As generally defined herein, B is an antibody or antibody fragment. It is generally understood that the antibody or antibody fragment B is a large molecule with many possible sites of attachment of the trioxacarcin-linker moiety, i.e., a [trioxacarcin-L$^1$-A-L$^2$-] moiety. In certain embodiments, the antibody or antibody fragment comprises 1 to 200 independent instances of a trioxacarcin-linker moiety attached thereto, inclusive, e.g., 1 to 150, 1 to 100, 1 to 75, 1 to 50, 1 to 25, 1 to 15, 1 to 10, inclusive, e.g., 1, 2, 3, 4, 5, 6, 7, 8, 9, or 10 independent instances.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three subdomains, $C_{H1}$, $C_{H2}$ and $C_{H3}$. Each light chain is comprised of a light chain variable region (abbreviated herein as $V_L$) and a light chain constant region. The light chain constant region is comprised of one subdomain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

As used herein, the term "monoclonal antibody" may refer to an antibody obtained from a single clonal population of immunoglobulins that bind to the same epitope of an antigen. Monoclonal antibodies have the same Ig gene rearrangement and thus demonstrate identical binding specificity. Methods for preparing monoclonal antibodies, as described herein, are known in the art. Monoclonal antibodies can be prepared by a variety of methods. For example, monoclonal antibodies may be made by a hybridoma method (see, e.g., Kohler et al., Nature, 1975, 256: 495), or may be made by recombinant DNA methods (see, e.g., U.S. Pat. No. 4,816,567). The monoclonal antibodies may also be isolated from phage antibody libraries. (See e.g., Clarkson et al., Nature, 1991, 352: 624-628 and Marks et al., J. Mol. Biol., 1991, 222: 581-597).

Human monoclonal antibodies may be made by any of the methods known in the art, including those disclosed in U.S. Pat. No. 5,567,610, U.S. Pat. No. 5,565,354, U.S. Pat. No. 5,571,893, Kozber, J. Immunol., 1984, 133: 3001, Brodeur, et al., Monoclonal Antibody Production Techniques and Applications, p. 51-63 (Marcel Dekker, Inc., new York, 1987), and Boerner et al., J. Immunol., 1991, 147: 86-95. Human antibodies may be obtained by recovering antibody-producing lymphocytes from the blood or other tissues of humans producing antibody to an antigen of interest (e.g., CD20 or EGFR). These lymphocytes can be treated to produce cells that grow independently in the laboratory under appropriate culture conditions. The cell cultures can be screened for production of antibodies to the antigen of interest and then cloned. Clonal cultures can be used to produce human monoclonal antibodies to CD20 and/or EGFR, or the genetic elements encoding the variable portions of the heavy and light chain of the antibodies can be cloned and inserted into nucleic acid vectors for production of antibodies of different types. In addition to the conventional methods for preparing human monoclonal antibodies, such antibodies may also be prepared by immunizing transgenic animals that are capable of producing human antibodies (e.g., Jakobovits et al., *PNAS USA*, 1993, 90: 2551; Jakobovits et al., *Nature*, 1993, 362: 255-258, Bruggermann et al., *Year in Immunol.*, 1993, 7:33 and U.S. Pat. No. 5,569,825).

As used herein, "humanized monoclonal antibody" may refer to monoclonal antibodies having at least human constant regions and an antigen-binding region, such as one, two, or three CDRs, from a non-human species. Humanized antibodies specifically recognize antigens of interest, but will not evoke an immune response in humans against the antibody itself. As an example, murine CDRs may be grafted into the framework region of a human antibody to prepare the humanized antibody (e.g., Riechmann et al., *Nature*, 1988, 332, 323, and Neuberger et al., *Nature*, 1985, 314, 268). Alternatively, humanized monoclonal antibodies may be constructed by replacing the non-CDR regions of non-human antibodies with similar regions of human antibodies while retaining the epitopic specificity of the original antibodies. For example, non-human CDRs and optionally some of the framework regions may be covalently joined to human FR and/or Fc/pFc' regions to produce functional antibodies.

As used herein, the term "chimeric antibody" may refer to a monoclonal antibody comprising a variable region from one source (e.g., species) and at least a portion of a constant region derived from a different source. In some embodiments, chimeric antibodies are prepared by recombinant DNA techniques. In some embodiments, the chimeric antibodies comprise a murine variable region and a human constant region. Such chimeric antibodies may, in some embodiments, be the product of expressed immunoglobulin genes comprising DNA segments encoding murine immunoglobulin variable regions and DNA segments encoding human immunoglobulin constant regions. Methods for producing chimeric antibodies involve conventional recombinant DNA and gene transfection techniques (see, e.g., Morrison et al., *Proc. Natl. Acad. Sci. USA*, 1984, 81: 6851-6855; U.S. Pat. No. 5,202,238; and U.S. Pat. No. 5,204,244).

An antibody fragment is a portion of an antibody such as F(ab').sub.2, F(ab).sub.2, Fab', Fab, Fv, scFv (single chain Fv) and the like. Such fragments may be prepared by standard methods. See, e.g., Coligan et al. *Current Protocols in Immunology*, John Wiley & Sons, 1991-1997. Regardless of structure, an antibody fragment binds with the same antigen that is recognized by the intact antibody. An antibody fragment may comprise one or more proteolytic fragments (i.e., fragments produced by cleavage with papain), e.g., a Fab fragment, each containing a light chain domain and a heavy chain domain (designated herein as a "Fab heavy chain domain"), and/or Fc fragment containing two Fc domains. Each light chain domain contains a $V_L$ and a $C_L$ subdomain, each Fab heavy chain domain contains a $V_H$ and a $C_{H1}$ subdomain, and each Fc domain contains a $C_{H2}$ and $C_{H3}$ subdomain.

In certain embodiments, antigen-binding antibody fragments is only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. An isolated F(ab')2 fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Further, Fab fragments consist of a covalently bound antibody light chain and a portion of the antibody heavy chain denoted Fd (heavy chain variable region, referred to herein as Fab heavy chain domain). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')2 and Fv are employed with either standard immunological meanings (Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)). Well-known functionally active antibody fragments include but are not limited to F(ab')2, Fab, Fv and Fd fragments of antibodies. These fragments, which lack the Fc fragment of intact antibody, clear more rapidly from the circulation, and may have less non-specific tissue binding than an intact antibody (Wahl et al., J. Nucl. Med. 24:316-325 (1983)). For example, single-chain antibodies may be constructed in accordance with the methods described in U.S. Pat. No. 4,946,778. Such single-chain antibodies include the variable regions of the light and heavy chains joined by a flexible linker moiety. Methods for obtaining a single domain antibody ("Fd") which comprises an isolated variable heavy chain single domain, also have been reported (see, e.g., Ward et al., *Nature*, 1989, 341:644-646, disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, (see, e.g., Moore et al., U.S. Pat. No. 4,462,334). Other references describing the use and generation of antibody fragments include, e.g., Fab fragments (Tijssen, Practice and Theory of Enzyme Immunoassays (Elsevieer, Amsterdam, 1985)), Fv fragments (Hochman et al., *Biochemistry*, 1973, 12: 1130; Sharon et al., *Biochemistry*, 1976, 15: 1591; Ehrilch et al., U.S. Pat. No. 4,355,023) and portions of antibody molecules (Audilore-Hargreaves, U.S. Pat. No. 4,470,925). Thus, antibody fragments may be constructed from intact antibodies without destroying the specificity of the antibodies for the CD20 or EGFR epitope.

In certain embodiments, the antibody fragment is a camelid antibody; e.g., a functional antibody devoid of light chains of which the single N-terminal domain is fully capable of antigen binding; i.e., a single-domain antibody fragment.

Exemplary antibodies and their cell markers (targets) contemplated for use include, but are not limited to, antibodies listed in Table A, and antibody fragments thereof.

TABLE A

| Antibody | Target |
|---|---|
| Adecatumumab (MT201) | EpCAM - CD326 |
| Afutuzumab | CD20 |
| Alemtuzumab (CAMPATH) | CD52 |
| Bavituximab | phosphatidylserine |
| Belimumab | BAFF, BLyS |
| Bevacizumab (AVASTIN) | VEGF-A |
| Brentuximab | CD30 |
| Cantuzumab | MUC1 |
| Cetuximab (ERBITUX) | EGF receptor |
| Citatuzumab | TACSTD1 |
| Cixutumumab | IGF-1 receptor |
| Conatumumab | TRAIL-R2 (CD262) |
| Dacetuzumab | CD40 |
| Elotuzumab | SLAMF7 (CD319) |
| Etaracizumab | alpha-v beta-3 integrin |
| Farletuzumab | FR-alpha |
| Figitumumab | IGF-1 receptor |
| Gemtuzumab | CD33 |
| Ibritumomab | CD20 |
| Inotuzumab (CMC-533) | CD22 |
| Ipilimumab (YERVOY) | CTLA-4 |
| Iratumumab | CD30 |
| Labetuzumab | carcinoembryonic antigen |
| Lexatumumab | TRAIL-R2 |
| Lintuzumab | CD33 |
| Lucatumumab | CD40 |
| Mapatumumab | TRAIL-receptor (death receptor 4) |
| Matuzumab | EGFR |
| Milatuzumab | CD74 |
| Necitumumab | EGFR |
| Nimotuzumab | EGFR |
| Ofatumumab (ARZERRA) | CD20 |
| Olaratumab | PDGF-R α |
| Oportuzumab | EpCAM |
| Panitumumab (VECTIBIX) | EGFR |
| Pertuzumab (PERJETA) | HER2 |
| Pritumumab | vimentin |
| Rituximab (RITUXAN) | CD20 |
| Robatumumab | CD221 |
| Sibrotuzumab | FAP |
| Siltuximab | IL-6 |
| Tacatuzumab | α-fetoprotein |
| Tigatuzumab | TNFRSF10B (TRAIL-R2) |
| Tositumomab (BEXXAR) | CD20 |
| Trastuzumab (HERCEPTIN) | HER2/neu |
| Tucotuzumab | EpCAM |
| Veltuzumab | CD20 |
| Votumumab | mor antigen CTAA16.88 |
| Zalutumumab | EGFr |

In certain embodiments, the antibody is Trastuzumab (HERCEPTIN) or an antibody fragment thereof.

Groups A, a, X, and Y and Methods of Preparation

As is generally understood from the above disclosure, the compound of Formula (P-I), comprising at least one -L$^1$-X group attached thereto, is coupled to a compound of formula Y-L$^2$-B or iteratively coupled to one or more independent instances of a compound of formula Y-L$_2$-X before being coupled (capped) with a compound of formula Y-L$^2$-B. See, e.g., Schemes 1 and 2. In certain embodiments, the coupling comprises a reaction typically referred to as "click chemistry." Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition).

Scheme 1.

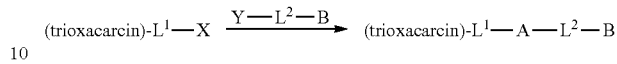

Scheme 2.

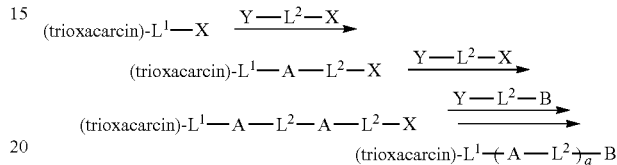

In general, for the compound of Formula (P-I), the group Y should be complimentary and reactive with the group X present on the precursor compound in order to form the compound of Formula (A), (I), and (II). For example, the if the group Y of Y-L$^2$-B or Y-L$^2$-X is a nucleophilic group, the group X must be a electrophilic group. Likewise, if the group Y of Y-L$^2$-B or Y-L$^2$-X is an electrophilic group, the group X must be a nucleophilic group. While X and Y are defined the same, it is thus understood that such groups are paired compliments.

As generally defined herein, X and Y may be selected from the group consisting of:

—SH, —OH, —NH$_2$, —NH—NH$_2$, —N$_3$, —O—NH$_2$, halogen (or other leaving group),

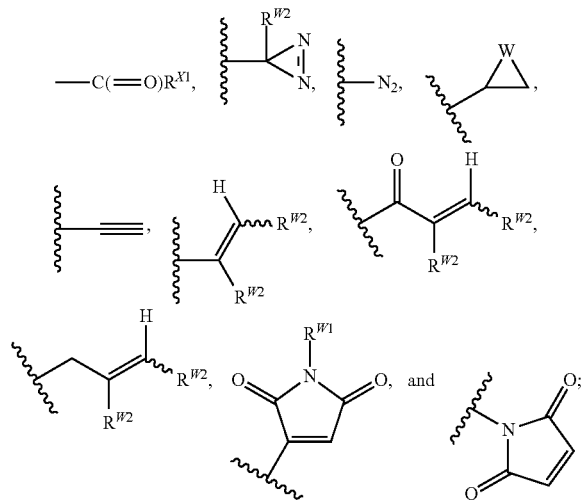

wherein:

R$^{X1}$ is hydrogen, halogen, or —OR$^{X2}$, wherein R$^{X2}$ is hydrogen; substituted or unsubstituted alkyl; substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; an oxygen protecting group;

W is O, S, or NR$^{W1}$;

R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group; and R$^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl, or two R$^{W2}$ groups are joined to form a 5-6 membered ring.

In certain embodiments, Y is —SH. In certain embodiments, X is —SH.

In certain embodiments, Y is —OH. In certain embodiments, X is —OH.

In certain embodiments, Y is —NH$_2$. In certain embodiments, X is —NH$_2$.

In certain embodiments, Y is —NH—NH$_2$. In certain embodiments, X is —NH—NH$_2$.

In certain embodiments, Y is —O—NH$_2$. In certain embodiments, X is —O—NH$_2$.

In certain embodiments, Y is —N$_3$. In certain embodiments, X is —N$_3$.

In certain embodiments, Y is halogen, e.g., —Cl, —Br, or —I. In certain embodiments, X is halogen, e.g., —Cl, —Br, or —I.

In certain embodiments, Y is —C(=O)R$^{X1}$, wherein R$^{X1}$ is hydrogen, i.e., to provide Y as an aldehyde —CHO. In certain embodiments, X is —C(=O)R$^{X1}$, wherein R$^{X1}$ is hydrogen, i.e., to provide X as an aldehyde —CHO.

In certain embodiments, Y is —C(=O)R$^{X1}$, wherein R$^{X1}$ is halogen (e.g., "Hal" representing —Cl, —Br, and —I), i.e., to provide Y as an acyl halide —C(=O)—Hal.

In certain embodiments, X is —C(=O)R$^{X1}$, wherein R$^{X1}$ is halogen (e.g., "Hal" representing —Cl, —Br, and —I), i.e., to provide X as an acyl halide —C(=O)—Hal.

In certain embodiments, Y is —C(=O)R$^{X1}$, wherein R$^{X1}$ is —OR$^{X2}$, and wherein R$^{X2}$ is hydrogen, i.e., to provide Y as a carboxylic acid —C(=O)OH.

In certain embodiments, X is —C(=O)R$^{X1}$, wherein R$^{X1}$ is —OR$^{X2}$, and wherein R$^{X2}$ is hydrogen, i.e., to provide X as a carboxylic acid —C(=O)OH.

In certain embodiments, Y is —C(=O)R$^{X1}$, wherein R$^{Z1}$ is —OR$^{X2}$, and wherein R$^{X2}$ is a substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or an oxygen protecting group, i.e., to provide Y as an ester —C(=O)OR$^{X2}$.

In certain embodiments, X is —C(=O)R$^{X1}$, wherein R$^{Z1}$ is —OR$^{X2}$, and wherein R$^{X2}$ is a substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or an oxygen protecting group, i.e., to provide X as an ester —C(=O)OR$^{X2}$.

In certain embodiments, Y is an oxiranyl, thiorenyl, or azirdinyl group of formula:

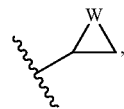

wherein W is O, S, or NR$^{W1}$. In certain embodiments, W is O. In certain embodiments, W is S. In certain embodiments, W is NR$^{W1}$.

In certain embodiments, X is an oxiranyl, thiorenyl, or azirdinyl group of formula:

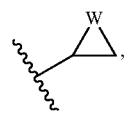

wherein W is O, S, or NR$^{W1}$. In certain embodiments, W is O. In certain embodiments, W is S. In certain embodiments, W is NR$^{W1}$.

In certain embodiments, X or Y is ethynyl:

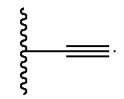

In certain embodiments, X or Y is ethenyl or propenyl:

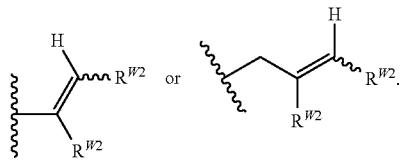

In certain embodiments, X or Y is an α,β-unsaturated carbonyl:

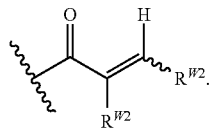

In certain embodiments X or Y is a maleimide group:

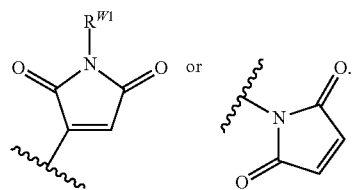

In certain embodiments, X or Y is a group:

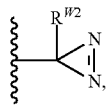

wherein $R^{W2}$ is alkyl, e.g., methyl.

In certain embodiments, X or Y is a group:

Furthermore, as generally defined herein, X and Y react together to form a group A, wherein A is a group of the formula:

—NH—, —NH—NH—, —NH—O—, —O—NH—, —S—, —O—,

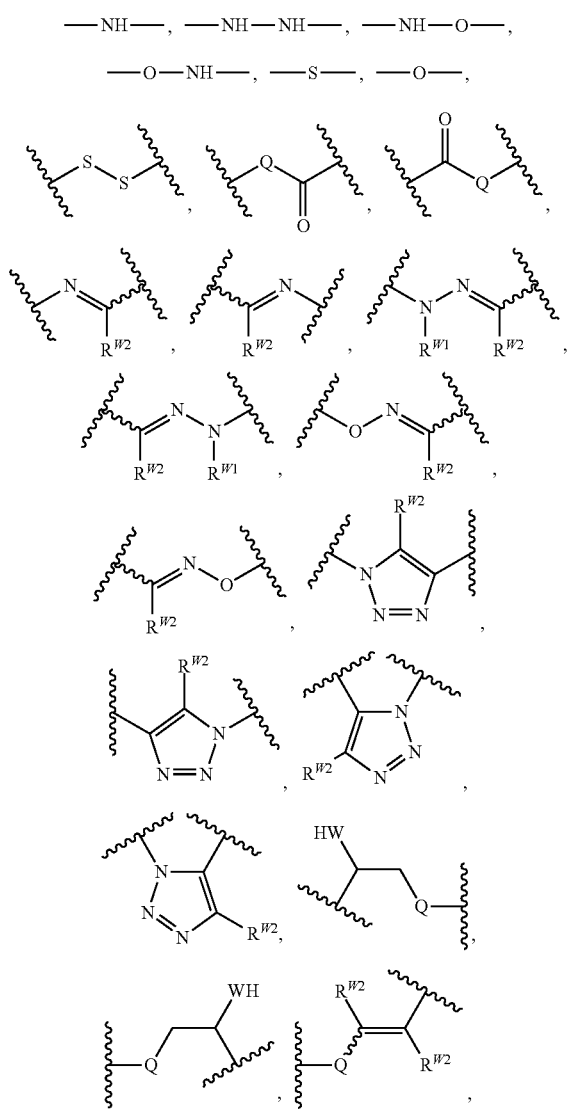

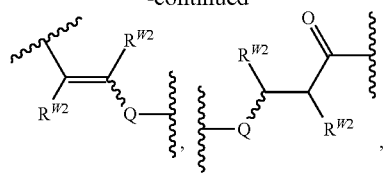

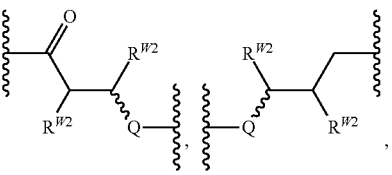

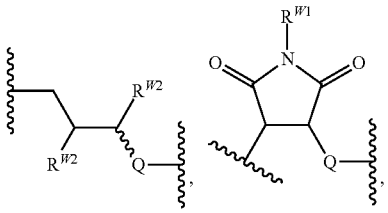

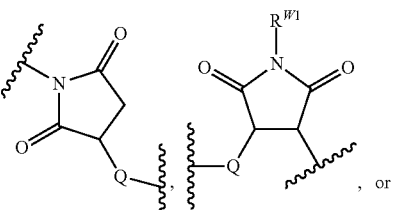

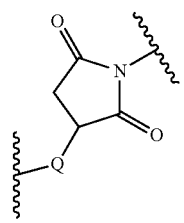

wherein:

Q is —NH—, —NH—NH—, —O—NH—, —NH—O—, —S—, —O—;

W is O, S, or $NR^{W1}$;

$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group; and $R^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl, or two $R^{W2}$ groups are joined to form a 5-6 membered ring;

In certain embodiments, A is —NH—.

In certain embodiments, A is —NH—NH—.

In certain embodiments, A is —S—.

In certain embodiments, A is —O—.

In certain embodiments, A is a disulfide group

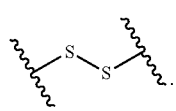 [SMILES: *SS*]

In certain embodiments, A is

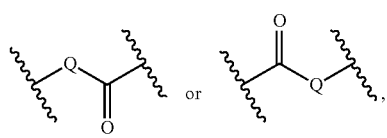

wherein Q is —NH—, —NH—NH—, —O—NH—, —NH—O—, —S—, —O—. For example, in certain embodiments, wherein Q is —NH—, A is an amide group of the formula

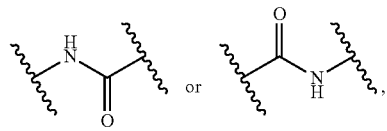 [SMILES: *NC(*)=O ; *NC(*)=O]

In certain embodiments, wherein Q is —NH—NH—, A is an amide hydrazide group of the formula

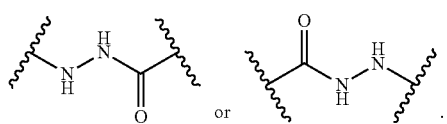 [SMILES: *NNC(*)=O ; *NNC(*)=O]

In certain embodiments, wherein Q is —S—, A is an thioester group of the formula

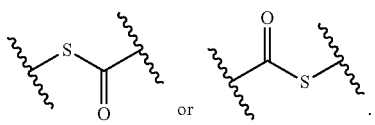 [SMILES: *SC(*)=O ; *SC(*)=O]

In certain embodiments, wherein Q is —O—, A is an ester group of the formula

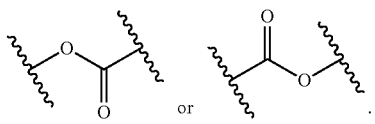 [SMILES: *OC(*)=O ; *OC(*)=O]

In certain embodiments, A is

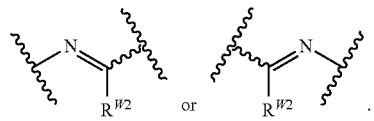

In certain embodiments, $R^{W2}$ is alkyl, e.g., methyl.

In certain embodiments, A is

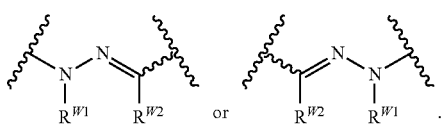

In certain embodiments, $R^{W2}$ is alkyl, e.g., methyl. In certain embodiments, $R^{W1}$ is hydrogen.

In certain embodiments, A is

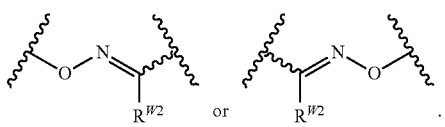

In certain embodiments, $R^{W2}$ is alkyl, e.g., methyl.

In certain embodiments, A is:

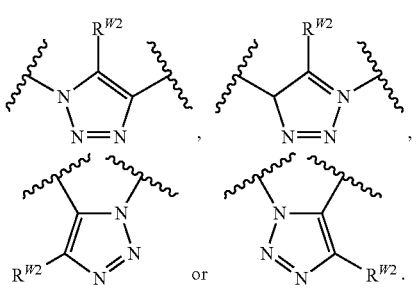

In certain embodiments, A is:

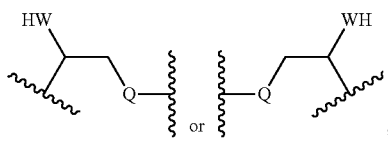

wherein W is O, S, or $NR^{W1}$, $R^{W1}$ is hydrogen, substituted or unsubstituted alkyl, or an amino protecting group; and Q is —NH—, —NH—NH—, —O—NH—, —NH—O—, —S—, or —O—. In certain embodiments, W is O. In certain embodiments, W is S. In certain embodiments, W is $NR^{W1}$. In certain embodiments, Q is —NH—. In certain embodiments, Q is —NH—NH—. In certain embodiments, Q is —S—. In certain embodiments, Q is —O—.

In certain embodiments, A is:

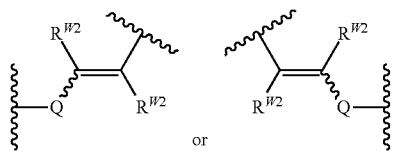

or wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, A is:

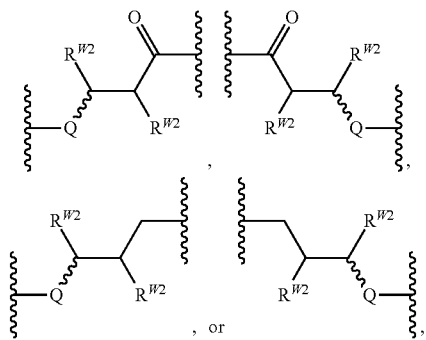

, or wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, A is:

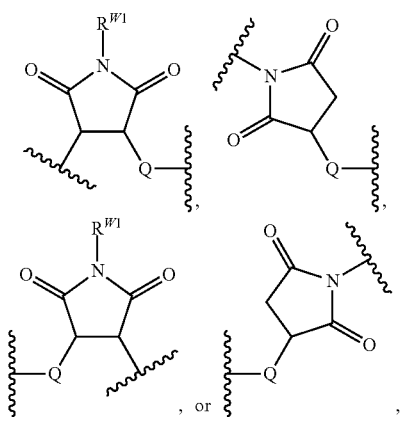

, or wherein W is O, S, or $NR^{W1}$, $R^{W1}$ is hydrogen, substituted or unsubstituted alkyl, or an amino protecting group; and Q is —NH—, —NH—NH—, —O—NH—, —NH—O—, —S—, or —O—. In certain embodiments, W is O. In certain embodiments, W is S. In certain embodiments, W is $NR^{W1}$. In certain embodiments, Q is —NH—. In certain embodiments, Q is —NH—NH—. In certain embodiments, Q is —S—. In certain embodiments, Q is —O—.

In one aspect, provided is a method of preparing a compound of Formula (A), (I), and (II), or pharmaceutically acceptable salt thereof, comprising at least one group $-L^1$-$(A-L^2)_a$-B attached thereto, the method comprising optionally coupling a precursor compound of Formula (P-I), or pharmaceutically acceptable salt thereof, comprising at least one group $-L^1$-X attached thereto, with 1, 2, 3, 4, 5, 6, 7, 8, 9 independent iterations of a compound of formula Y-$L_2$-X, followed by coupling (capping) with a compound of formula Y-$L_2$-B.

It is understood that if the interative method of reacting the precursor compound with one Y-$L_2$-X is employed, followed by coupling (capping) with Y-$L_2$-B, a group of formula $-L^1$-$(A-L^2)_a$-B will be provided wherein a is 2. It is further understood that if the interative method of reacting the precursor compound with 2, 3, 4, 5, 6, 7, 8, or 9 independent iterations of Y-$L_2$-X is employed, followed by coupling (capping) with Y-$L_2$-B, a group of formula $-L^1$-$(A-L^2)_a$-B will be provided wherein a is 3, 4, 5, 6, 7, 8, 9, or 10, respectively.

It is further understood that if the method does not employ the optional interative method, as described above, but instead comprises reacting the precursor compound with Y-$L_2$-B, a group of formula $-L^1$-$(A-L^2)_a$-B will be provided wherein a is 1.

For simplicity, the below described methods do not describe the optional interative method, as described above, but instead describe the reaction of a precursor compound with Y-$L_2$-B to provide a group of formula $-L^1$-A-$L^2$-B, i.e., wherein a is 1. However, it is fully within the scope of the present method to modify any of the methods described below, with the iterative approach, to arrive at compounds of Formula (A), (I), and (II) comprising a group of formula $-L^1$-$(A-L^2)_a$-B attached thereto, wherein a is 2, 3, 4, 5, 6, 7, 8, 9, or 10.

In certain embodiments, the method of preparing a compound of Formula (A), (I), and (II) comprises coupling a precursor compound of Formula (P-I) with a compound of formula Y-$L_2$-B, wherein one of X and Y is —C(=O)$R^{X1}$, wherein $R^{X1}$ is halogen or —$OR^{X2}$, and the other of X and Y is —SH, —OH, —$NH_2$, or —NH—$NH_2$ to provide a compound of Formula (A), (I), and (II), wherein A is an amide, thioester, or ester group. See, for example, Scheme 3 and Table 1.

Scheme 3. Preparation of compounds of Formula (A), (I), and (II) via amide, thioester, and ester formation

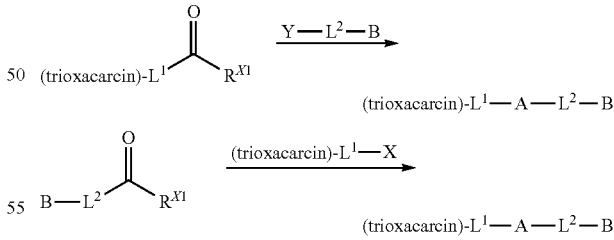

TABLE 1

| $R^{X1}$ | Y | X | A<br>—C(=O)Q-, -QC(=O)— |
|---|---|---|---|
| halogen or —$OR^{X2}$ | —SH | — | —C(=O)S— |
|  | — | —SH | —SC(=O)— |
|  | —OH | — | —C(=O)O— |
|  | — | —OH | —OC(=O)— |

TABLE 1-continued

| $R^{X1}$ | Y | X | A<br>—C(=O)Q-, -QC(=O)— |
|---|---|---|---|
|  | —NH₂ | — | —C(=O)NH— |
|  | — | —NH₂ | —NHC(=O)— |
|  | —NH—NH₂ | — | —C(=O)NHNH— |
|  | — | —NH—NH₂ | —NHNHC(=O)— |

In certain embodiments, the method of preparing a compound of Formula (A), (I), and (II) comprises coupling a precursor compound of Formula (P-I) with a compound of formula Y-L₂-B, wherein one of X and Y is halogen or another leaving group, and the other of X and Y is —SH, —OH, —NH₂, or —NH—NH₂ to provide a compound of Formula (A), (I), and (II), wherein A is, respectively, —S—, —O—, —NH—, or —NH—NH—. See, for example, Scheme 4 and Table 2.

Scheme 4. Nucleophilic displacement of a halide or other leaving group (trioxacarcin)-L¹—Hal $\xrightarrow{\text{Y—L}^2\text{—B}}$ (trioxacarcin)-L¹—A—L²—B B—L²—Hal $\xrightarrow{\text{X—L}^1\text{-(trioxacarcin)}}$ (trioxacarcin)-L¹—A—L²—B

TABLE 2

| Y | X | A |
|---|---|---|
| Hal or other leaving group | —SH | —S— |
|  | —OH | —O— |
|  | —NH₂ | —NH— |
|  | —NH—NH₂ | —NH—NH— |
|  | —O—NH₂ | —O—NH— |
| —SH | Hal or other leaving group | —S— |
| —OH |  | —O— |
| —NH₂ |  | —NH— |
| —NH—NH₂ |  | —NH—NH— |
| —O—NH₂ |  | —NH—O— |

In certain embodiments, the method of preparing a compound of Formula (A), (I), and (II) comprises coupling a precursor compound of Formula (P-I) with a compound of formula Y-L₂-B, wherein one of X and Y is

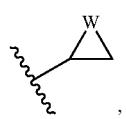

and the other of X and Y is —SH, —OH, —NH₂, or —NH—NH₂ to provide the coupled compound of Formula (A), (I), and (II). See, for example, Scheme 5 and Table 3.

Scheme 5. Nucleophilic addition to strained ring systems

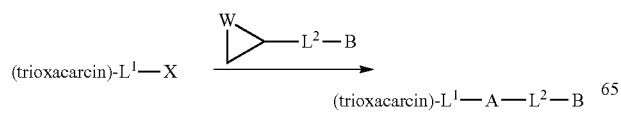

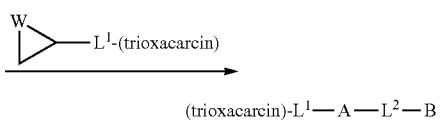

TABLE 3

| W | Y | X | A |
|---|---|---|---|
| O,S,NR^{W1} | —SH | — | (HW-CH-CH₂-S-) |
|  | —OH | — | (HW-CH-CH₂-O-) |
|  | —NH₂ | — | (HW-CH-CH₂-HN-) |
|  | —NH—NH₂ | — | (HW-CH-CH₂-HN—NH-) |
|  | —O—NH₂ | — | (HW-CH-CH₂-HN—O-) |
| O,S,NR^{W1} | — | —SH | (-S-CH₂-CH-WH) |
|  | — | —OH | (-O-CH₂-CH-WH) |
|  | — | —NH₂ | (-NH-CH₂-CH-WH) |
|  | — | —NH—NH₂ | (-HN-NH-CH₂-CH-WH) |

TABLE 3-continued

| W | Y | X | A |
|---|---|---|---|
| — | — | —O—NH$_2$ | 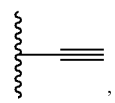 |

In certain embodiments, the method of preparing a compound of Formula (A), (I), and (II) comprises coupling (azide-alkyne Huisgen cycloaddition of) a precursor compound of Formula (P-I) with a compound of formula Y-L$_2$-B, wherein one of X and Y is

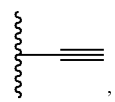

and the other of X and Y is —N$_3$ to provide the compound of Formula (A), (I), and (II). See, for example, Scheme 6 and Table 4.

Scheme 6.1 Azide-alkyne Huisgen cycloaddition (trioxacarcin)-L$^1$—X $\xrightarrow{\equiv\!\!\!\equiv\!\!\!\equiv\text{—L}^2\text{—B}}$ (trioxacarcin)-L$^1$—A—L$^2$—B B—L$^2$—Y $\xrightarrow{\equiv\!\!\!\equiv\!\!\!\equiv\text{—L}^1\text{-(trioxacarcin)}}$ (trioxacarcin)-L$^1$—A—L$^2$—B

TABLE 4

| X | Y | A (1,4-adduct) | A (1,5-adduct) |
|---|---|---|---|
| — | —N$_3$ | 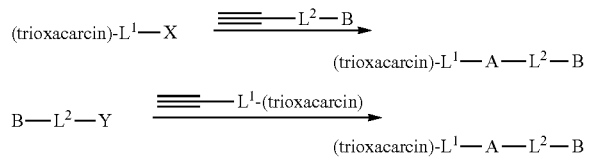 | |
| —N$_3$ | — | | |

In certain embodiments, the method of preparing a compound of Formula (A), (I), and (II) comprises coupling (via thiol-yne addition of) a precursor compound of Formula (P-I) with a compound of formula Y-L$_2$-B, wherein one of X and Y is and the other of X and Y is —SH to provide the compound of Formula (A), (I), and (II). See, for example, Scheme 7 and Table 5.

Scheme 7. Thiol-yne addition (trioxacarcin)-L$^1$—X $\xrightarrow{\equiv\!\!\!\equiv\!\!\!\equiv\text{—L}^2\text{—B}}$ (trioxacarcin)-L$^1$—A—L$^2$—B B—L$^2$—Y $\xrightarrow{\equiv\!\!\!\equiv\!\!\!\equiv\text{—L}^1\text{-(trioxacarcin)}}$ (trioxacarcin)-L$^1$—A—L$^2$—B

TABLE 5

| X | Y | A |
|---|---|---|
| — | —SH | 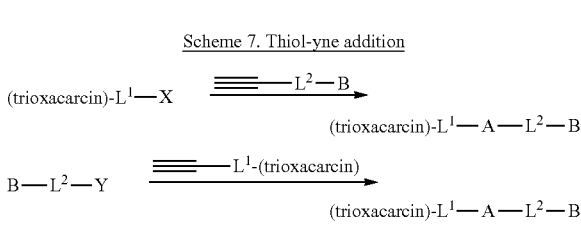 |
| —SH | — | |

In certain embodiments, the method of preparing a compound of Formula (A), (I), and (II) comprises coupling a precursor compound of Formula (P-I) with a compound of formula Y-L$_2$-B, wherein one of X and Y is an aldehyde —CHO or ketone, and the other of X and Y is —NH$_2$, —NH—NH$_2$, or —O—NH$_2$ to provide the compound of Formula (A), (I), and (II). See, for example, Scheme 8 and Table 6.

Scheme 8. Imine formation (trioxacarcin)-L$^1$—X $\xrightarrow{\overset{O}{\underset{H}{\|}}\text{—L}^2\text{—B}}$ (trioxacarcin)-L$^1$—A—L$^2$—B B—L$^2$—Y $\xrightarrow{\overset{O}{\underset{H}{\|}}\text{—L}^1\text{-(trioxacarcin)}}$ (trioxacarcin)-L$^1$—A—L$^2$—B

TABLE 6

| X | Y | A |
|---|---|---|
| — | —NH$_2$ | 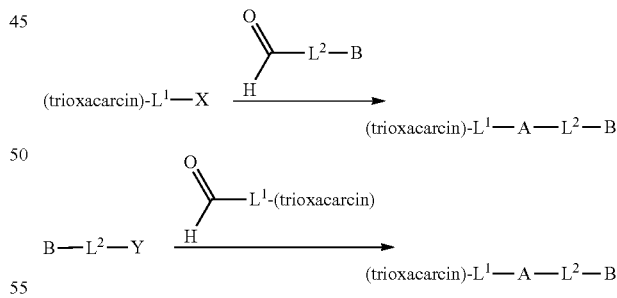 |

TABLE 6-continued

| X | Y | A |
|---|---|---|
| — | —NH—NH$_2$ | (structure: hydrazone with R$^{W2}$ and R$^{W1}$) |
| — | —O—NH$_2$ | (structure: oxime with R$^{W2}$) |
| —NH$_2$ | — | (structure: imine with R$^{W2}$) |
| —NH—NH$_2$ | — | (structure: hydrazone with R$^{W1}$ and R$^{W2}$) |
| —O—NH$_2$ | — | (structure: oxime with R$^{W2}$) |

In certain embodiments, the method of preparing a compound of Formula (A), (I), and (II) comprises coupling a precursor compound of Formula (P-I) with a compound of formula Y-L$_2$-B, wherein one of X and Y is an α,β-unsaturated carbonyl, and the other of X and Y is —OH, —SH, —NH$_2$, —NHNH$_2$, or —O—NH$_2$ to provide the compound of Formula (A), (I), and (II). See, for example, Scheme 9 and Table 7.

Scheme 9. Michael addition

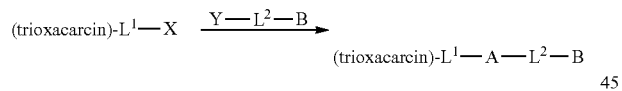

TABLE 7

| X | Y | A |
|---|---|---|
| (α,β-unsaturated ketone with R$^{W2}$, R$^{W2}$) | —OH,—SH,—NH$_2$, —NHNH$_2$,—O—NH$_2$ | (saturated ketone with R$^{W2}$, R$^{W2}$, Q) |
| —OH,—SH,—NH$_2$, —NHNH$_2$,—O—NH$_2$ | (α,β-unsaturated ketone with R$^{W2}$, R$^{W2}$) | (saturated ketone with R$^{W2}$, Q, R$^{W2}$) |

In certain embodiments, the method of preparing a compound of Formula (A), (I), and (II) comprises coupling a precursor compound of Formula (P-I) with a compound of formula Y-L$_2$-B, wherein one of X and Y is a maleimide group, and the other of X and Y is —OH, —SH, —NH$_2$, —NHNH$_2$, or —O—NH$_2$ to provide the compound of Formula (A), (I), and (II). See, for example, Scheme 10 and Table 8.

Scheme 10. Maleimide addition

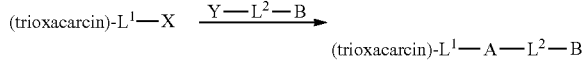

TABLE 8

| X | Y | A |
|---|---|---|
| (maleimide with R$^{W1}$) | —OH,—SH,—NH$_2$, —NHNH$_2$,—O—NH$_2$ | (succinimide with R$^{W1}$, Q) |
| (maleimide N-substituted) | —OH,—SH,—NH$_2$, —NHNH$_2$,—O—NH$_2$ | (succinimide N-substituted with Q) |
| —OH,—SH,—NH$_2$, —NHNH$_2$,—O—NH$_2$ | (maleimide with R$^{W1}$) | (succinimide with R$^{W1}$, Q) |

TABLE 8-continued

| X | Y | A |
|---|---|---|
| —OH, —SH, —NH$_2$, —NHNH$_2$, —O—NH$_2$ | | |

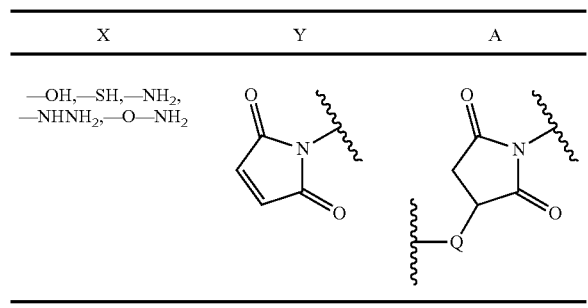

In certain embodiments, the method of preparing a compound of Formula (A), (I), and (II) comprises coupling a precursor compound of Formula (P-I) with a compound of formula Y-L$_2$-B, wherein each of X and Y is —SH to provide, upon treatment with an oxidant, a compound of Formula (A), (I), and (II), wherein A is a disulfide bond. See, for example, Scheme 11.

Scheme 9. Disulfide formation

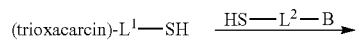

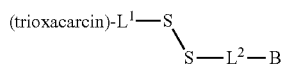

Additional Embodiments of the Preparative Method

Particular sites of the trioxacarcin scaffold are specifically contemplated for attachment of one or more groups -L$^1$-X to provide a compound of Formula (P-A), (P-I), and (P-II) and further provide a antibody-drug conjugate of Formula (A), (I), and (II). As would be appreciated by one of skill in the art, there are many sites on the trioxacarcin scaffold which are considered to be suitable for attachment of the group -L$^1$-X, and the below discussion should not be considered limiting in any way to the scope of the present invention.

In certain embodiments, the northern or southern glycosides functionalized with a group -L$^1$-X may be attached employing standard glycosylation conditions. See, for example, Schemes 12 and 13. For Scheme 12, see also Lear et al., *Angew. Chem.*, Int. Ed. (2001) 113: 972-975; and Ren et al., *J. Am. Chem. Soc.* (2007) 129:5381-5383. For Scheme 13, see also Kimura et al., *Chem. Lett.* (1984) 501-504; Kimura et al., *Bull. Chem. Soc. Jpn.* (1986) 59:423-431.

Scheme 12. Attachment of the Northern Glycoside functionalized with —L$^1$—X

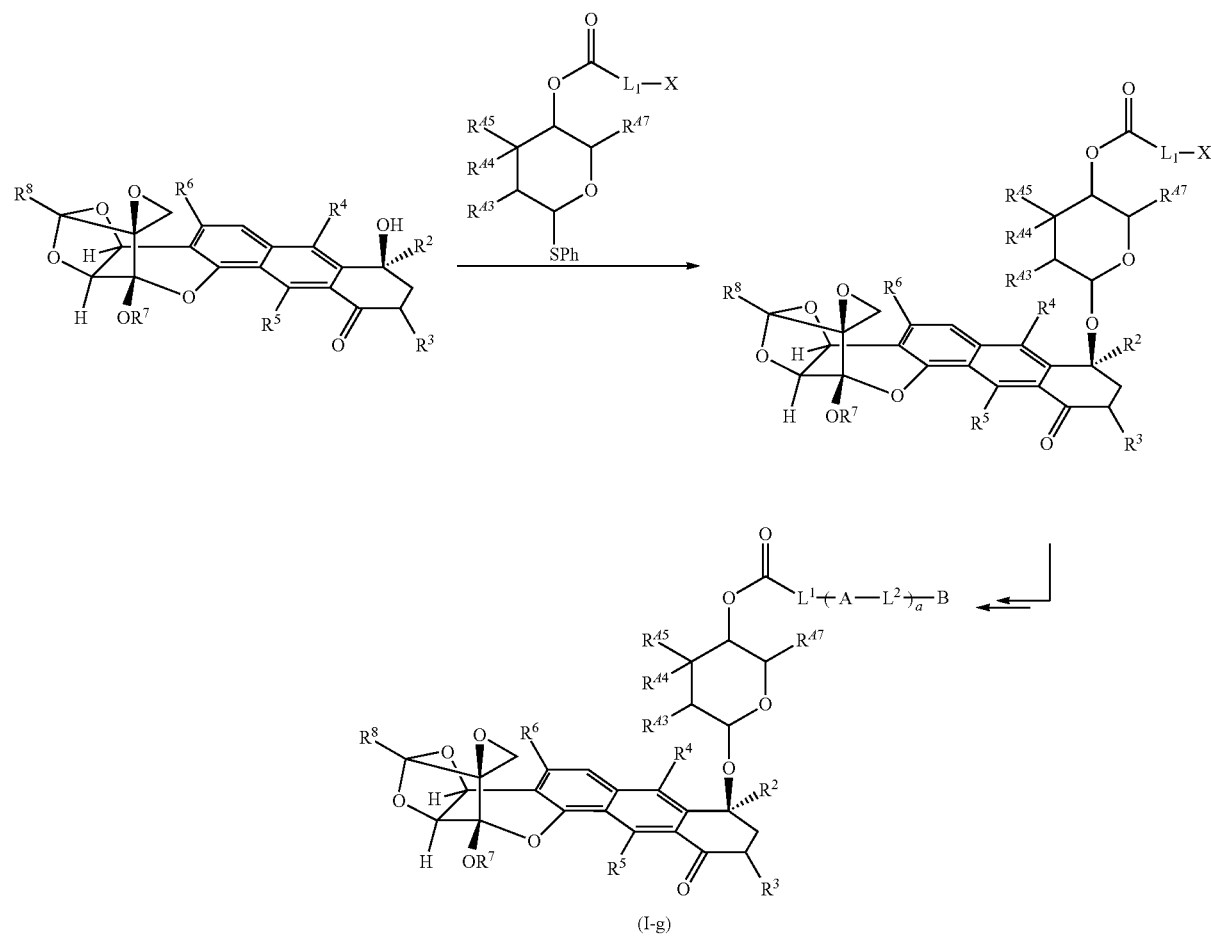

Scheme 13. Attachment of the Southern Glycoside functionalized with —L¹—X

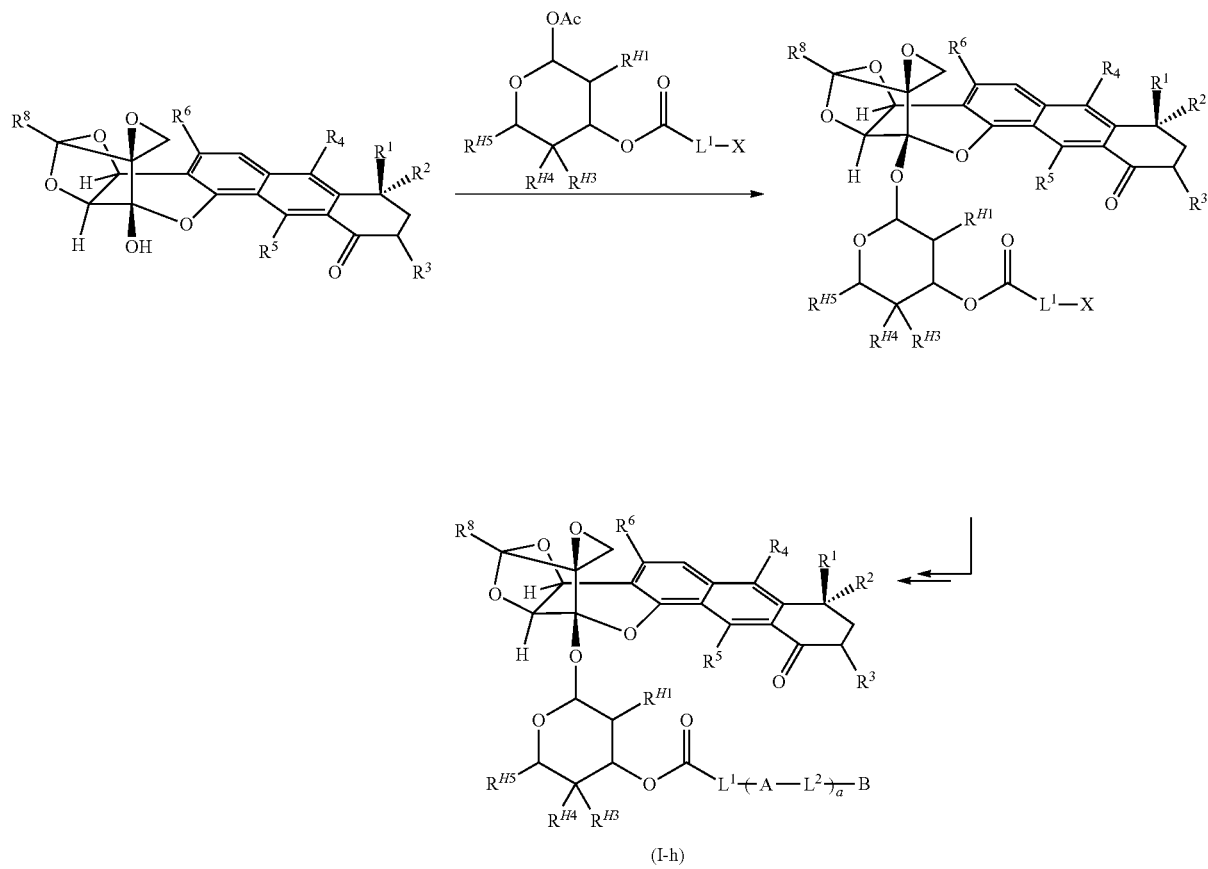

(I-h)

In certain embodiments, the glycosides already attached to the trioxacarcin scaffold may be synthetically manipulated. For example, manipulation of the southern glycoside by oxime formation, hydrazone formation, reductive amination, or ester formation, provides a trioxacarcin functionalized with a group -L¹-X. See Schemes 14-1

Scheme 14. Oxime Modification of the Southern Glycoside

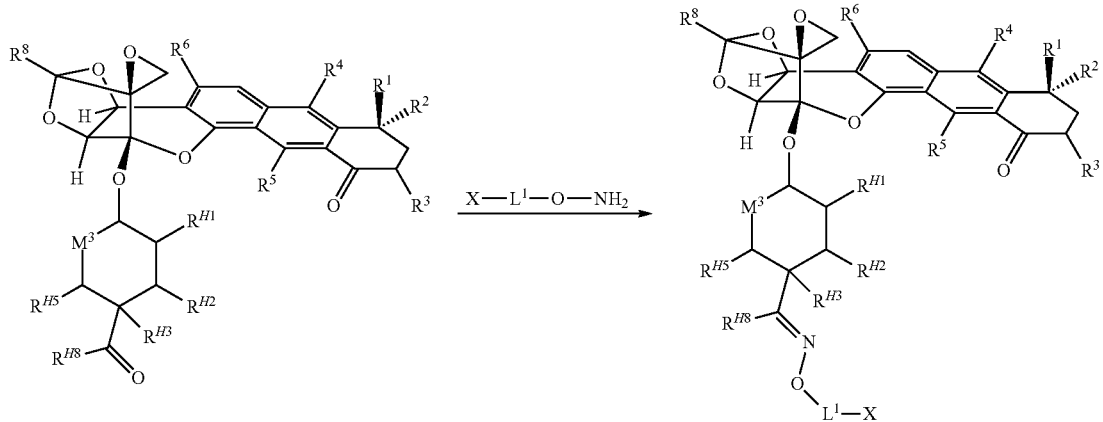

-continued
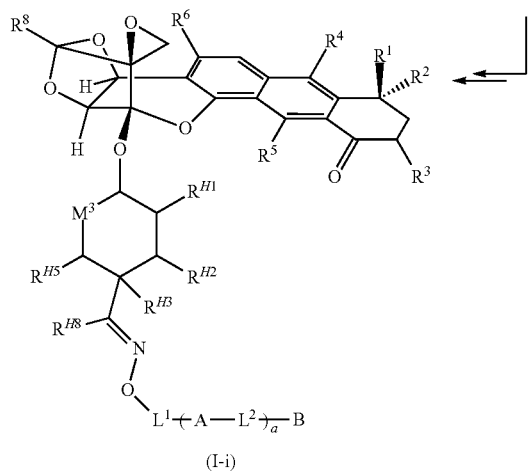
(I-i)
Scheme 15. Hydrazone Modification of the Southern Glycoside
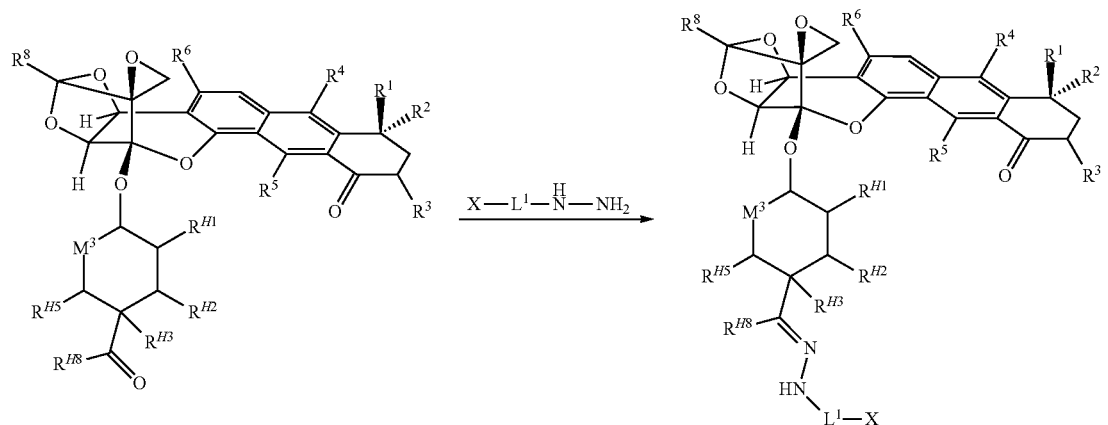
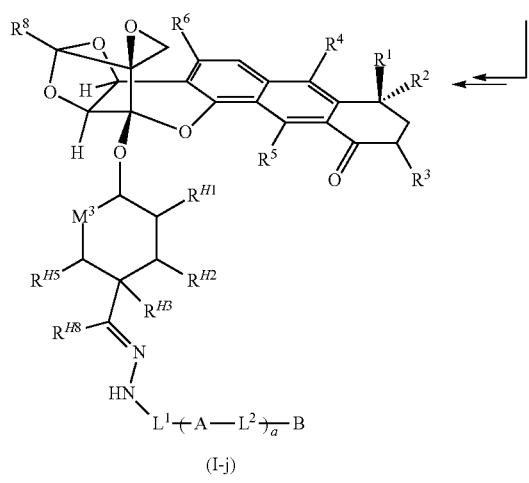
(I-j)

Scheme 16. Reductive Amination of the Southern Glycoside
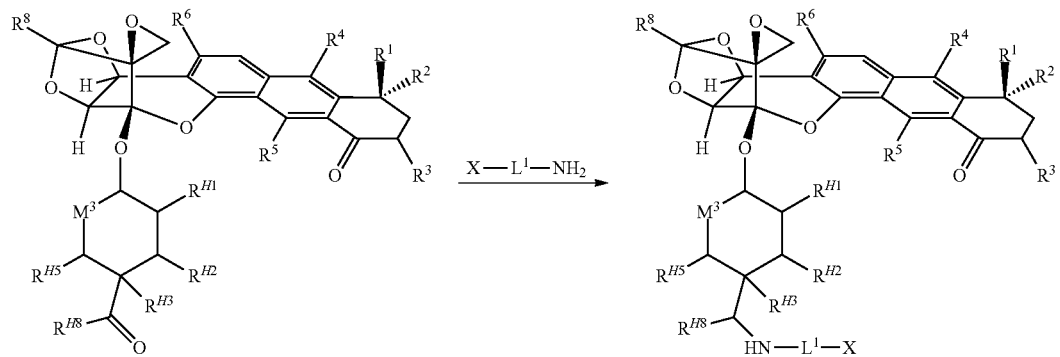
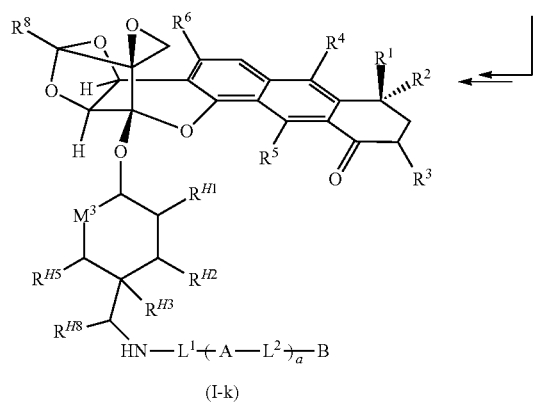
(I-k)
Scheme 17. Ester Formation of the Southern Glycoside
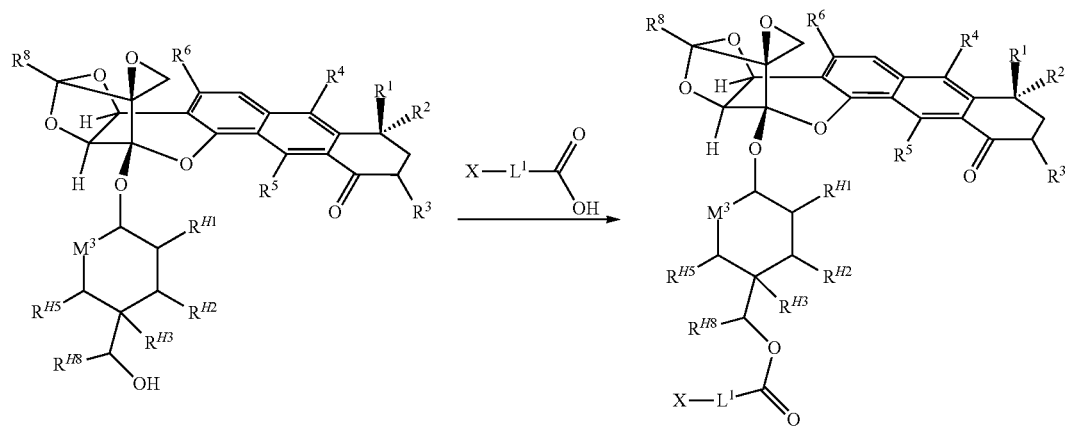

-continued

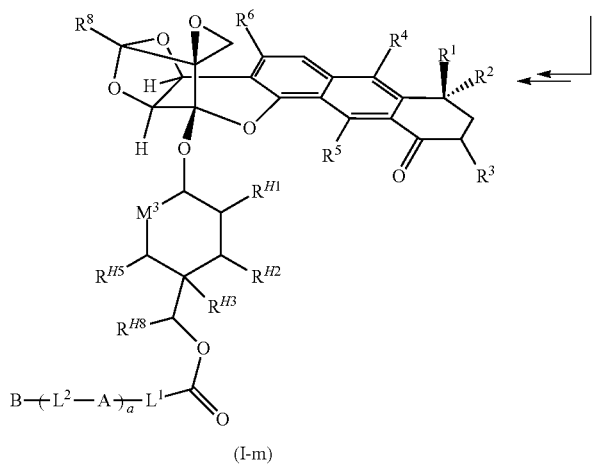

(I-m)

In certain embodiments, the western hemisphere of the trioxacarcin scaffold may be manipulated. For example, attachment of the group -$L^1$-X via ester formation provides a functionalized trioxacarcin. See Scheme 18.

Scheme 18. Ester Formation at the Western Hemisphere

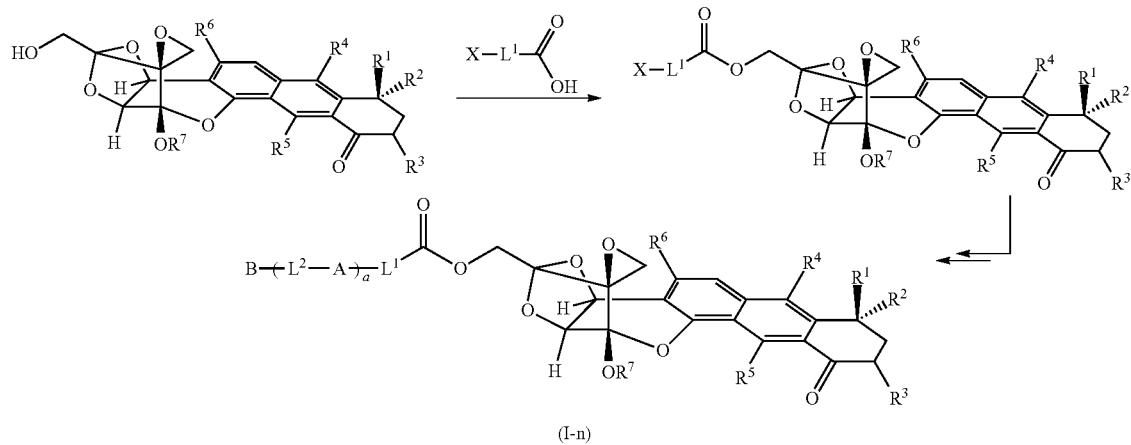

(I-n)

Trioxacarcin Compounds without an Antibody Conjugated Thereto

The present invention also recognizes certain trioxacarcin compounds which are novel and active even without an antibody conjugated thereto.

For example, the inventors have discovered that simplified analogs which remove the oxygenation of the right-hand ring are quite potent and in some cases more so than their oxygenated counterparts. See, e.g., compounds disclosed in FIG. 10. Particular compounds of this family include compounds of Formula (I-x), (I-c), (I-f), and (I-d), (II-x), (II-c), (II-f), and (II-d), and pharmaceutically acceptable salts thereof, wherein $R^G$, $R^{A1}$, $R^{C1}$, $R^{D1}$, $R^{E1}$, $R^6$, $R^7$, and $R^8$ are as defined herein, provided that the compound does not comprise an antibody conjugated thereto.

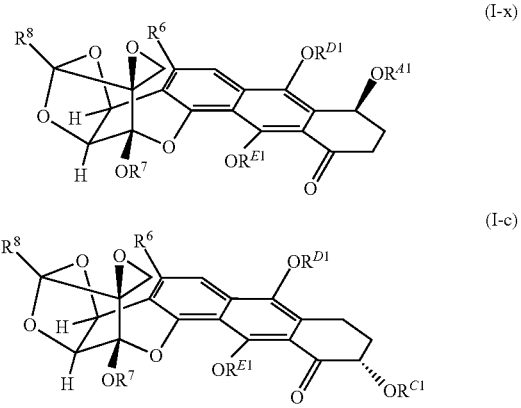

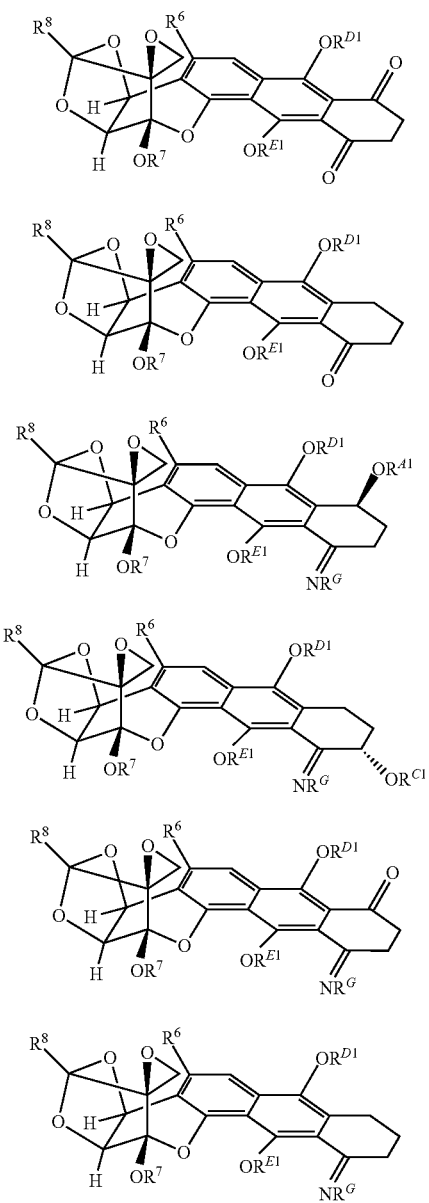

Pharmaceutical Compositions

In certain embodiments, the present invention provides a pharmaceutical composition comprising an active ingredient and, optionally, a pharmaceutically acceptable excipient. In certain embodiments, the active ingredient is present in an effective amount, e.g., a therapeutically effective amount or a prophylactically effective amount.

An "active ingredient," as used herein, refers to trioxacarcin-antibody conjugates of Formula (A), (I), and (II), precursor compounds of Formula (P-A), (P-I), or (P-II), or novel trioxacarcin compounds without an antibody conjugated thereto, and pharmaceutically acceptable salts thereof.

A pharmaceutical composition of the present disclosure can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by epidermal administration (e.g., by injection or infusion). The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, the pharmaceutical composition can be administered via a non-parenteral route, such as a topical, epidermal or mucosal route of administration, for example, intranasally, orally, vaginally, rectally, sublingually or topically.

Depending on the route of administration, the pharmaceutical composition or active ingredient may be coated in a material to protect the compound from the action of acids and other natural conditions that may inactivate the compound.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutical compositions described herein can be prepared by any method known in the art of pharmacology. In general, such preparatory methods include the steps of bringing the active ingredient into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility.

The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes.

The active ingredient can be prepared with carriers that will protect the active ingredient against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Pharmaceutical compositions can be administered with medical devices known in the art. For example, in a preferred embodiment, a pharmaceutical composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

The exact amount of the active ingredient required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an active ingredient for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of the active ingredient per unit dosage form.

In certain embodiments, the active ingredient may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that the active ingredient or composition, as described herein, can be administered in combination with one or more additional therapeutically active agents. The active ingredient or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-cancer agent, etc.), and/or it may achieve different effects (e.g., control of adverse side-effects, e.g., emesis controlled by an anti-emetic).

The active ingredient or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the active ingredient with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, cancer therapies, antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestant, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants/anti-epileptics (e.g., Neurontin, Lyrica, valproates (e.g., Depacon), and other neuro-stabilizing agents), muscle relaxants, anti-spasmodics, muscle contractants, channel blockers, miotic agents, antisecretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g., cell growth inhibitors and anti-adhesion molecules), or inhibitors/intercalators of DNA, RNA, protein-protein interactions, protein-receptor interactions, etc. Therapeutically active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutic agent is a cancer therapy. Cancer therapies include, but are not limited to, surgery and surgical treatments, radiation therapy, and administration of additional therapeutic cancer agents (e.g., biotherapeutic and chemotherapeutic cancer agents).

Exemplary biotherapeutic cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic cancer agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichlorometotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g., 1-methyl-4-phenylpyridinium ion), cell cycle inhibitors (e.g. staurosporine), actinomycin (e.g., actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In other embodiments, the additional therapeutically active agent is an anti-inflammatory agent. Exemplary anti-inflammatory agents include, but are not limited to, aspirin; ibuprofen; ketoprofen; naproxen; etodolac (LODINE®); COX-2 inhibitors such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl) cyclopenta-2,4-dien-3-yl)benzene, 4-(1,5-Dihydro-6-fluoro-7-methoxy-3-(trifluoromethyl)-(2)-benzothiopyrano(4,3-c) pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIAPED® prednisolone sodium phosphate oral solution, SOLU-MEDROL® methylprednisolone sodium succinate for injection, PRELONE® brand prednisolone syrup.

Further examples of anti-inflammatory agents include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-Tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

In certain embodiments, the additional therapeutically active agent is a pain-relieving agent. Exemplary pain relieving agents include, but are not limited to, analgesics such as non-narcotic analgesics [e.g., salicylates such as aspirin, ibuprofen (MOTRIN®, ADVIL®), ketoprofen (ORUDIS®), naproxen (NAPROSYN®), acetaminophen, indomethacin] or narcotic analgesics [e.g., opioid analgesics such as tramadol, fentenyl, sufentanil, morphine, hydromorphone, codeine, oxycodone, and buprenorphine]; non-steroidal anti-inflammatory agents (NSAIDs) [e.g., aspirin, acetaminophen, COX-2 inhibitors]; steroids or anti-rheumatic agents; migraine preparations such as beta adrenergic blocking agents, ergot derivatives; tricyclic antidepressants (e.g., amitryptyline, desipramine, imipramine); anti-epileptics (e.g., clonaxepam, valproic acid, phenobarbital, phenytoin, tiagaine, gabapentin, carbamazepine, topiramate, sodium valproate); $\alpha_2$ agonists; selective serotonin reuptake inhibitors (SSRIs), selective norepinepherine uptake inhibitors; benzodiazepines; mexiletine (MEXITIL); flecainide (TAMBOCOR); NMDA receptor antagonists (e.g., ketamine, detromethorphan, methadone); and topical agents (e.g., capsaicin (Zostrix), EMLA cream, lidocaine, prilocaine).

Kits

Still further contemplated herein are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Use and Treatment

Further provided are methods of using compounds as described herein (e.g., trioxacarcin-antibody conjugates of Formula (A), (I), and (II), precursor compounds of Formula (P-A), (P-I), or (P-II), or novel trioxacarcin compounds which do not comprise an antibody conjugated thereto, and pharmaceutically acceptable salts thereof).

For example, in one aspect, provided is a method of treating a disease, disorder, or condition selected from the group consisting of cardiovascular diseases, proliferative diseases (e.g., cancer, benign tumors), diabetic retinopathy, inflammatory diseases, autoimmune diseases, and infectious diseases (e.g., bacterial infections, fungal infections, parasitic infections) comprising administering an effective amount of a compound of the present invention to a subject in need thereof.

In certain embodiments, the compound of the present invention is useful in the treatment of cardiovascular disease. Exemplary cardiovascular diseases include, but are not limited to, coronary heart disease, cardiomyopathy, hypertensive heart disease, heart failure, inflammatory heart disease, valvular heart disease, stroke, cerebrovascular disease, and peripheral arterial disease.

In certain embodiments, the compound of the present invention is useful in the treatment of a proliferative disease. Exemplary proliferative diseases include, but are not limited to, cancers and benign neoplasms. In certain embodiments, the proliferative disease is cancer. Exemplary cancers include, but are not limited to, acoustic neuroma, adenocarcinoma, adrenal gland cancer, anal cancer, angiosarcoma (e.g., lymphangiosarcoma, lymphangio-endotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrim's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above, e.g., mixed leukemia lymphoma (MLL); and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Trioxacarcins are known to be useful in the treatment of various cancers, such as ovarian, colorectal, hepatocellular, pancreatic cancer, and andenocarcinomas. See, e.g., Cassidy et al., *Cancer Chemother. Pharmacol.* (1993) 31:395-400; Tomita et al., *J. Antibiot.* (1981) 34:1519-1524. It is contemplated that various compounds of Formula (A), (I), and (II), conjugated to an antibody, will have even higher efficacy against these and other cancers as described herein.

In certain embodiments, the compound of the present invention is useful in the treatment of diabetic retinopathy.

In certain embodiments, the compound of the present invention is useful in the treatment of an inflammatory disease. Exemplary inflammatory diseases include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatitis.

In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, the compound of the present invention is useful in the treatment of an autoimmune disease. Exemplary autoimmune diseases include, but are not limited to, arthritis (e.g., including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the inflammatory disorder and/or the immune disorder is a gastrointestinal disorder. In some embodiments, the gastrointestinal disorder is selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS).

In certain embodiments, the compound of the present invention is useful in the treatment of an infectious disease (e.g., bacterial infection, fungal infection, and/or parasitic infection). In certain embodiments, the compound is useful in treating a parasitic infection (e.g., malaria). In certain embodiments, the compound is useful in treating a bacterial infection. In certain embodiments, the compound is useful in treating a fungal infection.

Trioxacarcins are known to have antibiotic and antiparasitic (e.g., anti-malarial) activity. See, e.g., U.S. Pat. No. 4,459,291; U.S. Pat. No. 4,511,560; Fujimoto et al., *J. Antibiot*. (1983) 36:1216-1221; Maiese et al. *J. Antibiot*. (1990) 43:253-258; Tomita et al., *J. Antibiot*. (1981) 34:1519-1524; and Maskey et al. *J. Antibiot*. (2004) 57:771-779 (antibacterial and antimalarial activity). It is contemplated that various compounds of Formula (A), (I), and (II), conjugated to an antibody, will have even higher efficacy against an infectious disease, such as a bacterial infection, and other infectious diseases as described herein.

Adducts

Figure 7:
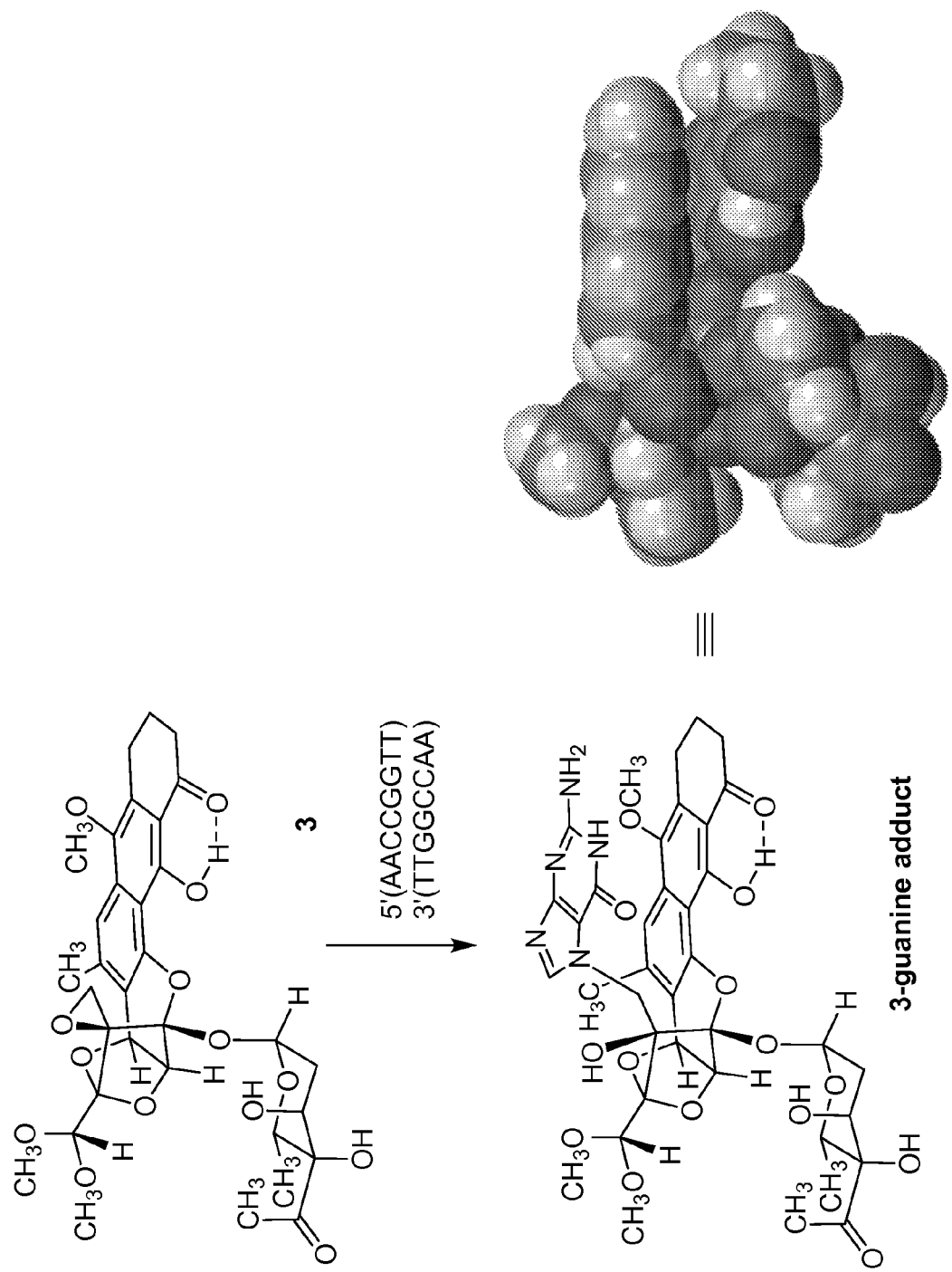
FIG. 7 depicts the guanine adduct formed from DNA alkylation of compound 3.
Figure 8:
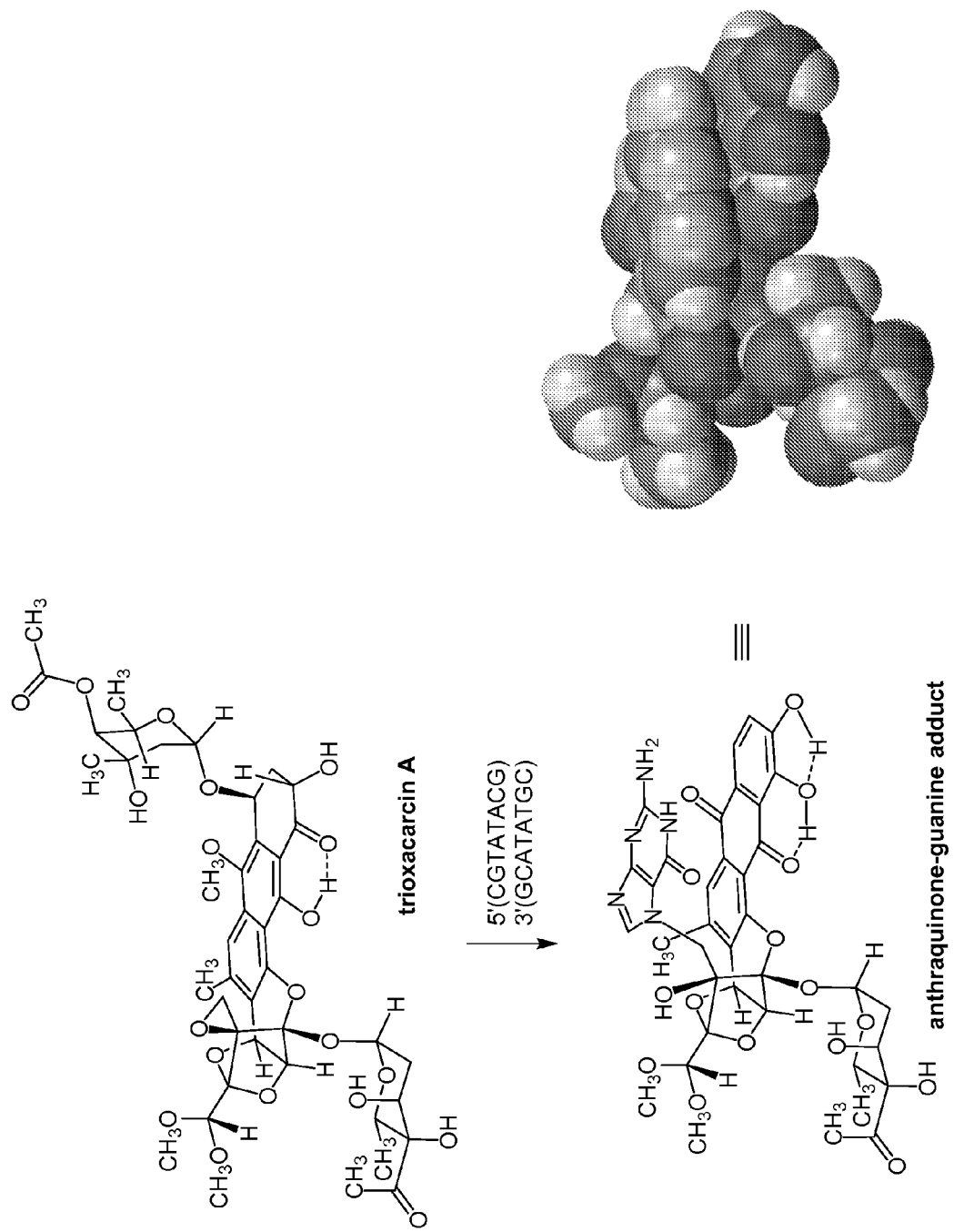
FIG. 8 depicts the anthraquinone-guanine adduct formed from DNA alkylation of trioxacarcin A.
Figure 9:
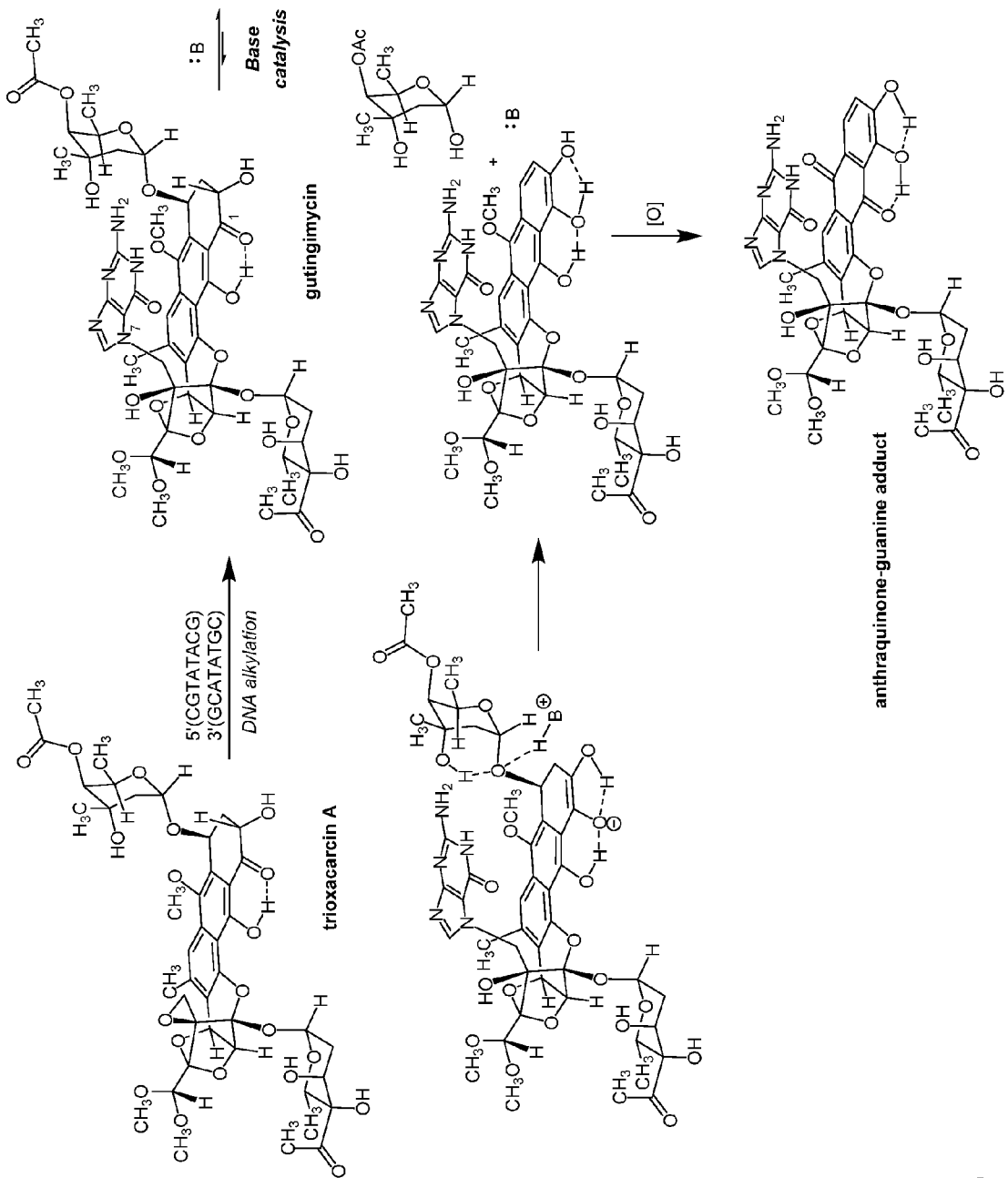
FIG. 9 depicts the proposed mechanism to form gutingimycin and the anthraquinone-guanine adduct from DNA alkylation of trioxacarcin A.

Further provided are products of nucleophilic addition, e.g., by water or hydroxide addition or by addition of guanine via DNA alkylation, of the trioxacarcins as described herein, contemplated useful, for example, as control compounds for assay and compound development. See, e.g., FIGS. 7-9, depicting adducts provided from guanine addition. One exemplary use contemplated is running a trioxacarcin compound of interest along side the corresponding guanine adduct (as a negative control), and confirming that the trioxacarcin compound of interest has a higher activity than the corresponding adduct. This result would suggest that the antiproliferative activity of the trioxacarcin of interest is due to its ability to form the guanine adduct.

In certain embodiments, provided are adducts of Formula (Adduct-I):

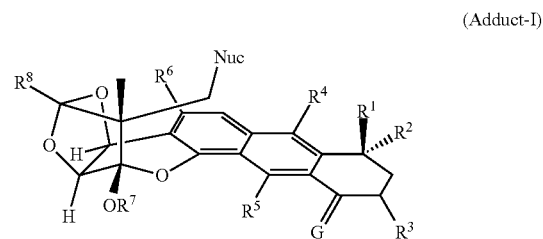

(Adduct-I)

wherein Nuc is —OH or the guanine radical:

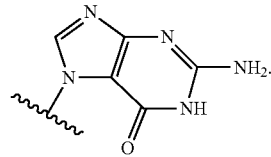 [SMILES: *n1cnc2nc(N)[nH]c(=O)c21]

Exemplary compounds of Formula (Adduct-I) include, but are not limited to,

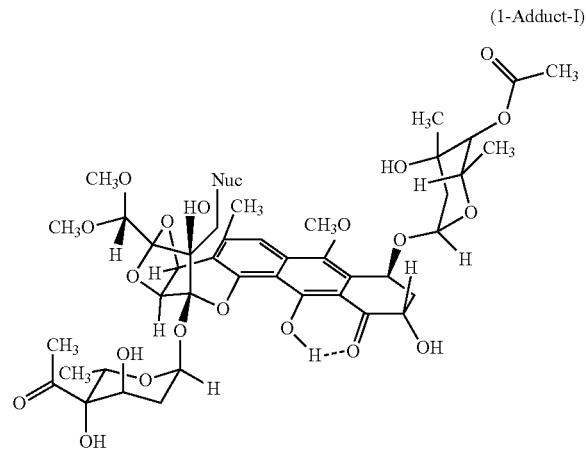

(1-Adduct-I)

Figure 10:
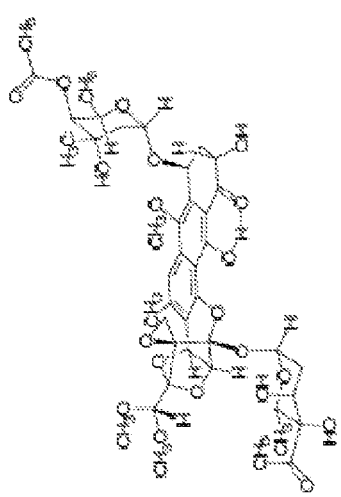
FIG. 10 compares the growth inhibition ($GI_{50}$) of some of the trioxacarcins studied in H460 cells, a large-cell lung carcinoma cell line; T-47D cells, a mammary ductal carcinoma cell line; HEK293 cells, an embryonic kidney cell line; N87 cells, a gastric carcinoma cell line; MDA-MB-361/DYT2 cells, a mammary adenocarcinoma cell line; HT-29 cells, a colorectal carcinoma cell line; HL-60 cells, an acute promyelocytic leukemia cell line; and HEL 92.1.7 cells, an erythroleukemia cell line
Figure 10:
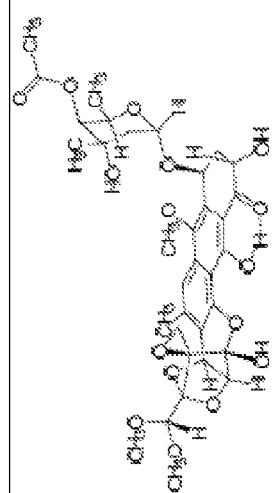
Figure 10:
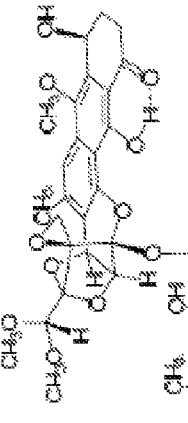
Figure 10:
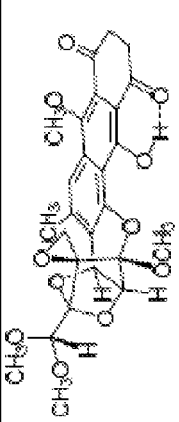
Figure 10:
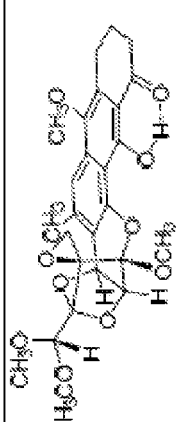
Figure 10:
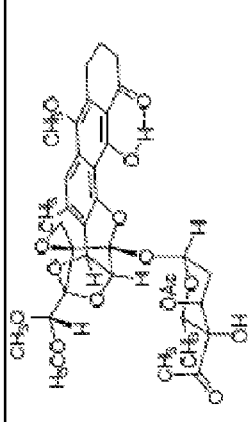
Figure 10:
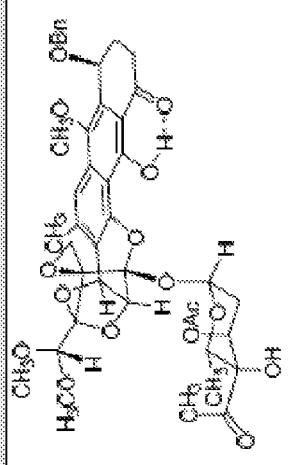
Figure 10:
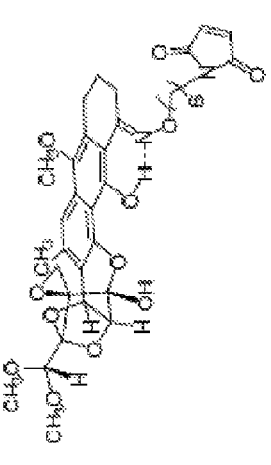
Figure 10:
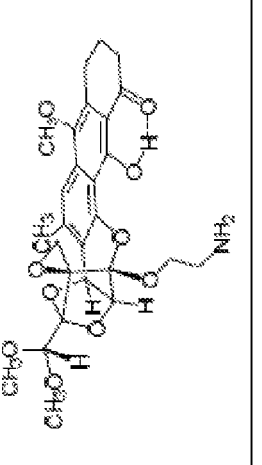
Figure 10:
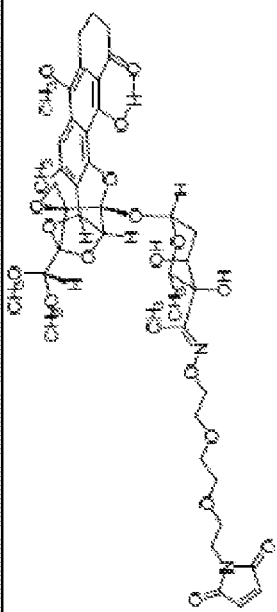
Figure 10:
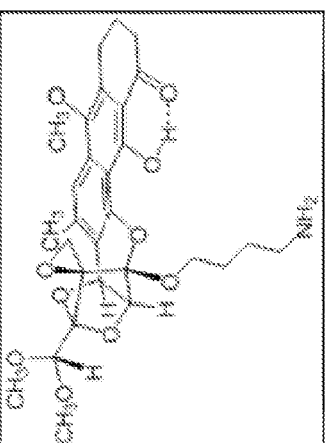

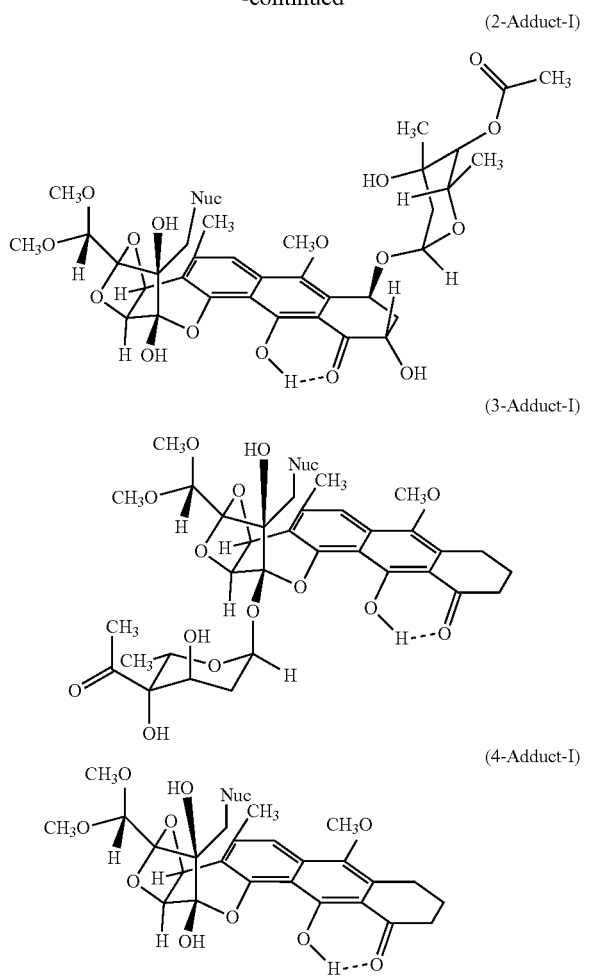

and the like. Adducts of compounds provided in FIG. 10 are further contemplated herein. In certain embodiments, the compound of Formula (Adduct-I) is not the trioxacarcin A-guanine adduct, gutingimycin, as depicted in FIG. 9.

Alternatively, in certain embodiments, provided are adducts of Formula (Adduct-II):

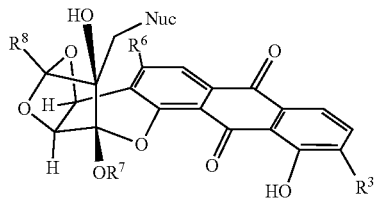

wherein Nuc is —OH or the guanine radical:

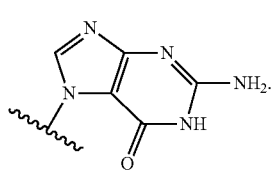 [SMILES: *n1cnc2nc(N)[nH]c(=O)c21]

Exemplary compounds of Formula (Adduct-II) include, but are not limited to,

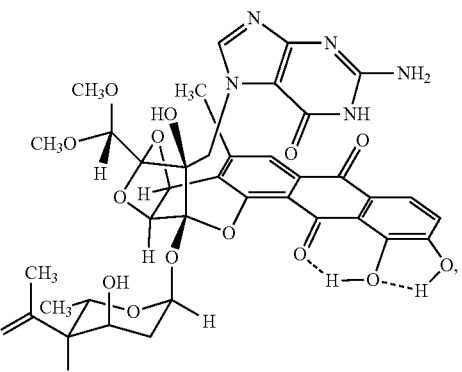

also referred to herein as the anthraquinone-guanine adduct of trioxacarcin A.

EXAMPLES

In order that the invention described herein may be more fully understood, the following examples are set forth. It should be understood that these examples are for illustrative purposes only and are not to be construed as limiting this invention in any manner.

Development of Trioxacarcin-Antibody Conjugates

Figure 3:
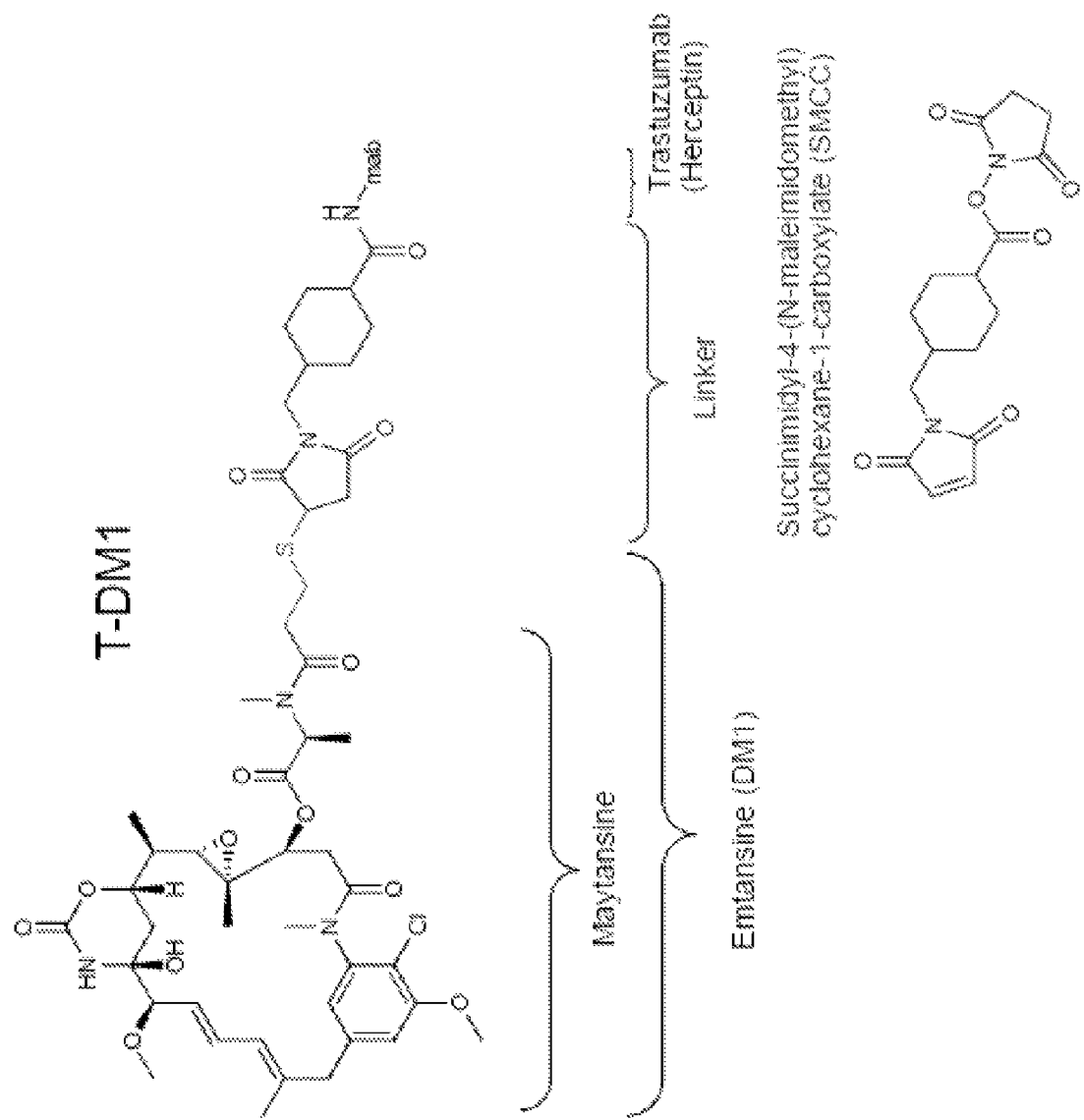
FIG. 3 depicts the linker strategy in T-DM1.
Figure 4:
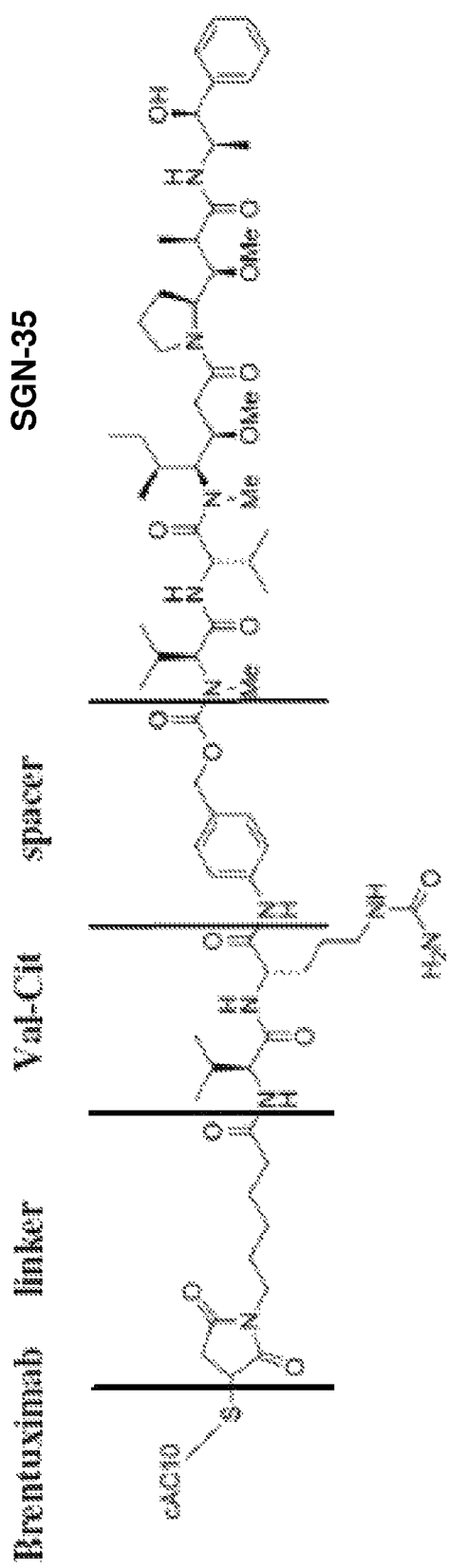
FIG. 4 depicts the linker strategy in SGN-35.

The most recent linker strategies for ADCs which have been applied in late-stage clinical trials were developed by ImmunoGen and Seattle Genetics. See, e.g., Teicher et al., *Clin. Cancer Res.* (2011) 17:6389-6397. Trastuzumab emtansine (T-DM1) consists of the cytotoxic drug DM1 from ImmunoGen and is attached via an SMCC-linker to lysines in the HER2-binding antibody trastuzumab. See, e.g., FIG. 3. Seattle Genetics's Adcetris consists of the drug SGN-35 attached via a peptide containing linker to the cysteines in the antibody Brentuximab. See, e.g., FIG. 4. These strategies use lysine or cysteine in the monoclonal antibody for conjugating to provide the ADC. In T-DM1 for example it is known that there are 1-8 drugs (DM1) per antibody (T). See, e.g., U.S. 2011/0165155.

An alternative strategy from Bertozzi et al. reports of site-specific chemical modification of monoclonal antibodies using a genetically encoded aldehyde tag. See, e.g., Bertozzi et al., *PNAS* (2008) 1-6; Bertozzi et al., *ACIE* (2012) 51:4161; Bertozzi et al., *Nature Protocols* (2012) 7:1052-1067. See also FIG. 5. Such aldehydes can react with an aminooxy reagent to form oximes, which are reported to be stable up to pH of 4-5. See, e.g., Zhu et al., *Biomacromolecules* (2011) 12:3460-3468.

Figure 6:
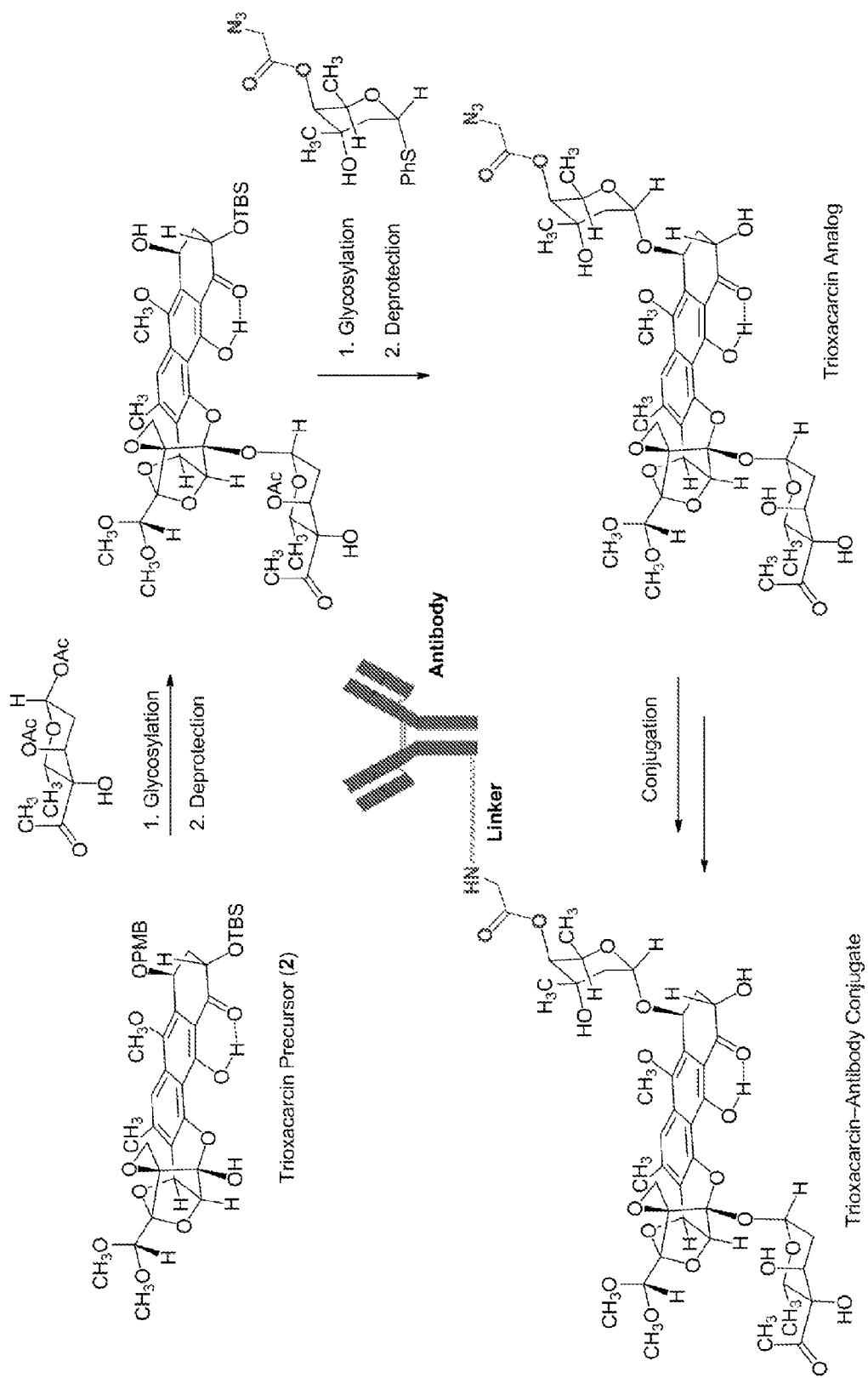
FIG. 6 depicts an exemplary synthesis of an α-azidoacetate analog of trioxacarcin A to provide a chemical handle for conjugation to an antibody. Other exemplary syntheses of trioxacarcin ADCs are provided in the Examples. See, e.g., Examples 1 to 21.

The trioxacarcin compound may be coupled to an antibody using any of the above described and other known methods for coupling known in the art. See, e.g., FIG. 6. For example, the trioxacarcin may be coupled to an antibody using one or more linkers terminally modified with reactive functional groups. Various linkers are contemplated, for example:

(a) Linking amine and thiol functionalities:

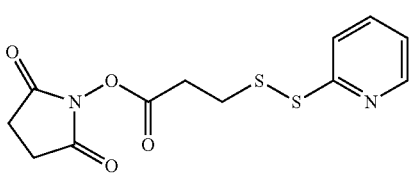

-continued

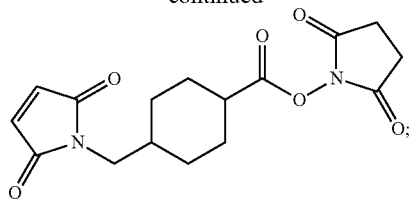

(b) Linking alcohol and thiol functionalities:

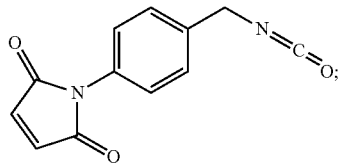 [SMILES: O=C=NCc1ccc(N2C(=O)C=CC2=O)cc1]

(c) Linking amine functionality to another, nonspecific functionality:

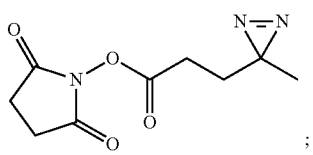 [SMILES: CC1(CCC(=O)ON2C(=O)CCC2=O)N=N1]

(d) Linking thiol and carbonyl functionalities:

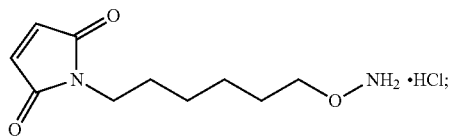 [SMILES: NOCCCCCCN1C(=O)C=CC1=O]

(e) Linking two thiol functionalities:

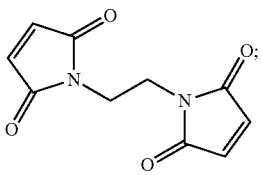 [SMILES: O=C1C=CC(=O)N1CCN1C(=O)C=CC1=O]

(f) Linking two amine functionalities:

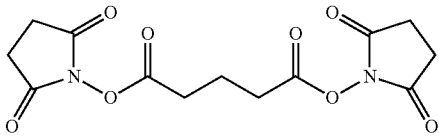 [SMILES: O=C(CCCC(=O)ON1C(=O)CCC1=O)ON1C(=O)CCC1=O]

The linkers listed above are all likely to be "non-cleavable" in vivo. The linkers could be modified in many ways, for example, by increasing or decreasing linker length, linker hydrophilicity (e.g., poly(ethylene glycol) instead of simple alkyl), and/or including moieties such as peptides, polypeptides, hydrazones, and/or disulfides in the linker to render the linker cleavable in vivo.

Example 1

Trioxacarcin Ketone Functionalization by Oxime Formation and Michael Addition of the Antibody

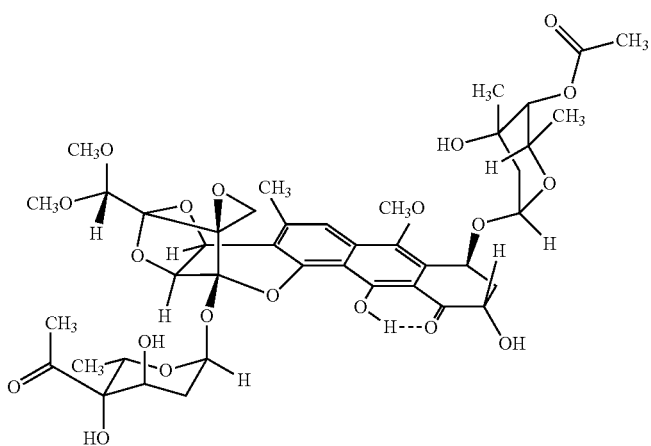

131     132
-continued
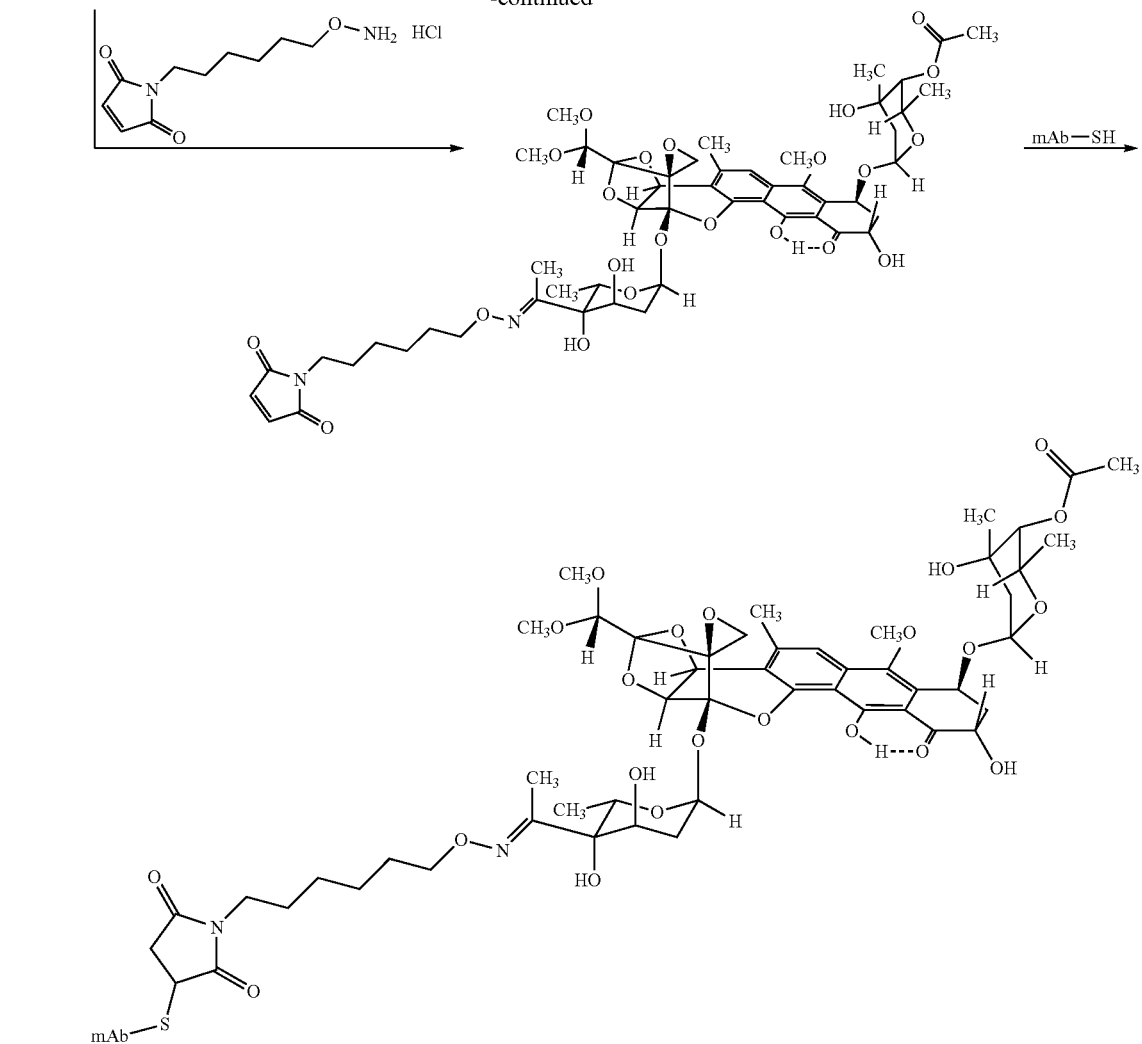
Example 2
Trioxacarcin Ketone Functionalization by Oxime Formation and Michael Addition of the Antibody
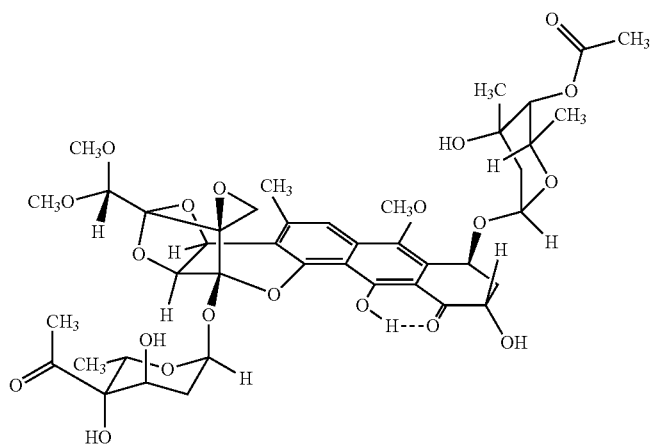

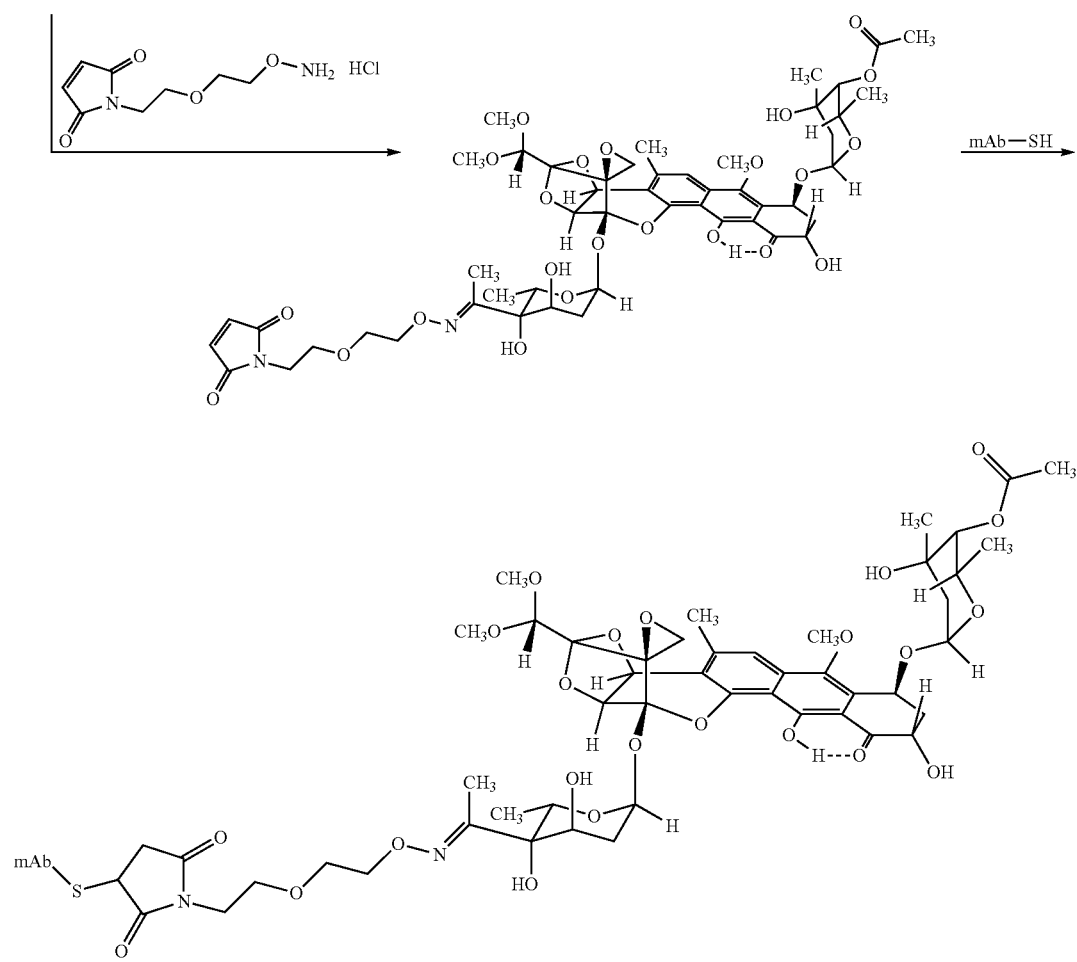
Example 3
Trioxacarcin Ketone Functionalization by Hydrazone Formation and Michael Addition of the Antibody
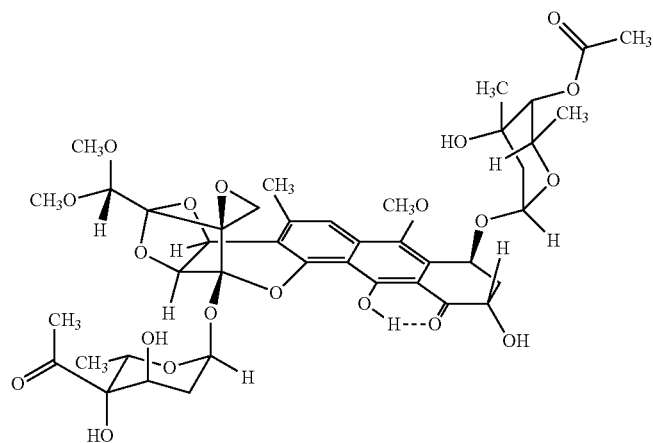

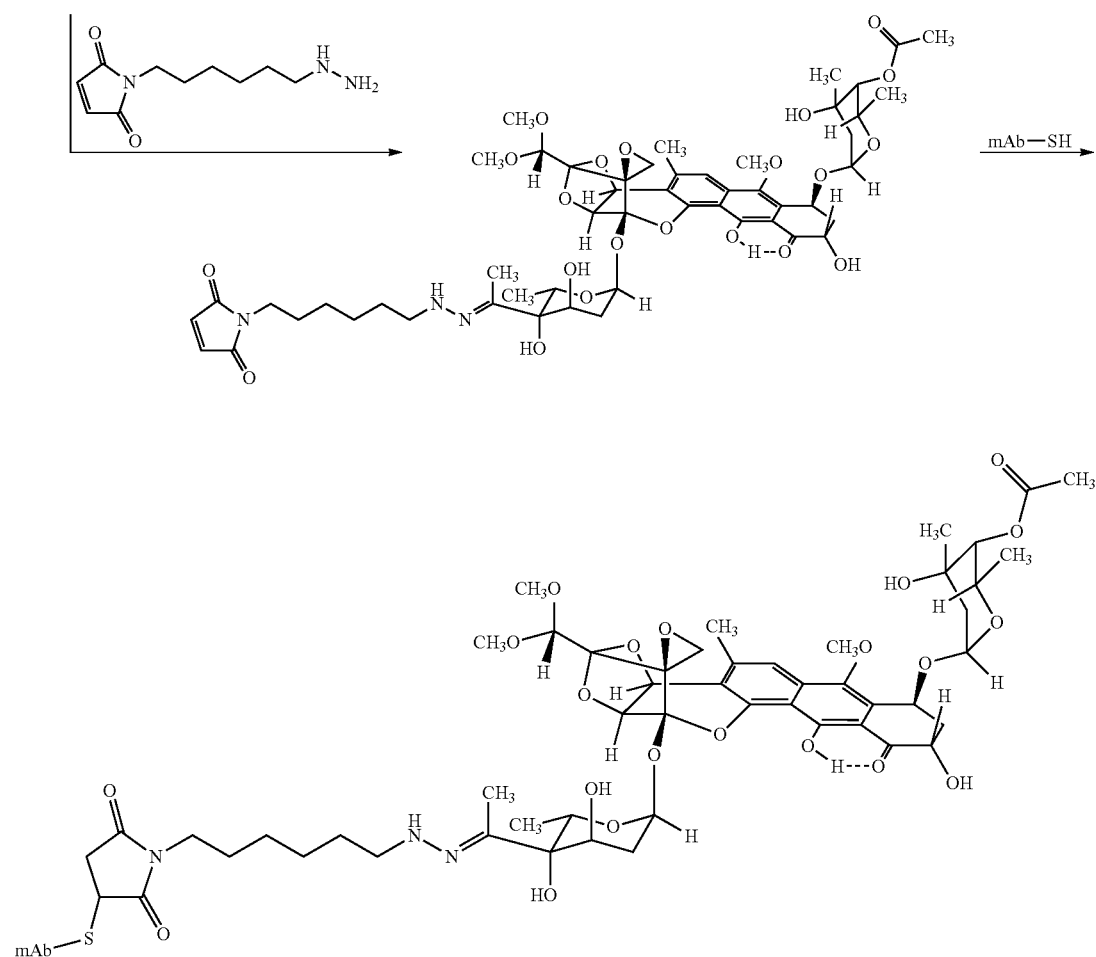
Example 4
Trioxacarcin Ketone Functionalization by Reductive Amination and Michael Addition of the Antibody
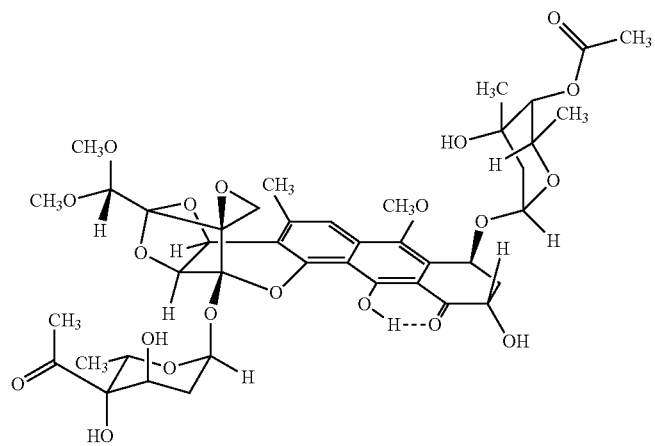

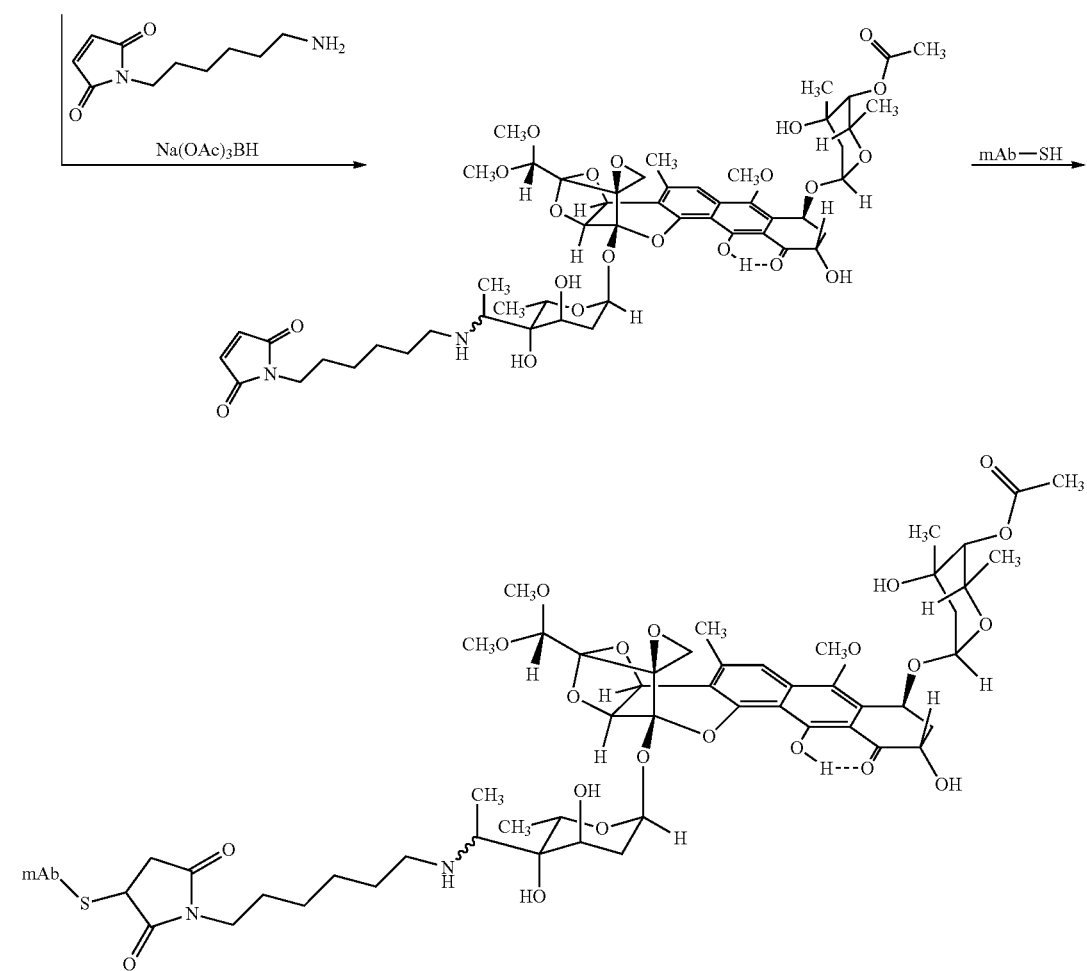
Example 5
Trioxacarcin Ketone Functionalization by Reduction, Ester Formation, and Michael Addition of the Antibody
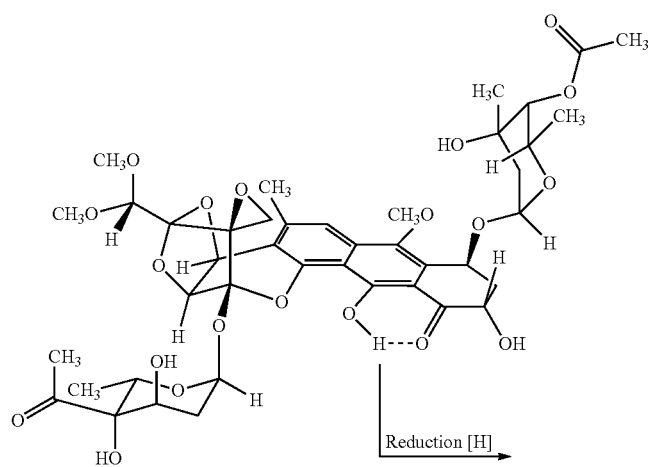

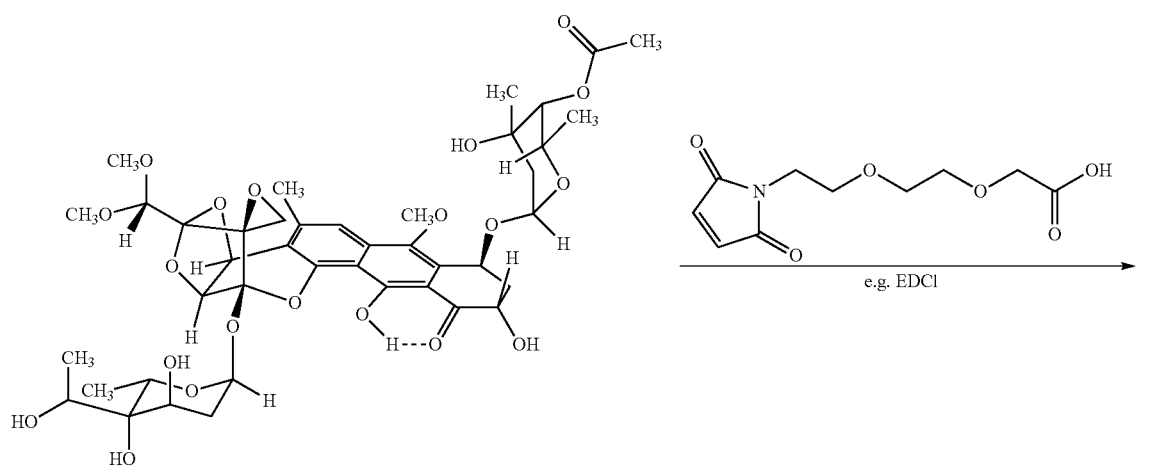
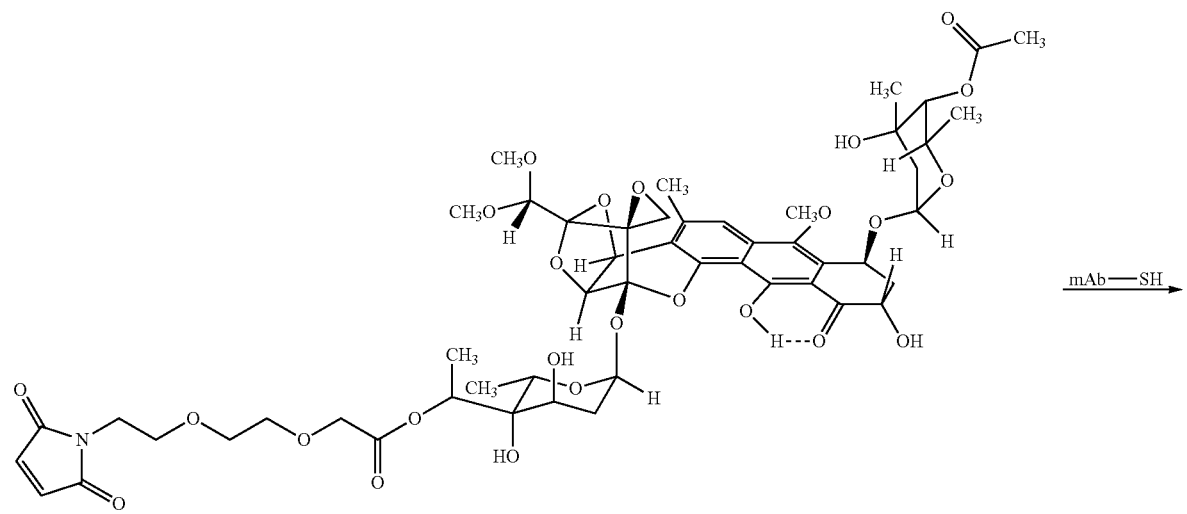
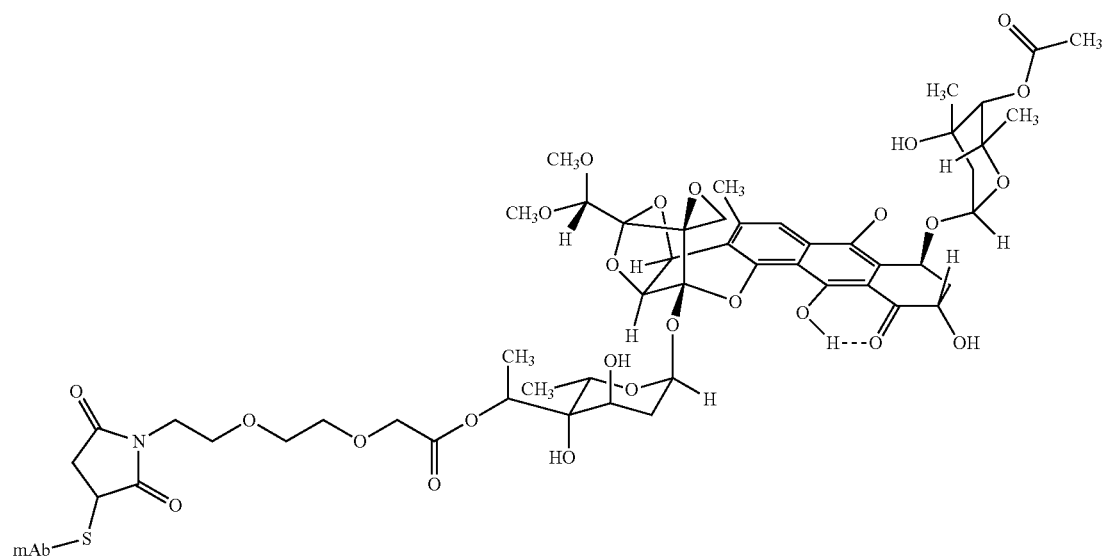

Example 6
Trioxacarcin Ketone Functionalization by Oxime Formation, Michael Addition, and Peptide Coupling of the Antibody
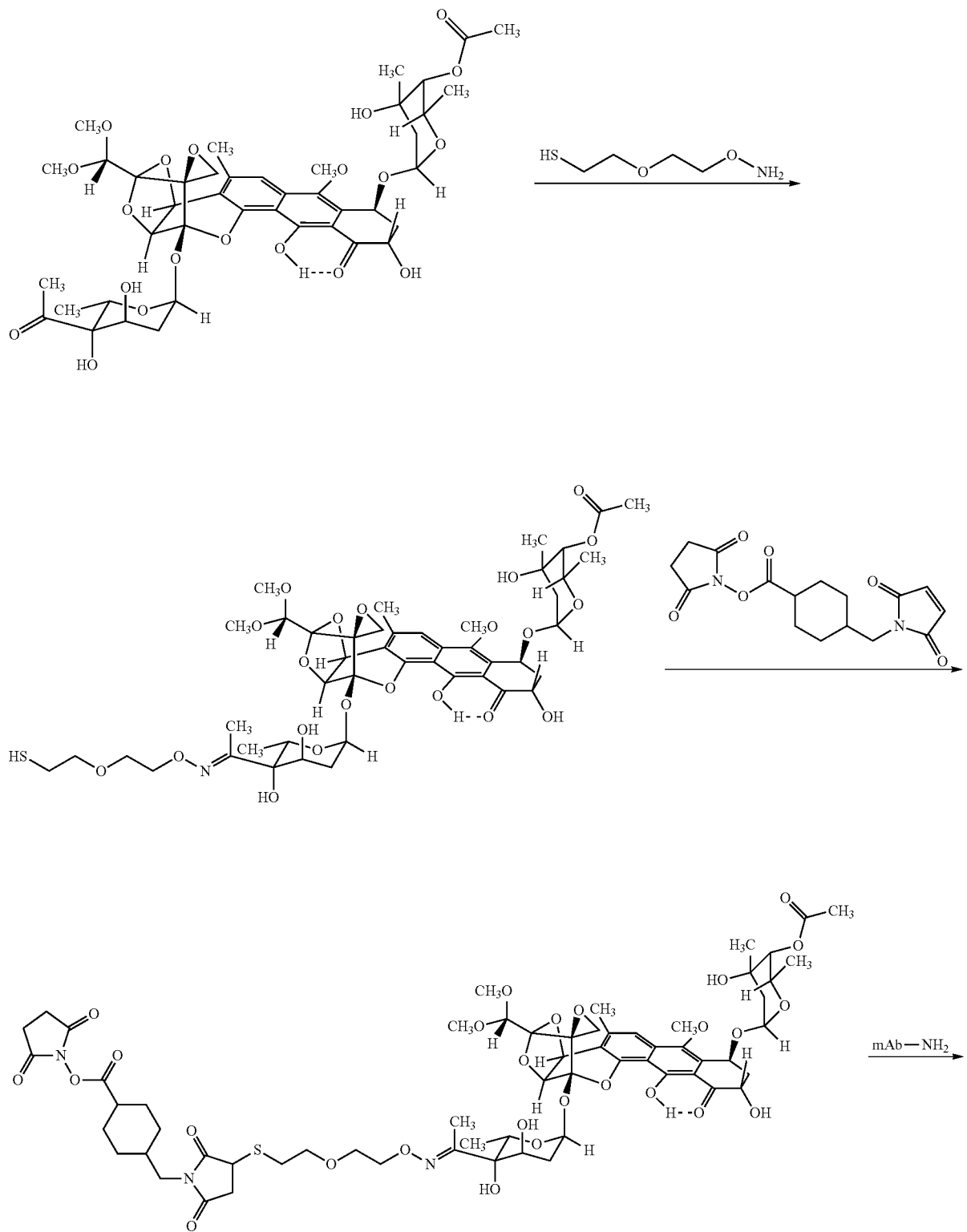

-continued
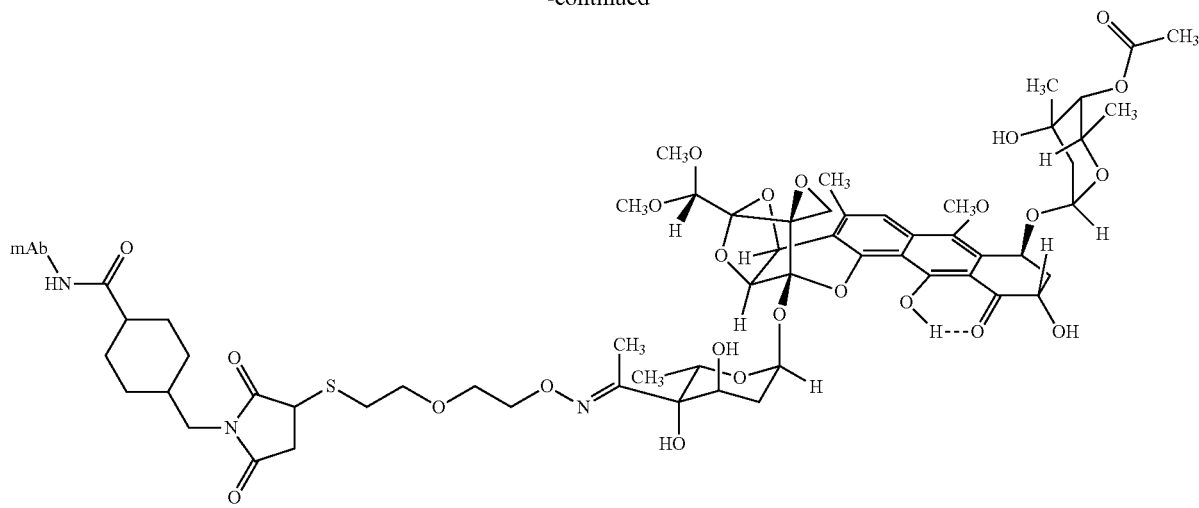
Example 7
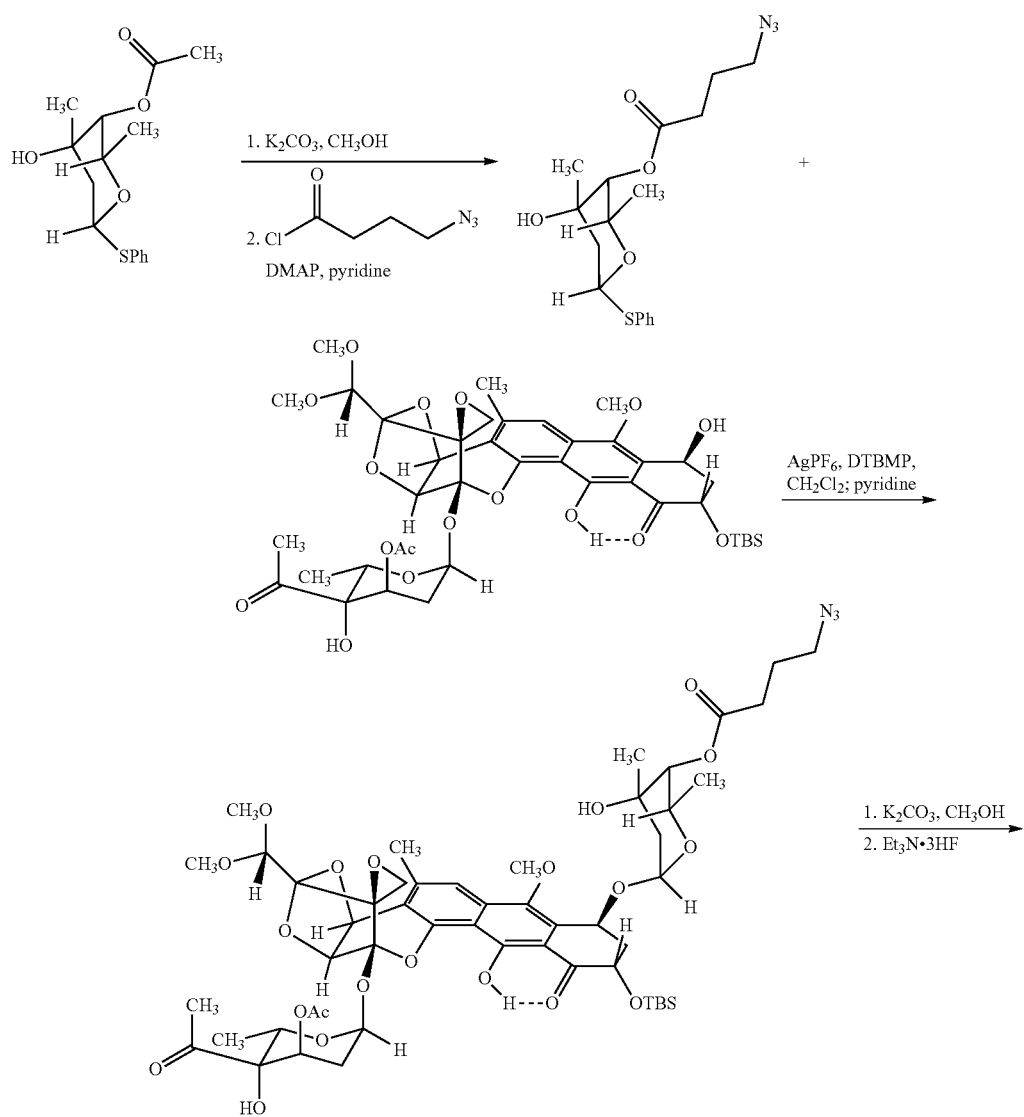

-continued
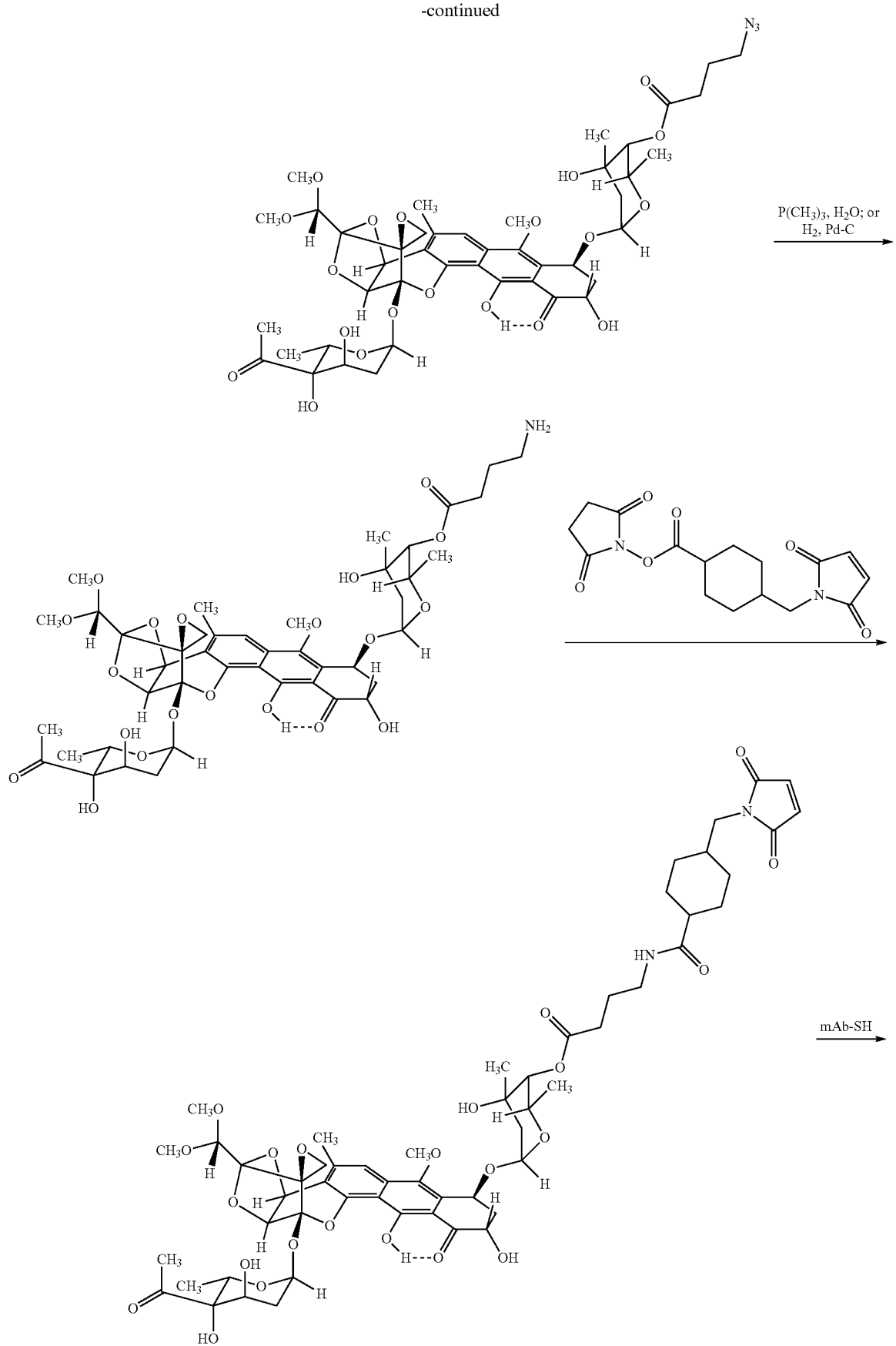

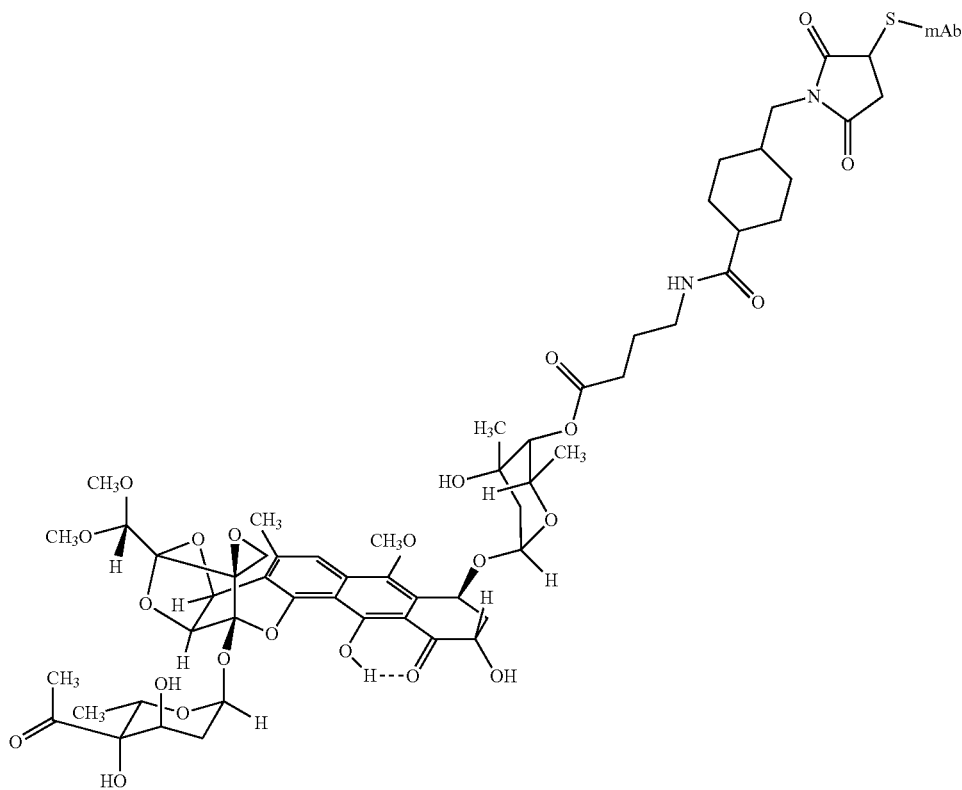
Example 8
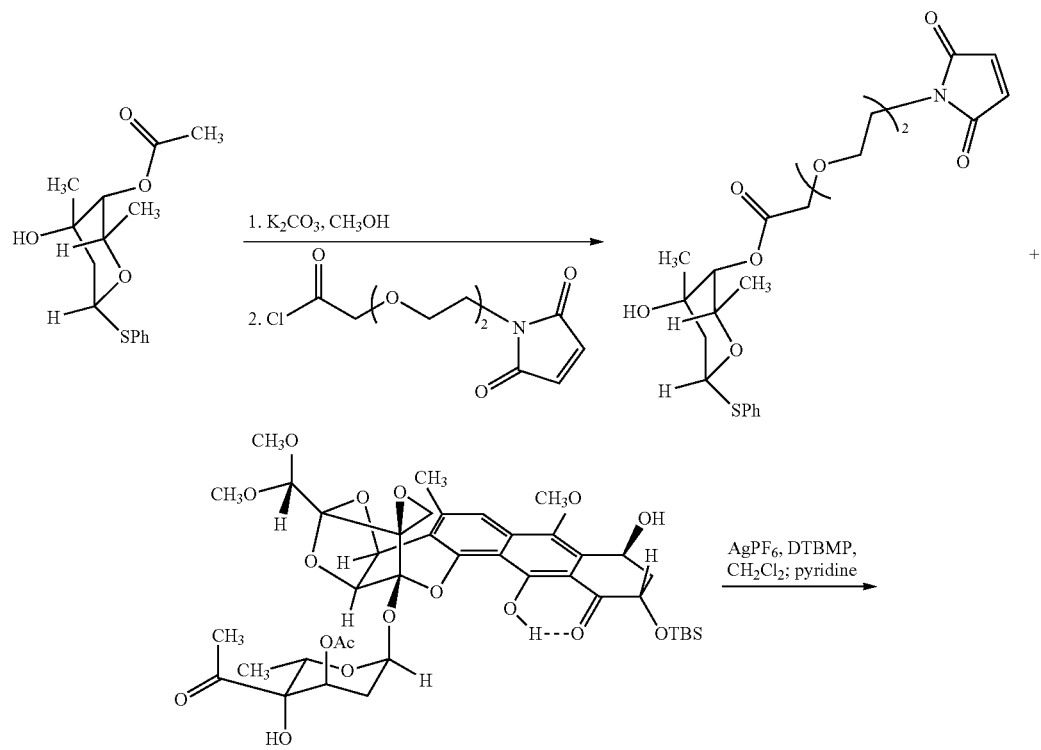

-continued
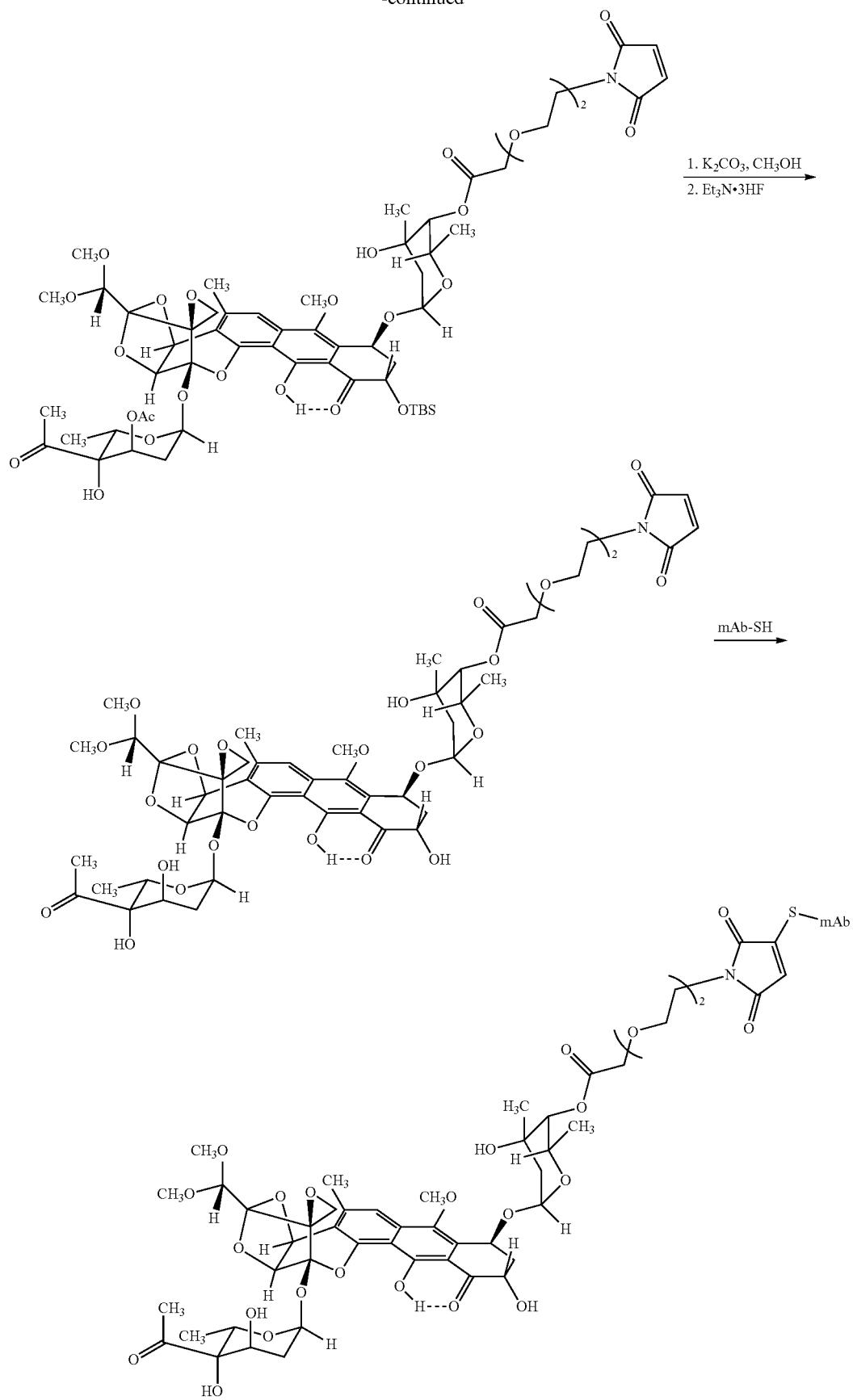

151 152
Example 9
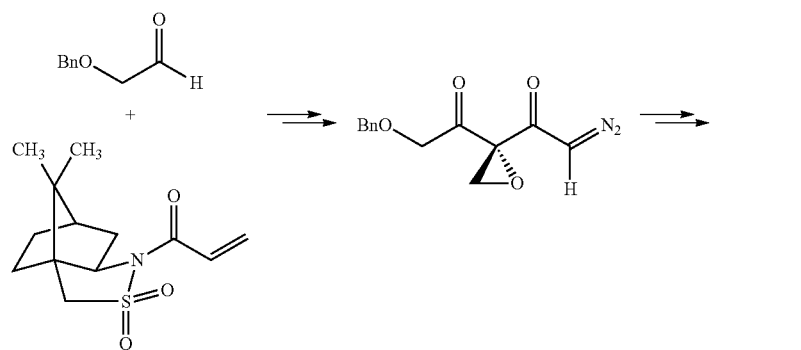
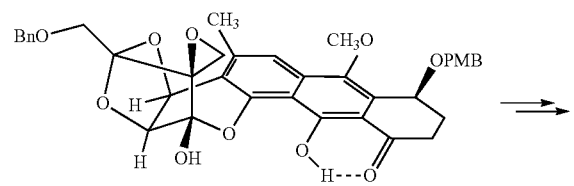
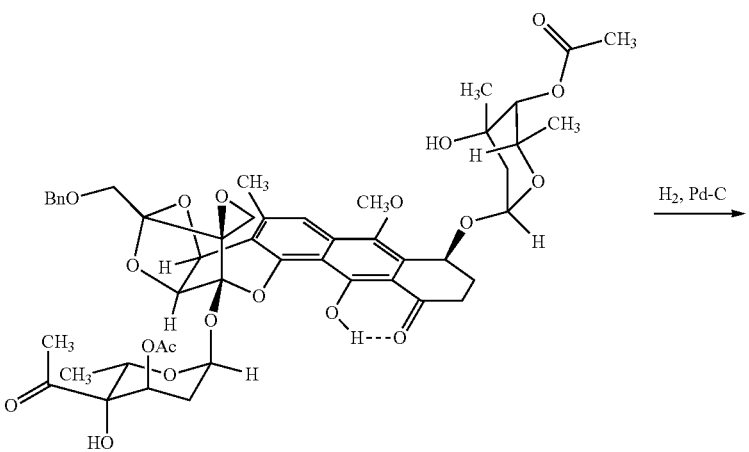
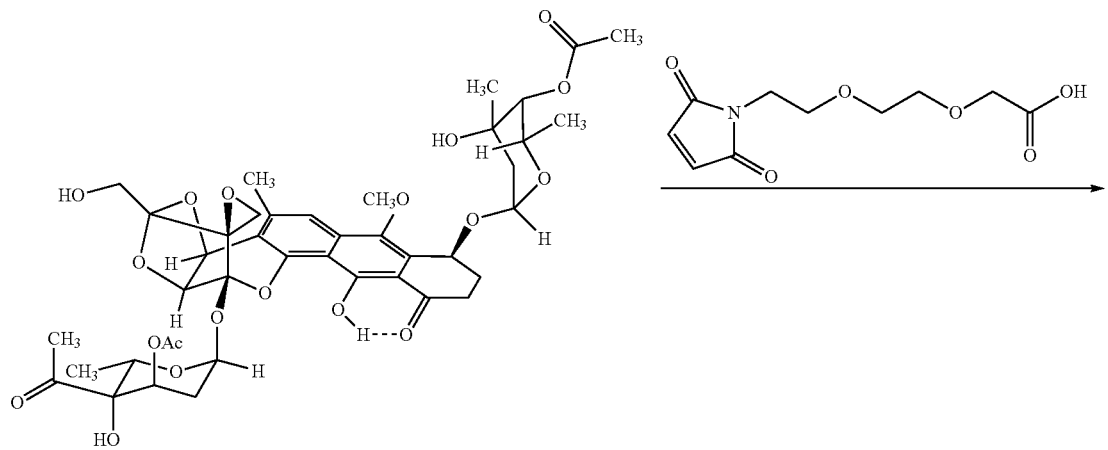

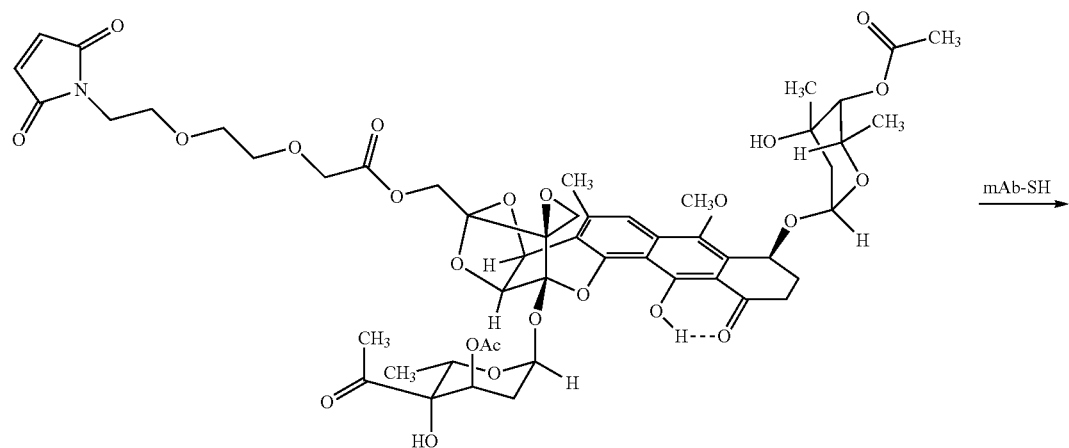
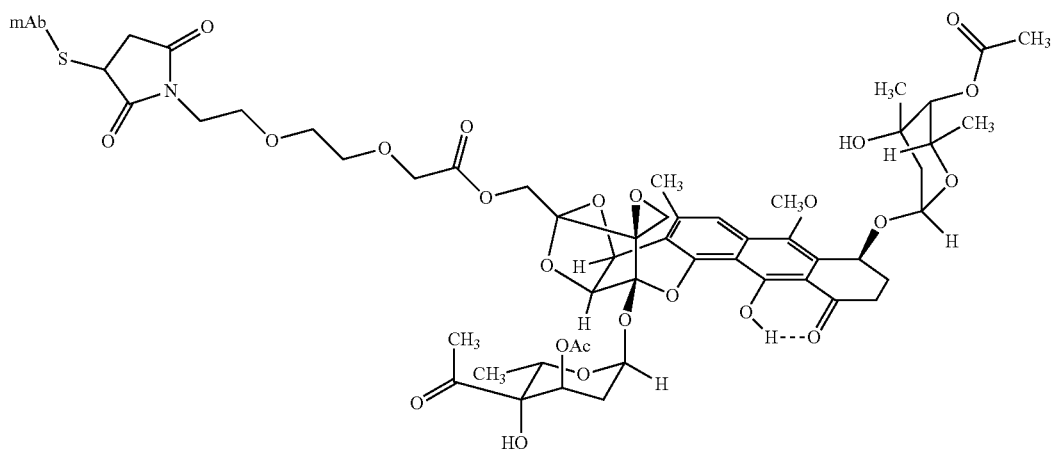
Example 10
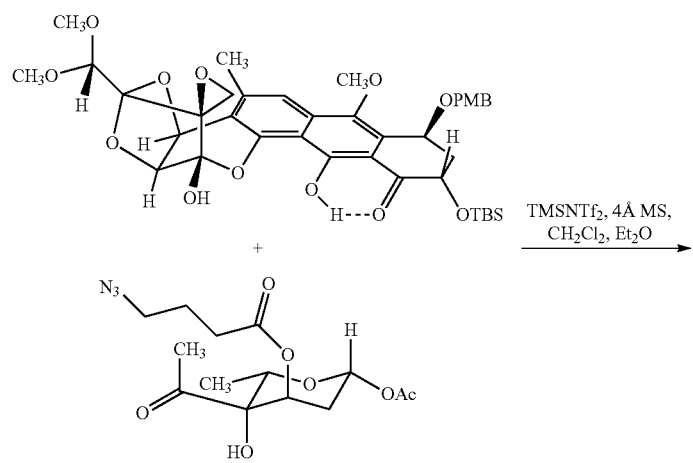

-continued
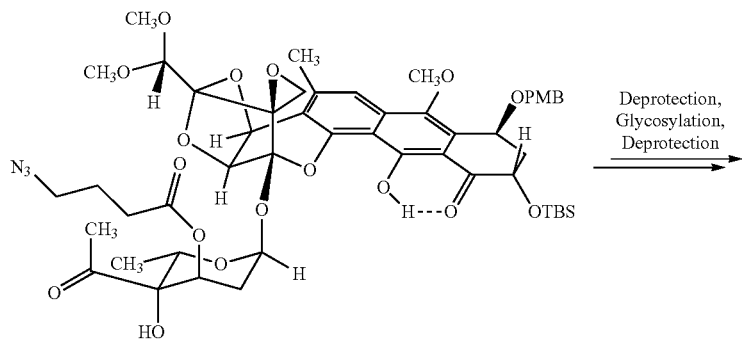
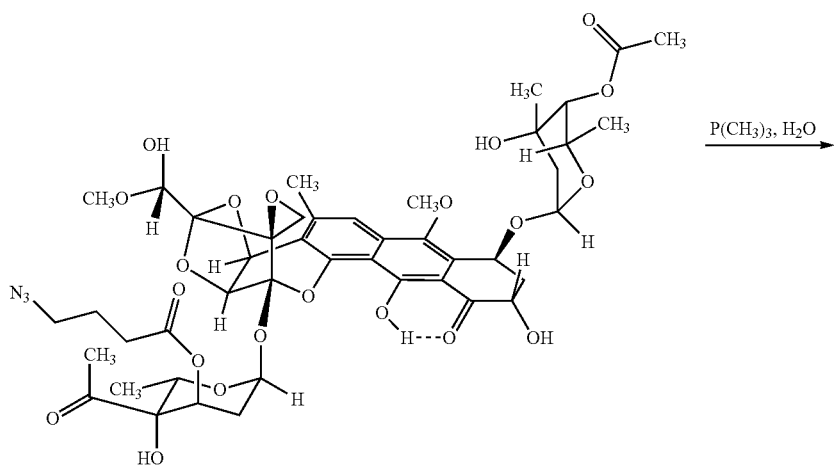
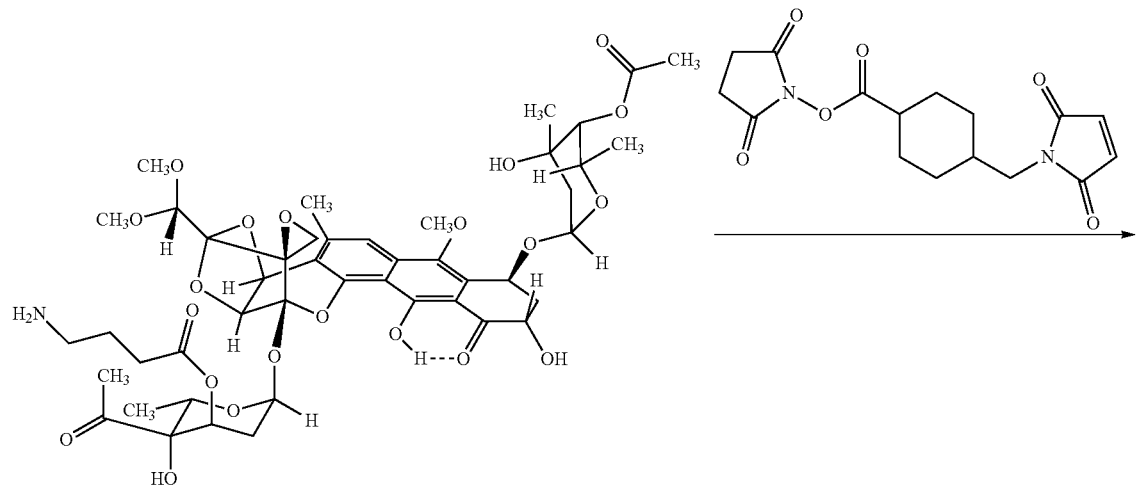

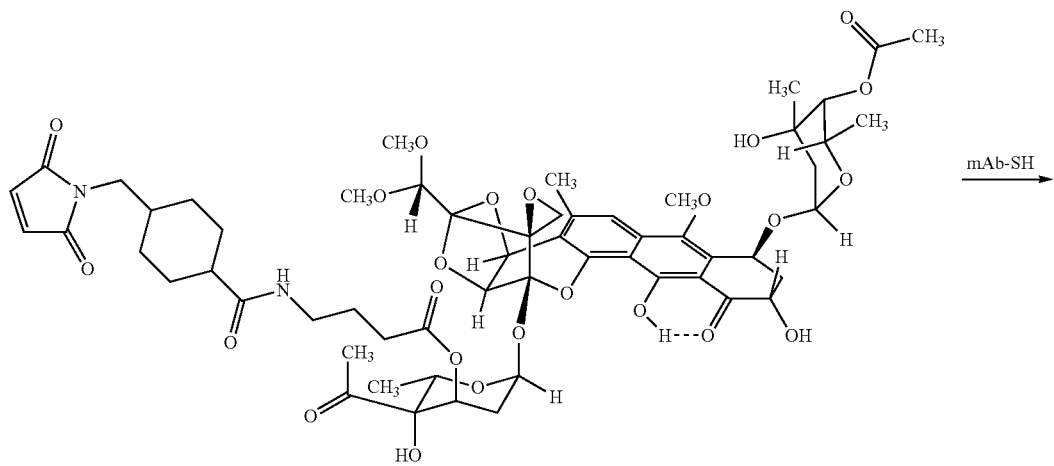
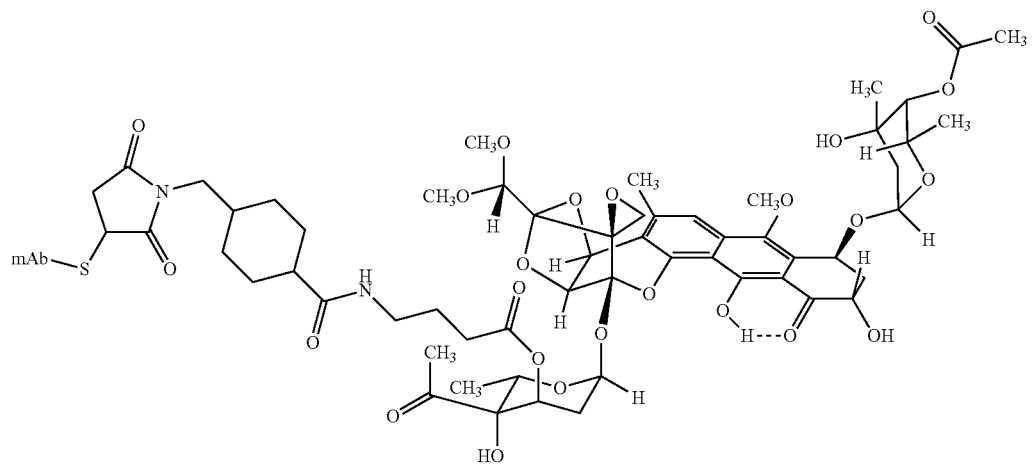
Example 11
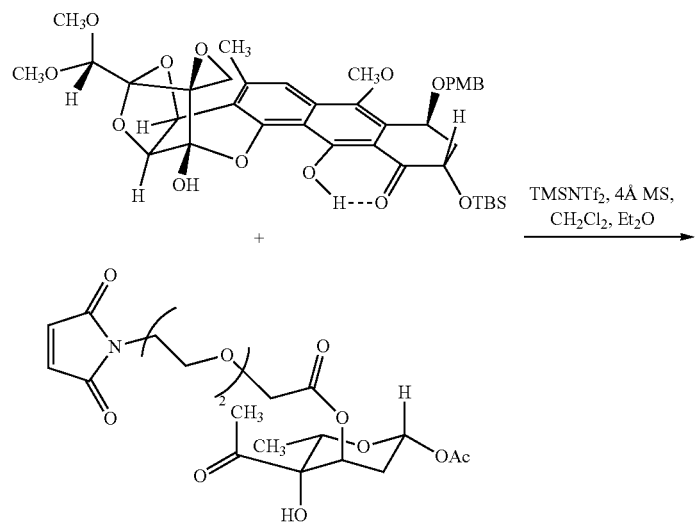

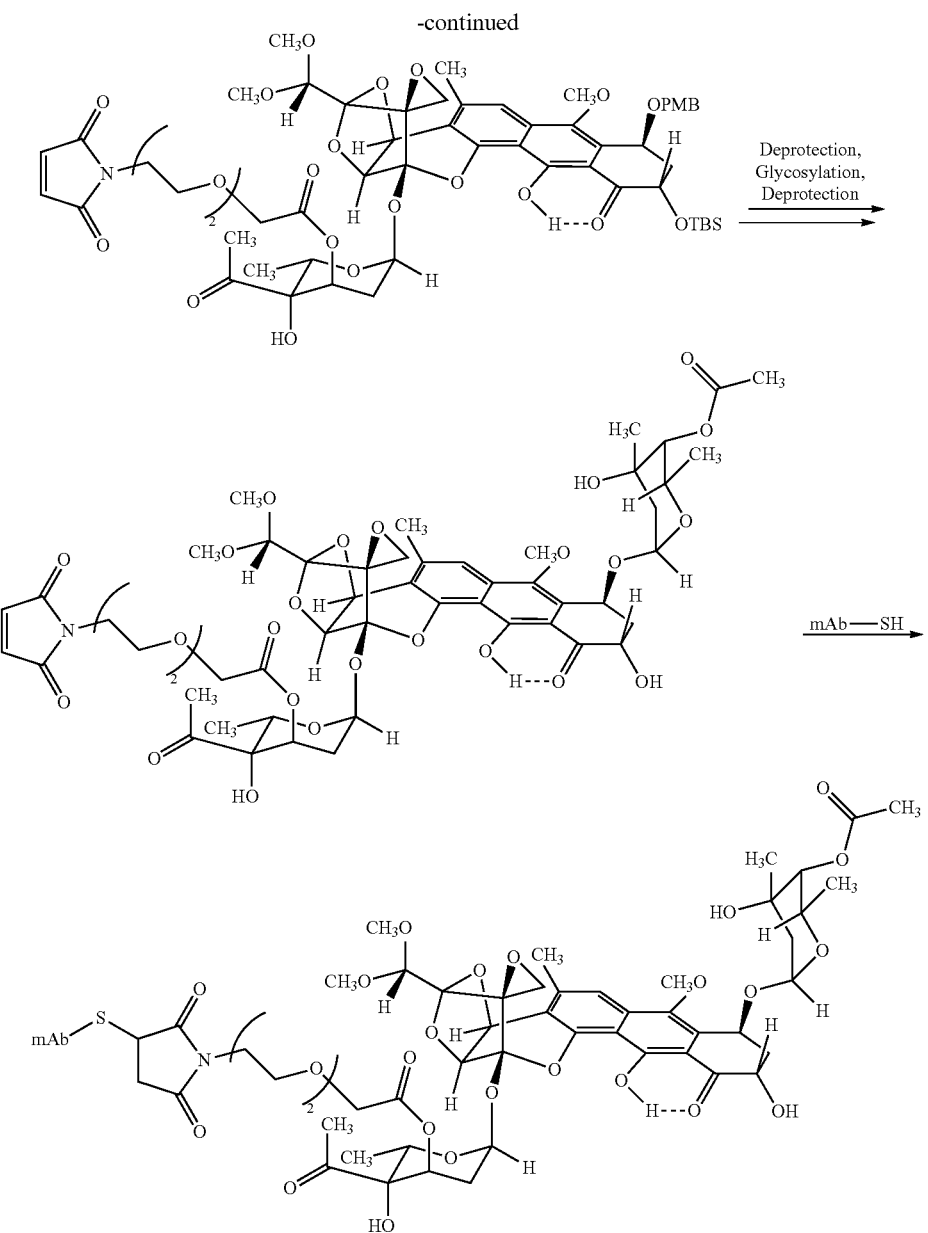

Example 12

Trioxacarcinose B Ketone Functionalization Via Oxime Formation

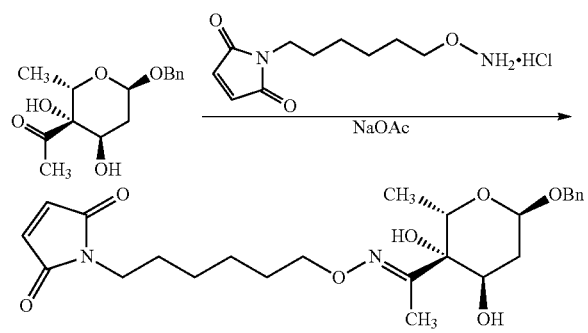

1-(6-(Aminooxy)hexyl)-1H-pyrrole-2,5-dione hydrochloride (13.3 mg, 53.5 μmol, 5.0 equiv) was added to a suspension of anhydrous sodium acetate (4.4 mg, 54 μmol, 5.0 equiv) and benzyl trioxacarcinose B (3.0 mg, 11 μmol, 1 equiv) in anhydrous methanol (0.5 mL) at 23° C. After 15 h, the mixture was concentrated. The residue was partitioned between dichloromethane (5 mL) and saturated aqueous sodium chloride solution (5 mL). The layers were separated. The aqueous layer was extracted with dichloromethane (3×3 mL). The organic layers were combined, and the combined solution was dried over magnesium sulfate. The dried solution was filtered and the filtrate was concentrated. The residue was purified by flash-column chromatography (2.0:3.0:0.1 ethyl acetate-hexanes-triethylamine) to provide the product as a colorless oil (4.60 mg, 9.69 μmol, 91%). TLC: (50% ethyl acetate-hexane) $R_f$=0.51 (UV); $^1$H NMR (600 MHz, CDCl$_3$) δ: 7.41-7.29 (m, 5H), 6.68 (s, 2H), 5.06 (app d, J=3.3 Hz, 1H), 4.77 (d, J=12.0 Hz, 1H), 4.56 (d, J=12.0 Hz, 1H), 4.46 (q, J=6.4 Hz, 1H), 4.06 (t, J=6.6 Hz, 2H), 4.00

(s, OH), 3.86 (d, J=9.3 Hz, OH), 3.69-3.64 (m, 1H), 3.51 (t, J=7.3 Hz, 2H), 2.42-2.37 (m, 1H), 1.94 (s, 3H), 1.91-1.86 (m, 1H), 1.66-1.54 (m, 4H), 1.41-1.28 (m, 4H), 1.09 (d, J=6.4 Hz, 3H); $^{13}$C NMR (125 MHz, CDCl$_3$), δ: 12.7, 14.3, 25.5, 26.5, 28.5, 28.8, 31.9, 37.8, 40.2 (2 C), 63.0, 69.6, 72.6, 74.1, 97.1 (2 C), 127.8 (2 C), 127.9, 128.0, 128.5, 134.0 (2 C), 171.9 (2 C); HRMS (ESI): Calcd for (C$_{25}$H$_{34}$N$_2$O$_7$+H)$^+$: 475.2439. Found: 475.2452.

Example 13

Dideoxy Trioxacarcin Ketone Functionalization Via Oxime Formation

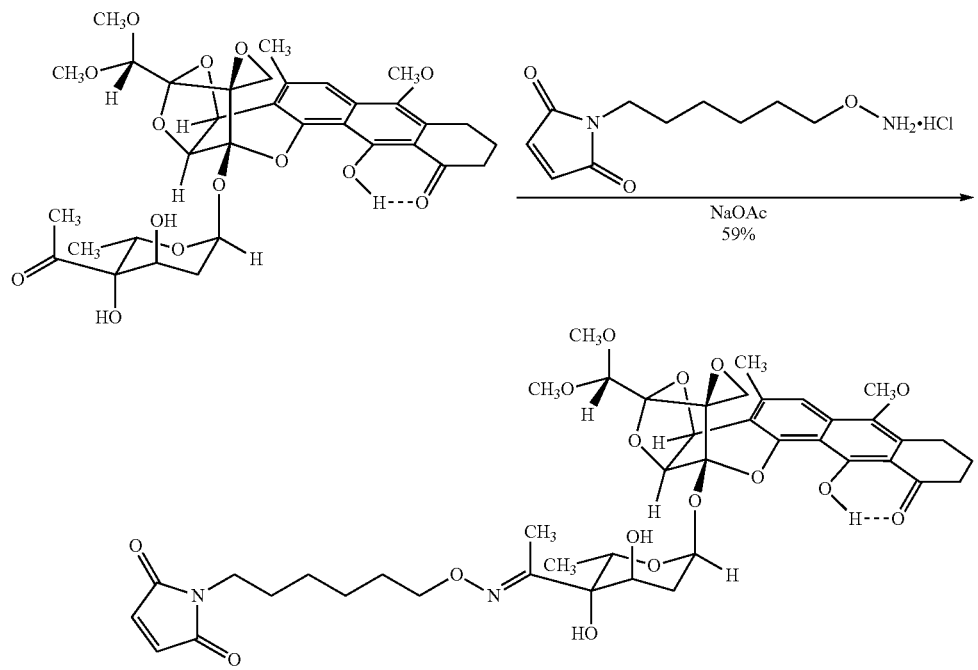

1-(6-(aminooxy)hexyl)-1H-pyrrole-2,5-dione hydrochloride (15.1 mg, 60.8 μmol, 20.0 equiv) was added to a solution of dideoxy trioxacarcin glycoside (2.00 mg, 3.04 μmol, 1 equiv) and anhydrous sodium acetate (4.98 mg, 60.8 μmol, 20.0 equiv) in anhydrous methanol (1.0 mL) at 23° C. The reaction flask was covered with aluminum foil to exclude light. After 32 h, the mixture was concentrated. To remove unreacted starting material, the residue was purified by reparative TLC (silica gel, 67% ethyl acetate-hexanes). The product was further purified by filtration through a short path of silica gel (hexanes initially, grading to ethyl acetate) to provide the oxime product (1.52 mg, 59%). TLC: (75% ethyl acetate-hexane) R$_f$=0.63 (UV); $^1$H NMR (600 MHz, CDCl$_3$) δ: 14.67 (s, 1H). 7.44 (s, 1H), 6.69 (s, 2H) 5.84 (t, J=3.6 Hz, 1H), 5.35 (d, J=4.2 Hz, 1H), 5.22 (d, J=4.2 Hz, 1H), 4.86 (q, J=6.6 Hz, 1H), 4.74 (s, 1H), 4.22 (s, OH), 4.08 (dt, J=6.6, 1.6 Hz, 2H), 3.77 (s, 3H), 3.75 (s, OH), 3.62 (s, 3H), 3.52 (app t, J=7.3 Hz, 2H), 3.48 (s, 3H), 3.03 (app q, J=5.7 Hz, 2H), 2.95 (d, J=5.7 Hz, 1H), 2.89 (d, J=5.7 Hz, 1H), 2.72 (app t, J=6.6 Hz, 2H), 2.58 (s, 3H), 2.59 (s, 3H), 2.51-2.47 (m, 1H), 2.24-2.05 (m, 4H), 1.65-1.20 (m, 8H), 1.12 (d, J=6.3 Hz, 3H); HRMS (ESI): Calcd for (C$_{43}$H$_{52}$N$_2$O$_{16}$+Na)$^+$: 875.3215. Found: 875.3112.

Example 14

Synthesis of Various Linker Groups

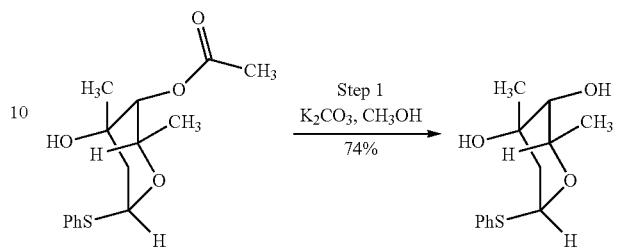

-continued

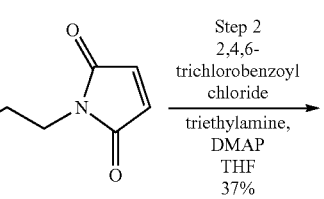

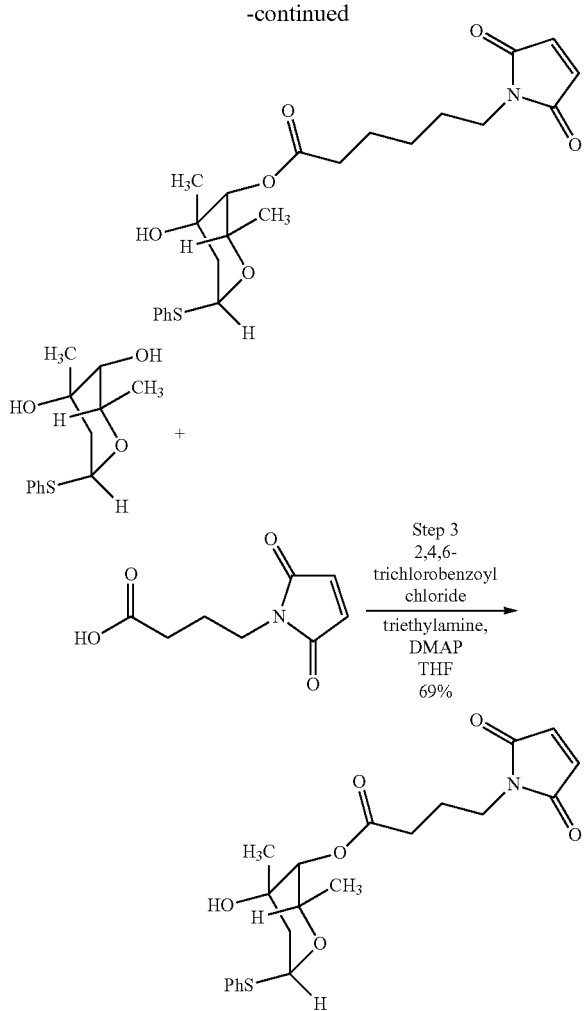

Step 1. Potassium carbonate (823 mg, 5.96 mmol, 5.0 equiv) was added to a solution of 1-thiophenyltrioxacarcinoside A (353 mg, 1.19 mmol, 1 equiv, a 2.4:1 mixture of α- and β-anomers, respectively) in methanol (24 mL) at 23° C. After 4 h, pH 7 aqueous phosphate buffer solution (20 mL) was added. The mixture was concentrated to a volume of ~20 mL. The concentrate was extracted with ethyl acetate (3×40 mL). The organic layers were combined. The combined solution was washed with saturated aqueous sodium chloride solution (40 mL) and the washed solution was dried over sodium sulfate. The dried solution was filtered and the filtrate was concentrated to provide the product, 1-thiophenylaxenoside, as a 2.0:1 mixture of α- and β-anomers, respectively (223 mg, 74%). $^1$H NMR (600 MHz, CDCl$_3$) δ: α-anomer (major): 7.49 (m, 2H), 7.32-7.24 (m, 3H), 5.57 (d, 1H, J=7.0 Hz), 4.81 (q, 1H, J=6.5 Hz), 3.16 (d, 1H, J=8.8 Hz), 2.33 (dd, 1H, J=15.0, 6.7 Hz), 2.17 (s, 1H), 1.86 (d, 1H, J=14.7 Hz), 1.35 (s, 3H), 1.25 (d, 3H, J=6.5 Hz); β-anomer (minor): 7.49 (m, 2H), 7.32-7.24 (m, 3H), 5.13 (dd, 1H, J=11.7, 2.3 Hz), 4.21 (q, 1H, J=7.0 Hz), 3.03 (d, 1H, J=10.0 Hz), 2.14 (s, 1H), 1.87-1.75 (m, 2H), 1.35 (s, 3H), 1.29 (d, 3H, J=7.0 Hz).

Step 2. 2,4,6-trichlorobenzoyl chloride (77 mg, 0.32 mmol, 4.0 equiv) was added to a solution of 6-maleimidohexanoic acid (66 mg, 0.32 mmol, 4.0 equiv) and triethylamine (219 µL, 1.57 mmol, 20.0 equiv) in tetrahydrofuran (800 µL). After 1 h, the suspension was filtered through a short pad of Celite, eluting with tetrahydrofuran (5 mL). The filtrate was concentrated. The residue was dissolved in toluene (1.0 mL) and the resulting solution was added to neat 1-thiophenylaxenoside (20 mg, 0.079 mmol, 1 equiv, a 2.0:1 mixture of α- and β-anomers, respectively). 4-Dimethylaminopyridine (58 mg, 0.47 mmol, 6.0 equiv) was added. After 10 min, the mixture was partitioned between ethyl acetate (30 mL) and pH 7 aqueous phosphate buffer solution (10 mL). The layers were separated. The aqueous layer was extracted with ethyl acetate (30 mL). The organic layers were combined. The combined solution was washed with saturated aqueous sodium chloride solution (10 mL) and the washed solution was dried over sodium sulfate. The dried solution was filtered and the filtrate was concentrated. The residue was purified by flash-column chromatography (40% ethyl acetate-hexanes initially, grading to 70% ethyl acetate-hexanes) to provide the pure thioglycoside ester as a 4.5:1 mixture of α- and β-anomers, respectively (13 mg, 37%). $^1$H NMR (500 MHz, CDCl$_3$) δ: α-anomer (major): 7.49 (m, 2H), 7.31-7.24 (m, 3H), 6.67 (s, 2H), 5.64 (d, 1H, J=6.4 Hz), 4.78 (q, 1H, J=6.4 Hz), 4.72 (s, 1H), 3.51 (m, 2H), 2.41-2.31 (m, 3H), 1.92 (d, 1H, J=14.7 Hz), 1.71-1.58 (m, 4H), 1.33 (m, 2H), 1.19 (s, 3H), 1.09 (d, 3H, J=6.8 Hz).

Step 3. 2,4,6-trichlorobenzoyl chloride (44 mg, 0.18 mmol, 4.0 equiv) was added to a solution of 4-maleimidobutanoic acid (33 mg, 0.18 mmol, 4.0 equiv) and triethylamine (126 µL, 0.901 mmol, 20.0 equiv) in tetrahydrofuran (450 µL). After 75 min, the suspension was filtered through a short pad of Celite, washing with tetrahydrofuran (2 mL). The filtrate was concentrated. The residue was dissolved in toluene (300 µL) and the resulting solution was added to neat 1-thiophenylaxenoside (11.5 mg, 0.045 mmol, 1 equiv, a 3.3:1 mixture of α- and β-anomers, respectively). 4-Dimethylaminopyridine (33 mg, 0.27 mmol, 6.0 equiv) was added. After 10 min, the mixture was partitioned between ethyl acetate (15 mL) and saturated aqueous ammonium chloride solution (5 mL). The layers were separated. The aqueous layer was extracted with ethyl acetate (15 mL). The organic layers were combined and the combined solution was dried over sodium sulfate. The dried solution was filtered and the filtrate was concentrated. The residue was purified by flash-column chromatography (30% ethyl acetate-hexanes) to provide the pure thioglycoside ester as a ~7:1 mixture of α- and β-anomers, respectively (13 mg, 69%). $^1$H NMR (500 MHz, CDCl$_3$) δ: α-anomer (major): 7.48 (m, 2H), 7.31-7.23 (m, 3H), 6.70 (s, 2H), 5.64 (d, 1H, J=6.3 Hz), 4.78 (q, 1H, J=6.8 Hz), 4.73 (s, 1H), 3.06 (m, 2H), 2.45-2.33 (m, 3H), 1.98-1.90 (m, 3H), 1.21 (s, 3H), 1.10 (d, 3H, J=6.3 Hz).

Example 15

Synthesis of Compound (24)

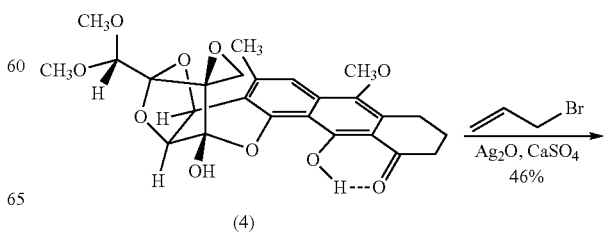

(4)

-continued

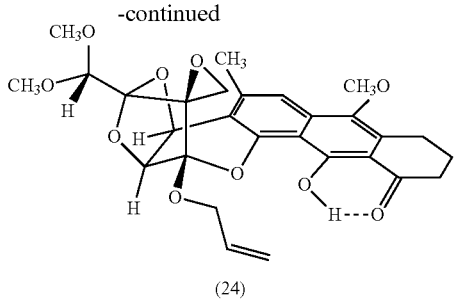

(24)

Silver(I) oxide (29 mg, 0.12 mmol, 2.0 equiv) was added to a suspension of dideoxy-DC-45-A2 (30 mg, 0.062 mmol, 1 equiv) and anhydrous calcium sulfate (34 mg, 0.25 mmol, 4.0 equiv) in allyl bromide (2 mL) at 23° C. After 21 h, the mixture was diluted with ethyl acetate (20 mL) and the diluted suspension was filtered through a short pad of Celite. The filtrate was concentrated. The residue was purified by preparatory HPLC (Agilent Prep-C18 column, 10 μm, 30×150 mm, UV detection at 270 nm, gradient elution with 40→90% acetonitrile in water, flow rate: 15 mL/min) to provide after concentration the pure O-allyl ketal (14.9 mg, 46%). $^1$H NMR (500 MHz, CDCl$_3$) δ: 14.79 (s, 1H), 7.43 (s, 1H), 6.1 (m, 1H), 5.39 (dd, 1H, J=17.7, 1.4 Hz), 5.21 (m, 2H), 4.81 (d, 1H, J=4.4 Hz), 4.76 (s, 1H), 4.55 (m, 2H), 3.78 (s, 3H), 3.63 (s, 3H), 3.44 (s, 3H), 3.06 (m, 2H), 2.89 (d, 1H, J=5.6 Hz), 2.86 (d, 1H, J=6.0 Hz), 2.73 (t, 2H, J=6.5 Hz), 2.59 (s, 3H), 2.10 (m, 2H).

Example 16

Synthesis of Compound (55)

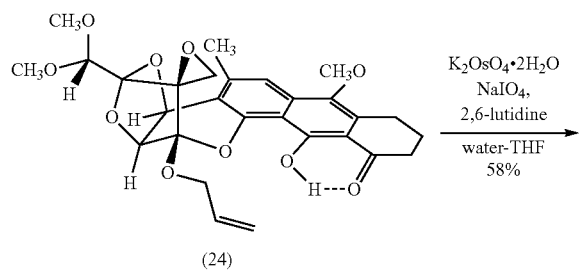

-continued (55)

Sodium periodate (48 mg, 0.23 mmol, 8.0 equiv) was added to an ice-cooled suspension of O-allyl hemiketal (14.9 mg, 0.028 mmol, 1 equiv), 2,6-lutidine (6.6 μL, 0.057 mmol, 2.0 equiv), and potassium osmate dihydrate (0.5 mg, 0.001 mmol, 0.05 equiv) in a mixture of THF (2 mL) and water (1 mL). After 5 min, the cooling bath was removed and the reaction flask was allowed to warm to 23° C. After 21 h, the suspension was diluted with dichloromethane (20 mL) and the diluted suspension was filtered through a short pad of Celite. The filtrate was concentrated. The residue was purified by preparatory HPLC (Agilent Prep-C18 column, 10 μm, 30×150 mm, UV detection at 270 nm, gradient elution with 40→90% acetonitrile in water, flow rate: 15 mL/min) to provide after concentration the pure aldehyde (8.6 mg, 58%). $^1$H NMR (500 MHz, CDCl$_3$) δ: 14.81 (s, 1H), 9.85 (s, 1H), 7.46 (s, 1H), 5.23 (d, 1H, J=4.4 Hz), 4.83 (d, 1H, J=4.4 Hz), 4.73 (s, 1H), 4.55 (m, 2H), 3.78 (s, 3H), 3.63 (s, 3H), 3.45 (s, 3H), 3.04 (m, 2H), 2.92 (d, 1H, J=5.2 Hz), 2.83 (d, 1H, J=5.2 Hz), 2.73 (t, 2H, J=6.3 Hz), 2.59 (s, 3H), 2.09 (m, 2H); HRMS (ESI): Calcd for $(C_{27}H_{28}O_{11}+Na)^+$ 551.1529, found 551.1538.

Example 17

Synthesis of Compound (29)

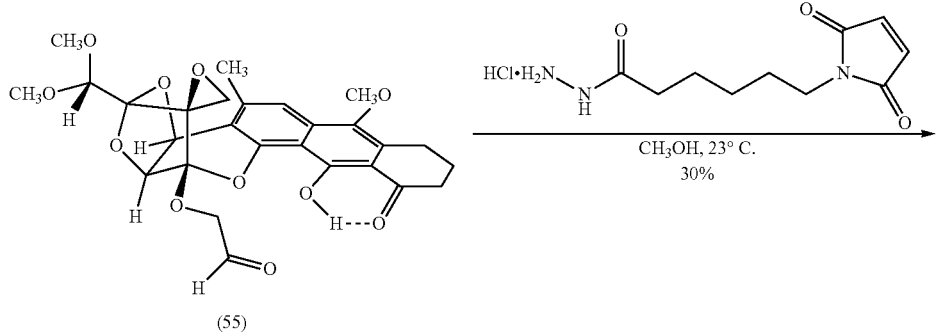

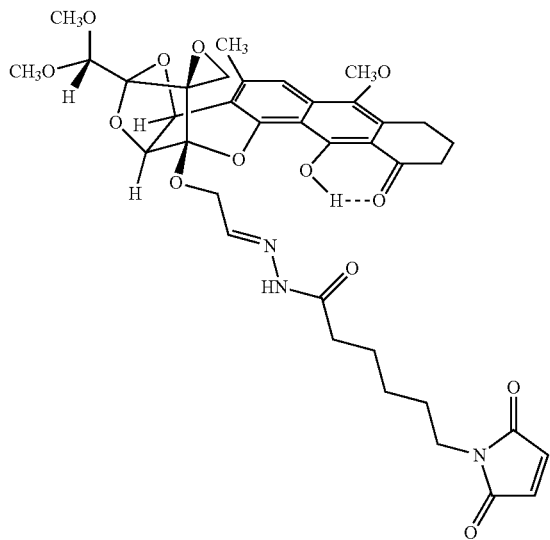

(29)

6-(2,5-Dioxo-2,5-dihydro-1H-pyrrol-1-yl)hexanehydrazide hydrochloride (9.9 mg, 38 μmol, 5.0 equiv) was added to a solution of aldehyde (4.0 mg, 7.6 μmol, 1 equiv) in methanol (0.5 mL) at 23° C. After 90 min, ether (30 mL) was added, and the diluted solution was filtered through a short pad of Celite. The filtrate was concentrated. The residue was purified by preparatory HPLC (Agilent Prep-C18 column, 10 pin, 30×150 mm, UV detection at 270 nm, gradient elution with 40→90% acetonitrile in water, flow rate: 15 mL/min) to provide after concentration the pure N-acyl hydrazone (1.7 mg, 30%). $^1$H NMR (500 MHz, CDCl$_3$) δ:14.88 (s, 1H), 8.33 (s, 1H), 7.46 (s, 1H), 7.31 (t, 1H, J=5.2 Hz), 6.67 (s, 2H), 5.22 (d, 1H, J=4.0 Hz), 4.80 (d, 1H, J=4.0 Hz), 4.74 (s, 1H), 4.65 (m, 2H), 3.78 (s, 3H), 3.63 (s, 3H), 3.51 (m, 2H), 3.45 (s, 3H), 3.05 (m, 2H), 2.92 (d, 1H, J=5.6 Hz), 2.86 (d, 1H, J=5.2 Hz), 2.74 (m, 2H), 2.59 (m, 2H), 2.59 (s, 3H), 2.10 (m, 2H), 1.70-1.58 (m, 4H), 1.34 (m, 2H).

Example 18

Synthesis of Compound (41)

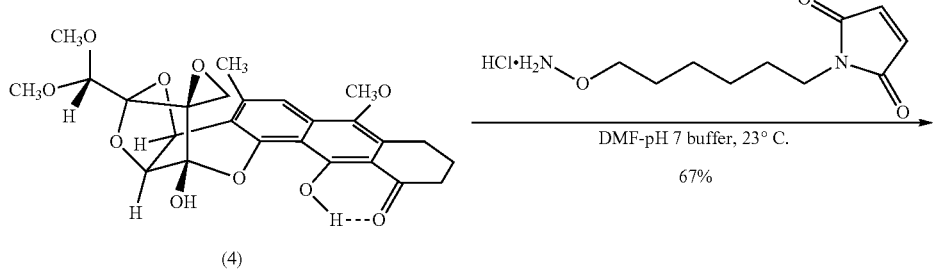

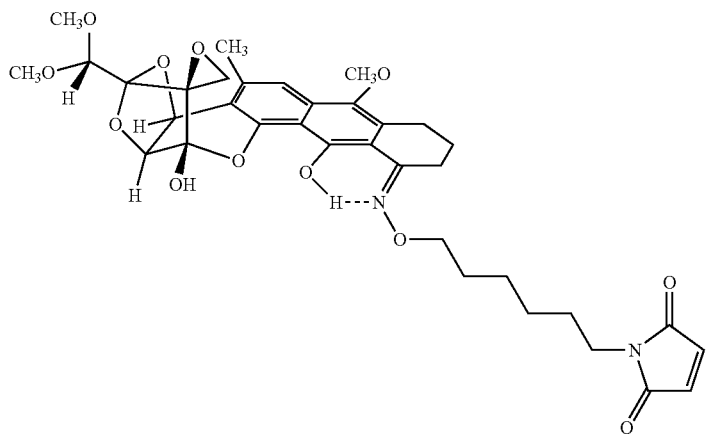

(41)

2-Aminobenzoic acid (4.2 mg, 31 μmol, 5.0 equiv) was added to a solution of dideoxy-DC-45-A2 (3.0 mg, 6.2 μmol, 1 equiv) and 1-(6-(aminooxy)hexyl)-1H-pyrrole-2,5-dione hydrochloride (31 mg, 120 μmol, 20 equiv) in a mixture of N,N-dimethylformamide (300 μL) and pH 7 aqueous phosphate buffer solution (200 μL) at 23° C. After 16 h, the suspension was diluted with 20% acetonitrile-water (10 mL) and the diluted solution was purified by preparatory HPLC (Agilent Prep-C18 column, 10 μm, 30×150 mm, UV detection at 270 nm, gradient elution with 20→90% acetonitrile in water over 60 min, flow rate: 15 mL/min) to provide after concentration the pure oxime (2.8 mg, 67%). $^1$H NMR (500 MHz, CDCl$_3$) δ: 12.77 (s, 1H), 7.43 (s, 1H), 6.69 (s, 2H), 5.27 (d, 1H, J=4.1 Hz), 4.81 (d, 1H, J=3.8 Hz), 4.71 (s, 1H), 4.44 (s, 1H), 4.18 (m, 2H), 3.75 (s, 3H), 3.62 (s, 3H), 3.53 (m, 2H), 3.47 (s, 3H), 3.12 (d, 1H, J=5.5 Hz), 3.07 (d, 1H, J=5.5 Hz), 2.92 (m, 2H), 2.85 (m, 2H), 2.56 (s, 3H), 1.85 (m, 2H), 1.74 (m, 2H), 1.61 (m, 2H), 1.44 (m, 2H), 1.35 (m, 2H); HRMS (ESI): Calcd for $(C_{35}H_{40}N_2O_{12}+H)^+$ 681.2654, found 681.2648.

Example 19

Synthesis of Compound (49)

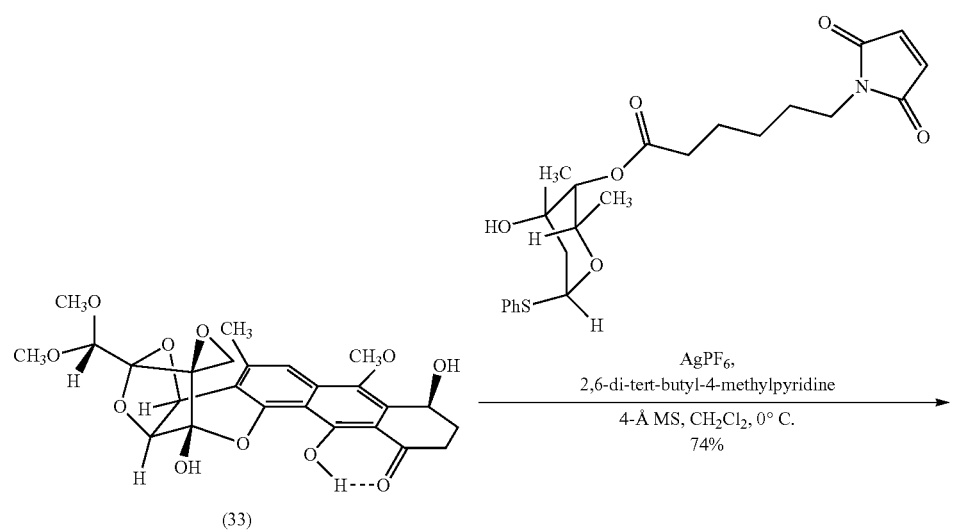

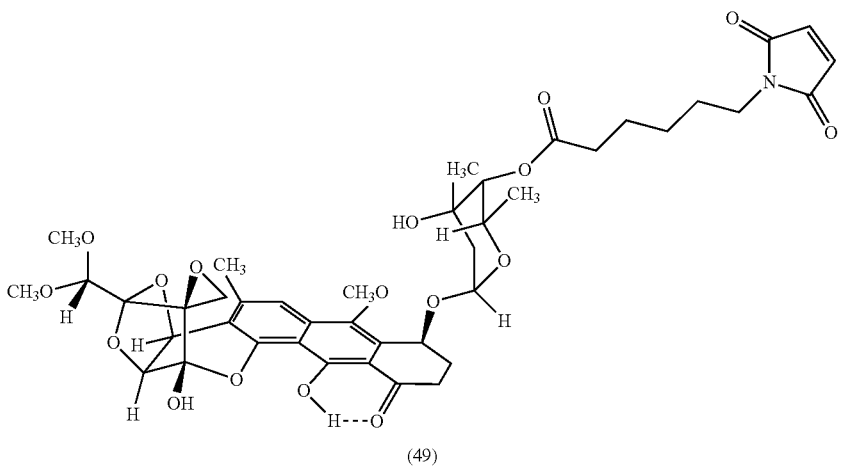

(49)

2,6-di-tert-butyl-4-methylpyridine (16 mg, 77 mol, 8.0 equiv) was added to a solution of thioglycoside (13 mg, 29 mol, 3.0 equiv, a 4.5:1 mixture of α and β anomers, respectively) and 2-deoxy trioxacarcin (5 mg, 10 mol, 1 equiv) in benzene (2 mL). The solution was concentrated and the residue was blanketed with argon. Dichloromethane (500 μL) and crushed 4-A molecular sieves (20 mg) were added sequentially at 23° C. After 20 min, the suspension was cooled in an ice-water bath. Silver hexafluorophosphate (15 mg, 58 mol, 6.0 equiv) was added. After 25 min, the cold suspension was partitioned between dichloromethane (30 mL) and saturated aqueous sodium chloride solution (10 mL). The mixture was shaken vigorously and the layers were separated. The organic layer was dried over sodium sulfate. The dried solution was filtered and the filtrate was concentrated. The residue was purified by preparatory HPLC (Agilent Prep-C18 column, 10 m, 30×150 mm, UV detection at 270 nm, gradient elution with 40-100% acetonitrile in water over 40 min, flow rate: 15 mL/min) to provide after concentration the pure α-glycoside (6 mg, 74%). $^1$H NMR (500 MHz, CDCl$_3$) δ: 15.03 (s, 1H), 7.50 (s, 1H), 6.69 (s, 2H), 5.37 (s, 1H), 5.27 (s, 2H), 4.83 (d, 1H, J=3.7 Hz), 4.74 (s, 1H), 4.71 (s, 1H), 4.49 (q, 1H, J=6.6 Hz), 4.38 (s, 1H), 4.09 (s, 1H), 3.85 (s, 3H), 3.62 (s, 3H), 3.52 (m, 2H), 3.47 (s, 3H), 3.16 (m, 1H), 3.08 (d, 1H, J=5.5 Hz), 3.01 (ddd, 1H, J=17.9, 15.0, 5.9 Hz), 2.68 (dd, 1H, J=18.1, 3.8 Hz), 2.61 (s, 3H), 2.44-2.36 (m, 3H), 2.33 (m, 1H), 1.92 (dd, 1H, J=14.6, 3.7 Hz), 1.71-1.58 (m, 5H), 1.14 (m, 5H), 1.04 (s, 3H); HRMS (ESI): Calcd for (C$_{42}$H$_{49}$NO$_{17}$+Na)$^+$ 862.2893, found 862.2892.

Example 20

Synthesis of Compound (39)

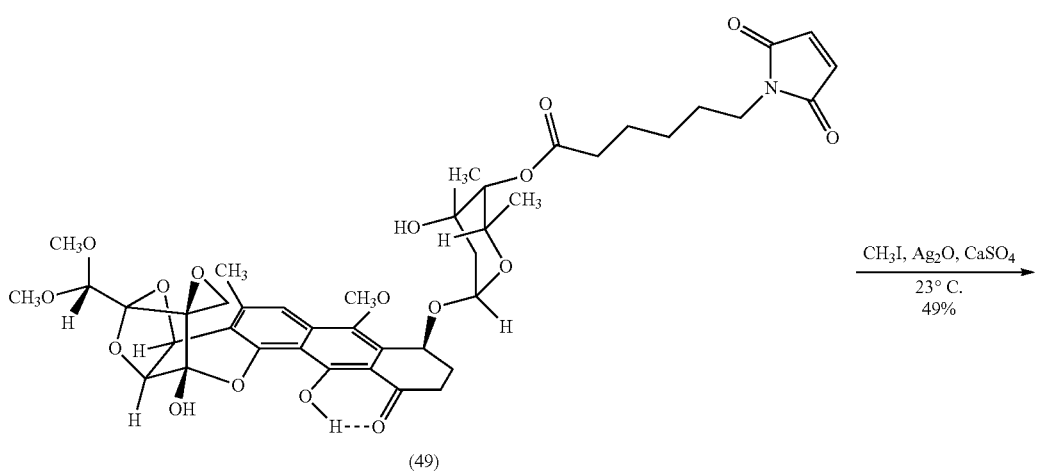

(49)

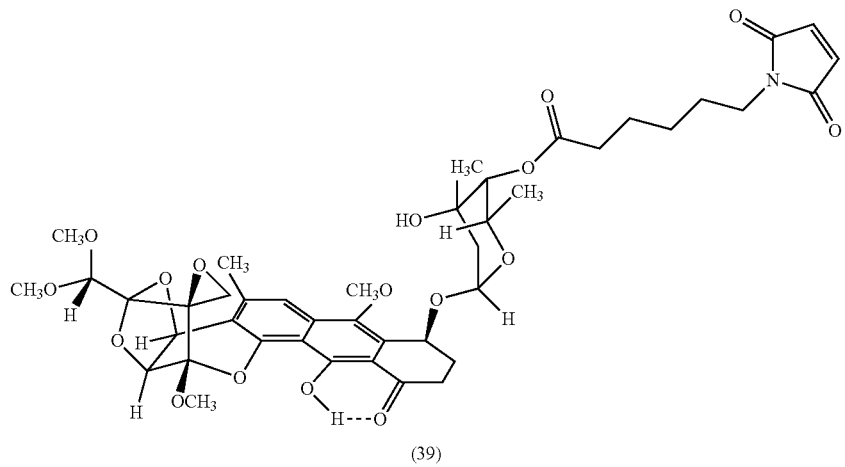

(39)

Silver(I) oxide (1 mg, 4 μmol, 2 equiv) and anhydrous calcium sulfate (1 mg, 7 μmol, 3 equiv) were added sequentially to a solution of α-glycoside (2 mg, 2 mol, 1 equiv) in iodomethane (200 μmol). After 2 h, the mixture was concentrated. The residue was suspended in dichloromethane (5 mL) and filtered through a short pad of Celite. The filtrate was concentrated. The residue was purified by preparatory HPLC (Agilent Prep-C18 column, 10 μm, 30×150 mm, UV detection at 270 nm, gradient elution with 40-100% acetonitrile in water, flow rate: 15 mL/min) to provide after concentration the pure methylated hemiketal (1 mg, 49%). $^1$H NMR (500 MHz, CDCl$_3$) δ: 14.92 (s, 1H), 7.49 (s, 1H), 6.69 (s, 2H), 5.38 (t, 1H, J=2.7 Hz), 5.27 (d, 1H, J=3.3 Hz), 5.22 (d, 1H, J=4.0 Hz), 4.83 (d, 1H, J=4.0 Hz), 4.75 (s, 1H), 4.74 (br, 1H), 4.49 (q, 1H, J=6.2 Hz), 4.1 (br, 1H), 3.85 (s, 3H), 3.76 (s, 3H), 3.64 (s, 3H), 3.52 (t, 2H, J=7.1 Hz), 3.45 (s, 3H), 3.03 (ddd, 1H, J=18.3, 14.3, 5.5 Hz), 2.90 (m, 2H), 2.68 (m, 1H), 2.61 (s, 3H), 2.45-2.34 (m, 3H), 2.22 (m, 1H), 1.92 (dd, 1H, J=14.5, 3.8 Hz), 1.71-1.40 (m, 5H), 1.29 (m, 2H), 1.20 (d, 3H, J=6.6 Hz), 1.05 (s, 3H); HRMS (ESI): Calcd for (C$_{43}$H$_{51}$NO$_{17}$+Na)$^+$ 876.3049, found 876.3028.

Example 21

Synthesis of Compound (48)

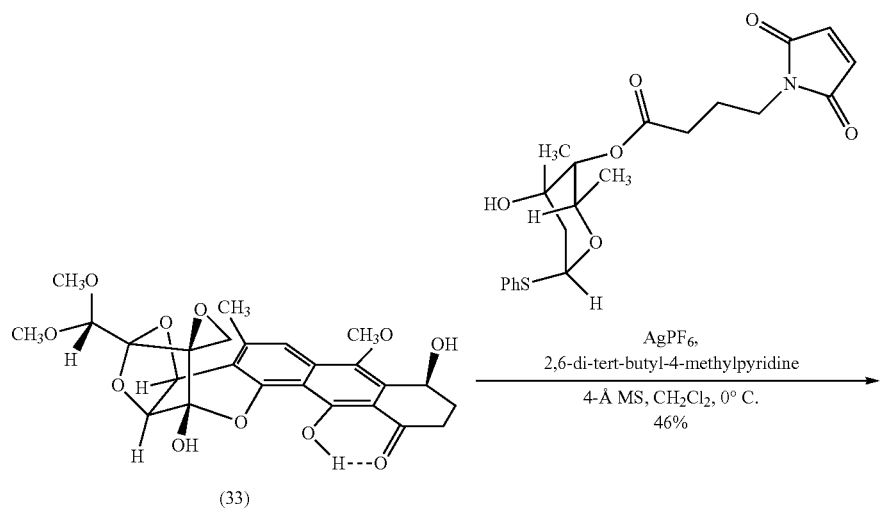

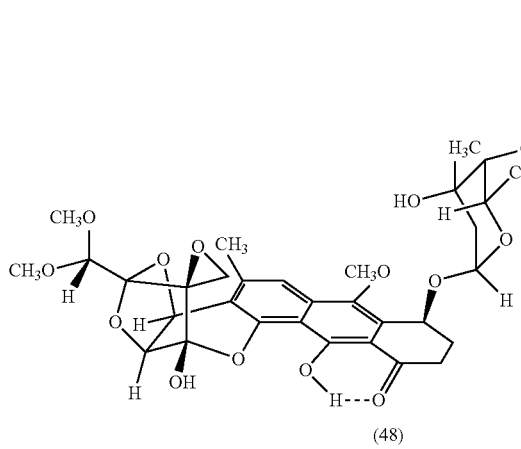

(48)

2,6-di-tert-butyl-4-methylpyridine (6.5 mg, 32 μmol, 4.0 equiv) was added to a solution of thioglycoside (6.7 mg, 16 μmol, 2.0 equiv, a ~7:1 mixture of α and β anomers, respectively) and 2-deoxy trioxacarcin (4.0 mg, 8.0 μmol, 1 equiv) in benzene (2 mL). The solution was concentrated and the residue was blanketed with argon. Dichloromethane (400 μL) and crushed 4-Å molecular sieves (20 mg) were added sequentially at 23° C. After 20 min, the suspension was cooled in an ice-water bath. Silver hexafluorophosphate (6.0 mg, 24 μmol, 3.0 equiv) was added. After 20 min, the cold suspension was partitioned between dichloromethane (30 mL) and saturated aqueous sodium chloride solution (20 mL). The mixture was shaken vigorously and the layers were separated. The organic layer was dried over sodium sulfate. The dried solution was filtered and the filtrate was concentrated. The residue was purified by preparatory HPLC (Agilent Prep-C18 column, 10 μm, 30×150 mm, UV detection at 270 nm, gradient elution with 20→90% acetonitrile in water over 60 min, flow rate: 15 mL/min) to provide after concentration the pure α-glycoside (3 mg, 46%). $^1$H NMR (500 MHz, CDCl$_3$) δ: 15.03 (s, 1H), 7.50 (s, 1H), 6.71 (s, 2H), 5.36 (app s, 1H), 5.26 (d, 1H, J=4.0 Hz), 4.83 (d, 1H, J=4.0 Hz), 4.75 (s, 1H), 4.71 (s, 1H), 4.49 (q, 1H, J=6.6 Hz), 3.84 (s, 3H), 3.62 (s, 3H), 3.60 (m, 2H), 3.47 (s, 3H), 3.16 (d, 1H, J=5.1 Hz), 3.07 (d, 1H, J=5.1 Hz), 3.01 (m, 1H), 2.69 (s, 1H), 2.67 (m, 1H), 2.61 (s, 3H), 2.45-2.35 (m, 3H), 2.22 (m, 1H), 1.98-1.91 (m, 3H), 1.59 (d, 1H, J=14.3 Hz), 1.21 (d, 3H, J=6.6 Hz), 1.06 (s, 3H); HRMS (ESI): Calcd for $(C_{40}H_{45}NO_{17}+Na)^+$ 834.2580, *found 834.2569.

Example 22

Antiproliferative Assays

Cell Culture. H460 cells were purchased from American Type Culture Collection (ATCC). H460 cells were maintained in RPMI-1640 medium supplemented with 10% fetal bovine serum (FBS).

Cell Proliferation Assay. A suspension of H460 cells (3000 cells/well) in growth medium was seeded onto a 96-well plate. The 96-well plate was incubated for 24 h at 37° C. Stock solutions of each compound were diluted serially and the resulting solutions were administrated to cells to achieve final concentrations of 110 pM to 250 nM (trioxacarcin A) or 1.1 nM to 2.5 μM (all other compounds). After incubating at 37° C. for 72 h, 20 μL of resazurin solution (Promega CellTiter-Blue® Cell Viability Assay) was added to each well. After incubating at 37° C. for 2.0 h, the fluorescence (560 nm excitation/590 nm emission) was recorded using a microplate reader (SpectraMax PLUS$^{384}$) as a measure of viable cells. Percent growth inhibition was calculated for each well, based upon the following formula: Percent growth inhibition=100×(S–B$_0$)/(B$_t$–B$_0$); where S is the sample fluorescence, B$_t$ is the average fluorescence for a vehicle-treated population of cells at the completion of the assay, and B$_0$ is the average fluorescence for an untreated population of cells at the beginning of the assay. The average percent inhibition at each concentration was plotted against log(concentration), and a curve fit was generated using a four-parameter logistic equation. GI$_{50}$ values were computed to reflect the concentrations at which the resulting curves pass through 50% inhibition.

FIG. 10 compares the growth inhibition (GI$_{50}$) of some of the trioxacarcins studied in H460 cells, a large-cell lung carcinoma cell line; T-47D cells, a mammary ductal carcinoma cell line; HEK293 cells, an embryonic kidney cell line; N87 cells, a gastric carcinoma cell line; MDA-MB-361/DYT2 cells, a mammary adenocarcinoma cell line; HT-29 cells, a colorectal carcinoma cell line; HL-60 cells, an acute promyelocytic leukemia cell line; and HEL 92.1.7 cells, an erythroleukemia cell line. Substantial variation at the sites of glycosylation appears to be well tolerated. The total absence of the northern glycoside or the southern glycoside (e.g., DC-45-A1) produces compounds which, while less active than trioxacarcin A, remain highly potent antiproliferative agents. Interestingly, simplified analogs which remove the oxygenation of the right-hand ring are quite potent and in some cases more so than their oxygenated counterparts. Of significance for the development of antibody-trioxacarcin conjugates, the C$_4$ hydroxyl group of the northern glycoside is acetylated in trioxacarcin A, and the presence of this ester group appears to increase the antiproliferative activity relative to, for example, trioxacarcin D. Acetylation of the C$_3$ hydroxyl group of the southern glycoside produces compounds that retain potent activity. Compounds disclosed in FIG. 10 which are novel are also contemplated as part of the present invention, and may be useful, for example, as a compound for in any of the methods of treatment or use as described herein.

Example 23

Crystalline Guanine Adducts of Natural and Synthetic Trioxacarcins Suggest a Common Biological Mechanism and Reveal a Basis for the Instability of Trioxacarcin A The trioxacarcins are structurally complex bacterial metabolites that exhibit potent cytotoxicity in cultured human cancer cells and have demonstrated antibacterial and antimalarial activities. See, e.g., Tomita et al., *J. Antibiot.* (1981) 34:1519-1524; Tamaoki et al., *J. Antibiot.* (1981) 34:1525-1530; Maskey et al., *J. Antibiot.* (2004) 57:771-779. Trioxacarcin A (see FIG. 2A) is the most potent natural trioxacarcin yet identified, with subnanomolar $IC_{70}$ values in many human cancer cell lines. See, e.g., Maskey et al., *J. Antibiot.* (2004) 57:771-779. The biological activity of the trioxacarcins is thought to arise from their ability to irreversibly alkylate N7 of guanosine residues of duplex DNA mediated by their spiro epoxide function. Compelling evidence supporting this proposal was obtained by X-ray crystallographic analysis of a 2:1 covalent adduct of trioxacarcin A and a self-complementary DNA duplex oligonucleotide containing two guanosine residues. See, e.g., Pfoh et al., *Nucleic Acids Res.* (2008) 36:3508-3514. Furthermore, it was shown that under physiological conditions, or more rapidly upon heating, depurination of this DNA lesion occurred to provide a 1:1 adduct of trioxacarcin A and guanine (gutingimycin, see FIG. 9), which has also been characterized crystallographically. See, e.g., Maskey et al., *Ang. Chem. Int. Ed.* (2004) 43:1281-1283.

Recently, we reported a fully synthetic, component-based route to trioxacarcin A and used this platform to prepare a number of non-natural trioxacarcin analogs. See, e.g., Magauer et al., *Nat. Chem.* (2013) 5:886-893. Many of these analogs were substantially structurally modified relative to trioxacarcin A yet retained potent cytotoxicity. For example, the monoglycoside analog, compound 3 (See FIG. 10, and below), is deoxygenated at the C2- and C4-positions compared to Trioxacarcin A, and lacks the trioxacarcinose A glycosyl residue, but is nevertheless a potent cytotoxic agent ($GI_{50}$ 19±7 nM, H460 cells). See, e.g., Magauer et al., *Nat. Chem.* (2013) 5:886-893; for trioxacarcin A, we measured a $GI_{50}$ value of 0.85±0.36 nM; see also Magauer et al., *Nat. Chem.* (2013) 5:886-893. In this work, we provide evidence that analog 3 also produces DNA lesions by alkylation of guanosine residues within a self-complementary 8-mer duplex DNA, by crystallographic characterization of a 1:1 adduct of 3 and guanine. See, e.g., FIG. 7. In addition, we have crystallographically characterized a novel guanine adduct of trioxacarcin A, which reveals a heretofore unrecognized pathway for molecular degradation of 1, by elimination of the trioxacarcinose A residue and aromatization/oxidation to form an anthraquinone.

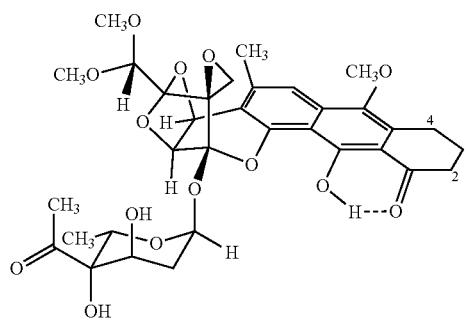

3

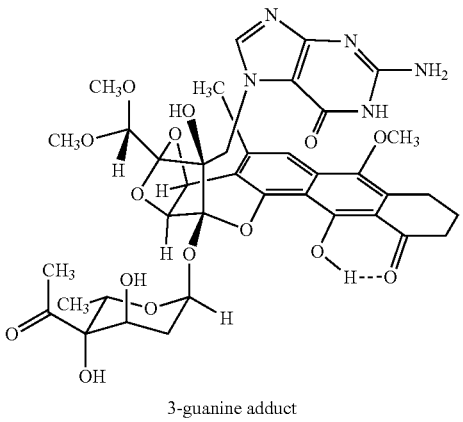

3-guanine adduct

In their seminal studies, Pfoh and coworkers characterized by X-ray crystallography the 2:1 covalent intercalation complex of trioxacarcin A with the self-complementary duplex oligonucleotide d(AACCGGTT). See, e.g., Pfoh et al., *Nucleic Acids Res.* (2008) 36:3508-3514. To prepare the crystalline complex, the DNA duplex was treated with trioxacarcin A (2.2 equiv) in 25% methanol-water at 4° C. for 3 days. Hanging drops of the resulting solution were equilibrated against an aqueous solution containing 1.55 M ammonium citrate and 30% dimethyl sulfoxide at 40° C. for 24 h, producing yellow crystals of the alkylated intercalation complex.

We conducted DNA-alkylation experiments with the fully synthetic trioxacarcin analog 3 by a similar protocol. Incubation of analog 3 with the self-complementary duplex oligonucleotide d(AACCGGTT) in 25% methanol-water for 3 days at 4° C. followed by equilibration with an aqueous solution containing 1.65 M triammonium citrate (pH 7.0) and 30% DMSO (2 weeks at 40° C. and 2 weeks at 23° C.) produced crystals of guanine adduct suitable for X-ray diffraction.

Separately, we conducted studies of the reaction of trioxacarcin A with duplex DNA oligonucleotides of different sequences. In one experiment, we incubated trioxacarcin A with the self-complementary duplex oligonucleotide d(CG-TATACG) in 25% methanol-water for 3 days at 4° C. Hanging drops of the resulting solution were allowed to equilibrate at 40° C. with an aqueous solution containing 5% 2-methyl-2,4-pentanediol, 20 mM sodium dimethylarsinate, 6 mM spermine tetrahydrochloride, 40 mM sodium chloride, and 10 mM magnesium chloride. After 2 weeks, a dark red crystalline product was obtained; X-ray crystallographic analysis revealed this to be a novel guanine adduct in which the planar core of the trioxacarcin residue had undergone substantial modification to form an anthraquinone-guanine adduct (See FIGS. 8 and 9, and below).

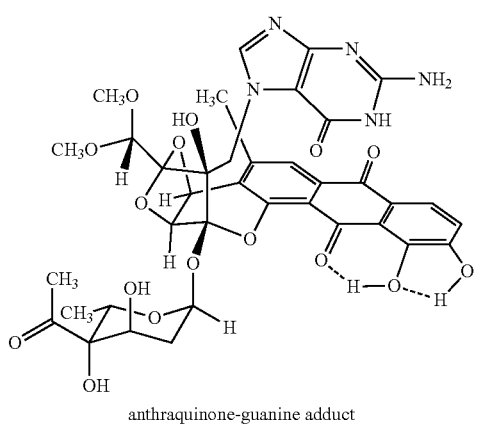

anthraquinone-guanine adduct

We and others have observed that trioxacarcin A is unstable under basic conditions in aqueous or alcoholic solvents, made evident by rapid darkening of the initially yellow solutions to dark red. See, e.g., Magauer et al., *Nat. Chem.* (2013) 5:886-893; Shirahata et al., *Symposium on the Chemistry of Natural Products* (1981) 24:199-206. The anthroquinone-guanine adduct formed from DNA alkylation of trioxacarcin A leads us to propose a potential chemical basis for this instability, outlined in FIG. 9. As shown, we propose that base-catalyzed enolization of the C1 ketone promotes elimination of trioxacarcinose A and aromatization. Autoxidation, which we expect to be facile, would then produce the anthraquinone product. While conceivably the dark red adduct anthraquinone product could have been formed by base-promoted elimination of the trioxacarcinose A residue prior to DNA binding and then alkylation we believe the sequence depicted in FIG. 9 is more probable. Regardless of the sequencing, the anthraquinone product suggests a link between the base instability of trioxacarcin A and its heretofore unrecognized propensity to undergo elimination of the trioxacarcinose A residue followed by autoxidation. Further supporting this proposal is the observation that compound 3, which has no capacity to undergo the elimination-autoxidation pathway, is not unstable towards base and is generally much more stable than trioxacarcin A. Furthermore, compound 3 retains a capacity to abstract guanine from duplex DNA, yet exhibits superior stability in aqueous solutions. With evidence that simplified constructs such as compound 3 produce DNA lesions analogous to trioxacarcin A yet exhibit greater chemical stability we believe that compounds of this novel chemical series present a promising avenue for further exploration in potential chemotherapeutic constructs such as antibody-drug conjugates.

X-ray Measurements

Crystallographic data for the 3-guanine adduct and the anthraquinone-quanine adduct were measured at the Swiss Light Source synchrotron at the macromolecular beamline X10SA using a wavelength of 0.6358 Å. Fine slicing data collection was performed according to a previously described protocol. See Mueller et al., *Acta Crystallogr. D* (2012) 68:42-56. Due to the small crystal size the use of synchrotron radiation was necessary. Data integration was performed with the XDS software. See Kabsch *Acta Crystallogr. D* (2010) 66:125-132. Structure solution and refinement were carried out with SHELXS and SHELXL. See Sheldrick, *Acta Crystallogr. A* (2008) 64:112-122. The structure of the 3-guanine adduct (PDB ID 4HP7) has been deposited at the Protein Data Bank. Crystallographic analysis established that the 3-guanine adduct was structurally similar to gutingimycin, supporting a common mechanism of action.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

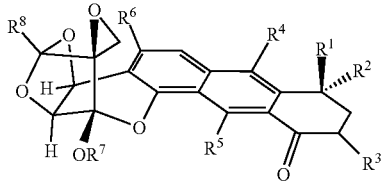

(I)

or a pharmaceutically acceptable salt thereof; wherein:

a is an integer between 1 and 10, inclusive;

$L^1$ is absent or is a linking group selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; peptidyl groups; dipeptidyl groups; polypeptidyl groups; and combinations thereof;

$L^2$ is absent or is a linking group selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; peptidyl groups; dipeptidyl groups; polypeptidyl groups; and combinations thereof;

A is a group of the formula —NH—, —NH—NH—, —NH—O—, —O—NH—, —S—, —O—,

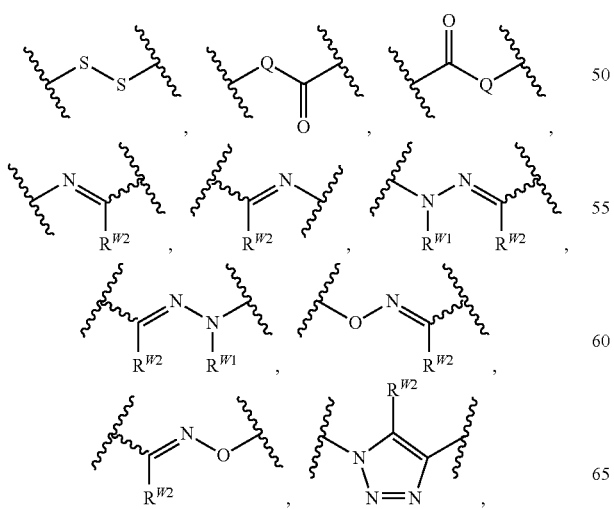

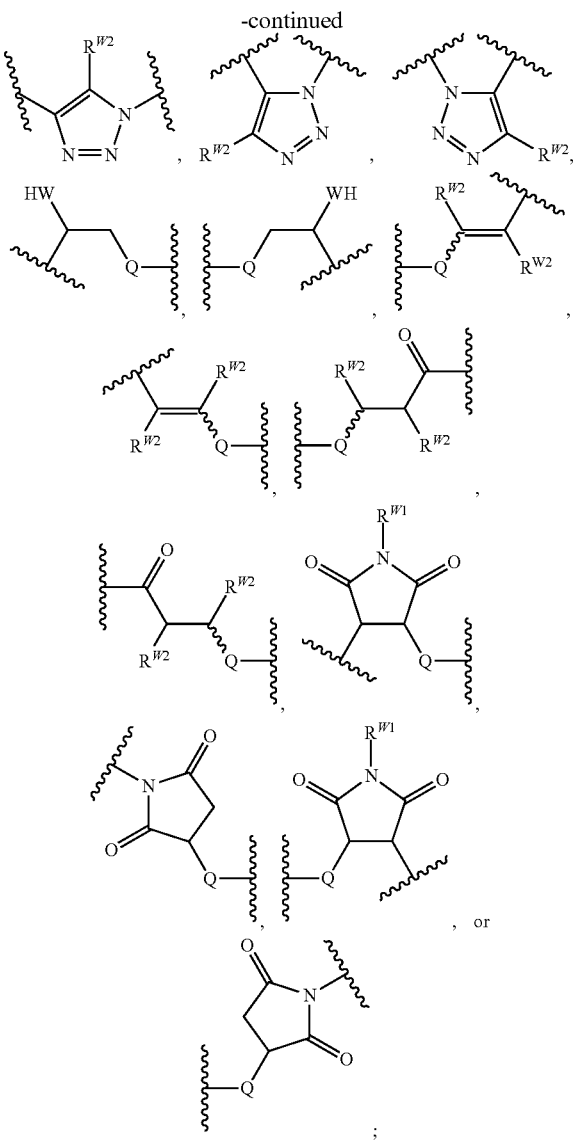

Q is —NH—, —NH—NH—, —O—NH—, —NH—O—, —S—, or —O—;

W is —O—, —S—, or —NR$^{W1}$—, wherein R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

R$^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two R$^{W2}$ groups are joined to form a 5-6 membered ring;

B is an antibody or an antibody fragment;

$R^1$ is hydrogen or —OR$^{41}$; and $R^2$ is hydrogen; or $R^1$ and $R^2$ are joined to form =O;

$R^{41}$ is hydrogen; an oxygen protecting group; or substituted or unsubstituted alkyl;

or $R^{A1}$ is a group of Formula (i):

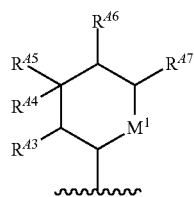

(i)

wherein each occurrence of $R^{A3}$, $R^{A4}$, $R^{A5}$, $R^{A6}$, and $R^{A7}$ is independently hydrogen, substituted or unsubstituted alkyl; —$OR^{A9}$; —$OC(=O)R^{A9}$; —$N(R^{A9})_2$; or —$NHC(=O)R^{A9}$; wherein each occurrence of $R^{A9}$ is independently hydrogen; substituted or unsubstituted alkyl; an oxygen protecting group when attached to an oxygen atom; or a nitrogen protecting group when attached to a nitrogen atom; or two $R^{A9}$ groups are joined to form a substituted or unsubstituted heterocyclic or substituted or unsubstituted heteroaryl ring; and $M^1$ is —O—;

$R^3$ is hydrogen or —$OR^{C1}$, wherein $R^{C1}$ is hydrogen; an oxygen protecting group; or substituted or unsubstituted alkyl;

$R^4$ is hydrogen or —$OR^{D1}$, wherein $R^{D1}$ is hydrogen; an oxygen protecting group; or substituted or unsubstituted alkyl;

$R^5$ is hydrogen or —$OR^{E1}$, wherein $R^{E1}$ is hydrogen; an oxygen protecting group; or substituted or unsubstituted alkyl;

$R^6$ is substituted or unsubstituted alkyl;

$R^7$ is -$L^1$-$(A-L^2)_a$-B;

$R^8$ is —$CH(OR^{I1})_2$;

each occurrence of $R^{I1}$ is substituted or unsubstituted alkyl;

wherein substituted, when on a carbon atom, independently refers to substitution with halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$ —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, or 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$, or =$NOR^{cc}$; and wherein substituted, when on a nitrogen atom, independently refers to substitution with —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, or 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, or 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, or 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, or 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, or 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form =O or =S; wherein $X^-$ is a counterion.

2. The compound of claim 1, or a pharmaceutically acceptable salt thereof, wherein $L^1$ is absent or is a linking group consisting of one or more groups of the formula:

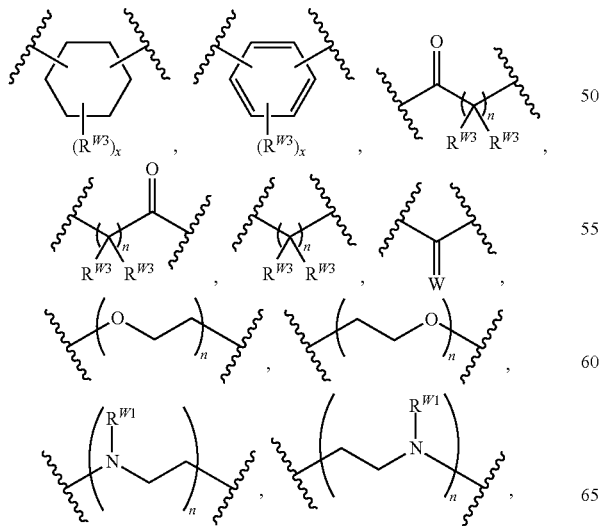

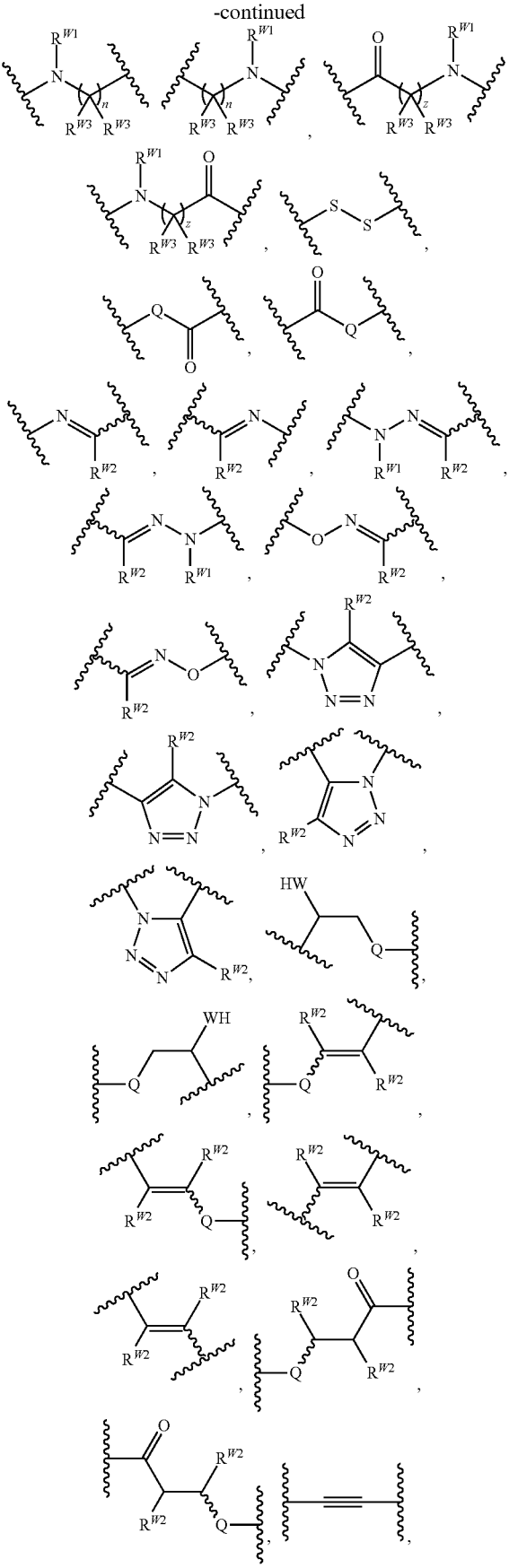

-continued

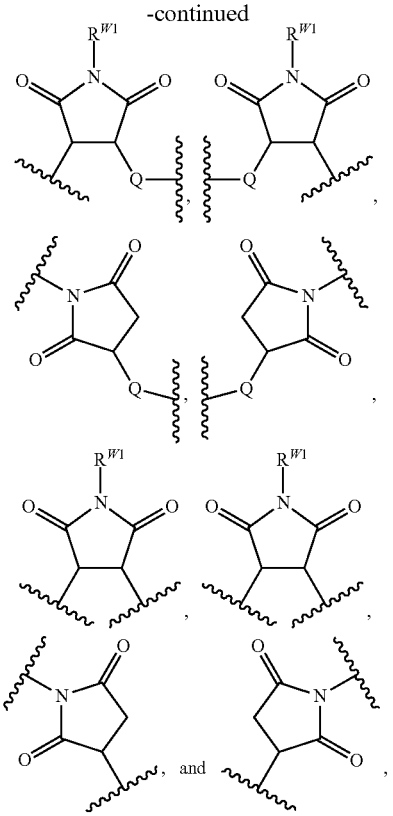

wherein:
n is an integer between 1 to 10, inclusive;
x is 0, 1 or 2;
z is 1 or 2;
Q is —NH—, —NH—NH—, —O—NH—, —NH—O—, —S—, —O—;
W is O, S, or $NR^{w1}$;
$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;
$R^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl; or two $R^{W2}$ groups are joined to form a 5-6 membered ring; and
each instance of $R^{W3}$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two $R^{W3}$ groups are joined to form a 3-6 membered ring;
or $R^{W1}$ and $R^{W3}$ are joined to form a 5-6 membered heterocyclic ring.

3. The compound of claim 2, or a pharmaceutically acceptable salt thereof, wherein $L^1$ is absent or is a linking group consisting of one or more groups of the formula:

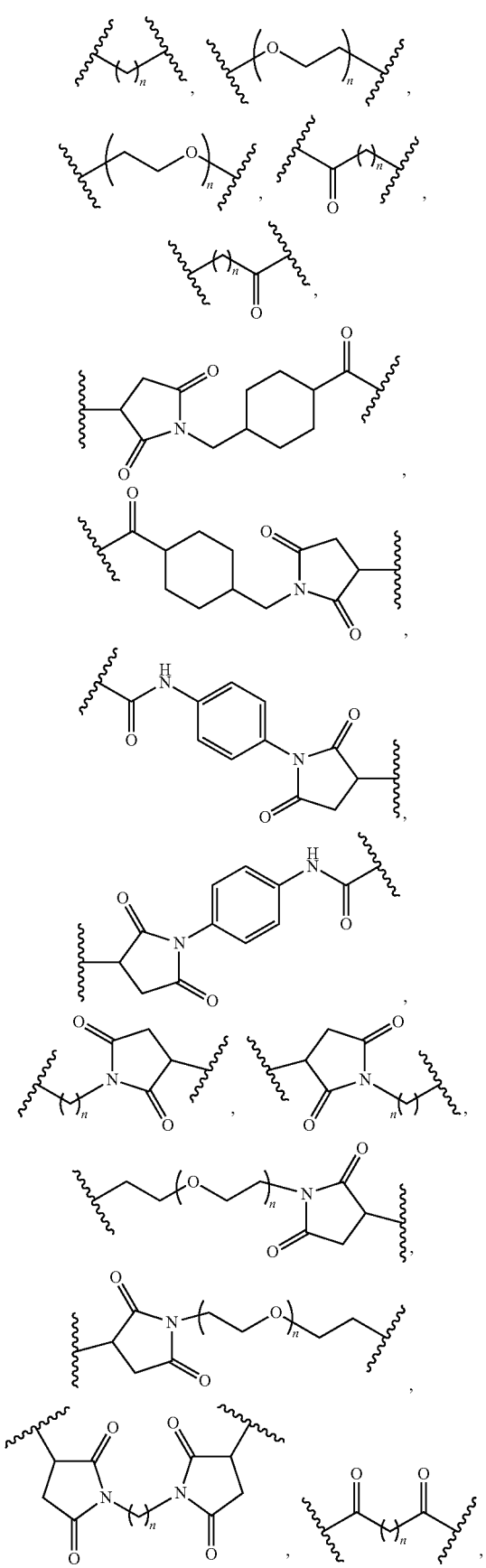

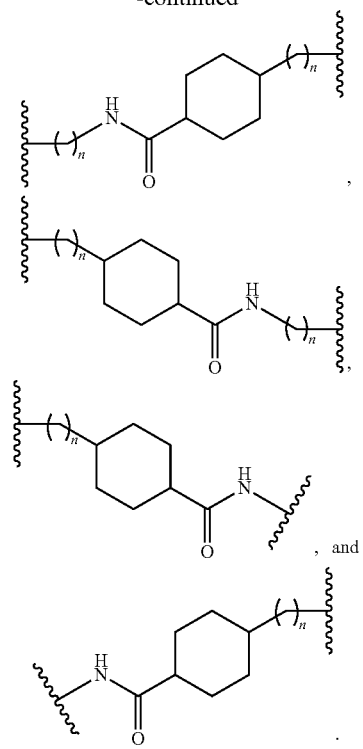
4. The compound of claim 1, or a pharmaceutically acceptable salt thereof, wherein $L^2$ is absent or is a linking group consisting of one or more groups of the formula:
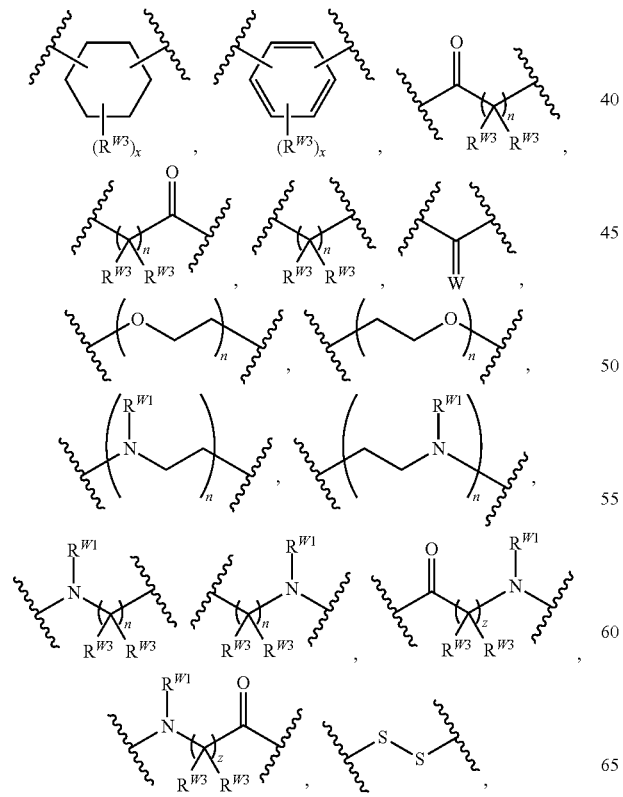
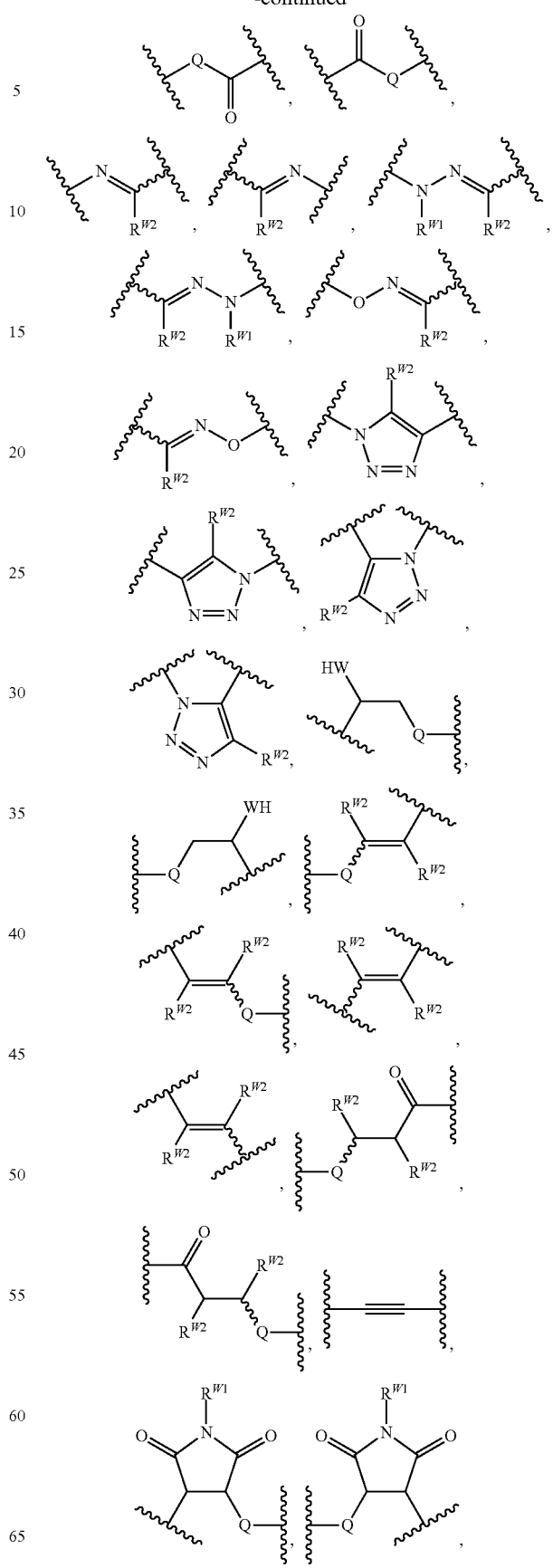

191

-continued

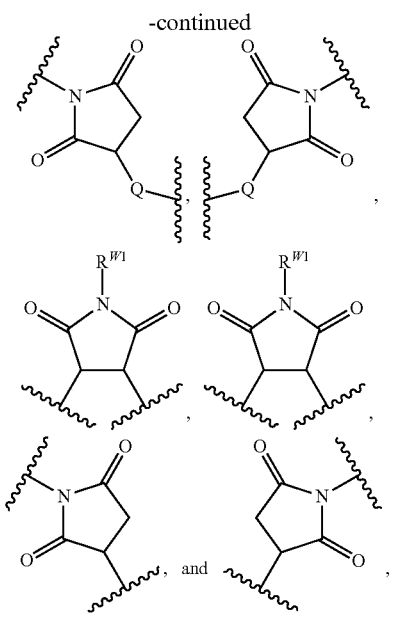

wherein:
n is an integer between 1 to 10, inclusive;
x is 0, 1 or 2;
z is 1 or 2;
Q is —NH—, —NH—NH—, —O—NH—, —NH—O—, —S—, or —O—;
W is O, S, or $NR^{w1}$;
$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;
$R^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; or substituted or unsubstituted aryl; substituted or unsubstituted heteroaryl; or two $R^{W2}$ groups are joined to form a 5-6 membered ring; and
each instance of $R^{W3}$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two $R^{W3}$ groups are joined to form a 3-6 membered ring; or $R^{W1}$ and $R^{W3}$ are joined to form a 5-6 membered heterocyclic ring.

5. The compound of claim 1 of Formula (I-a):

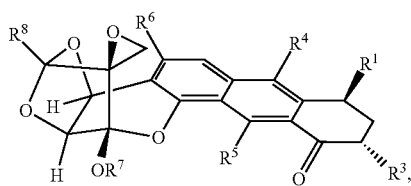

(I-a)

or a pharmaceutically acceptable salt thereof.

6. The compound of claim 1, or a pharmaceutically acceptable salt thereof, wherein $R^1$ is hydrogen or —$OR^{41}$; and $R^2$ is hydrogen.

7. The compound of claim 1, or a pharmaceutically acceptable salt thereof, wherein $R^1$ and $R^2$ are joined to form =O.

8. The compound of claim 1, or a pharmaceutically acceptable salt thereof, wherein $R^3$ is hydrogen.

9. The compound of claim 1, or a pharmaceutically acceptable salt thereof, wherein $R^1$, $R^2$, and $R^3$ are each hydrogen.

10. The compound of claim 1, or a pharmaceutically acceptable salt thereof, wherein $R^4$ is —$OCH_3$.

11. The compound of claim 1, or a pharmaceutically acceptable salt thereof, wherein $R^5$ is —OH.

12. The compound of claim 1, or a pharmaceutically acceptable salt thereof, wherein $R^6$ is —$CH_3$.

13. The compound of claim 1, or a pharmaceutically acceptable salt thereof, wherein $R^8$ is —$CH(OCH_3)_2$.

14. The compound of claim 1, or a pharmaceutically acceptable salt thereof, wherein B is an antibody selected from the group consisting of Adecatumumab, Afutuzumab, Alemtuzumab (CAMPATH), Bavituximab, Belimumab, Bevacizumab (AVASTIN), Brentuximab, Cantuzumab, Cetuximab (ERBITUX), Citatuzumab, Cixutumumab, Conatumumab, Dacetuzumab, Elotuzumab, Etaracizumab, Farletuzumab, Figitumumab, Gemtuzumab, Ibritumomab, Inotuzumab, Ipilimumab (YERVOY), Iratumumab, Labetuzumab, Lexatumumab, Lintuzumab, Lucatumumab, Mapatumumab, Matuzumab, Milatuzumab, Necitumumab, Nimotuzumab, Ofatumumab (ARZERRA), Olaratumab, Oportuzumab, Panitumumab (VECTIBIX), Pertuzumab (PERJETA), Pritumumab, Rituximab (RITUXAN), Robatumumab, Sibrotuzumab, Siltuximab, Tacatuzumab, Tigatuzumab, Tositumomab (BEXXAR), Trastuzumab (HERCEPTIN), Tucotuzumab, Veltuzumab, Votumumab, Zalutumumab, and antibody fragments thereof.

15. A pharmaceutical composition comprising a compound of claim 1 or pharmaceutically acceptable salt thereof, and a pharmaceutically acceptable excipient.

16. A method of treating a condition selected from the group consisting of proliferative diseases, inflammatory diseases, autoimmune diseases, and infectious diseases from which a subject is suffering from, comprising administering to the subject an amount of a compound of claim 1 or pharmaceutically acceptable salt thereof, effective to treat the condition.

17. The method of claim 16, wherein the proliferative disease is a cancer.

18. A method of preparing a compound of Formula (I) of claim 1:

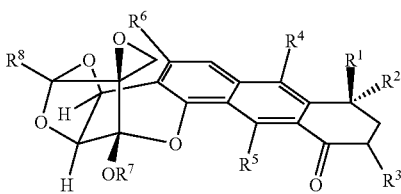

(I)

or a pharmaceutically acceptable salt thereof,
the method comprising coupling a compound of Formula (PI):

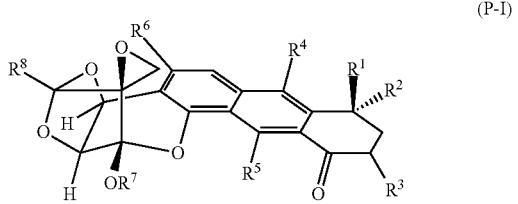

(P-I)

or a salt thereof,
with (i) a compound of formula Y-L²-X, followed by coupling with a compound of formula Y-L²-B, or with (ii) a compound of formula Y-L²-B;
wherein:
each of X and Y are independently selected from the group consisting of —SH, —OH, —NH₂, —NH—NH₂, —N₃, —O—NH₂, halogen (or other leaving group), —C(=O)R$^{X1}$,

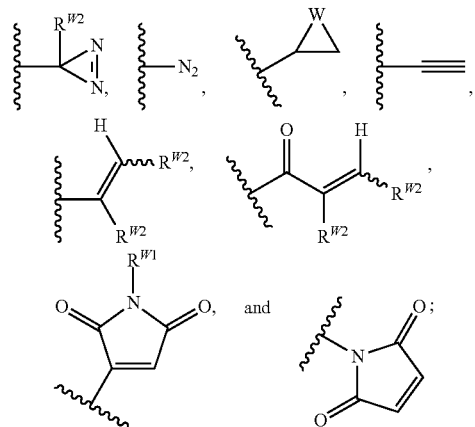

wherein:
R$^{X1}$ is hydrogen, halogen, or —OR$^{X2}$, wherein R$^{X2}$ is hydrogen, substituted or unsubstituted alkyl, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or an oxygen protecting group;
W is O, S, or NR$^{W1}$;
R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;
R$^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two R$^{W2}$ groups are joined to form a 5-6 membered ring;
a is an integer between 1 and 10, inclusive;
L¹ is absent or is a linking group selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; peptidyl groups; dipeptidyl groups; polypeptidyl groups; and combinations thereof;
L² is absent or is a linking group selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; peptidyl groups; dipeptidyl groups; polypeptidyl groups; and combinations thereof;
A is a group of the formula —NH—, —NH—NH—, —NH—O—, —O—NH—, —S—, —O—,

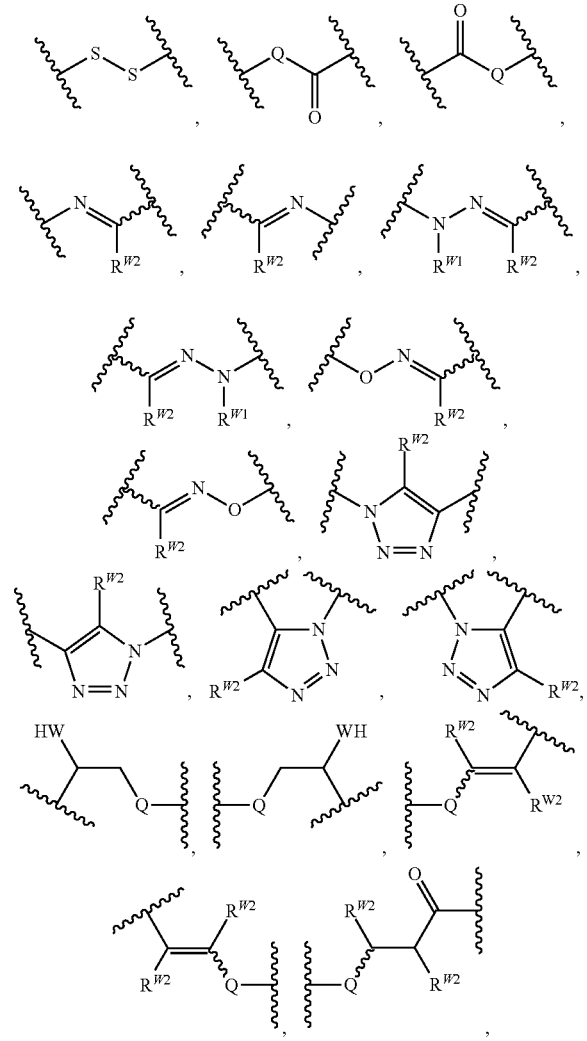

-continued

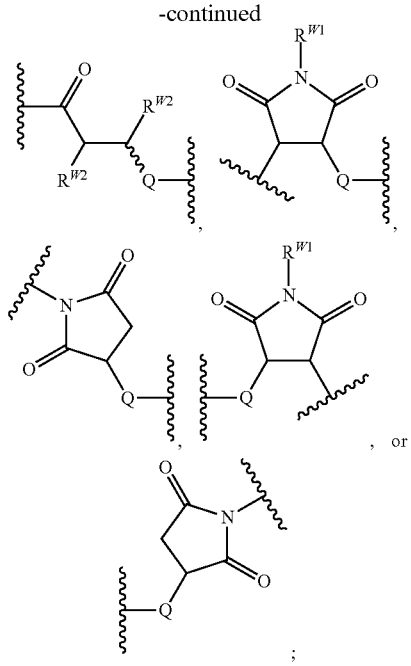

Q is —NH—, —NH—NH—, —O—NH—, —NH—O—, —S—, or —O—;

W is —O—, —S—, or —NR$^{W1}$—, wherein R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

R$^{W2}$ is hydrogen, substituted or unsubstituted alkyl; or substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two R$^{W2}$ groups are joined to form a 5-6 membered ring;

B is an antibody or an antibody fragment;

R$^1$ is hydrogen or —OR$^{A1}$; and R$^2$ is hydrogen; or R$^1$ and R$^2$ are joined to form =O;

R$^{A1}$ is hydrogen; an oxygen protecting group or substituted or unsubstituted alkyl;

or R$^{A1}$ is a group of Formula (i):

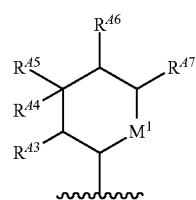

(i)

wherein each occurrence of R$^{43}$, R$^{44}$, R$^{45}$, R$^{46}$, and R$^{47}$ is independently hydrogen, substituted or unsubstituted alkyl; —OR$^{49}$; —OC(=O)R$^{49}$; —N(R$^{49}$)$_2$; or —NHC(=O)R$^{49}$; wherein each occurrence of R$^{49}$ is independently hydrogen; substituted or unsubstituted alkyl; an oxygen protecting group when attached to an oxygen atom; or a nitrogen protecting group when attached to a nitrogen atom; or two R$^{49}$ groups are joined to form a substituted or unsubstituted heterocyclic or substituted or unsubstituted heteroaryl ring; and M$^1$ is —O—;

R$^3$ is hydrogen or —OR$^{C1}$, wherein R$^{C1}$ is hydrogen; an oxygen protecting group; or substituted or unsubstituted alkyl;

R$^4$ is hydrogen or —OR$^{D1}$, wherein R$^{D1}$ is hydrogen; an oxygen protecting group; or substituted or unsubstituted alkyl;

R$^5$ is hydrogen or —OR$^{E1}$, wherein R$^{E1}$ is hydrogen; an oxygen protecting group; or substituted or unsubstituted alkyl;

R$^6$ is substituted or unsubstituted alkyl;

R$^7$ is -L$^1$-(A-L$^2$)$_a$-B for Formula (I), or a group -L$^1$-X for Formula (P-I);

R$^8$ is —CH(OR$^{J1}$)$_2$;

each occurrence of R$^{J1}$ is independently substituted or unsubstituted alkyl;

wherein substituted, when on a carbon atom, independently refers to substitution with halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$_{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, or 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; and wherein substituted, when on a nitrogen atom, independently refers to substitution with —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, or 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, or 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, or 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, or 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, or 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl) $^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form =O or =S; wherein X$^-$ is a counterion.

19. The compound of claim 1 of Formula (I-b):

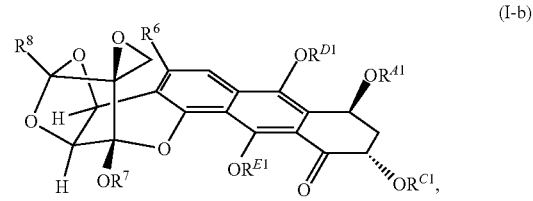

(I-b)

or a pharmaceutically acceptable salt thereof.

20. The compound of claim 1 of Formula (I-c):

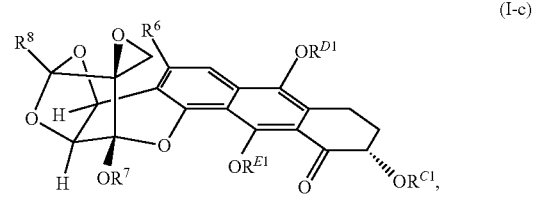

(I-c)

or a pharmaceutically acceptable salt thereof.

21. The compound of claim 1 of Formula (I-d):

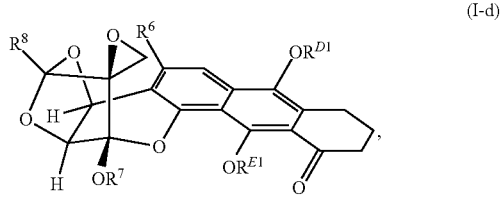

(I-d)

or a pharmaceutically acceptable salt thereof.

22. The compound of claim 1 of Formula (I-e):
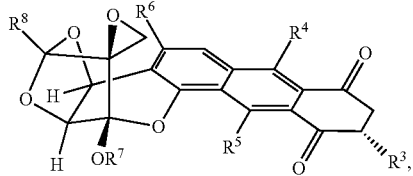
or a pharmaceutically acceptable salt thereof.
23. The compound of claim 1 of Formula (I-f):
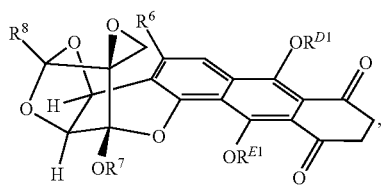
or a pharmaceutically acceptable salt thereof.
24. A compound selected from the group consisting of
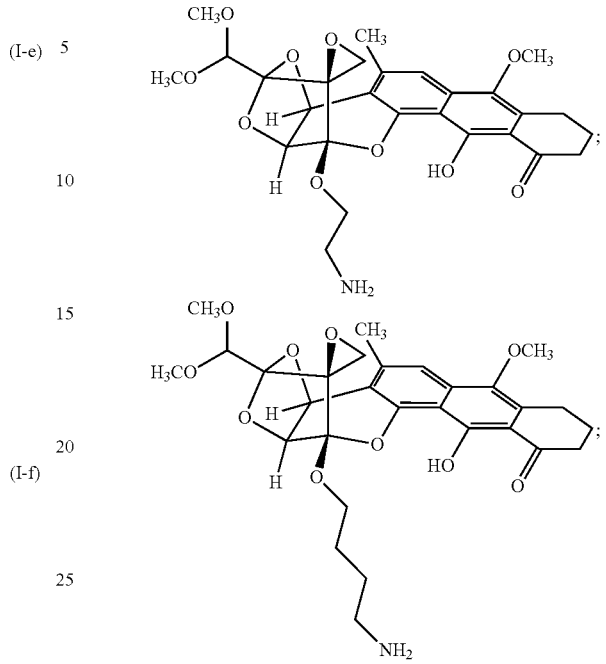
and salts thereof.

UNITED STATES PATENT AND TRADEMARK OFFICE
CERTIFICATE OF CORRECTION

PATENT NO.       : 9,775,915 B2
APPLICATION NO.  : 14/647198
DATED            : October 3, 2017
INVENTOR(S)      : Andrew G. Myers et al.

It is certified that error appears in the above-identified patent and that said Letters Patent is hereby corrected as shown below:

In the Claims

In Claim 1, at Column 183, Line 26, the text: "oxygen protecting group;or substituted or unsubstituted" should be replaced with: -- oxygen protecting group; or substituted or unsubstituted --.

In Claim 1, at Column 183, Line 53, the text: "$(R^{3aa})_3-C(=S)N(R^{bb})_2$," should be replaced with: -- $(R^{aa})_3, -C(=S)N(R^{bb})_2$, --.

In Claim 1, at Column 184, Lines 24-25, the text: "$-N(R^{cc})_2, -CN, -C(=O)R^{aa}, -C(=O\ )N(R^{cc})_2$," should be replaced with: -- $-N(R^{cc})_2, -CN, -C(=O)R^{aa}, -C(=O)N(R^{cc})_2$, --.

In Claim 1, at Column 185, Line 21, the text: "$-SS(C_{1-6}\ alkyl), -C(=O)(C_{1-6}\ alkyl)$," should be replaced with: -- $-SS(C_{1-6}alkyl), -C(=O)(C_{1-6}alkyl)$, --.

In Claim 1, at Column 185, Lines 29-30, the text: ",$-NHC(NH)N(C_{1-6}\ alkyl)_2$" should be replaced with: -- , $-NHC(NH)N(C_{1-6}alkyl)_2$ --.

In Claim 1, at Column 185, Line 35, the text: "$-OSi(C_{1-6}alkyl)_3 -C(=S)N(C_{1-6}alkyl)_2$" should be replaced with: -- $-OSi(C_{1-6}alkyl)_3, -C(=S)N(C_{1-6}alkyl)_2$ --.

In Claim 1, at Column 185, Line 40, the text: "=0" should be replaced with: -- =O --.

In Claim 2, at Column 187, Line 36, the text: "x is 0, 1 or 2;" should be replaced with: -- x is 0, 1, or 2; --.

In Claim 2, at Column 187, Line 40, the text: "O—, —S, —O—;" should be replaced with: -- —O—, —S, or —O—; --.

Signed and Sealed this
First Day of May, 2018

Andrei Iancu
*Director of the United States Patent and Trademark Office*

CERTIFICATE OF CORRECTION (continued)
U.S. Pat. No. 9,775,915 B2

In Claim 2, at Column 187, Line 62, the text: "3-6membered" should be replaced with: -- 3-6 membered --.

In Claim 4, at Column 191, Lines 42-44, the text: "or substituted or unsubstituted aryl, substituted or unsubstituted heteroaryl" should be replaced with: -- substituted or unsubstituted aryl, or substituted or unsubstituted heteroaryl --.

In Claim 18, at Column 192, Line 67, the text: "(PI)" should be replaced with: -- (P-I) --.

In Claim 18, at Column 195, Lines 37-38, the text: "alkyl; or substituted" should be replaced with: -- alkyl; substituted --.

In Claim 18, at Column 196, Line 26, the text: "—OC(=OR$^{aa}$," should be replaced with: -- —OC(=O)R$^{aa}$, --.

In Claim 18, at Column 196, Lines 34-35, the text: "—OSi(R$^{aa}$)$_3$ —C(=S)N(R$^{bb}$)$_2$," should be replaced with: -- —OSi(R$^{aa}$)$_3$, —C(=S)N(R$^{bb}$)$_2$, --.

In Claim 18, at Column 197, Line 8, the text: "—C(=NR$^{cc}$)R$^{aa}$," should be replaced with: -- —C(=NR$^{cc}$)OR$^{aa}$, --.

In Claim 18, at Column 198, Line 3, the text: "—SS(C$_{1-6}$ alkyl), —C(=O)(C$_{1-6}$ alkyl)," should be replaced with: -- —SS(C$_{1-6}$alkyl), —C(=O)(C$_{1-6}$alkyl), --.